US010287359B2

(12) United States Patent
Hoogenraad et al.

(10) Patent No.: US 10,287,359 B2
(45) **Date of Patent: *May 14, 2019**

(54) FN14 BINDING PROTEINS AND USES THEREOF

(71) Applicant: La Trobe University, Bundoora, Victoria (AU)

(72) Inventors: Nicholas Johannes Hoogenraad, Melbourne (AU); Amelia Jane Johnston, Melbourne (AU); John Silke, Melbourne (AU)

(73) Assignee: La Trobe University, Bundoora, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/790,618

(22) Filed: Oct. 23, 2017

(65) Prior Publication Data

US 2018/0057599 A1 Mar. 1, 2018

Related U.S. Application Data

(63) Continuation of application No. 15/236,676, filed on Aug. 15, 2016, now abandoned, which is a continuation of application No. 14/529,890, filed on Oct. 31, 2014, now abandoned, which is a continuation of application No. 13/851,153, filed on Mar. 27, 2013, now Pat. No. 9,006,397, which is a continuation of application No. PCT/AU2012/000989, filed on Aug. 23, 2012.

(60) Provisional application No. 61/526,599, filed on Aug. 23, 2011.

(51) Int. Cl.
*A61K 39/00* (2006.01)
*C07K 16/28* (2006.01)

(52) U.S. Cl.
CPC .... *C07K 16/2878* (2013.01); *A61K 2039/505* (2013.01); *C07K 2317/24* (2013.01); *C07K 2317/33* (2013.01); *C07K 2317/34* (2013.01); *C07K 2317/55* (2013.01); *C07K 2317/56* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 9,006,397 | B2 | 4/2015 | Hoogenraad et al. |
| 2005/0208046 | A1 | 9/2005 | Kim et al. |
| 2013/0273036 | A1 | 10/2013 | Hoogenraad et al. |
| 2015/0218278 | A1 | 8/2015 | Hoogenraad et al. |
| 2017/0029519 | A1 | 2/2017 | Hoogenraad et al. |

FOREIGN PATENT DOCUMENTS

| | | |
|---|---|---|
| WO | 03086311 | 10/2003 |
| WO | 2003086311 | 10/2003 |
| WO | 2009020933 | 2/2009 |
| WO | 2009140177 | 11/2009 |
| WO | 2013026099 | 2/2013 |

OTHER PUBLICATIONS

Scher (JNCI, 92(23):1866-1868, 2000).*
U.S. Appl. No. 13/851,153 , “Advisory Action”, dated Nov. 3, 2014, 3 pages.
U.S. Appl. No. 13/851,153 , “Final Office Action”, dated May 27, 2014, 11 pages.
U.S. Appl. No. 13/851,153 , “Non-Final Office Action”, dated Dec. 4, 2013, 21 Pages.
U.S. Application No. 13/851,153 , “Notice of Allowance”, dated Dec. 8, 2014, 12 pages.
U.S. Appl. No. 14/529,890 , “Non-Final Office Action”, dated May 13, 2016, 33 pages.
U.S. Appl. No. 14/529,890 , “Restriction Requirement”, dated Jan. 22, 2016, 5 pages.
U.S. Appl. No. 15/236,676 , “Non-Final Office Action”, dated Jul. 25, 2017, 29 pages.
U.S. Appl. No. 15/236,676 , “Restriction Requirement”, dated May 26, 2017, 5 pages.
Australian Patent Application No. 2012300191, “First Examination Report”, dated Mar. 13, 2013.
Australian Patent Application No. 2014203658, “First Examination Report” dated Jun. 17, 2015.
Chorianopoulos et al., “FGF-inducible 14-kDa protein (Fn14) is regulated via the RhoA/Rock kinase pathway in cardiomyocytes and mediates nuclear factor-kappaB activation by Tweak”, Basic Research in Cardiology, Steinkopff-Verlag, DA, (Jul. 23, 2009), vol. 105, No. 2, ISSN 1435-1803, pp. 301-313, XP019780543 [Y] 1-5,10-14.
European Patent Application No. 12826494.2, “First Examination Report” dated Nov. 23, 2016.
European Patent Application No. 12826494.2, “Supplemental EP Search Report”, dated Mar. 13, 2015.
Feng et al., “Tumor Necrosis Factor-Like Weak Inducer of Apoptosis Attenuates the Action of Insulin in Hepatocytes”, Endocrinology, (Apr. 1, 2008), vol. 149, No. 4, doi:10.1210/en.2007-1119, ISSN 0013-7227, pp. 1505-1513, XP055176016 [Y] 1-5,10-14.
Giusti et al., “Somatic diversificatio n of S107 from an antiphosphocholine to an anti-DNA autoantibody is due to a single base change in its heavy chain variable region”, Proc. Nati. Acad. Sci . USA vol. 84, May 1987, pp. 2926-2930.
Gussow et al., Methods in Enzymology, vol. 203, 1991, pp. 99-121.
Jones , Pharmacogenomics Journal, vol. 1, 2001, pp. 126-134.
Kumar et al., “Tweak/Fn14 system is a critical regulator of denervation-induced skeletal muscle atrophy”, The FASEB journal, vol. 24 (meeting abstract supplement), (Apr. 2010), URL: http://ajp.amjpathol.org/article/S0002-9440%2810%2960226-X/pdf, (Mar. 11, 2015), XP055176019 [Y] 1-5,10-14.

(Continued)

*Primary Examiner* — Brad Duffy
(74) *Attorney, Agent, or Firm* — Kilpatrick Townsend & Stockton, LLP

(57) ABSTRACT

The present disclosure provides proteins comprising antibody antigen binding domains that bind to Fn14 and uses thereof. The present disclosure also provides methods for treating wasting disorders, such as cachexia.

5 Claims, 82 Drawing Sheets

Specification includes a Sequence Listing.

(56) References Cited

OTHER PUBLICATIONS

Lippincott-Schwartz , “Antibodies as Cell Biological Tools”, Current Protocols in Cell Biology, 2002, pp. 16.0.1-16.0.2.
Mariuzza et al., “The Structural Basis of Antigen-Antibody Recognition”, Annual Review of Biophysics and Biophysical Chemistry, vol. 16, Jun. 1987, pp. 139-159.
Michaelson et al., “Therapeutic targeting of Tweak/FnI4 in cancer: exploiting the intrinsic tumor cell killing capacity of the pathwa”, Results and Problems in Cell Differentiation, vol. 48, Jan. 1, 2009, pp. 145-160.
Mittal et al., “The Tweak-Fn14 system is a critical regulator of denervation-induced skeletal muscle atrophy in mice”, The Rockefeller University Press, JCB vol. 188 No. 6, Mar. 22, 2010, pp. 833-839.
Mittal et al., “Genetic Ablation of Tweak Augments Regeneration and Post-Injury Growth of Skeletal Muscle in Mice”, The American Journal of Pathology, (Oct. 1, 2010), vol. 177, No. 4, doi:10.2353/ajpath.2010.100335, ISSN 0002-9440, pp. 1732-1742, XP055176014 [Y] 1-5,10-14.
International Application No. PCT/AU2012/000989 , International Search Report and Written Opinion dated Sep. 24, 2012.
Rudikoff et al., “Single Amino Acid Substitution altering Antigen-binding Specificity”, Proc. Natl Acad Sci., vol. 79,No. 6, 1982, pp. 1979-1983.
Singapore Patent Application No. 2014010334, “Examiner’s Written Opinion”, dated Mar. 18, 2015.
Tosatto et al., Current Pharmaceutical Design, vol. 12, 2006, pp. 2067-2086.
Winkler et al., “Changing the antigen binding specificity by single point mutations of an anti-p24 (HIV-1) antibody”, J. Immunol., vol. 165 (8), Oct. 15, 2000, pp. 4505-4514.

* cited by examiner

Light chain sequences:

| | FR1 | CDR1 | FR2 | CDR2 | FR3 |
|---|---|---|---|---|---|
| 001 | DIVMTQTPASLAVSLGQRATISC | **RASQSVSTSTYSYMH** | WYQQKPGQPPKLLIK | **YASSLES** | GVPARFSGSGSGTDFTLNIHPVEEDDTATYYC |
| 002 | DTVLTQSPASLVVSLGQRATISC | **RASQSVSTSDYSYIH** | WYQQKPGQPPKFLIK | **YASNRDS** | GVPARFSGSGSGTDFTLNIHPVEEDDTAIYYC |
| 005 | DIVLTQTTASLTVSLGQRATISC | **RASQSVSTSTYSYMH** | WYQQTPGQPPTVLIK | **YASSLES** | GVPTRFSGSGSGTDFTLNIHPVEEEDTATYYC |
| 006 | DIVITQSPASLTVSLGQRATISC | **RASQSVSTSTYSYMH** | WYQQTPGQPPTVLIK | **YASSLES** | GVPTRFSGSGSGTDFTLNIHPVEEEDTATYYC |
| 007 | DIVMTQSTASLAVSLGQRATISC | **RASQSVSTSSYSYMH** | WYQQKPGQPPKVLIK | **YASNLES** | GVPARFSGSGSGTDFTLNIHPVEEEDAATYYC |
| | | | | | |
| 003 | DIVMTQTTALMAASPGEKVTITC | SVNSSI SSSYLHW | YQQKSGISPNPGFMAHPTWLLESLLASVAVDLGPLTLSHSAAWRLKMLPLITVNSGVVPH | | |
| 004 | DIVLTQSPALMAASPGEKVTITC | SVNSSI SSSYLHW | YQQKSGISPNPGFMAHPTWLLESLLASVAVDLGPLTLSHSAAWRLKMLPLITVNSGVVPH | | |

| | CDR3 | FR4 | |
|---|---|---|---|
| 001 | **QHSWEIPYT** | FGGGTKLEIKR | SEQ ID NO: 22 |
| 002 | **QHSWEIPPT** | FGAGTKLELQR | SEQ ID NO: 23 |
| 005 | **QHSWEIPYT** | FGGGTKLEIKR | SEQ ID NO: 26 |
| 006 | **QHSWEIPYT** | FGGGTKLEIKR | SEQ ID NO: 27 |
| 007 | **QHSWEIPYT** | FGGGTKLEIKR | SEQ ID NO: 28 |
| | | | |
| 003 | | GSGTKLEIKR | SEQ ID NO: 24 |
| 004 | | GSGTKLEIKR | SEQ ID NO: 25 |

Figure 11A

Light chain sequences:

```
                       FR1              CDR1            FR2           CDR2          FR3
    001   DIVMTQTPASLAVSLGQRATISC RASQSVSTSTYSYMH WYQQKPGQPPKLLIK    YASSLES  GVPARFSGSGSGTDFTLNIHPVEEDDTATYYC
    002   DTVLTQSPASLVVSLGQRATISC RASQSVSTSDYSYIH WYQQKPGQPPKFLIK    YASNRDS  GVPARFSGSGSGTDFTLNIHPVEEDDTAIYYC
    005   DIVLTQTTASLTVSLGQRATISC RASQSVSTSTYSYMH WYQQTPGQPPTVLIK    YASSLES  GVPTRFSGSGSGTDFTLNIHPVEEEDTATYYC
    006   DIVITQSPASLTVSLGQRATISC RASQSVSTSTYSYMH WYQQTPGQPPTVLIK    YASSLES  GVPTRFSGSGSGTDFTLNIHPVEEEDTATYYC
    007   DIVMTQSTASLAVSLGQRATISC RASQSVSTSSYSYMH WYQQKPGQPPKVLIK    YASNLES  GVPARFSGSGSGTDFTLNIHPVEEEDAATYYC

CONSENSUS DIVXTQXXASLXVSLGQRATISC RASQSVSTSXYSYXH WYQQXPGQPPXXLIK    YASXXXS  GVPXRFSGSGSGTDFTLNIHPVEEXDTAXYYC
             I  TP   T                     T   M      K     KL          SLE      A                    D   T
             L  ST   A                     D   T      T     TV          NRD      T                    E   I
             M       V                                       F

             CDR3        FR4
    001   QHSWEIPYT FGGGTKLEIKR  SEQ ID NO: 22
    002   QHSWEIPPT FGAGTKLELQR  SEQ ID NO: 23
    005   QHSWEIPYT FGGGTKLEIKR  SEQ ID NO: 26
    006   QHSWEIPYT FGGGTKLEIKR  SEQ ID NO: 27
    007   QHSWEIPYT FGGGTKLEIKR  SEQ ID NO: 28

CONSENSUS QHSWEIPXT FXGGTKLEXXR  SEQ ID NO: 14
                 P   G      LQ
                 Y   A      IK
```

Figure 11B

Heavy chain sequences:

| | FR1 | CDR1 | FR2 | CDR2 | FR3 |
|---|---|---|---|---|---|
| 001 | QVQLQQSGGGLVQPGGSMKLSCIAS | GFTFS**SYWMS** | WVRQSPEKGLEWVA | **EIRSKSDNYATHYAESVKG** | KFTISRDDSKSRFFLQMNNLRAEDTGIYYCSS |
| 002 | EVKLQQSGGGLVQPGGSMKLSCVAS | GFTFS**YYWMN** | WVRQSPEQGLEWIA | **EIRLQSNDYPTHYAESVKG** | RFTISRDDSKNSVYLQMNNLRPEDTGIYYCAC |
| 005 | QVQLQESGGGLVQPGGSMKLSCVAS | GFTFS**YYWMN** | WVRQSPEQGLEWIA | **EIRLQSNDYPTHYAESVKG** | RFTISRDDSKNSVYLQMNNLRPEDTGIYYCAC |
| 006 | QVQLQESGGGLVQPGGSMKLSCVAS | GFTFS**YYWMN** | WVRQSPEQGLEWIA | **EIRLQSNDYPTHYAESVKG** | RFTISRDDSKNSVYLQMNNLRPEDTGIYYCAC |
| 007 | QVKLEESGGVLVQPGGSMKLSCIAS | GFSFS**KYWMN** | WVRQSPEKGLEWVA | **EIRVKSNNYATHYAESVKG** | RFIISRDDSKSSVYLQMNNLRAEDTGIYYCTK |
| 003 | QVKLEQSGGGLVQPGGSMKLSCVAS | GFTFS**HYWMS** | WVRQSPEKGLEWVA | **EIRLKSDNYATHYAESVKG** | KFTISRDDSKSRLYLQMSSLRAEDTGIYYCTG |
| 004 | QVQLQQSGGGLVQPGGSMKLSCVAS | GFTFS**HYWMS** | WVRQSPEKGLEWVA | **EIRLKSDNYATHYAESVKG** | KFTISRDDSKSRLYLQMSSLRAEDTGIYYCTG |

| | CDR3 | FR4 | |
|---|---|---|---|
| 001 | **TYADYFHY** | WGQGTDLTVSS | SEQ ID NO: 15 |
| 002 | **RYADYFDH** | WGQGTTLTVSS | SEQ ID NO: 16 |
| 005 | **RYADYFDH** | WGQGTTLTVSS | SEQ ID NO: 19 |
| 006 | **RYADYFDH** | WGQGTTLTVSS | SEQ ID NO: 20 |
| 007 | **SYADYFDY** | WGQGTTLTVSS | SEQ ID NO: 21 |
| 003 | **RYSDYFDY** | WGQGTTLTVSS | SEQ ID NO: 17 |
| 004 | **RYSDYFDY** | WGQGTTLTVSS | SEQ ID NO: 18 |

Figure 11C

Heavy chain sequences:

| | FR1 | CDR1 | FR2 | CDR2 | FR3 |
|---|---|---|---|---|---|
| 001 | QVQLQQSGGGLVQPGGSMKLSCIAS | GFTFSSYWMS | WVRQSPEKGLEWVA | EIRSKSDNYATHYAESVKG | KFTISRDDSKSRFFLQMNNLRAEDTGIYYCSS |
| 002 | EVKLQQSGGGLVQPGGSMKLSCVAS | GFTFSYYWMN | WVRQSPEQGLEWIA | EIRLQSNDYPTHYAESVKG | RFTISRDDSKNSVYLQMNNLRPEDTGIYYCAC |
| 005 | QVQLQESGGGLVQPGGSMKLSCVAS | GFTFSYYWMN | WVRQSPEQGLEWIA | EIRLQSNDYPTHYAESVKG | RFTISRDDSKNSVYLQMNNLRPEDTGIYYCAC |
| 006 | QVQLQESGGGLVQPGGSMKLSCVAS | GFTFSYYWMN | WVRQSPEQGLEWIA | EIRLQSNDYPTHYAESVKG | RFTISRDDSKNSVYLQMNNLRPEDTGIYYCAC |
| 007 | QVKLEESGGVLVQPGGSMKLSCIAS | GFSFSKYWMN | WVRQSPEKGLEWVA | EIRVKSNNYATHYAESVKG | RFIISRDDSKSSVYLQMNNLRAEDTGIYYCTK |
| 003 | QVKLEQSGGGLVQPGGSMKLSCVAS | GFTFSHYWMS | WVRQSPEKGLEWVA | EIRLKSDNYATHYAESVKG | KFTISRDDSKSRLYLQMSSLRAEDTGIYYCTG |
| 004 | QVQLQQSGGGLVQPGGSMKLSCVAS | GFTFSHYWMS | WVRQSPEKGLEWVA | EIRLKSDNYATHYAESVKG | KFTISRDDSKSRLYLQMSSLRAEDTGIYYCTG |
| CONSENSUS | XVXLXXSGGXLVQPGGSMKLSCXAS | GFXFXXYWMX | WVRQSPEXGLEWXA | EIRXXSXXYXTHYAESVKG | XFXISRDDSXXXXXLQMXXLRXEDTGIYYCXX |
| | Q K QQ V I | T SS S | Q V | VK NN A | K T KNRFY NN P TS |
| | E Q EE G V | S NY N | K I | LQ DD P | R I ESSVF SS A AC |
| | | K | | SR E | CL SR |
| | | H | | | K |

| | CDR3 | FR4 | |
|---|---|---|---|
| 001 | TYADYFHY | WGQGTDLTVSS | SEQ ID NO: 15 |
| 002 | RYADYFDH | WGQGTTLTVSS | SEQ ID NO: 16 |
| 005 | RYADYFDH | WGQGTTLTVSS | SEQ ID NO: 19 |
| 006 | RYADYFDH | WGQGTTLTVSS | SEQ ID NO: 20 |
| 007 | SYADYFDY | WGQGTTLTVSS | SEQ ID NO: 21 |
| 003 | RYSDYFDY | WGQGTTLTVSS | SEQ ID NO: 17 |
| 004 | RYSDYFDY | WGQGTTLTVSS | SEQ ID NO: 18 |
| CONSENSUS | XYXDYFXX | WGQGTXLTVSS | SEQ ID NO: 13 |
| | T A HH | T | |
| | R S DY | D | |
| | S | | |

| | | |
|---|---|---|
| RW91 | DFCLGCAAAPPAPFRLLWP | SEQ ID NO: 12 |
| RW95 | SRGSSWSADLDKCMDCASCRARPHSDFCLGCAAAPPAPFRLLWPILGGALSLTF | SEQ ID NO: 11 |
| RW98 | LRSVAGEQAPGTAPCSRGSSWSADLDKCMDCASCRARPHSDFCLGCAAAPPAPFRLLWPILGGALSLTPVLGL | SEQ ID NO: 10 |
| RW114 | PGTAPCSRGSSWSADLDKCMDCASCRARPHSDFCLGCAAA | SEQ ID NO: 9 |
| RW118 | LLRSVAGEQAPGTAPCSRGSSWSADLDKCMDCASCRARPHSDFCLGCAAAPPA | SEQ ID NO: 8 |
| RW120 | PGTAPCSRGSSWSADLDKCMDCASCRARPHSDFCLGCAAAPPAPVD | SEQ ID NO: 7 |
| RW125 | PGTAPCSRGSSWSADLDKCMDCASCRARPHSDFCLGCAAAPPAP | SEQ ID NO: 6 |
| RW127 | WLALLRSVAGEQAPGTAPCSRGSSWSADLDKCMDCASCRARPHSDFCLGCAA | SEQ ID NO: 5 |
| **RW129** | **GTAPCSRGSSWSADLDKCMDCASCRARPHSDFCLGCAAAPPAP** | SEQ ID NO: 3 |
| RW131 | RSVAGEQAPGTAPCSRGSSWSADLDKCMDCASCRARPHSDFCLGCAA | SEQ ID NO: 4 |

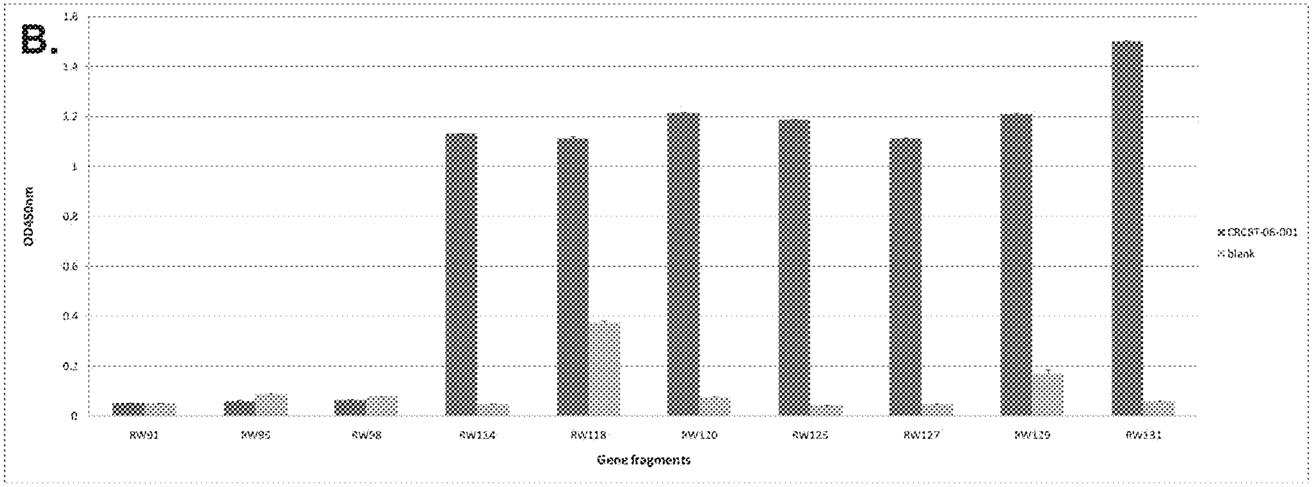

Figure 13

| | | |
|---|---|---|
| Fn14 Ectodomain | EQAPGTAPCSRGSSWSADLDKCMDCASCRARPHSDFCLGCAAAPPAPFRL | SEQ ID NO: 2 |
| D45A | EQAPGTAPCSRGSSWSAALDKCMDCASCRARPHSDFCLGCAAAPPAPFRL | SEQ ID NO: 29 |
| K48A | EQAPGTAPCSRGSSWSADLDACMDCASCRARPHSDFCLGCAAAPPAPFRL | SEQ ID NO: 30 |
| M50A | EQAPGTAPCSRGSSWSADLDKCADCASCRARPHSDFCLGCAAAPPAPFRL | SEQ ID NO: 31 |
| D62E | EQAPGTAPCSRGSSWSADLDKCMDCASCRARPHSEFCLGCAAAPPAPFRL | SEQ ID NO: 32 |
| Fn14 Sub-domain 1 | PGTAPCSRGSSWSADLDKCM | SEQ ID NO: 33 |
| Fn14 Sub-domain 2 | DCASCRARPHSDFCLGCAAA | SEQ ID NO: 34 |
| Fn14 Sub-domain 3 | ASCRARPHSDFCLG | SEQ ID NO: 35 |

EQAPGTAPCSRGSSWSADLDKCMDCASCRARPHSDFCLGCAAAPPAPFRL SEQ ID NO: 2

B.

EQAPGTAPCSRGSSWSADLDKCMD    SEQ ID NO: 46

C.

DCASCRARPHSDFCLGCAAA    SEQ ID NO: 34

D.

ASCRARPHSDFCLG    SEQ ID NO: 35

E.
DSASCRARPHSDFCLGSAAA    SEQ ID NO: 47

F.
DCASSRARPHSDFSLGCAAA    SEQ ID NO: 48

Protein sequence of Fn14-GPI control 1 70
MARGSLRRLLRLLVLGLWLALLRSVAGEQAPGTAPCSRGSSWSADLDKCMDCASCRARPHSDFCLGCAAA

71 126
PLAPFRLLW*MTTSPGTPAPAAEETMTT*S*PGTPASSHYLSCTIVGIIVLIVLLIVFV* SEQ ID NO: 36
↑

Figure 34A

SEQUENCE LISTING

```
<160> NUMBER OF SEQ ID NOS: 70

<210> SEQ ID NO 1
<211> LENGTH: 103
<212> TYPE: PRT
<213> ORGANISM: Homo sapiens

<400> SEQUENCE: 1

Gly Glu Gln Ala Pro Gly Thr Ala Pro Cys Ser Arg Gly Ser Ser Trp
1               5                   10                  15

Ser Ala Asp Leu Asp Lys Cys Met Asp Cys Ala Ser Cys Arg Ala Arg
            20                  25                  30
```

-continued

```
Pro His Ser Asp Phe Cys Leu Gly Cys Ala Ala Ala Pro Pro Ala Pro
        35                  40                  45

Phe Arg Leu Leu Trp Pro Ile Leu Gly Gly Ala Leu Ser Leu Thr Phe
    50                  55                  60

Val Leu Gly Leu Leu Ser Gly Phe Leu Val Trp Arg Arg Cys Arg Arg
65                  70                  75                  80

Arg Glu Lys Phe Thr Thr Pro Ile Glu Glu Thr Gly Gly Glu Gly Cys
                85                  90                  95

Pro Ala Val Ala Leu Ile Gln
            100


<210> SEQ ID NO 2
<211> LENGTH: 50
<212> TYPE: PRT
<213> ORGANISM: artificial
<220> FEATURE:
<223> OTHER INFORMATION: amino acid sequence of Fn14 ectodomain (Mus
      musculus)

<400> SEQUENCE: 2

Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Ala Pro Pro Ala Pro Phe
        35                  40                  45

Arg Leu
    50


<210> SEQ ID NO 3
<211> LENGTH: 43
<212> TYPE: PRT
<213> ORGANISM: artificial
<220> FEATURE:
<223> OTHER INFORMATION: amino acid sequence of Fn14 gene fragment RW129
      (Mus musculus)

<400> SEQUENCE: 3

Gly Thr Ala Pro Cys Ser Arg Gly Ser Ser Trp Ser Ala Asp Leu Asp
1               5                   10                  15

Lys Cys Met Asp Cys Ala Ser Cys Arg Ala Arg Pro His Ser Asp Phe
            20                  25                  30

Cys Leu Gly Cys Ala Ala Ala Pro Pro Ala Pro
        35                  40


<210> SEQ ID NO 4
<211> LENGTH: 47
<212> TYPE: PRT
<213> ORGANISM: artificial
<220> FEATURE:
<223> OTHER INFORMATION: amino acid sequence of Fn14 gene fragment RW131
      (Mus musculus)

<400> SEQUENCE: 4

Arg Ser Val Ala Gly Glu Gln Ala Pro Gly Thr Ala Pro Cys Ser Arg
1               5                   10                  15

Gly Ser Ser Trp Ser Ala Asp Leu Asp Lys Cys Met Asp Cys Ala Ser
            20                  25                  30

Cys Arg Ala Arg Pro His Ser Asp Phe Cys Leu Gly Cys Ala Ala
        35                  40                  45
```

```
<210> SEQ ID NO 5
<211> LENGTH: 52
<212> TYPE: PRT
<213> ORGANISM: artificial
<220> FEATURE:
<223> OTHER INFORMATION: amino acid sequence of Fn14 gene fragment RW127
      (Mus musculus)

<400> SEQUENCE: 5

Trp Leu Ala Leu Leu Arg Ser Val Ala Gly Glu Gln Ala Pro Gly Thr
1               5                   10                  15

Ala Pro Cys Ser Arg Gly Ser Ser Trp Ser Ala Asp Leu Asp Lys Cys
            20                  25                  30

Met Asp Cys Ala Ser Cys Arg Ala Arg Pro His Ser Asp Phe Cys Leu
        35                  40                  45

Gly Cys Ala Ala
    50


<210> SEQ ID NO 6
<211> LENGTH: 44
<212> TYPE: PRT
<213> ORGANISM: artificial
<220> FEATURE:
<223> OTHER INFORMATION: amino acid sequence of Fn14 gene fragment RW125
      (Mus musculus)

<400> SEQUENCE: 6

Pro Gly Thr Ala Pro Cys Ser Arg Gly Ser Ser Trp Ser Ala Asp Leu
1               5                   10                  15

Asp Lys Cys Met Asp Cys Ala Ser Cys Arg Ala Arg Pro His Ser Asp
            20                  25                  30

Phe Cys Leu Gly Cys Ala Ala Ala Pro Pro Ala Pro
        35                  40


<210> SEQ ID NO 7
<211> LENGTH: 46
<212> TYPE: PRT
<213> ORGANISM: artificial
<220> FEATURE:
<223> OTHER INFORMATION: amino acid sequence of Fn14 gene fragment RW120
      (Mus musculus)

<400> SEQUENCE: 7

Pro Gly Thr Ala Pro Cys Ser Arg Gly Ser Ser Trp Ser Ala Asp Leu
1               5                   10                  15

Asp Lys Cys Met Asp Cys Ala Ser Cys Arg Ala Arg Pro His Ser Asp
            20                  25                  30

Phe Cys Leu Gly Cys Ala Ala Ala Pro Pro Ala Pro Val Asp
        35                  40                  45


<210> SEQ ID NO 8
<211> LENGTH: 53
<212> TYPE: PRT
<213> ORGANISM: artificial
<220> FEATURE:
<223> OTHER INFORMATION: amino acid sequence of Fn14 gene fragment RW118
      (Mus musculus)

<400> SEQUENCE: 8

Leu Leu Arg Ser Val Ala Gly Glu Gln Ala Pro Gly Thr Ala Pro Cys
1               5                   10                  15

Ser Arg Gly Ser Ser Trp Ser Ala Asp Leu Asp Lys Cys Met Asp Cys
            20                  25                  30
```

```
Ala Ser Cys Arg Ala Arg Pro His Ser Asp Phe Cys Leu Gly Cys Ala
        35                  40                  45

Ala Ala Pro Pro Ala
    50


<210> SEQ ID NO 9
<211> LENGTH: 40
<212> TYPE: PRT
<213> ORGANISM: artificial
<220> FEATURE:
<223> OTHER INFORMATION: amino acid sequence of Fn14 gene fragment RW114
      (Mus musculus)

<400> SEQUENCE: 9

Pro Gly Thr Ala Pro Cys Ser Arg Gly Ser Ser Trp Ser Ala Asp Leu
1               5                   10                  15

Asp Lys Cys Met Asp Cys Ala Ser Cys Arg Ala Arg Pro His Ser Asp
            20                  25                  30

Phe Cys Leu Gly Cys Ala Ala Ala
        35                  40


<210> SEQ ID NO 10
<211> LENGTH: 73
<212> TYPE: PRT
<213> ORGANISM: artificial
<220> FEATURE:
<223> OTHER INFORMATION: amino acid sequence of Fn14 gene fragment RW98
      (Mus musculus)

<400> SEQUENCE: 10

Leu Arg Ser Val Ala Gly Glu Gln Ala Pro Gly Thr Ala Pro Cys Ser
1               5                   10                  15

Arg Gly Ser Ser Trp Ser Ala Asp Leu Asp Lys Cys Met Asp Cys Ala
            20                  25                  30

Ser Cys Arg Ala Arg Pro His Ser Asp Phe Cys Leu Gly Cys Ala Ala
        35                  40                  45

Ala Pro Pro Ala Pro Phe Arg Leu Leu Trp Pro Ile Leu Gly Gly Ala
    50                  55                  60

Leu Ser Leu Thr Phe Val Leu Gly Leu
65                  70


<210> SEQ ID NO 11
<211> LENGTH: 54
<212> TYPE: PRT
<213> ORGANISM: artificial
<220> FEATURE:
<223> OTHER INFORMATION: amino acid sequence of Fn14 gene fragment RW95
      (Mus musculus)

<400> SEQUENCE: 11

Ser Arg Gly Ser Ser Trp Ser Ala Asp Leu Asp Lys Cys Met Asp Cys
1               5                   10                  15

Ala Ser Cys Arg Ala Arg Pro His Ser Asp Phe Cys Leu Gly Cys Ala
            20                  25                  30

Ala Ala Pro Pro Ala Pro Phe Arg Leu Leu Trp Pro Ile Leu Gly Gly
        35                  40                  45

Ala Leu Ser Leu Thr Phe
    50


<210> SEQ ID NO 12
<211> LENGTH: 19
<212> TYPE: PRT
```

<213> ORGANISM: artificial
<220> FEATURE:
<223> OTHER INFORMATION: amino acid sequence of Fn14 gene fragment RW91
(Mus musculus)

<400> SEQUENCE: 12

Asp Phe Cys Leu Gly Cys Ala Ala Ala Pro Pro Ala Pro Phe Arg Leu
1 5 10 15

Leu Trp Pro

<210> SEQ ID NO 13
<211> LENGTH: 119
<212> TYPE: PRT
<213> ORGANISM: artificial
<220> FEATURE:
<223> OTHER INFORMATION: amino acid sequence for consensus sequence for
VH (Mus musculus)
<220> FEATURE:
<221> NAME/KEY: VARIANT
<222> LOCATION: (1)..(1)
<223> OTHER INFORMATION: X is E or Q
<220> FEATURE:
<221> NAME/KEY: VARIANT
<222> LOCATION: (3)..(3)
<223> OTHER INFORMATION: X is K or Q
<220> FEATURE:
<221> NAME/KEY: VARIANT
<222> LOCATION: (5)..(6)
<223> OTHER INFORMATION: X is Q or E
<220> FEATURE:
<221> NAME/KEY: VARIANT
<222> LOCATION: (10)..(10)
<223> OTHER INFORMATION: X is V or G
<220> FEATURE:
<221> NAME/KEY: VARIANT
<222> LOCATION: (23)..(23)
<223> OTHER INFORMATION: X is I or V
<220> FEATURE:
<221> NAME/KEY: VARIANT
<222> LOCATION: (28)..(28)
<223> OTHER INFORMATION: X is T or S
<220> FEATURE:
<221> NAME/KEY: VARIANT
<222> LOCATION: (30)..(30)
<223> OTHER INFORMATION: X is S or N
<220> FEATURE:
<221> NAME/KEY: VARIANT
<222> LOCATION: (31)..(31)
<223> OTHER INFORMATION: X is S or Y or K or H
<220> FEATURE:
<221> NAME/KEY: VARIANT
<222> LOCATION: (35)..(35)
<223> OTHER INFORMATION: X is S or N
<220> FEATURE:
<221> NAME/KEY: VARIANT
<222> LOCATION: (43)..(43)
<223> OTHER INFORMATION: X is K o rQ
<220> FEATURE:
<221> NAME/KEY: VARIANT
<222> LOCATION: (48)..(48)
<223> OTHER INFORMATION: X is V or I
<220> FEATURE:
<221> NAME/KEY: VARIANT
<222> LOCATION: (53)..(53)
<223> OTHER INFORMATION: X is V or L or S
<220> FEATURE:
<221> NAME/KEY: VARIANT
<222> LOCATION: (54)..(54)
<223> OTHER INFORMATION: X is K or Q or R
<220> FEATURE:
<221> NAME/KEY: VARIANT
<222> LOCATION: (56)..(57)
<223> OTHER INFORMATION: X is N or D
<220> FEATURE:
<221> NAME/KEY: VARIANT
<222> LOCATION: (59)..(59)

<223> OTHER INFORMATION: X is A or P or E
<220> FEATURE:
<221> NAME/KEY: VARIANT
<222> LOCATION: (69)..(69)
<223> OTHER INFORMATION: X is K or R
<220> FEATURE:
<221> NAME/KEY: VARIANT
<222> LOCATION: (71)..(71)
<223> OTHER INFORMATION: X is T or E
<220> FEATURE:
<221> NAME/KEY: VARIANT
<222> LOCATION: (78)..(78)
<223> OTHER INFORMATION: X is K or E
<220> FEATURE:
<221> NAME/KEY: VARIANT
<222> LOCATION: (79)..(79)
<223> OTHER INFORMATION: X is N or S
<220> FEATURE:
<221> NAME/KEY: VARIANT
<222> LOCATION: (80)..(80)
<223> OTHER INFORMATION: X is R or S or C
<220> FEATURE:
<221> NAME/KEY: VARIANT
<222> LOCATION: (81)..(81)
<223> OTHER INFORMATION: X is F or V or L
<220> FEATURE:
<221> NAME/KEY: VARIANT
<222> LOCATION: (82)..(82)
<223> OTHER INFORMATION: X is Y or F
<220> FEATURE:
<221> NAME/KEY: VARIANT
<222> LOCATION: (86)..(87)
<223> OTHER INFORMATION: X is N or S
<220> FEATURE:
<221> NAME/KEY: VARIANT
<222> LOCATION: (90)..(90)
<223> OTHER INFORMATION: X is P or A
<220> FEATURE:
<221> NAME/KEY: VARIANT
<222> LOCATION: (99)..(99)
<223> OTHER INFORMATION: X is T or A or S
<220> FEATURE:
<221> NAME/KEY: VARIANT
<222> LOCATION: (100)..(100)
<223> OTHER INFORMATION: X is S ro C or R or K
<220> FEATURE:
<221> NAME/KEY: VARIANT
<222> LOCATION: (100)..(100)
<223> OTHER INFORMATION: X is S or C or R or K
<220> FEATURE:
<221> NAME/KEY: VARIANT
<222> LOCATION: (101)..(101)
<223> OTHER INFORMATION: X is T or R or S
<220> FEATURE:
<221> NAME/KEY: VARIANT
<222> LOCATION: (103)..(103)
<223> OTHER INFORMATION: X is A or S
<220> FEATURE:
<221> NAME/KEY: VARIANT
<222> LOCATION: (107)..(107)
<223> OTHER INFORMATION: X is H or D
<220> FEATURE:
<221> NAME/KEY: VARIANT
<222> LOCATION: (108)..(108)
<223> OTHER INFORMATION: X is H or Y
<220> FEATURE:
<221> NAME/KEY: VARIANT
<222> LOCATION: (114)..(114)
<223> OTHER INFORMATION: X is T or D

<400> SEQUENCE: 13

```
Xaa Val Xaa Leu Xaa Xaa Ser Gly Gly Xaa Leu Val Gln Pro Gly Gly
1               5                   10                  15

Ser Met Lys Leu Ser Cys Xaa Ala Ser Gly Phe Xaa Phe Xaa Xaa Tyr
            20                  25                  30

Trp Met Xaa Trp Val Arg Gln Ser Pro Glu Xaa Gly Leu Glu Trp Xaa
```

```
        35                  40                  45

Ala Glu Ile Arg Xaa Xaa Ser Xaa Xaa Tyr Xaa Thr His Tyr Ala Glu
    50                  55                  60

Ser Val Lys Gly Xaa Phe Xaa Ile Ser Arg Asp Asp Ser Xaa Xaa Xaa
65                  70                  75                  80

Xaa Xaa Leu Gln Met Xaa Xaa Leu Arg Xaa Glu Asp Thr Gly Ile Tyr
                85                  90                  95

Tyr Cys Xaa Xaa Xaa Tyr Xaa Asp Tyr Phe Xaa Xaa Trp Gly Gln Gly
            100                 105                 110

Thr Xaa Leu Thr Val Ser Ser
        115


<210> SEQ ID NO 14
<211> LENGTH: 112
<212> TYPE: PRT
<213> ORGANISM: artificial
<220> FEATURE:
<223> OTHER INFORMATION: amino acid sequence for consensus sequence for
      VL (Mus musculus)
<220> FEATURE:
<221> NAME/KEY: VARIANT
<222> LOCATION: (4)..(4)
<223> OTHER INFORMATION: X is I or L or M
<220> FEATURE:
<221> NAME/KEY: VARIANT
<222> LOCATION: (7)..(7)
<223> OTHER INFORMATION: X is T or S
<220> FEATURE:
<221> NAME/KEY: VARIANT
<222> LOCATION: (8)..(8)
<223> OTHER INFORMATION: X is P or T
<220> FEATURE:
<221> NAME/KEY: VARIANT
<222> LOCATION: (12)..(12)
<223> OTHER INFORMATION: X is T or A or V
<220> FEATURE:
<221> NAME/KEY: VARIANT
<222> LOCATION: (33)..(33)
<223> OTHER INFORMATION: X is T or D
<220> FEATURE:
<221> NAME/KEY: VARIANT
<222> LOCATION: (37)..(37)
<223> OTHER INFORMATION: X is M or T
<220> FEATURE:
<221> NAME/KEY: VARIANT
<222> LOCATION: (43)..(43)
<223> OTHER INFORMATION: X is K o rT
<220> FEATURE:
<221> NAME/KEY: VARIANT
<222> LOCATION: (49)..(49)
<223> OTHER INFORMATION: X is K o rT
<220> FEATURE:
<221> NAME/KEY: VARIANT
<222> LOCATION: (49)..(49)
<223> OTHER INFORMATION: X is K or T
<220> FEATURE:
<221> NAME/KEY: VARIANT
<222> LOCATION: (50)..(50)
<223> OTHER INFORMATION: X is L or V or F
<220> FEATURE:
<221> NAME/KEY: VARIANT
<222> LOCATION: (57)..(57)
<223> OTHER INFORMATION: X is S or N
<220> FEATURE:
<221> NAME/KEY: VARIANT
<222> LOCATION: (58)..(58)
<223> OTHER INFORMATION: X is L or R
<220> FEATURE:
<221> NAME/KEY: VARIANT
<222> LOCATION: (59)..(59)
<223> OTHER INFORMATION: X is E or D
<220> FEATURE:
<221> NAME/KEY: VARIANT
```

```
<222> LOCATION: (64)..(64)
<223> OTHER INFORMATION: X is A or T
<220> FEATURE:
<221> NAME/KEY: VARIANT
<222> LOCATION: (85)..(85)
<223> OTHER INFORMATION: X is D or E
<220> FEATURE:
<221> NAME/KEY: VARIANT
<222> LOCATION: (89)..(89)
<223> OTHER INFORMATION: X is T or I
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: VARIANT
<222> LOCATION: (103)..(103)
<223> OTHER INFORMATION: X is P or Y
<220> FEATURE:
<221> NAME/KEY: VARIANT
<222> LOCATION: (103)..(103)
<223> OTHER INFORMATION: X is G or A
<220> FEATURE:
<221> NAME/KEY: VARIANT
<222> LOCATION: (110)..(110)
<223> OTHER INFORMATION: X is L or I
<220> FEATURE:
<221> NAME/KEY: VARIANT
<222> LOCATION: (111)..(111)
<223> OTHER INFORMATION: X is Q or K

<400> SEQUENCE: 14

Asp Ile Val Xaa Thr Gln Xaa Xaa Ala Ser Leu Xaa Val Ser Leu Gly
1               5                   10                  15

Gln Arg Ala Thr Ile Ser Cys Arg Ala Ser Gln Ser Val Ser Thr Ser
            20                  25                  30

Xaa Tyr Ser Tyr Xaa His Trp Tyr Gln Gln Xaa Pro Gly Gln Pro Pro
        35                  40                  45

Xaa Xaa Leu Ile Lys Tyr Ala Ser Xaa Xaa Xaa Ser Gly Val Pro Xaa
    50                  55                  60

Arg Phe Ser Gly Ser Gly Ser Gly Thr Asp Phe Thr Leu Asn Ile His
65                  70                  75                  80

Pro Val Glu Glu Xaa Asp Thr Ala Xaa Tyr Tyr Cys Gln His Ser Trp
                85                  90                  95

Glu Ile Pro Xaa Thr Phe Xaa Gly Gly Thr Lys Leu Glu Xaa Xaa Arg
            100                 105                 110


<210> SEQ ID NO 15
<211> LENGTH: 119
<212> TYPE: PRT
<213> ORGANISM: artificial
<220> FEATURE:
<223> OTHER INFORMATION: heavy chain amino acid sequence of CRCBT-06-001
      (Mus musculus)

<400> SEQUENCE: 15

Gln Val Gln Leu Gln Gln Ser Gly Gly Gly Leu Val Gln Pro Gly Gly
1               5                   10                  15

Ser Met Lys Leu Ser Cys Ile Ala Ser Gly Phe Thr Phe Ser Ser Tyr
            20                  25                  30

Trp Met Ser Trp Val Arg Gln Ser Pro Glu Lys Gly Leu Glu Trp Val
        35                  40                  45

Ala Glu Ile Arg Ser Lys Ser Asp Asn Tyr Ala Thr His Tyr Ala Glu
    50                  55                  60

Ser Val Lys Gly Lys Phe Thr Ile Ser Arg Asp Asp Ser Lys Ser Arg
65                  70                  75                  80
```

```
Phe Phe Leu Gln Met Asn Asn Leu Arg Ala Glu Asp Thr Gly Ile Tyr
                85                  90                  95

Tyr Cys Ser Ser Thr Tyr Ala Asp Tyr Phe His Tyr Trp Gly Gln Gly
            100                 105                 110

Thr Asp Leu Thr Val Ser Ser
        115


<210> SEQ ID NO 16
<211> LENGTH: 119
<212> TYPE: PRT
<213> ORGANISM: artificial
<220> FEATURE:
<223> OTHER INFORMATION: heavy chain amino acid sequence of CRCBT-06-002
      (Mus musculus)

<400> SEQUENCE: 16

Glu Val Lys Leu Gln Gln Ser Gly Gly Gly Leu Val Gln Pro Gly Gly
1               5                   10                  15

Ser Met Lys Leu Ser Cys Val Ala Ser Gly Phe Thr Phe Ser Tyr Tyr
            20                  25                  30

Trp Met Asn Trp Val Arg Gln Ser Pro Glu Gln Gly Leu Glu Trp Ile
        35                  40                  45

Ala Glu Ile Arg Leu Gln Ser Asn Asp Tyr Pro Thr His Tyr Ala Glu
    50                  55                  60

Ser Val Lys Gly Arg Phe Thr Ile Ser Arg Asp Asp Ser Lys Asn Ser
65                  70                  75                  80

Val Tyr Leu Gln Met Asn Asn Leu Arg Pro Glu Asp Thr Gly Ile Tyr
                85                  90                  95

Tyr Cys Ala Cys Arg Tyr Ala Asp Tyr Phe Asp His Trp Gly Gln Gly
            100                 105                 110

Thr Thr Leu Thr Val Ser Ser
        115


<210> SEQ ID NO 17
<211> LENGTH: 119
<212> TYPE: PRT
<213> ORGANISM: artificial
<220> FEATURE:
<223> OTHER INFORMATION: heavy chain amino acid sequence of CRCBT-06-003
      (Mus musculus)

<400> SEQUENCE: 17

Gln Val Lys Leu Glu Gln Ser Gly Gly Gly Leu Val Gln Pro Gly Gly
1               5                   10                  15

Ser Met Lys Leu Ser Cys Val Ala Ser Gly Phe Thr Phe Ser His Tyr
            20                  25                  30

Trp Met Ser Trp Val Arg Gln Ser Pro Glu Lys Gly Leu Glu Trp Val
        35                  40                  45

Ala Glu Ile Arg Leu Lys Ser Asp Asn Tyr Ala Thr His Tyr Ala Glu
    50                  55                  60

Ser Val Lys Gly Lys Phe Thr Ile Ser Arg Asp Asp Ser Lys Ser Arg
65                  70                  75                  80

Leu Tyr Leu Gln Met Ser Ser Leu Arg Ala Glu Asp Thr Gly Ile Tyr
                85                  90                  95

Tyr Cys Thr Gly Arg Tyr Ser Asp Tyr Phe Asp Tyr Trp Gly Gln Gly
            100                 105                 110

Thr Thr Leu Thr Val Ser Ser
        115
```

<210> SEQ ID NO 18
<211> LENGTH: 119
<212> TYPE: PRT
<213> ORGANISM: artificial
<220> FEATURE:
<223> OTHER INFORMATION: heavy chain amino acid sequence of CRCBT-06-004
(Mus musculus)

<400> SEQUENCE: 18

Gln Val Gln Leu Gln Gln Ser Gly Gly Gly Leu Val Gln Pro Gly Gly
1 5 10 15

Ser Met Lys Leu Ser Cys Val Ala Ser Gly Phe Thr Phe Ser His Tyr
20 25 30

Trp Met Ser Trp Val Arg Gln Ser Pro Glu Lys Gly Leu Glu Trp Val
35 40 45

Ala Glu Ile Arg Leu Lys Ser Asp Asn Tyr Ala Thr His Tyr Ala Glu
50 55 60

Ser Val Lys Gly Lys Phe Thr Ile Ser Arg Asp Asp Ser Lys Ser Arg
65 70 75 80

Leu Tyr Leu Gln Met Ser Ser Leu Arg Ala Glu Asp Thr Gly Ile Tyr
85 90 95

Tyr Cys Thr Gly Arg Tyr Ser Asp Tyr Phe Asp Tyr Trp Gly Gln Gly
100 105 110

Thr Thr Leu Thr Val Ser Ser
115

<210> SEQ ID NO 19
<211> LENGTH: 119
<212> TYPE: PRT
<213> ORGANISM: artificial
<220> FEATURE:
<223> OTHER INFORMATION: heavy chain amino acid sequence of CRCBT-06-005
(Mus musculus)

<400> SEQUENCE: 19

Gln Val Gln Leu Gln Glu Ser Gly Gly Gly Leu Val Gln Pro Gly Gly
1 5 10 15

Ser Met Lys Leu Ser Cys Val Ala Ser Gly Phe Thr Phe Ser Tyr Tyr
20 25 30

Trp Met Asn Trp Val Arg Gln Ser Pro Glu Gln Gly Leu Glu Trp Ile
35 40 45

Ala Glu Ile Arg Leu Gln Ser Asn Asp Tyr Pro Thr His Tyr Ala Glu
50 55 60

Ser Val Lys Gly Arg Phe Thr Ile Ser Arg Asp Asp Ser Lys Asn Ser
65 70 75 80

Val Tyr Leu Gln Met Asn Asn Leu Arg Pro Glu Asp Thr Gly Ile Tyr
85 90 95

Tyr Cys Ala Cys Arg Tyr Ala Asp Tyr Phe Asp His Trp Gly Gln Gly
100 105 110

Thr Thr Leu Thr Val Ser Ser
115

<210> SEQ ID NO 20
<211> LENGTH: 119
<212> TYPE: PRT
<213> ORGANISM: artificial
<220> FEATURE:
<223> OTHER INFORMATION: heavy chain amino acid sequence of CRCBT-06-006
(Mus musculus)

<400> SEQUENCE: 20

```
Gln Val Gln Leu Gln Glu Ser Gly Gly Gly Leu Val Gln Pro Gly Gly
1               5                   10                  15

Ser Met Lys Leu Ser Cys Val Ala Ser Gly Phe Thr Phe Ser Tyr Tyr
            20                  25                  30

Trp Met Asn Trp Val Arg Gln Ser Pro Glu Gln Gly Leu Glu Trp Ile
        35                  40                  45

Ala Glu Ile Arg Leu Gln Ser Asn Asp Tyr Pro Thr His Tyr Ala Glu
    50                  55                  60

Ser Val Lys Gly Arg Phe Thr Ile Ser Arg Asp Asp Ser Lys Asn Ser
65                  70                  75                  80

Val Tyr Leu Gln Met Asn Asn Leu Arg Pro Glu Asp Thr Gly Ile Tyr
                85                  90                  95

Tyr Cys Ala Cys Arg Tyr Ala Asp Tyr Phe Asp His Trp Gly Gln Gly
            100                 105                 110

Thr Thr Leu Thr Val Ser Ser
        115
```

<210> SEQ ID NO 21
<211> LENGTH: 119
<212> TYPE: PRT
<213> ORGANISM: artificial
<220> FEATURE:
<223> OTHER INFORMATION: heavy chain amino acid sequence of CRCBT-06-007 (Mus musculus)

<400> SEQUENCE: 21

```
Gln Val Lys Leu Glu Glu Ser Gly Gly Val Leu Val Gln Pro Gly Gly
1               5                   10                  15

Ser Met Lys Leu Ser Cys Ile Ala Ser Gly Phe Ser Phe Ser Lys Tyr
            20                  25                  30

Trp Met Asn Trp Val Arg Gln Ser Pro Glu Lys Gly Leu Glu Trp Val
        35                  40                  45

Ala Glu Ile Arg Val Lys Ser Asn Asn Tyr Ala Thr His Tyr Ala Glu
    50                  55                  60

Ser Val Lys Gly Arg Phe Ile Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Lys Ser Tyr Ala Asp Tyr Phe Asp Tyr Trp Gly Gln Gly
            100                 105                 110

Thr Thr Leu Thr Val Ser Ser
        115
```

<210> SEQ ID NO 22
<211> LENGTH: 112
<212> TYPE: PRT
<213> ORGANISM: Artificial Sequence
<220> FEATURE:
<223> OTHER INFORMATION: light chain amino acid sequence of CRCBT-06-001 (Mus musculus)

<400> SEQUENCE: 22

```
Asp Ile Val Met Thr Gln Thr Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30
```

-continued

```
Thr Tyr Ser Tyr Met His Trp Tyr Gln Gln Lys Pro Gly Gln Pro Pro
        35                  40                  45

Lys Leu Leu Ile Lys Tyr Ala Ser Ser Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Asp Asp Thr Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110


<210> SEQ ID NO 23
<211> LENGTH: 112
<212> TYPE: PRT
<213> ORGANISM: Artificial Sequence
<220> FEATURE:
<223> OTHER INFORMATION: light chain amino acid sequence of CRCBT-06-002
      (Mus musculus)

<400> SEQUENCE: 23

Asp Thr Val Leu Thr Gln Ser Pro Ala Ser Leu Val Val Ser Leu Gly
1               5                   10                  15

Gln Arg Ala Thr Ile Ser Cys Arg Ala Ser Gln Ser Val Ser Thr Ser
            20                  25                  30

Asp Tyr Ser Tyr Ile His Trp Tyr Gln Gln Lys Pro Gly Gln Pro Pro
        35                  40                  45

Lys Phe Leu Ile Lys Tyr Ala Ser Asn Arg Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Asp Asp Thr Ala Ile Tyr Tyr Cys Gln His Ser Trp
                85                  90                  95

Glu Ile Pro Pro Thr Phe Gly Ala Gly Thr Lys Leu Glu Leu Gln Arg
            100                 105                 110


<210> SEQ ID NO 24
<211> LENGTH: 106
<212> TYPE: PRT
<213> ORGANISM: artificial
<220> FEATURE:
<223> OTHER INFORMATION: light chain amino acid sequence of CRCBT-06-003
      (Mus musculus)

<400> SEQUENCE: 24

Asp Ile Val Met Thr Gln Thr Thr Ala Leu Met Ala Ala Ser Pro Gly
1               5                   10                  15

Glu Lys Val Thr Ile Thr Cys Ser Val Asn Ser Ser Ile Ser Ser Ser
            20                  25                  30

Tyr Leu His Trp Tyr Gln Gln Lys Ser Gly Ile Ser Pro Asn Pro Gly
        35                  40                  45

Phe Met Ala His Pro Thr Trp Leu Leu Glu Ser Leu Leu Ala Ser Val
    50                  55                  60

Ala Val Asp Leu Gly Pro Leu Thr Leu Ser His Ser Ala Ala Trp Arg
65                  70                  75                  80

Leu Lys Met Leu Pro Leu Ile Thr Val Asn Ser Gly Val Val Pro His
                85                  90                  95

Gly Ser Gly Thr Lys Leu Glu Ile Lys Arg
            100                 105
```

-continued

```
<210> SEQ ID NO 25
<211> LENGTH: 106
<212> TYPE: PRT
<213> ORGANISM: artificial
<220> FEATURE:
<223> OTHER INFORMATION: light chain amino acid sequence of CRCBT-06-004
      (Mus musculus)

<400> SEQUENCE: 25

Asp Ile Val Leu Thr Gln Ser Pro Ala Leu Met Ala Ala Ser Pro Gly
1               5                   10                  15

Glu Lys Val Thr Ile Thr Cys Ser Val Asn Ser Ser Ile Ser Ser Ser
            20                  25                  30

Tyr Leu His Trp Tyr Gln Gln Lys Ser Gly Ile Ser Pro Asn Pro Gly
        35                  40                  45

Phe Met Ala His Pro Thr Trp Leu Leu Glu Ser Leu Leu Ala Ser Val
    50                  55                  60

Ala Val Asp Leu Gly Pro Leu Thr Leu Ser His Ser Ala Ala Trp Arg
65                  70                  75                  80

Leu Lys Met Leu Pro Leu Ile Thr Val Asn Ser Gly Val Val Pro His
                85                  90                  95

Gly Ser Gly Thr Lys Leu Glu Ile Lys Arg
            100                 105


<210> SEQ ID NO 26
<211> LENGTH: 112
<212> TYPE: PRT
<213> ORGANISM: artificial
<220> FEATURE:
<223> OTHER INFORMATION: light chain amino acid sequence of CRCBT-06-005
      (Mus musculus)

<400> SEQUENCE: 26

Asp Ile Val Leu Thr Gln Thr Thr Ala Ser Leu Thr Val Ser Leu Gly
1               5                   10                  15

Gln Arg Ala Thr Ile Ser Cys Arg Ala Ser Gln Ser Val Ser Thr Ser
            20                  25                  30

Thr Tyr Ser Tyr Met His Trp Tyr Gln Gln Thr Pro Gly Gln Pro Pro
        35                  40                  45

Thr Val Leu Ile Lys Tyr Ala Ser Ser Leu Glu Ser Gly Val Pro Thr
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110


<210> SEQ ID NO 27
<211> LENGTH: 112
<212> TYPE: PRT
<213> ORGANISM: artificial
<220> FEATURE:
<223> OTHER INFORMATION: light chain amino acid sequence of CRCBT-06-006
      (Mus musculus)

<400> SEQUENCE: 27

Asp Ile Val Ile Thr Gln Ser Pro Ala Ser Leu Thr Val Ser Leu Gly
1               5                   10                  15

Gln Arg Ala Thr Ile Ser Cys Arg Ala Ser Gln Ser Val Ser Thr Ser
```

```
            20                  25                  30

Thr Tyr Ser Tyr Met His Trp Tyr Gln Gln Thr Pro Gly Gln Pro Pro
        35                  40                  45

Thr Val Leu Ile Lys Tyr Ala Ser Ser Leu Glu Ser Gly Val Pro Thr
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110


<210> SEQ ID NO 28
<211> LENGTH: 112
<212> TYPE: PRT
<213> ORGANISM: artificial
<220> FEATURE:
<223> OTHER INFORMATION: light chain amino acid sequence of CRCBT-06-007
      (Mus musculus)

<400> SEQUENCE: 28

Asp Ile Val Met Thr Gln Ser Thr Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Val Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110


<210> SEQ ID NO 29
<211> LENGTH: 50
<212> TYPE: PRT
<213> ORGANISM: artificial
<220> FEATURE:
<223> OTHER INFORMATION: amino acid sequence of hFn14 ectodomain mutant
      construct D45A (Mus musculus)

<400> SEQUENCE: 29

Glu Gln Ala Pro Gly Thr Ala Pro Cys Ser Arg Gly Ser Ser Trp Ser
1               5                   10                  15

Ala Ala Leu Asp Lys Cys Met Asp Cys Ala Ser Cys Arg Ala Arg Pro
            20                  25                  30

His Ser Asp Phe Cys Leu Gly Cys Ala Ala Ala Pro Pro Ala Pro Phe
        35                  40                  45

Arg Leu
    50


<210> SEQ ID NO 30
<211> LENGTH: 50
<212> TYPE: PRT
<213> ORGANISM: artificial
<220> FEATURE:
<223> OTHER INFORMATION: amino acid sequence of hFn14 ectodomain mutant
```

construct K48A (Mus musculus)

<400> SEQUENCE: 30

```
Glu Gln Ala Pro Gly Thr Ala Pro Cys Ser Arg Gly Ser Ser Trp Ser
1               5                   10                  15

Ala Asp Leu Asp Ala Cys Met Asp Cys Ala Ser Cys Arg Ala Arg Pro
            20                  25                  30

His Ser Asp Phe Cys Leu Gly Cys Ala Ala Ala Pro Pro Ala Pro Phe
        35                  40                  45

Arg Leu
    50
```

<210> SEQ ID NO 31
<211> LENGTH: 50
<212> TYPE: PRT
<213> ORGANISM: artificial
<220> FEATURE:
<223> OTHER INFORMATION: amino acid sequence of hFn14 ectodomain mutant construct M50A (Mus musculus)

<400> SEQUENCE: 31

```
Glu Gln Ala Pro Gly Thr Ala Pro Cys Ser Arg Gly Ser Ser Trp Ser
1               5                   10                  15

Ala Asp Leu Asp Lys Cys Ala Asp Cys Ala Ser Cys Arg Ala Arg Pro
            20                  25                  30

His Ser Asp Phe Cys Leu Gly Cys Ala Ala Ala Pro Pro Ala Pro Phe
        35                  40                  45

Arg Leu
    50
```

<210> SEQ ID NO 32
<211> LENGTH: 50
<212> TYPE: PRT
<213> ORGANISM: Artificial Sequence
<220> FEATURE:
<223> OTHER INFORMATION: amino acid sequence of hFn14 ectodomain mutant construct D62E (Mus musculus)

<400> SEQUENCE: 32

```
Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Glu Phe Cys Leu Gly Cys Ala Ala Ala Pro Pro Ala Pro Phe
        35                  40                  45

Arg Leu
    50
```

<210> SEQ ID NO 33
<211> LENGTH: 20
<212> TYPE: PRT
<213> ORGANISM: artificial
<220> FEATURE:
<223> OTHER INFORMATION: amino acid sequence of hFn14 subdomain 1 (Mus musculus)

<400> SEQUENCE: 33

```
Pro Gly Thr Ala Pro Cys Ser Arg Gly Ser Ser Trp Ser Ala Asp Leu
1               5                   10                  15

Asp Lys Cys Met
            20
```

<210> SEQ ID NO 34
<211> LENGTH: 20
<212> TYPE: PRT
<213> ORGANISM: artificial
<220> FEATURE:
<223> OTHER INFORMATION: amino acid sequence of hFn14 subdomain 2 (Mus musculus)

<400> SEQUENCE: 34

```
Asp Cys Ala Ser Cys Arg Ala Arg Pro His Ser Asp Phe Cys Leu Gly
1               5                   10                  15

Cys Ala Ala Ala
            20
```

<210> SEQ ID NO 35
<211> LENGTH: 14
<212> TYPE: PRT
<213> ORGANISM: artificial
<220> FEATURE:
<223> OTHER INFORMATION: amino acid sequene of hFn14 subdomain 3 (Mus musculus)

<400> SEQUENCE: 35

```
Ala Ser Cys Arg Ala Arg Pro His Ser Asp Phe Cys Leu Gly
1               5                   10
```

<210> SEQ ID NO 36
<211> LENGTH: 126
<212> TYPE: PRT
<213> ORGANISM: artificial
<220> FEATURE:
<223> OTHER INFORMATION: amino acid sequence of Fn14-GPI control (Mus musculus)

<400> SEQUENCE: 36

```
Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ala Ser Cys Arg Ala Arg Pro His Ser Asp Phe Cys
    50                  55                  60

Leu Gly Cys Ala Ala Ala Pro Leu Ala Pro Phe Arg Leu Leu Trp Met
65                  70                  75                  80

Thr Thr Ser Pro Gly Thr Pro Ala Pro Ala Ala Glu Glu Thr Met Thr
                85                  90                  95

Thr Ser Pro Gly Thr Pro Ala Ser Ser His Tyr Leu Ser Cys Thr Ile
            100                 105                 110

Val Gly Ile Ile Val Leu Ile Val Leu Leu Ile Val Phe Val
        115                 120                 125
```

<210> SEQ ID NO 37
<211> LENGTH: 30
<212> TYPE: DNA
<213> ORGANISM: artificial
<220> FEATURE:
<223> OTHER INFORMATION: nucleotide sequence of a primer for amplifying nucleic acid encoding extracellular domain of Fn14 (Mus musculus)

<400> SEQUENCE: 37

```
cgcggatcca tggctcgggg ctcgctgcgc                                        30
```

-continued

```
<210> SEQ ID NO 38
<211> LENGTH: 36
<212> TYPE: DNA
<213> ORGANISM: artificial
<220> FEATURE:
<223> OTHER INFORMATION: nucleotide sequence of a primer for amplifying
      nucleic acid encoding extracellular domain of Fn14 (Mus musculus)

<400> SEQUENCE: 38

gctggtggtc atccaaagca gccggaaggg ggcagg                              36


<210> SEQ ID NO 39
<211> LENGTH: 36
<212> TYPE: DNA
<213> ORGANISM: artificial
<220> FEATURE:
<223> OTHER INFORMATION: nucleotide sequence of a primer for amplifying
      Trail R3 GPI anchor coding region (Mus musculus)

<400> SEQUENCE: 39

cggctgcttt ggatgaccac cagcccgggg actcct                              36


<210> SEQ ID NO 40
<211> LENGTH: 33
<212> TYPE: DNA
<213> ORGANISM: artificial
<220> FEATURE:
<223> OTHER INFORMATION: nucleotide sequence of a primer for amplifying
      Trail R3 GPI anchor coding region (Mus musculus)

<400> SEQUENCE: 40

cgcgctagct tatcaaacaa acacaatcag aag                                 33


<210> SEQ ID NO 41
<211> LENGTH: 32
<212> TYPE: DNA
<213> ORGANISM: artificial
<220> FEATURE:
<223> OTHER INFORMATION: nucleotide sequence of a primer for amplifying
      light chain variable region of an antibody (Mus musculus)

<400> SEQUENCE: 41

gggagctcga yattgtgmts acmcarwctm ca                                  32


<210> SEQ ID NO 42
<211> LENGTH: 30
<212> TYPE: DNA
<213> ORGANISM: artificial
<220> FEATURE:
<223> OTHER INFORMATION: nucleotide sequence of a primer for amplifying
      light chain variable region of an antibody (Mus musculus)

<400> SEQUENCE: 42

ggtgcatgcg gatacagttg gtgcagcatc                                     30


<210> SEQ ID NO 43
<211> LENGTH: 32
<212> TYPE: DNA
<213> ORGANISM: artificial
<220> FEATURE:
<223> OTHER INFORMATION: nucleotide sequence of a primer for amplifying
      heavy chain variable region of an antibody (Mus musculus)
<220> FEATURE:
<221> NAME/KEY: misc_feature
<222> LOCATION: (18)..(18)
<223> OTHER INFORMATION: n is a, c, g, or t

<400> SEQUENCE: 43
```

```
cttccggaat tcsargtnma gctgsagsag tc                                 32


<210> SEQ ID NO 44
<211> LENGTH: 35
<212> TYPE: DNA
<213> ORGANISM: artificial
<220> FEATURE:
<223> OTHER INFORMATION: nucleotide sequence of a primer for amplifying
      heavy chain variable region of an antibody (Mus musculus)
<220> FEATURE:
<221> NAME/KEY: misc_feature
<222> LOCATION: (18)..(18)
<223> OTHER INFORMATION: n is a, c, g, or t

<400> SEQUENCE: 44

cttccggaat tcsargtnma gctgsagsag tcwgg                              35


<210> SEQ ID NO 45
<211> LENGTH: 36
<212> TYPE: DNA
<213> ORGANISM: artificial
<220> FEATURE:
<223> OTHER INFORMATION: nucleotide sequence of a primer for amplifying
      heavy chain variable region of an antibody (Mus musculus)

<400> SEQUENCE: 45

ggaagatcta tagacagatg ggggtgtcgt tttggc                             36


<210> SEQ ID NO 46
<211> LENGTH: 24
<212> TYPE: PRT
<213> ORGANISM: artificial
<220> FEATURE:
<223> OTHER INFORMATION: amino acid sequence of hFn14 subdomain 1p (Mus
      musculus)

<400> SEQUENCE: 46

Glu Gln Ala Pro Gly Thr Ala Pro Cys Ser Arg Gly Ser Ser Trp Ser
1               5                   10                  15

Ala Asp Leu Asp Lys Cys Met Asp
            20


<210> SEQ ID NO 47
<211> LENGTH: 20
<212> TYPE: PRT
<213> ORGANISM: artificial
<220> FEATURE:
<223> OTHER INFORMATION: Fn14 sub-domain 2 in which the third and sixth
      cysteine residues in Fn14 ECD that form disulfide bonds are
      mutated to serine (designated herein "Sub-domain 2 Cys 3&6 delta
      S") (Mus musculus)

<400> SEQUENCE: 47

Asp Ser Ala Ser Cys Arg Ala Arg Pro His Ser Asp Phe Cys Leu Gly
1               5                   10                  15

Ser Ala Ala Ala
            20


<210> SEQ ID NO 48
<211> LENGTH: 20
<212> TYPE: PRT
<213> ORGANISM: artificial
<220> FEATURE:
<223> OTHER INFORMATION: Fn14 sub-domain 2 in which the fourth and fifth
      cysteine residues in Fn14 ECD that form disulfide bonds are
      mutated to serine (designated herein "Sub-domain 2 Cys 4&5 delta
      S") (Mus musculus)
```

<400> SEQUENCE: 48

Asp Cys Ala Ser Ser Arg Ala Arg Pro His Ser Asp Phe Ser Leu Gly
1 5 10 15

Cys Ala Ala Ala
20

<210> SEQ ID NO 49
<211> LENGTH: 50
<212> TYPE: PRT
<213> ORGANISM: artificial
<220> FEATURE:
<223> OTHER INFORMATION: Fn14 ECD T33N mutant (Mus musculus)

<400> SEQUENCE: 49

Glu Gln Ala Pro Gly Asn Ala Pro Cys Ser Arg Gly Ser Ser Trp Ser
1 5 10 15

Ala Asp Leu Asp Lys Cys Met Asp Cys Ala Ser Cys Arg Ala Arg Pro
20 25 30

His Ser Asp Phe Cys Leu Gly Cys Ala Ala Ala Pro Pro Ala Pro Phe
35 40 45

Arg Leu
50

<210> SEQ ID NO 50
<211> LENGTH: 50
<212> TYPE: PRT
<213> ORGANISM: artificial
<220> FEATURE:
<223> OTHER INFORMATION: Fn14 ECD A34S mutant (Mus musculus)

<400> SEQUENCE: 50

Glu Gln Ala Pro Gly Thr Ser Pro Cys Ser Arg Gly Ser Ser Trp Ser
1 5 10 15

Ala Asp Leu Asp Lys Cys Met Asp Cys Ala Ser Cys Arg Ala Arg Pro
20 25 30

His Ser Asp Phe Cys Leu Gly Cys Ala Ala Ala Pro Pro Ala Pro Phe
35 40 45

Arg Leu
50

<210> SEQ ID NO 51
<211> LENGTH: 50
<212> TYPE: PRT
<213> ORGANISM: artificial
<220> FEATURE:
<223> OTHER INFORMATION: Fn14 ECD R38S mutant (Mus musculus)

<400> SEQUENCE: 51

Glu Gln Ala Pro Gly Thr Ala Pro Cys Ser Ser Gly Ser Ser Trp Ser
1 5 10 15

Ala Asp Leu Asp Lys Cys Met Asp Cys Ala Ser Cys Arg Ala Arg Pro
20 25 30

His Ser Asp Phe Cys Leu Gly Cys Ala Ala Ala Pro Pro Ala Pro Phe
35 40 45

Arg Leu
50

<210> SEQ ID NO 52
<211> LENGTH: 50
<212> TYPE: PRT

-continued

<213> ORGANISM: artificial
<220> FEATURE:
<223> OTHER INFORMATION: Fn14 ECD R56P mutant (Mus musculus)

<400> SEQUENCE: 52

Glu Gln Ala Pro Gly Thr Ala Pro Cys Ser Arg Gly Ser Ser Trp Ser
1 5 10 15

Ala Asp Leu Asp Lys Cys Met Asp Cys Ala Ser Cys Pro Ala Arg Pro
20 25 30

His Ser Asp Phe Cys Leu Gly Cys Ala Ala Ala Pro Pro Ala Pro Phe
35 40 45

Arg Leu
50

<210> SEQ ID NO 53
<211> LENGTH: 50
<212> TYPE: PRT
<213> ORGANISM: artificial
<220> FEATURE:
<223> OTHER INFORMATION: Fn14 ECD L77M mutant (Mus musculus)

<400> SEQUENCE: 53

Glu Gln Ala Pro Gly Thr Ala Pro Cys Ser Arg Gly Ser Ser Trp Ser
1 5 10 15

Ala Asp Leu Asp Lys Cys Met Asp Cys Ala Ser Cys Arg Ala Arg Pro
20 25 30

His Ser Asp Phe Cys Leu Gly Cys Ala Ala Ala Pro Pro Ala Pro Phe
35 40 45

Arg Met
50

<210> SEQ ID NO 54
<211> LENGTH: 50
<212> TYPE: PRT
<213> ORGANISM: artificial
<220> FEATURE:
<223> OTHER INFORMATION: Fn14 ECD R56A mutant (Mus musculus)

<400> SEQUENCE: 54

Glu Gln Ala Pro Gly Thr Ala Pro Cys Ser Arg Gly Ser Ser Trp Ser
1 5 10 15

Ala Asp Leu Asp Lys Cys Met Asp Cys Ala Ser Cys Ala Ala Arg Pro
20 25 30

His Ser Asp Phe Cys Leu Gly Cys Ala Ala Ala Pro Pro Ala Pro Phe
35 40 45

Arg Leu
50

<210> SEQ ID NO 55
<211> LENGTH: 50
<212> TYPE: PRT
<213> ORGANISM: artificial
<220> FEATURE:
<223> OTHER INFORMATION: Fn14 ECD R56K mutant (Mus musculus)

<400> SEQUENCE: 55

Glu Gln Ala Pro Gly Thr Ala Pro Cys Ser Arg Gly Ser Ser Trp Ser
1 5 10 15

Ala Asp Leu Asp Lys Cys Met Asp Cys Ala Ser Cys Lys Ala Arg Pro
20 25 30

His Ser Asp Phe Cys Leu Gly Cys Ala Ala Ala Pro Pro Ala Pro Phe 35 40 45

Arg Leu
50

<210> SEQ ID NO 56
<211> LENGTH: 50
<212> TYPE: PRT
<213> ORGANISM: artificial
<220> FEATURE:
<223> OTHER INFORMATION: Fn14 ECD R58A mutant (Mus musculus)

<400> SEQUENCE: 56

Glu Gln Ala Pro Gly Thr Ala Pro Cys Ser Arg Gly Ser Ser Trp Ser
1 5 10 15

Ala Asp Leu Asp Lys Cys Met Asp Cys Ala Ser Cys Arg Ala Ala Pro
20 25 30

His Ser Asp Phe Cys Leu Gly Cys Ala Ala Ala Pro Pro Ala Pro Phe
35 40 45

Arg Leu
50

<210> SEQ ID NO 57
<211> LENGTH: 50
<212> TYPE: PRT
<213> ORGANISM: artificial
<220> FEATURE:
<223> OTHER INFORMATION: Fn14 ECD W42A mutant (Mus musculus)

<400> SEQUENCE: 57

Glu Gln Ala Pro Gly Thr Ala Pro Cys Ser Arg Gly Ser Ser Ala Ser
1 5 10 15

Ala Asp Leu Asp Lys Cys Met Asp Cys Ala Ser Cys Arg Ala Arg Pro
20 25 30

His Ser Asp Phe Cys Leu Gly Cys Ala Ala Ala Pro Pro Ala Pro Phe
35 40 45

Arg Leu
50

<210> SEQ ID NO 58
<211> LENGTH: 50
<212> TYPE: PRT
<213> ORGANISM: artificial
<220> FEATURE:
<223> OTHER INFORMATION: Fn14 ECD L46A mutant (Mus musculus)

<400> SEQUENCE: 58

Glu Gln Ala Pro Gly Thr Ala Pro Cys Ser Arg Gly Ser Ser Trp Ser
1 5 10 15

Ala Asp Ala Asp Lys Cys Met Asp Cys Ala Ser Cys Arg Ala Arg Pro
20 25 30

His Ser Asp Phe Cys Leu Gly Cys Ala Ala Ala Pro Pro Ala Pro Phe
35 40 45

Arg Leu
50

<210> SEQ ID NO 59
<211> LENGTH: 50
<212> TYPE: PRT
<213> ORGANISM: artificial
<220> FEATURE:
<223> OTHER INFORMATION: Fn14 ECD D51A (Mus musculus)

<400> SEQUENCE: 59

```
Glu Gln Ala Pro Gly Thr Ala Pro Cys Ser Arg Gly Ser Ser Trp Ser
1               5                   10                  15

Ala Asp Leu Asp Lys Cys Met Ala Cys Ala Ser Cys Arg Ala Arg Pro
            20                  25                  30

His Ser Asp Phe Cys Leu Gly Cys Ala Ala Ala Pro Pro Ala Pro Phe
        35                  40                  45

Arg Leu
    50
```

<210> SEQ ID NO 60
<211> LENGTH: 50
<212> TYPE: PRT
<213> ORGANISM: artificial
<220> FEATURE:
<223> OTHER INFORMATION: Fn14 ECD S54A mutant (Mus musculus)

<400> SEQUENCE: 60

```
Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ala Cys Arg Ala Arg Pro
            20                  25                  30

His Ser Asp Phe Cys Leu Gly Cys Ala Ala Ala Pro Pro Ala Pro Phe
        35                  40                  45

Arg Leu
    50
```

<210> SEQ ID NO 61
<211> LENGTH: 50
<212> TYPE: PRT
<213> ORGANISM: artificial
<220> FEATURE:
<223> OTHER INFORMATION: Fn14 ECD A57G mutant (Mus musculus)

<400> SEQUENCE: 61

```
Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Gly Arg Pro
            20                  25                  30

His Ser Asp Phe Cys Leu Gly Cys Ala Ala Ala Pro Pro Ala Pro Phe
        35                  40                  45

Arg Leu
    50
```

<210> SEQ ID NO 62
<211> LENGTH: 50
<212> TYPE: PRT
<213> ORGANISM: artificial
<220> FEATURE:
<223> OTHER INFORMATION: Fn14 ECD P59A mutant (Mus musculus)

<400> SEQUENCE: 62

```
Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Ala
            20                  25                  30

His Ser Asp Phe Cys Leu Gly Cys Ala Ala Ala Pro Pro Ala Pro Phe
        35                  40                  45

Arg Leu
    50
```

<210> SEQ ID NO 63
<211> LENGTH: 50
<212> TYPE: PRT
<213> ORGANISM: artificial
<220> FEATURE:
<223> OTHER INFORMATION: Fn14 ECD H60A mutant (Mus musculus)

<400> SEQUENCE: 63

```
Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

Ala Ser Asp Phe Cys Leu Gly Cys Ala Ala Ala Pro Pro Ala Pro Phe
        35                  40                  45

Arg Leu
    50
```

<210> SEQ ID NO 64
<211> LENGTH: 50
<212> TYPE: PRT
<213> ORGANISM: artificial
<220> FEATURE:
<223> OTHER INFORMATION: Fn14 ECD S61A mutant (Mus musculus)

<400> SEQUENCE: 64

```
Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ala Asp Phe Cys Leu Gly Cys Ala Ala Ala Pro Pro Ala Pro Phe
        35                  40                  45

Arg Leu
    50
```

<210> SEQ ID NO 65
<211> LENGTH: 50
<212> TYPE: PRT
<213> ORGANISM: artificial
<220> FEATURE:
<223> OTHER INFORMATION: Fn14 ECD D62A mutant (Mus musculus)

<400> SEQUENCE: 65

```
Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Ala Phe Cys Leu Gly Cys Ala Ala Ala Pro Pro Ala Pro Phe
        35                  40                  45

Arg Leu
    50
```

<210> SEQ ID NO 66
<211> LENGTH: 50
<212> TYPE: PRT
<213> ORGANISM: artificial
<220> FEATURE:
<223> OTHER INFORMATION: Fn14 ECD F63A mutant (Mus musculus)

<400> SEQUENCE: 66

```
Glu Gln Ala Pro Gly Thr Ala Pro Cys Ser Arg Gly Ser Ser Trp Ser
1               5                   10                  15
```

```
Ala Asp Leu Asp Lys Cys Met Asp Cys Ala Ser Cys Arg Ala Arg Pro
            20                  25                  30

His Ser Asp Ala Cys Leu Gly Cys Ala Ala Ala Pro Pro Ala Pro Phe
        35                  40                  45

Arg Leu
    50


<210> SEQ ID NO 67
<211> LENGTH: 50
<212> TYPE: PRT
<213> ORGANISM: artificial
<220> FEATURE:
<223> OTHER INFORMATION: Fn14 ECD L65A mutant (Mus musculus)

<400> SEQUENCE: 67

Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Ala Gly Cys Ala Ala Ala Pro Pro Ala Pro Phe
        35                  40                  45

Arg Leu
    50


<210> SEQ ID NO 68
<211> LENGTH: 50
<212> TYPE: PRT
<213> ORGANISM: artificial
<220> FEATURE:
<223> OTHER INFORMATION: Fn14 ECD H60K mutant (Mus musculus)

<400> SEQUENCE: 68

Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

Lys Ser Asp Phe Cys Leu Gly Cys Ala Ala Ala Pro Pro Ala Pro Phe
        35                  40                  45

Arg Leu
    50


<210> SEQ ID NO 69
<211> LENGTH: 28
<212> TYPE: DNA
<213> ORGANISM: artificial
<220> FEATURE:
<223> OTHER INFORMATION: primer for amplifying antibody light chain (Mus
      musculus)

<400> SEQUENCE: 69

atggagwcag acacactcct gytatggt                                        28


<210> SEQ ID NO 70
<211> LENGTH: 20
<212> TYPE: DNA
<213> ORGANISM: artificial
<220> FEATURE:
<223> OTHER INFORMATION: primer for amplifying antibody light chain (Mus
      musculus)
```

-continued

<400> SEQUENCE: 70

```
ttttatctcc agcttggtgc                                                20
```

FN14 BINDING PROTEINS AND USES THEREOF

RELATED APPLICATION DATA

This application is a continuation of U.S. patent application Ser. No. 15/236,676 entitled "FN14 Binding Proteins and Uses Thereof", filed Aug. 15, 2016, which is a continuation application of U.S. patent application Ser. No. 14/529,890, filed Oct. 31, 2014, which is a continuation application of U.S. patent application Ser. No. 13/851,153 filed Mar. 27, 2013, now U.S. Pat. No. 9,006,397, issued Apr. 14, 2015, which is a continuation application of PCT Application No. PCT/AU2012/000989, filed Aug. 23, 2012, which claims priority to U.S. Provisional Application No. 61/526,599 entitled "FN14 Binding Proteins and Uses Thereof", filed Aug. 23, 2011. The entire contents of each application are hereby incorporated by reference.

SEQUENCE LISTING

The present application is filed with a Sequence Listing in electronic form. The entire contents of the Sequence Listing is hereby incorporated by reference.

FIELD

The present disclosure relates to Fn14-binding proteins comprising antigen binding domains of anti-Fn14 antibodies and uses thereof and methods of treating, preventing, diagnosing or prognosing various conditions including wasting disorders, such as cachexia.

BACKGROUND

Fibroblast Growth Factor Inducible 14

Fibroblast growth factor inducible 14 (Fn14, also known as TNF-like weak inducer of apoptosis receptor [Tweak-R] or TNFRSF12A), is a member of the Tumor Necrosis Factor receptor superfamily. Expression of Fn14 is up-regulated by growth factors in vitro and in vivo in response to tissue injury, regeneration, and inflammation.

As one of the names for Fn14 suggests, this protein is a receptor for the protein designated Tweak. Tweak binding to Fn14, or constitutive Fn14 overexpression, activates the NFκB signaling pathway, which is known to play an important role in immune and inflammatory processes, oncogenesis, and cancer therapy resistance. This interaction also controls many cellular activities including, proliferation, migration, differentiation, apoptosis, angiogenesis and inflammation. Tweak and Fn14 are also involved in tissue repair and regulation of immune functions and tumor growth. Accordingly, Fn14-mediated signaling is involved in pathways that play important roles in human diseases. Fn14-mediated signaling has been suggested to play a role in numerous diseases, including, cancer, metastasis, immunological disorders (including autoimmune diseases, graft rejection and graft versus host disease, and chronic and acute neurological conditions [including stroke]).

Fn14 is expressed by many non-lymphoid cell types (epithelial, mesenchymal, endothelial cells and neurons), by many tissue progenitor cells, including all progenitor cells of the mesenchymal lineage. This protein is highly inducible by growth factors e.g., in serum that are encountered in vivo at sites of tissue injuries and/or tissue remodeling. As a consequence Fn14 expression is relatively low in most healthy tissues, but increased in injured and/or diseased tissues.

Based on the foregoing description, the skilled artisan will be aware that compounds that bind to Fn14 are desirable. These compounds can be used to treat, prevent, diagnose or prognose Fn14-mediated conditions. In addition, it is desirable to identify and further understand the role of Fn14 in various biological conditions and diseases. In particular, the role of Fn14 in wasting disorders has not been previously demonstrated.

Wasting Disorders

Wasting disorders are a class of disorders that are characterized by progressive loss of one or more tissues, e.g., muscle and/or fat. Wasting disorders can be classified into two types: (i) those in which the tissue that is lost is the site of the disorder (e.g., muscular dystrophy); and (ii) wasting disorders that are associated with or caused by other conditions. This latter type can be associated with a variety of conditions including motor neuron disease, denervation, and ageing. Wasting disorders associated with other disorders also includes a subclass of wasting disorders known as cachexia.

Cachexia is a metabolic disorder associated with underlying illness (i.e., a condition) and characterized by loss of body weight and loss of muscle with or without loss of fat mass. Cachexia is generally associated with increased protein catabolism due to underlying disease(s). Contributory factors to the onset of cachexia are anorexia and metabolic alterations (e.g., increased inflammatory status, increased muscle proteolysis and impaired carbohydrate, protein and lipid metabolism). Conditions associated with cachexia include, but are not limited to, cancer, certain infectious diseases (e.g. tuberculosis, AIDS), some autoimmune disorders (including diabetic neuropathic cachexia, and rheumatoid cachexia), or addiction to drugs such as amphetamines or cocaine, chronic alcoholism and cirrhosis of the liver. Cachexia physically weakens patients to a state of immobility stemming from loss of appetite, asthenia, and anemia, and response to standard treatment is usually poor. Cachexia is regularly seen associated with cancer, and in that context is called "cancer cachexia". There are also a cachectic syndromes observed in patients suffering from disorders, such as, but not limited to renal disease, congestive heart failure, chronic obstructive pulmonary disease, diabetes and some severe cases of schizophrenia can present this disorder where it is named vesanic cachexia.

A common form of cachexia is associated with cancer. In this regard, cachexia is one of the most common manifestations of cancer and is present in up to 80% of patients with advanced cancer, including, but not limited to cancers of the breast, lung, colon, prostate, pancreas and gastrointestinal tract. Cachexia is also present early in progression of cancer with, for example, 85% of patients with gastrointestinal cancers, 83% of patients with pancreatic cancer and 60% of patients with lung cancer presenting with cachexia upon diagnosis. Cachexia accounts for >20% of all cancer-related deaths and is associated with reduced mobility, increased risk of complications in surgery, impaired response to chemo-/radio-therapy, decreased survival time and increased psychological distress, leading to an overall reduction in quality of life for sufferers. Currently, the only definitive treatment of cancer cachexia is removal of the causative tumor. Short of achieving this goal, which is often compromised by the patients' inability to tolerate cancer treatments due to their cachexia, various measures have been undertaken to ameliorate cachexia, however with limited success. Various agents have been administered in attempts to retard or halt progressive cachexia in cancer patients. These agents include orexigenic agents (appetite stimulants), corticosteroids, cannabinoids, serotonin antagonists, prokinetic agents, androgens and anabolic agents, anticytokine agents, non-steroidal anti-inflammatory drugs, and regulators of circadian rhythm.

It will be apparent to the skilled artisan from the foregoing that the identification of improved Fn14-binding proteins for medical and diagnostic treatment would be useful. Furthermore, the treatment of wasting disorders, such as cachexia, is a significant unmet medical need. Thus, there is a need in the art for therapies that can ameliorate, delay or prevent wasting disorders, including, unintended body weight loss, cachexia, muscle and/or fat wasting, weakness and/or fatigue associated with one or more disorders. Desirably, such therapies reduce mortality and/or enhance and/or prolong patients' quality of life, which can assist with therapeutic and/or prophylactic methods, e.g., to treat a condition causing or associated with the wasting disorder.

SUMMARY

The inventors have produced a class of antibodies that bind specifically to Fn14 and reduce Tweak-induced NFκB-signaling in a cell expressing Fn14. Accordingly, these antibodies are antagonists of a Tweak-mediated activity through Fn14. Antibodies identified by the inventors are capable of antagonizing or reducing several Tweak-mediated activities (e.g., NFκB-signaling and/or Tweak-induced Kym1 cell death). Antibodies identified by the inventors do not induce NFκB-signaling when bound to Fn14, e.g., in the absence of Tweak, meaning that these antibodies could avoid undesirable side-effects in situations in which treatment of Tweak-mediated conditions using antibodies against Fn14 is desirable. This functional difference not only provides a practical benefit, but it also distinguishes the antibodies produced by the inventors from several known anti-Fn14 antibodies that may suffer from undesirable side effects (e.g., ITEM-1, ITEM-2 and ITEM-3 and derivatives thereof).

Some antibodies identified by the inventors are capable of inducing or agonizing some Tweak-mediated activities, such as cytokine secretion (e.g., interleukin (IL)-8 secretion).

The inventors have also determined that the antibodies bind to an epitope, e.g., a conformational epitope, contained within a common region of the extracellular domain of Fn14. Moreover, the inventors found that different residues within the epitope were involved in binding of different sub-classes of antibodies. In conducting these analyses, the inventors determined that they could distinguish antibodies particularly effective in treating wasting conditions (as discussed below) from antibodies that were ineffective or less effective based on the amino acid residues involved within the epitope in antibody binding.

In developing animal models to characterize the antibodies that they produced, the inventors were surprised to find that mice administered tumorigenic cells ectopically expressing Fn14 developed severe cachexia. The inventors also determined that a class of antibodies that modulated Fn14 activity is capable of treating cachexia, including inducing weight gain in a subject following progression of cachexia. Upon further characterization of this finding, the inventors determined that the antibodies were exerting a therapeutic effect by binding to and modulating Fn14 signaling on the tumor cells. Thus, by modulating Fn14-signaling on a tumor, the inventors were inducing a positive effect at a distinct tissue, e.g., skeletal muscle.

The inventors have extended these studies to show that anti-Fn14 antibodies they produced were capable of preventing or delaying cachexia in a colon cancer mouse model. An antibody tested by the inventors was also able to reduce the size of tumors in the mice.

The inventors additionally demonstrated that a class of antibodies was capable of extending the life of a subject suffering from cancer and/or cachexia.

The inventors have also shown that an antibody that they have produced prevents a cancer's ability to invade tissue, such as muscle, indicating utility in preventing tissue invasion or metastasis of cancer.

The inventors further extended their studies by showing that they could reduce or prevent muscle wasting in a mouse model of diabetes-induced wasting/cachexia. These data indicate that the inventors have produced antibodies useful for the treatment or prevention of a variety of wasting disorders.

When treating mice suffering from diabetes using an antibody, the inventors observed that the mice showed reduced water intake and blood glucose levels compared to untreated diabetic mice.

Thus, the present disclosure provides various reagents for diagnosing/prognosing/treating/preventing Fn14-mediated conditions, including wasting conditions, such as cachexia. The present disclosure also provides methods for treating or preventing wasting conditions, such as cachexia or tissue invasion or metastasis of cancer.

In one example, the present disclosure provides an Fn14-binding protein comprising an antigen binding domain, wherein the antigen binding domain binds specifically to Fn14 and wherein the protein antagonizes at least one Tweak-mediated Fn14 signaling effect, and wherein the protein does not detectably induce the Tweak-mediated Fn14 signaling effect when contacted to a cell expressing Fn14 in the absence of Tweak. In one example, the antigen binding domain is from or derived from a non-antibody Fn14 binding protein.

In one example, the present disclosure provides an Fn14-binding protein comprising an antigen binding domain of an anti-Fn14 antibody, wherein the antigen binding domain binds specifically to Fn14 and wherein the protein antagonizes at least one Tweak-mediated Fn14 signaling effect, and wherein the protein does not detectably induce the Tweak-mediated Fn14 signaling effect when contacted to a cell expressing Fn14 in the absence of Tweak.

In one example, the Tweak-mediated activity is Tweak-induced NFκB-signaling in a cell and/or Tweak-induced death of Kym1 cells.

In one example, the present disclosure provides an Fn14-binding protein comprising an antigen binding domain, wherein the antigen binding domain binds specifically to Fn14 and wherein the Fn14-binding protein reduces Tweak-induced NFκB-signaling in a cell expressing Fn14, and wherein the Fn14-binding protein does not detectably induce NFκB-signaling when contacted to a cell expressing Fn14 in the absence of Tweak.

In one example, the present disclosure provides an Fn14-binding protein comprising an antigen binding domain of an anti-Fn14 antibody, wherein the antigen binding domain binds specifically to Fn14 and wherein the Fn14-binding protein reduces Tweak-induced NFκB-signaling in a cell expressing Fn14, and wherein the Fn14-binding protein does not detectably induce NFκB-signaling when contacted to a cell expressing Fn14 in the absence of Tweak.

For example, NFκB-signaling is detected in a cell (e.g., a HEK293T cell) comprising a nucleic acid encoding fluorescent protein operably linked to a promoter that facilitates gene expression as a result of NFκB binding. For example, NFκB signaling is detected using fluorescence activated cell sorting. Tweak-induced NFκB-signaling can be induced by contacting the cell with Tweak (e.g., about 100 ng or 200 ng of Tweak) either in the presence or absence of the protein. In one example, the Fn14-binding protein reduces or prevents Tweak-induced NFκB-signaling (e.g., induced by 100 ng or 200 ng of Tweak) at a concentration of 100 ng/ml or 1 μg/ml.

For example, the Fn14-binding protein binds specifically to an epitope in Fn14 comprising residues contained within the sequence set forth in SEQ ID NO: 34.

In one example, the Fn14-binding protein does not detectably bind to a polypeptide comprising a region of Fn14, the region consisting of a sequence set forth in SEQ ID NO: 33 or 46. For example, the polypeptide is displayed on the surface of a phage.

In one example, the Fn14-binding protein does not detectably bind to a peptide consisting of a sequence set forth in SEQ ID NO: 33 or 46.

In one example, the Fn14-binding protein binds to an extracellular domain of Fn14 comprising a proline or alanine substituted for the arginine at position 56 of SEQ ID NO: 1. In one example, the Fn14-binding protein binds to an extracellular domain of Fn14 comprising a proline or alanine substituted for the arginine at position 56 of SEQ ID NO: 1 at a similar or substantially the same level as it binds to an extracellular domain of Fn14 (e.g., comprising a sequence set forth in SEQ ID NO: 2). For example, the Fn14-binding protein binds to a peptide consisting of the sequence set forth in SEQ ID NO: 52 or 54 optionally additionally comprising six histidine residues at a terminus, e.g., at a similar or substantially the same level as it binds to an extracellular domain of Fn14 (e.g., comprising a sequence set forth in SEQ ID NO: 2). In one example, the level of binding is assessed by immobilizing the peptide and contacting the peptide with the Fn14-binding protein. Exemplary Fn14-binding proteins described herein having such binding characteristics comprise the variable regions and/or CDRs of an antibody designated CRCBT-06-001, CRCBT-06-002 or CRCBT-06-005. Thus, in one example, the Fn14-binding protein binds to a peptide consisting of the sequence set forth in SEQ ID NO: 52 or 54 (optionally with an additional six histidine residues at a terminus) at a similar or substantially the same level or with a similar or substantially the same affinity as an antibody designated CRCBT-06-001 or CRCBT-06-002 or CRCBT-06-005. In another example, the Fn14-binding protein competitively inhibits binding of an antibody designated CRCBT-06-001 or CRCBT-06-002 or CRCBT-06-005 to a peptide consisting of the sequence set forth in SEQ ID NO: 52 or 54 (optionally with an additional six histidine residues at a terminus).

In one example, the Fn14-binding protein binds to an extracellular domain of Fn14 comprising an alanine substituted for the arginine at position 58 of SEQ ID NO: 1. In one example, the Fn14-binding protein binds to an extracellular domain of Fn14 comprising an alanine substituted for the arginine at position 58 of SEQ ID NO: 1 at a similar or substantially the same level as it binds to an extracellular domain of Fn14 (e.g., comprising a sequence set forth in SEQ ID NO: 2). For example, the Fn14-binding protein binds to a peptide consisting of the sequence set forth in SEQ ID NO: 56 optionally additionally comprising six histidine residues at a terminus, e.g., at a similar or substantially the same level as it binds to an extracellular domain of Fn14 (e.g., comprising a sequence set forth in SEQ ID NO: 2). In one example, the level of binding is assessed by immobilizing the peptide and contacting the peptide with the Fn14-binding protein or by expressing the peptide on the surface of a phage and contacting the phage to an immobilized Fn14 binding protein. Exemplary Fn14-binding proteins described herein having such binding characteristics comprise the variable regions and/or CDRs of an antibody designated CRCBT-06-001, CRCBT-06-002 or CRCBT-06-005. Thus, in one example, the Fn14-binding protein binds to a peptide consisting of the sequence set forth in SEQ ID NO: 56 (optionally with an additional six histidine residues at a terminus) at a similar or substantially the same level or with a similar or substantially the same affinity as an antibody designated CRCBT-06-001 or CRCBT-06-002 or CRCBT-06-005. In another example, the Fn14-binding protein competitively inhibits binding of an antibody designated CRCBT-06-001 or CRCBT-06-002 or CRCBT-06-005 to a peptide consisting of the sequence set forth in SEQ ID NO: 56 (optionally with an additional six histidine residues at a terminus).

In one example, the Fn14-binding protein binds to an extracellular domain of Fn14 comprising an alanine substituted for the histidine at position 60 of SEQ ID NO: 1. In one example, the Fn14-binding protein binds to an extracellular domain of Fn14 comprising an alanine substituted for the histidine at position 60 of SEQ ID NO: 1 at a similar or substantially the same level as it binds to an extracellular domain of Fn14 (e.g., comprising a sequence set forth in SEQ ID NO: 2). For example, the Fn14-binding protein binds to a peptide consisting of the sequence set forth in SEQ ID NO: 63 optionally additionally comprising six histidine residues at a terminus, e.g., at a similar or substantially the same level as it binds to an extracellular domain of Fn14 (e.g., comprising a sequence set forth in SEQ ID NO: 2). In one example, the level of binding is assessed by immobilizing the peptide and contacting the peptide with the Fn14-binding protein. Exemplary Fn14-binding proteins described herein having such binding characteristics comprise the variable regions and/or CDRs of an antibody designated CRCBT-06-001 or CRCBT-06-002. Thus, in one example, the Fn14-binding protein binds to a peptide consisting of the sequence set forth in SEQ ID NO: 63 (optionally with an additional six histidine residues at a terminus) at a similar or substantially the same level or with a similar or substantially the same affinity as an antibody designated CRCBT-06-001 or CRCBT-06-002. In another example, the Fn14-binding protein competitively inhibits binding of an antibody designated CRCBT-06-001 or CRCBT-06-002 to a peptide consisting of the sequence set forth in SEQ ID NO: 63 (optionally with an additional six histidine residues at a terminus).

In one example, the Fn14-binding protein binds to a peptide consisting of the sequence set forth in SEQ ID NO: 48 (optionally with an additional six histidine residues at a terminus). In one example, the Fn14-binding protein binds to a peptide consisting of the sequence set forth in SEQ ID NO: 48 (optionally with an additional six histidine residues at a terminus) at a similar or substantially the same level as it binds to an extracellular domain of Fn14 (e.g., comprising a sequence set forth in SEQ ID NO: 2). In one example, the level of binding is assessed by immobilizing the peptide and contacting the peptide with the Fn14-binding protein. Exemplary Fn14-binding proteins described herein having such binding characteristics comprise the variable regions and/or CDRs of an antibody designated CRCBT-06-001 or CRCBT-06-002. Thus, in one example, the Fn14-binding protein binds to a peptide consisting of the sequence set forth in SEQ ID NO: 48 (optionally with an additional six histidine residues at a terminus) at a similar or substantially the same level or with a similar or substantially the same affinity as an antibody designated CRCBT-06-001 or CRCBT-06-002. In another example, the Fn14-binding protein competitively inhibits binding of an antibody designated CRCBT-06-001 or CRCBT-06-002 to a peptide consisting of the sequence set forth in SEQ ID NO: 48 (optionally with an additional six histidine residues at a terminus).

In one example, the Fn14-binding protein binds to an extracellular domain of Fn14 comprising an alanine substituted for the tryptophan at position 42 of SEQ ID NO: 1. In one example, the Fn14-binding protein binds to an extracellular domain of Fn14 comprising an alanine substituted for the tryptophan at position 42 of SEQ ID NO: 1 at a similar or substantially the same level as it binds to an extracellular domain of Fn14 (e.g., comprising a sequence set forth in SEQ ID NO: 2). For example, the Fn14-binding protein binds to a peptide consisting of the sequence set forth in SEQ ID NO: 57 optionally additionally comprising six histidine residues at a terminus, e.g., at a similar or substantially the same level as it binds to an extracellular domain of Fn14 (e.g., comprising a sequence set forth in SEQ ID NO: 2). In one example, the level of binding is assessed by immobilizing the peptide and contacting the peptide with the Fn14-binding protein. Exemplary Fn14-binding proteins described herein having such binding characteristics comprise the variable regions and/or CDRs of an antibody designated CRCBT-06-001, CRCBT-06-002 or CRCBT-06-004. Thus, in one example, the Fn14-binding protein binds to a peptide consisting of the sequence set forth in SEQ ID NO: 57 (optionally with an additional six histidine residues at a terminus) at a similar or substantially the same level or with a similar or substantially the same affinity as an antibody designated CRCBT-06-001 or CRCBT-06-002 or CRCBT-06-004. In another example, the Fn14-binding protein competitively inhibits binding of an antibody designated CRCBT-06-001 or CRCBT-06-002 or CRCBT-06-004 to a peptide consisting of the sequence set forth in SEQ ID NO: 57 (optionally with an additional six histidine residues at a terminus).

In one example, the Fn14-binding protein binds to an extracellular domain of Fn14 comprising one of the following amino acid substitutions (numbering relative to SEQ ID NO: 1) T33N, A34S, R38S, R56P, L77M, R56A, R56K, R58A, W42A, L46A, D51A, S54A, A57G, P59A, H60A, S61A, D62A, F63A, L65A or H60K. In one example, the level of binding is similar or substantially the same level as the Fn14-binding protein binds to an extracellular domain of Fn14 (e.g., comprising a sequence set forth in SEQ ID NO: 2).

In one example, the Fn14-binding protein binds to an extracellular domain of Fn14 comprising one or more amino acid substitutions individually or collectively selected from the group consisting of (numbering relative to SEQ ID NO: 1) T33N, A34S, R38S, R56P, L77M, R56A, R56K, R58A, W42A, L46A, D51A, S54A, A57G, P59A, H60A, S61A, D62A, F63A, L65A or H60K. In one example, the level of binding is similar or substantially the same level as the Fn14-binding protein binds to an extracellular domain of Fn14 (e.g., comprising a sequence set forth in SEQ ID NO: 2).

In one example, the Fn14 binding protein is capable of binding to a peptide consisting of a sequence set forth in any one of SEQ ID NOs: 49-68, optionally with an additional six histidine residues at a terminus.

In one example, the Fn14-binding protein is capable of binding to a series of peptides, wherein the series comprises peptides having all of the sequences set forth in any one of SEQ ID NOs: 49-68, optionally with an additional six histidine residues at a terminus.

In one example, the Fn14 binding protein is capable of binding to a peptide consisting of a sequence set forth in SEQ ID NOs: 47, optionally with an additional six histidine residues at a terminus.

In one example, the Fn14 binding protein is capable of binding to a peptide consisting of a sequence set forth in SEQ ID NO: 48, optionally with an additional six histidine residues at a terminus.

In one example, the Fn14-binding protein binds to a peptide consisting of a sequence set forth in SEQ ID NO: 35 in an amount within 75% of the amount of bound by an antibody comprising a $V_H$ comprising a sequence set forth in SEQ ID NO: 19 and a $V_L$ comprising a sequence set forth in SEQ ID NO: 26. In one example, the amount of protein or antibody bound is assessed by contacting the Fn14-binding protein to a peptide consisting of the sequence set forth in SEQ ID NO: 35 and an amount of the Fn14-binding protein (e.g., 2 μg/ml) brought into contact with the peptide. The amount of Fn14-binding protein bound to the peptide is then determined and compared to the amount of an antibody comprising a $V_H$ comprising a sequence set forth in SEQ ID NO: 19 and a $V_L$ comprising a sequence set forth in SEQ ID NO: 26 bound to the peptide. In one example, the amount of Fn14-binding protein bound to the peptide is within about 73% or 60% or 45% of the amount of antibody bound.

In one example, the Fn14-binding protein binds to a peptide consisting of a sequence set forth in SEQ ID NO: 34 in an amount within 80% of the amount bound by an antibody comprising a $V_H$ comprising a sequence set forth in SEQ ID NO: 15 and a $V_L$ comprising a sequence set forth in SEQ ID NO: 22 or comprising a $V_H$ comprising a sequence set forth in SEQ ID NO: 16 and a $V_L$ comprising a sequence set forth in SEQ ID NO: 23. In one example, the amount of protein or antibody bound is assessed by contacting the Fn14-binding protein to a peptide consisting of the sequence set forth in SEQ ID NO: 34 and an amount of the Fn14-binding protein (e.g., 5 ng/ml) brought into contact with the peptide. The amount of Fn14-binding protein bound to the peptide is then determined and compared to the amount of the antibody bound to the peptide. In one example, the amount of Fn14-binding protein bound to the peptide is within about 50% or 48% or 45% or 40% of the amount of antibody bound.

The present disclosure also provides Fn14-binding protein comprising an antigen binding domain of an anti-Fn14 antibody, wherein the antigen binding domain binds specifically to a peptide comprising residues of an epitope bound by antibodies identified by the inventors. For example, the disclosure provides an Fn14-binding protein comprising an antigen binding domain of an of an anti-Fn14 antibody, wherein the antigen binding domain binds specifically to Fn14, wherein the antigen binding domain binds to an epitope in Fn14 comprising residues contained within the sequence set forth in SEQ ID NO: 34.

For example, the antigen binding domain binds specifically to an epitope in Fn14 comprising residues contained within one or more sequences set forth in SEQ ID NOs: 3 to 9 or 34.

In one example, the Fn14-binding protein binds to a conformational epitope in Fn14. For example, the conformational epitope is dependent on disulphide bond formation within Fn14. For example, the conformational epitope bound by the Fn14-binding protein is not present in an Fn14 protein lacking disulphide bonds, e.g., Fn14 in reduced form.

In one example, the Fn14-binding protein does not substantially bind to Fn14 in reduced form or reduced and alkylated form. In one example, the Fn14-binding protein does not substantially bind to a polypeptide comprising an extracellular domain of Fn14 fused to an Fc region of an antibody, wherein the polypeptide is reduced or reduced and alkylated. For example, the binding is detected by performing an enzyme-linked immunosorbent assay (ELISA) to detect binding of the Fn14-binding protein to the immobilized polypeptide.

For example, the Fn14-binding protein does not detectably bind to Fn14 in reduced form or reduced and alkylated form. In one example, the Fn14-binding protein does not detectably bind to a polypeptide comprising an extracellular domain of Fn14 fused to an Fc region of an antibody, wherein the polypeptide is reduced or reduced and alkylated.

In one example, the Fn14-binding protein reduces Tweak-induced interleukin-8 (IL-8) secretion from a cell (i.e., has IL-8 secretion antagonistic activity), e.g., an A375 human melanoma cell. In one example, the Fn14-binding protein (e.g., at a concentration of about 10 μg/ml) reduces IL-8 secretion by A375 melanoma cells (e.g., about $1\times10^4$ cells) contacted with Tweak fused to the Fc region of an antibody (e.g., at a concentration of about 300 ng/ml). An exemplary antibody having such activity comprises the variable regions or CDRs of an antibody selected from the group consisting of CRCBT-06-002, CRCBT-06-005 and CRCBT-06-007 or antibodies comprising CDRs thereof.

In the case of CRCBT-06-005, the antibody is, for example, mouse IgG2b (the equivalent of human IgG3). In this regard, the inventors have shown that CRCBT-06-005 and CRCBT-06-006 have very similar V regions, however differ in isotype and activity (e.g., CRCBT-06-006 [mouse IgG2a, equivalent of human IgG1] is an agonist of Tweak-induced IL-8 secretion).

In one example, the Fn14-binding protein has a level of antagonism of at least about 80% or 90% or 100% when assessed using the following equation (b−d)/(b−a), where a=the amount of IL-8 secreted in the presence of 10 μg/ml antibody, b=the amount of IL-8 secreted in the presence of 300 ng/ml Tweak-Fc, c=the amount of IL-8 secreted from cells in the absence of either antibody or Tweak-Fc, d=the amount of IL-8 secreted in the presence of 10 μg/ml antibody and 300 ng/ml Tweak-Fc.

In one example, the Fn14-binding protein induces Tweak-induced interleukin-8 (IL-8) secretion from a cell (i.e., has IL-8 secretion agonistic activity), e.g., an A375 human melanoma cell when the cell is contacted with the Fn14-binding protein in the absence of Tweak. In one example, the Fn14-binding protein (e.g., at a concentration of about 10, 1, 0.1 or 0.01 μg/ml) induces IL-8 secretion by A375 melanoma cells (e.g., about $1\times10^4$ cells) in the absence of Tweak. An exemplary antibody having such activity comprises the variable regions or CDRs of an antibody selected from the group consisting of CRCBT-06-001 and CRCBT-06-006.

In one example, the Fn14-binding protein has a level of agonism of at least about 80% or 90% when assessed using the following equation (a−c)/(b−c), where a=the amount of IL-8 secreted in the presence of 10 μg/ml antibody, b=the amount of IL-8 secreted in the presence of 300 ng/ml Tweak-Fc, c=the amount of IL-8 secreted from cells in the absence of either antibody or Tweak-Fc, d=the amount of IL-8 secreted in the presence of 10 μg/ml antibody and 300 ng/ml Tweak-Fc.

In one example, the Fn14-binding protein delays or prevents weight loss upon administration to a subject suffering from cancer or cancer-cachexia or diabetes or diabetes-induced cachexia.

In one example, the Fn14-binding protein binds to a protein comprising an extracellular domain of Fn14 fused to an Fc region of an antibody with an affinity dissociation constant ($K_D$) of 2 nM or less, such as, 1.5 nM or less, for example, 1 nM or less. In one example, the $K_D$ is assessed by immobilizing the Fn14-binding protein (e.g., a Fab or an antibody) and assessing binding of an extracellular region of Fn14 fused to an Fc to the immobilized Fn14-binding protein using surface plasmon resonance.

In one example, the $K_D$ is between about 0.01 nM to about 2 nM, such as between about 0.05 nM to about 1 nM, for example, between about 0.1 nM to about 1 nM, for example, between about 0.5 nM to about 1 nM. In one example, the $K_D$ is assessed by immobilizing the Fn14-binding protein (e.g., a Fab or an antibody) and assessing binding of an extracellular region of Fn14 fused to an Fc to the immobilized Fn14-binding protein using surface plasmon resonance.

An exemplary Fn14-binding protein of the disclosure has a $K_D$ of about 0.9 nM (e.g., +/−0.1 nM) for a protein comprising an extracellular domain of Fn14 fused to an Fc region of an antibody. Another exemplary Fn14-binding protein of the disclosure has a $K_D$ of about 0.7 nM (e.g., +/−0.1 nM) for a protein comprising an extracellular domain of Fn14 fused to an Fc region of an antibody.

In one example, the Fn14-binding protein binds to recombinant human Fn14 with a $K_D$ of 0.6 nM or less.

In one example, the Fn14-binding protein binds to recombinant human Fn14 with a $K_D$ of 1 nM or less, such as, 0.9 nM or less, for example, 0.8 nM or less, for example, 0.7 nM or less, for example, 0.6 nM or less. In one example, the $K_D$ is assessed by immobilizing the Fn14-binding protein (e.g., a Fab or an antibody) and assessing binding of human recombinant Fn14 to the immobilized Fn14-binding protein using surface plasmon resonance.

In one example, the $K_D$ is between about 0.01 nM and 1 nM, such as between about 0.05 nM and 0.9 nM, for example, between about 0.09 nM and 0.7 nM, for example, between about 0.1 nM and 0.6 nM.

An exemplary Fn14-binding protein of the disclosure has a $K_D$ of about 0.5 nM (e.g., +/−0.1 nM) for recombinant human Fn14. For example, the Fn-14 binding protein is CRCBT-06-001 or an antibody comprising the antigen binding domain, variable regions or CDRs thereof.

Another exemplary Fn14-binding protein of the disclosure has a $K_D$ of about 0.2 nM (e.g., +/−0.1 nM) for recombinant human Fn14. For example, the Fn-14 binding protein is CRCBT-06-002 or an antibody comprising the antigen binding domain, variable regions or CDRs thereof.

In one example, the Fn14-binding protein binds to a protein comprising an extracellular domain of Fn14 fused to an Fc region of an antibody with an on-rate (Ka) of $5\times10^3$ $M^{-1}s^{-1}$ or greater, such as about $2\times10^3$ $M^{-1}s^{-1}$ or greater, for example, about $1.5\times10^4$ $M^{-1}s^{-1}$ or greater. In one example, the Ka is assessed by immobilizing the Fn14-binding protein (e.g., a Fab or an antibody) and assessing binding of an extracellular region of Fn14 fused to an Fc to the immobilized Fn14-binding protein using surface plasmon resonance.

For example, the Ka is between about $5\times10^3$ $M^{-1}s^{-1}$ to about $5\times10^5$ $M^{-1}s^{-1}$, for example, between about $1\times10^4$ $M^{-1}s^{-1}$ to about $4\times10^5$ $M^{-1}s^{-1}$, for example, between about $2\times10^4$ $M^{-1}s^{-1}$ to about $4\times10^5$ $M^{-1}s^{-1}$. In one example, the Ka is assessed by immobilizing the Fn14-binding protein (e.g., a Fab or an antibody) and assessing binding of an extracellular region of Fn14 fused to an Fc to the immobilized Fn14-binding protein using surface plasmon resonance.

An exemplary Fn14-binding protein of the disclosure has a Ka of about $2.2\times10^{4}$ $M^{-1}s^{-1}$. A further exemplary Fn14-binding protein of the disclosure has a Ka of about $3.9\times10^{5}$ $M^{-1}s^{-1}$. In one example, the Ka is assessed by immobilizing the Fn14-binding protein (e.g., a Fab or an antibody) and assessing binding of an extracellular region of Fn14 fused to an Fc to the immobilized Fn14-binding protein using surface plasmon resonance.

In one example, the Fn14-binding protein binds to recombinant human Fn14 with a Ka of $1\times10^{5}$ $M^{-1}s^{-1}$ or greater, such as about $1.2\times10^{5}$ $M^{-1}s^{-1}$ or greater, for example, about $1.3\times10^{5}$ $M^{-1}s^{-1}$ or greater. In one example, the Ka is assessed by immobilizing the Fn14-binding protein (e.g., a Fab or an antibody) and assessing binding of recombinant human Fn14 to the immobilized Fn14-binding protein using surface plasmon resonance.

For example, the Ka is between about $1\times10^{5}$ $M^{-1}s^{-1}$ to about $3.5\times10^{5}$ $M^{-1}s^{-1}$. In one example, the Ka is assessed by immobilizing the Fn14-binding protein (e.g., a Fab or an antibody) and assessing binding of recombinant human Fn14 to the immobilized Fn14-binding protein using surface plasmon resonance.

An exemplary Fn14-binding protein of the disclosure has a Ka of about $1.8\times10^{5}$ $M^{-1}s^{-1}$ for recombinant human Fn14. For example, the Fn-14 binding protein is CRCBT-06-001 or an antibody comprising the antigen binding domain, variable regions or CDRs thereof. In one example, the Ka is assessed by immobilizing the Fn14-binding protein (e.g., a Fab or an antibody) and assessing binding of recombinant human Fn14 to the immobilized Fn14-binding protein using surface plasmon resonance.

A further exemplary Fn14-binding protein of the disclosure has a Ka of about $1.3\times10^{5}$ $M^{-1}s^{-1}$ for recombinant human Fn14. For example, the Fn-14 binding protein is CRCBT-06-002 or an antibody comprising the antigen binding domain, variable regions or CDRs thereof. In one example, the Ka is assessed by immobilizing the Fn14-binding protein (e.g., a Fab or an antibody) and assessing binding of recombinant human Fn14 to the immobilized Fn14-binding protein using surface plasmon resonance.

In one example, the Fn14-binding protein binds to a protein comprising an extracellular domain of Fn14 fused to an Fc region of an antibody with an off-rate (Kd) of $9\times10^{-5}$ $s^{-1}$ or less, such as, $7\times10^{-5}$ $s^{-1}$ or less, for example, $6\times10^{-5}$ $s^{-1}$ or less, for example, $5.5\times10^{-5}$ $s^{-1}$ or less. In one example, the Kd is assessed by immobilizing the Fn14-binding protein (e.g., a Fab or an antibody) and assessing binding of an extracellular region of Fn14 fused to an Fc to the immobilized Fn14-binding protein using surface plasmon resonance.

For example, the Kd is between about $1\times10^{-4}s^{-1}$ to about $1\times10^{-5}s^{-1}$, for example, between about $6\times10^{-5}s^{-1}$ to about $1\times10^{-5}s^{-1}$, for example, between about $5.5\times10^{-5}s^{-1}$ to about $1.4\times10^{-5}s^{-1}$, for example, between about $2\times10^{-5}s^{-1}$ to about $1.4\times10^{-5}s^{-1}$. In one example, the Kd is assessed by immobilizing the Fn14-binding protein (e.g., a Fab or an antibody) and assessing binding of an extracellular region of Fn14 fused to an Fc to the immobilized Fn14-binding protein using surface plasmon resonance.

An exemplary protein of the disclosure has a Kd of about $1.85\times10^{-5}s^{-1}$. A further exemplary Fn14-binding protein of the disclosure has a Kd of about $1.45\times10^{-5}s^{-1}$. In one example, the Kd is assessed by immobilizing the Fn14-binding protein (e.g., a Fab or an antibody) and assessing binding of an extracellular region of Fn14 fused to an Fc to the immobilized Fn14-binding protein using surface plasmon resonance.

In one example, the Fn14-binding protein binds to recombinant human Fn14 with a Kd of $3\times10^{-3}s^{-1}$ or less.

In one example, the Fn14-binding protein binds to recombinant human Fn14 with a Kd of about $8\times10^{-4}s^{-1}$ or less, such as, $5\times10^{-4}$ $s^{-1}$ or less, for example, $4\times10^{-4}$ $s^{-1}$ or less, for example, $2\times10^{-4}$ $s^{-1}$ or less. In one example, the Kd is assessed by immobilizing the Fn14-binding protein (e.g., a Fab or an antibody) and assessing binding of recombinant human Fn14 to the immobilized Fn14-binding protein using surface plasmon resonance.

For example, the Kd is between about $9\times10^{-4}s^{-1}$ to about $1\times10^{-5}s^{-1}$, for example, between about $5\times10^{-4}s^{-1}$ to about $1\times10^{-5}s^{-1}$, for example, between about $2\times10^{-4}s^{-1}$ to about $2\times10^{-5}$ $s^{-1}$. In one example, the Kd is assessed by immobilizing the Fn14-binding protein (e.g., a Fab or an antibody) and assessing binding of recombinant human Fn14 to the immobilized Fn14-binding protein using surface plasmon resonance.

An exemplary protein of the disclosure has a Kd of about $1.02\times10^{-4}s^{-1}$ for recombinant human Fn14. For example, the Fn14-binding protein is CRCBT-06-001 or an antibody comprising the antigen binding domain, variable regions or CDRs thereof. In one example, the Kd is assessed by immobilizing the Fn14-binding protein (e.g., a Fab or an antibody) and assessing binding of recombinant human Fn14 to the immobilized Fn14-binding protein using surface plasmon resonance.

A further exemplary Fn14-binding protein of the disclosure has a Kd of about $1.45\times10^{-5}$ $s^{-1}$ for recombinant human Fn14. For example, the Fn-14 binding protein is CRCBT-06-001 or an antibody comprising the antigen binding domain, variable regions or CDRs thereof. In one example, the Kd is assessed by immobilizing the Fn14-binding protein (e.g., a Fab or an antibody) and assessing binding of recombinant human Fn14 to the immobilized Fn14-binding protein using surface plasmon resonance.

In one example, the level of binding of the Fn14-binding protein of the disclosure to a polypeptide comprising a sequence set forth in any one of SEQ ID NOs: 29-32 is similar to the level of binding to a polypeptide comprising a sequence set forth in SEQ ID NO: 2.

In one example, Fn14-binding of the disclosure does not detectably bind to a peptide comprising one or more of the following sequences:

(i) an amino acid sequence in SEQ ID NO: 12, wherein the peptide does not comprise amino acids 1 to 61 of SEQ ID NO: 1;

(ii) an amino acid sequence set forth in SEQ ID NO: 10; and/or (iii) an amino acid sequence set forth in SEQ ID NO: 11.

In one example, an Fn14-binding protein of the disclosure binds to human Fn14 and mouse Fn14. In one example, the binding of the protein is assessed by ELISA using recombinant Fn14 extracellular domain.

In one example, the Fn14-binding protein competitively inhibits binding of any one of the following antibodies to Fn14 and/or human Fn14 and/or a polypeptide comprising a sequence set forth in SEQ ID NO: 1, 2 or 34:

(i) an antibody comprising a heavy chain variable region ($V_H$) comprising a sequence set forth in SEQ ID NO: 15 and a light chain variable region ($V_L$) comprising a sequence set forth in SEQ ID NO: 22;

(ii) an antibody comprising a $V_H$ comprising a sequence set forth in SEQ ID NO: 16 and a $V_L$ comprising a sequence set forth in SEQ ID NO: 23;

(iii) an antibody comprising a $V_H$ comprising a sequence set forth in SEQ ID NO: 17 and a $V_L$ comprising a sequence set forth in SEQ ID NO: 24;

(iv) an antibody comprising a $V_H$ comprising a sequence set forth in SEQ ID NO: 18 and a $V_L$ comprising a sequence set forth in SEQ ID NO: 25;

(v) an antibody comprising a $V_H$ comprising a sequence set forth in SEQ ID NO: 19 and a $V_L$ comprising a sequence set forth in SEQ ID NO: 26;

(vi) an antibody comprising a $V_H$ comprising a sequence set forth in SEQ ID NO: 20 and a $V_L$ comprising a sequence set forth in SEQ ID NO: 27; and (vii) an antibody comprising a $V_H$ comprising a sequence set forth in SEQ ID NO: 21 and a $V_L$ comprising a sequence set forth in SEQ ID NO: 28.

In one example, the Fn14-binding protein binds to the same epitope in Fn14 or to an epitope in Fn14 that overlaps with the epitope bound by any one or more of the following antibodies:

(i) an antibody comprising a heavy chain variable region ($V_H$) comprising a sequence set forth in SEQ ID NO: 15 and a light chain variable region ($V_L$) comprising a sequence set forth in SEQ ID NO: 22;

(ii) an antibody comprising a $V_H$ comprising a sequence set forth in SEQ ID NO: 16 and a $V_L$ comprising a sequence set forth in SEQ ID NO: 23;

(iii) an antibody comprising a $V_H$ comprising a sequence set forth in SEQ ID NO: 17 and a $V_L$ comprising a sequence set forth in SEQ ID NO: 24;

(iv) an antibody comprising a $V_H$ comprising a sequence set forth in SEQ ID NO: 18 and a $V_L$ comprising a sequence set forth in SEQ ID NO: 25;

(v) an antibody comprising a $V_H$ comprising a sequence set forth in SEQ ID NO: 19 and a $V_L$ comprising a sequence set forth in SEQ ID NO: 26;

(vi) an antibody comprising a $V_H$ comprising a sequence set forth in SEQ ID NO: 20 and a $V_L$ comprising a sequence set forth in SEQ ID NO: 27; and (vii) an antibody comprising a $V_H$ comprising a sequence set forth in SEQ ID NO: 21 and a $V_L$ comprising a sequence set forth in SEQ ID NO: 28.

In one example, the Fn14-binding protein neutralizes a Tweak activity in a cell expressing Fn14. For example, the Fn14-binding protein inhibits or reduces Tweak-mediated death of Kym1 cells.

For example, at a concentration of about 100 ng/ml, the Fn14-binding protein is capable of reducing cell death induced by about 50 ng/ml of a protein comprising Tweak fused to an Fc region of an antibody. In one example, the reduction in cell death is about a 1.5 fold reduction or a 2 fold reduction compared to the level of cell death in the presence of the same concentration of a protein comprising Tweak fused to an Fc region of an antibody and the absence of the Fn14-binding protein.

For example, at a concentration of about 1 μg/ml, the Fn14-binding protein is capable of reducing cell death induced by about 200 ng/ml of a protein comprising Tweak fused to an Fc region of an antibody. In one example, the reduction in cell death is about a 1.2 fold reduction or a 1.5 fold reduction or a 2 fold reduction or a 3 fold reduction compared to the level of cell death in the presence of the same concentration of a protein comprising Tweak fused to an Fc region of an antibody and the absence of the Fn14-binding protein.

Alternatively, or additionally, the Fn14-binding protein reduces or prevents Fn14 (e.g. hFn14)-mediated cytokine production, e.g., production of IL-6 by tumor cells, e.g., fibroblasts genetically modified to express v12Hras and hFn14. In one example, the Fn14-binding protein reduces Fn14 (e.g., hFn14)-mediated IL-6 production by fibroblasts genetically modified to express v12Hras and hFn14 (e.g., as described herein) by at least 1.5 fold or at least 2 fold when contacted to the cells at a concentration of about 0.5 μg/ml.

Alternatively, or additionally, the Fn14-binding protein reduces or inhibits Tweak-induced NFκB-signaling in a cell expressing Fn14 (e.g., hFn14), e.g., as described herein.

In one example, the Fn14-binding protein comprising a non-antibody antigen binding domain, such as a non-antibody-derived Fn-14 binding protein comprising one or more Ig folds (e.g., an immunoglobulin, such as a T cell receptor or a V domain or an IgNAR), an adnectin, an affibody, an atrimer, an evasin, a designed ankyrin-repeat protein (DARPin) or an anticalin.

In one example, the Fn14-binding protein comprises an antibody antigen binding domain.

In one example, the antigen binding domain comprises:

(i) a $V_H$ comprising a sequence set forth in any one of SEQ ID NOs: 13 or 15 to 21 or a humanized, chimeric or deimmunized version thereof; and/or (ii) a $V_L$ comprising a sequence set forth in any one of SEQ ID NOs: 14 or 22 to 28 or a humanized, chimeric or deimmunized version thereof.

In one example, the Fn14-binding protein comprises a $V_H$ and a $V_L$, wherein the $V_H$ and $V_L$ bind to form a Fv comprising the antigen binding domain. For example, the Fv comprises:

(i) a $V_H$ comprising three complementarity determining regions (CDRs) of a $V_H$ comprising a sequence set forth in SEQ ID NO: 13, wherein if the amino acid at a position corresponding to residue 101 of SEQ ID NO: 13 is a thymidine, the residue at position 107 is a histidine and/or the residue at position 53 of SEQ ID NO: 13 is a serine; and (ii) a $V_L$ comprising three CDRs of a $V_L$ comprising a sequence set forth in SEQ ID NO: 14.

In one example, the Fv comprises:

(i) a $V_H$ comprising CDRs 1, 2, and 3 of a $V_H$ comprising a sequence set forth in SEQ ID NO: 15 and a $V_L$ comprising CDRs 1, 2, and 3 of a $V_L$ comprising a sequence set forth in SEQ ID NO: 22;

(ii) a $V_H$ comprising CDRs 1, 2, and 3 of a $V_H$ comprising a sequence set forth in SEQ ID NO: 16 and a $V_L$ comprising CDRs 1, 2, and 3 of a $V_L$ comprising a sequence set forth in SEQ ID NO: 23;

(iii) a $V_H$ comprising CDRs 1, 2, and 3 of a $V_H$ comprising a sequence set forth in SEQ ID NO: 17 and a $V_L$ comprising CDRs 1, 2, and 3 of a $V_L$ comprising a sequence set forth in SEQ ID NO: 24;

(iv) a $V_H$ comprising CDRs 1, 2, and 3 of a $V_H$ comprising a sequence set forth in SEQ ID NO: 18 and a $V_L$ comprising CDRs 1, 2, and 3 of a $V_L$ comprising a sequence set forth in SEQ ID NO: 25;

(v) a $V_H$ comprising CDRs 1, 2, and 3 of a $V_H$ comprising a sequence set forth in SEQ ID NO: 19 and a $V_L$ comprising CDRs 1, 2, and 3 of a $V_L$ comprising a sequence set forth in SEQ ID NO: 26;

(vi) a $V_H$ comprising CDRs 1, 2, and 3 of a $V_H$ comprising a sequence set forth in SEQ ID NO: 20 and a $V_L$ comprising CDRs 1, 2, and 3 of a $V_L$ comprising a sequence set forth in SEQ ID NO: 27; and (vii) a $V_H$ comprising CDRs 1, 2, and 3 of a $V_H$ comprising a sequence set forth in SEQ ID NO: 21 and a $V_L$ comprising CDRs 1, 2, and 3 of a $V_L$ comprising a sequence set forth in SEQ ID NO: 28.

In one example, the CDRs are defined by the Kabat numbering system and are shown in FIGS. 11A-11D in bold text.

In one example, the CDRs are defined by the Chothia numbering system and are shown in FIGS. 11A-11D in underlined text.

In one example, an Fn14-binding protein of the disclosure is a domain antibody (e.g., comprises only a $V_H$ or a only a $V_L$, for example only a $V_H$, optionally linked to another moiety, such as one or more constant domains or a constant region or a Fc). In this regard, the inventors have produced CRCBT-06-003 and CRCBT-06-004, which have VL domains which contain frame-shift mutations meaning that CDRs2 and 3 are not readily identifiable. Thus, at least the majority of the binding of these proteins is expected to result from the $V_H$. The sequences of the $V_H$ domains is very similar to the $V_H$ sequences of other exemplary proteins of the disclosure.

In one example of an Fn14-binding protein of the disclosure, the $V_H$ and the $V_L$ are in a single polypeptide chain. For example, the Fn14-binding protein is:

(i) a single chain Fv fragment (scFv);

(ii) a dimeric scFv (di-scFv);

(iii) at least one of (i) and/or (ii) linked to a heavy chain constant region or an Fc or a heavy chain constant domain ($C_H$) 2 and/or $C_H3$; or (iv) at least one of (i) and/or (ii) linked to a protein that binds to an immune effector cell.

In another example, of the disclosure the $V_L$ and $V_H$ are in separate polypeptide chains. For example, the Fn14-binding protein is:

(i) a diabody;

(ii) a triabody;

(iii) a tetrabody;

(iv) a Fab;

(v) a $F(ab')_2$;

(vi) a Fv; or (vii) at least one of (i) to (vi) linked to a heavy chain constant region or an Fc or a heavy chain constant domain ($C_H$) 2 and/or $C_H3$.

(viii) at least one of (i) to (vi) linked to a protein that binds to an immune effector cell.

In one exemplary form of the disclosure, the Fn14-binding protein is an antibody.

The present disclosure additionally provides an anti-Fn14 antibody, the antibody comprising any one of the following:

(i) a $V_H$ comprising a sequence set forth in SEQ ID NO: 13 or a humanized, synhumanized or deimmunized version thereof and a $V_L$ comprising a sequence set forth in SEQ ID NO: 14 or a humanized, synhumanized or deimmunized version thereof;

(ii) a $V_H$ comprising a sequence set forth in SEQ ID NO: 15 or a humanized, synhumanized or deimmunized version thereof and a $V_L$ comprising a sequence set forth in SEQ ID NO: 22 or a humanized, synhumanized or deimmunized version thereof;

(iii) a $V_H$ comprising a sequence set forth in SEQ ID NO: 16 or a humanized, synhumanized or deimmunized version thereof and a $V_L$ comprising a sequence set forth in SEQ ID NO: 23 or a humanized, synhumanized or deimmunized version thereof;

(iv) a $V_H$ comprising a sequence set forth in SEQ ID NO: 17 or a humanized, synhumanized or deimmunized version thereof and a $V_L$ comprising a sequence set forth in SEQ ID NO: 24 or a humanized, synhumanized or deimmunized version thereof;

(v) a $V_H$ comprising a sequence set forth in SEQ ID NO: 18 or a humanized, synhumanized or deimmunized version thereof and a $V_L$ comprising a sequence set forth in SEQ ID NO: 25 or a humanized, synhumanized or deimmunized version thereof;

(vi) a $V_H$ comprising a sequence set forth in SEQ ID NO: 19 or a humanized, synhumanized or deimmunized version thereof and a $V_L$ comprising a sequence set forth in SEQ ID NO: 26 or a humanized, synhumanized or deimmunized version thereof;

(vii) a $V_H$ comprising a sequence set forth in SEQ ID NO: 20 or a humanized, synhumanized or deimmunized version thereof and a $V_L$ comprising a sequence set forth in SEQ ID NO: 27 or a humanized, synhumanized or deimmunized version thereof; or (viii) a $V_H$ comprising a sequence set forth in SEQ ID NO: 21 or a humanized, synhumanized or deimmunized version thereof and a $V_L$ comprising a sequence set forth in SEQ ID NO: 28 or a humanized, synhumanized or deimmunized version thereof.

The present disclosure additionally provides an anti-Fn14 antibody, the antibody comprising a $V_H$ comprising a sequence set forth in SEQ ID NO: 15 or a humanized, synhumanized or deimmunized version thereof and a $V_L$ comprising a sequence set forth in SEQ ID NO: 22 or a humanized, synhumanized or deimmunized version thereof.

The present disclosure additionally provides an anti-Fn14 antibody, the antibody comprising a $V_H$ comprising a sequence set forth in SEQ ID NO: 16 or a humanized, synhumanized or deimmunized version thereof and a $V_L$ comprising a sequence set forth in SEQ ID NO: 23 or a humanized, synhumanized or deimmunized version thereof.

The present disclosure also provides a chimeric antibody comprising a $V_H$ and a $V_L$ as discussed above (e.g., in the preceding lists), wherein the $V_H$ is linked to a human heavy chain constant region and the $V_L$ is linked to a human light chain constant region.

It will be apparent to the skilled person based on the disclosure herein that the present disclosure encompasses human, humanized, synhumanized, chimeric and primatized proteins.

The present disclosure also encompasses monoclonal antibodies. For example, the present disclosure provides an anti-Fn14 monoclonal antibody, the antibody comprising any one of the following:

(i) a $V_H$ comprising a sequence set forth in SEQ ID NO: 13 and a $V_L$ comprising a sequence set forth in SEQ ID NO: 14;

(ii) a $V_H$ comprising a sequence set forth in SEQ ID NO: 15 and a $V_L$ comprising a sequence set forth in SEQ ID NO: 22;

(iii) a $V_H$ comprising a sequence set forth in SEQ ID NO: 16 and a $V_L$ comprising a sequence set forth in SEQ ID NO: 23;

(iv) a $V_H$ comprising a sequence set forth in SEQ ID NO: 17 and a $V_L$ comprising a sequence set forth in SEQ ID NO: 24;

(v) a $V_H$ comprising a sequence set forth in SEQ ID NO: 18 and a $V_L$ comprising a sequence set forth in SEQ ID NO: 25;

(vi) a $V_H$ comprising a sequence set forth in SEQ ID NO: 19 and a $V_L$ comprising a sequence set forth in SEQ ID NO: 26;

(vii) a $V_H$ comprising a sequence set forth in SEQ ID NO: 20 and a $V_L$ comprising a sequence set forth in SEQ ID NO: 27; or (viii) a $V_H$ comprising a sequence set forth in SEQ ID NO: 21 and a $V_L$ comprising a sequence set forth in SEQ ID NO: 28.

In one example, an Fn14-binding protein or antibody of the present disclosure is conjugated to a compound. For example, the compound is selected from the group consisting of a radioisotope, a detectable label, a therapeutic compound, a colloid, a toxin, a nucleic acid, a peptide, a protein, a compound that increases the half life of the Fn14-binding protein in a subject and mixtures thereof.

The present disclosure also provides an isolated or recombinant nucleic acid encoding the Fn14-binding protein or antibody of the disclosure.

The present disclosure additionally provides an expression construct comprising the nucleic acid of the disclosure operably linked to a promoter.

Such an expression construct can be in a vector, e.g., a plasmid.

In examples of the disclosure directed to single polypeptide Fn14-binding proteins, the expression construct may comprise a promoter linked to a nucleic acid encoding that polypeptide chain.

In examples directed to multiple polypeptides that form an Fn14-binding protein, an expression construct of the disclosure comprises a nucleic acid encoding one of the polypeptides (e.g., comprising a $V_H$) operably linked to a promoter and a nucleic acid encoding another of the polypeptides (e.g., comprising a $V_L$) operably linked to another promoter.

In another example, the expression construct is a bicistronic expression construct, e.g., comprising the following operably linked components in 5' to 3' order:

(i) a promoter (ii) a nucleic acid encoding a first polypeptide;

(iii) an internal ribosome entry site; and (iv) a nucleic acid encoding a second polypeptide.

For example, the first polypeptide comprises a $V_H$ and the second polypeptide comprises a $V_L$, or the first polypeptide comprises a $V_L$ and the second polypeptide comprises a $V_H$.

The present disclosure also contemplates separate expression constructs one of which encodes a first polypeptide (e.g., comprising a $V_H$) and another of which encodes a second polypeptide (e.g., comprising a $V_L$). For example, the present disclosure also provides a composition comprising:

(i) a first expression construct comprising a nucleic acid encoding a polypeptide (e.g., comprising a $V_H$ operably linked to a promoter); and (ii) a second expression construct comprising a nucleic acid encoding a polypeptide (e.g., comprising a $V_L$ operably linked to a promoter), wherein the first and second polypeptides associate to form an Fn14-binding protein of the present disclosure.

The present disclosure additionally provides an isolated cell expressing the Fn14-binding protein or antibody of the present disclosure or a recombinant cell genetically-modified to express an Fn14-binding protein or antibody of the disclosure. In one example, the cell is an isolated hybridoma. In another example, the cell comprises the nucleic acid of or the expression construct of the disclosure or:

(i) a first expression construct comprising a nucleic acid encoding a polypeptide (e.g., comprising a $V_H$) operably linked to a promoter; and (ii) a second expression construct comprising a nucleic acid encoding a polypeptide (e.g., comprising a $V_L$) operably linked to a promoter, wherein the first and second polypeptides associate to form an Fn14-binding protein or antibody of the present disclosure The present disclosure additionally provides a composition comprising the Fn14-binding protein or the antibody or the nucleic acid or the expression construct or the cell of the present disclosure and a suitable carrier. In one example, the composition comprises the Fn14-binding protein or the antibody of the present disclosure.

In one example, the carrier is pharmaceutically acceptable.

The present disclosure additionally provides a method for treating or preventing an Fn14-mediated condition in a subject, the method comprising administering the Fn14-binding protein or the antibody or the nucleic acid or the expression construct or the cell or the composition of the present disclosure to the subject.

In one example, the Fn14-mediated condition is cancer, metastasis, tissue invasion by a cancer, excessive vascularization or angiogenesis, an autoimmune disease, an inflammatory disease, a neurodegenerative diseases, a wasting disorder, keloid scarring, graft versus host disease, graft rejection or ischemia.

In one example, the Fn14-mediated condition is an inflammatory disease or an autoimmune disease. In one example, the condition is a connective tissue disease (including inflammatory arthritis, such as rheumatoid arthritis, psoriatic arthritis, reactive arthritis or gout), lupus (including systemic lupus erythematosus), type 1 diabetes, multiple sclerosis, vasculitis (including Wegener's granulomatosis and Henoch Schonlein Syndrome), nephritis (including glomerulonephritis and pneumonitis), atherosclerosis or inflammation of the eye (including uveitis).

In one example, the condition is cardiovascular disease.

In one example, the Fn14-mediated condition is selected from graft versus host disease, cardiac allograft vasculopathy, intramyocardial infarction, ischemic reperfusion injury, connective tissue disease (such as rheumatoid arthritis) or scleroderma.

As exemplified herein, the inventors have demonstrated that an Fn14-binding protein disclosed herein is useful for reducing or preventing invasiveness of a cancer into tissue of a subject. Such invasiveness is a component of cancer progression or metastasis. Accordingly, in one example, the Fn14-mediated condition is invasiveness of a cancer into tissue.

In one example, the Fn14-binding protein binds to recombinant human Fn14 with a $K_D$ of 1 nM or less, such as, 0.9 nM or less, for example, 0.8 nM or less, for example, 0.7 nM or less, for example, 0.6 nM or less. In one example, the $K_D$ is assessed by immobilizing the Fn14-binding protein (e.g., a Fab or an antibody) and assessing binding of human recombinant Fn14 to the immobilized Fn14-binding protein using surface plasmon resonance.

In one example, the $K_D$ is between about 0.01 nM and 1 nM, such as between about 0.05 nM and 0.9 nM, for example, between about 0.09 nM and 0.7 nM, for example, between about 0.1 nM and 0.6 nM.

An exemplary Fn14-binding protein of the disclosure has a $K_D$ of about 0.5 nM (e.g., +/−0.1 nM) for recombinant human Fn14. For example, the Fn14-binding protein is CRCBT-06-001 or an antibody comprising the antigen binding domain, variable regions or CDRs thereof.

Another exemplary Fn14-binding protein of the disclosure has a $K_D$ of about 0.2 nM (e.g., +/−0.1 nM) for recombinant human Fn14. For example, the Fn-14 binding protein is CRCBT-06-002 or an antibody comprising the antigen binding domain, variable regions or CDRs thereof.

In one example, the Fn14-binding protein binds to an extracellular domain of Fn14 comprising a proline or alanine substituted for the arginine at position 56 of SEQ ID NO: 1 at a similar or substantially the same level as it binds to an extracellular domain of Fn14 (e.g., comprising a sequence set forth in SEQ ID NO: 2). For example, the Fn14-binding protein binds to a peptide consisting of the sequence set forth in SEQ ID NO: 52 or 54 optionally additionally comprising six histidine residues at a terminus at a similar or substantially the same level as it binds to an extracellular domain of Fn14 (e.g., comprising a sequence set forth in SEQ ID NO: 2). In one example, the level of binding is assessed by immobilizing the peptide and contacting the peptide with the Fn14-binding protein. Exemplary Fn14-binding proteins described herein having such binding characteristics comprise the variable regions and/or CDRs of an antibody designated CRCBT-06-001, CRCBT-06-002 or CRCBT-06-005. Thus, in one example, the Fn14-binding protein binds to a peptide consisting of the sequence set forth in SEQ ID NO: 52 or 54 (optionally with an additional six histidine residues at a terminus) at a similar or substantially the same level or with a similar or substantially the same affinity as an antibody designated CRCBT-06-001 or CRCBT-06-002 or CRCBT-06-005. In another example, the Fn14-binding protein competitively inhibits binding of an antibody designated CRCBT-06-001 or CRCBT-06-002 or CRCBT-06-005 to a peptide consisting of the sequence set forth in SEQ ID NO: 52 or 54 (optionally with an additional six histidine residues at a terminus).

In one example, the Fn14-binding protein binds to an extracellular domain of Fn14 comprising an alanine substituted for the arginine at position 58 of SEQ ID NO: 1 at a similar or substantially the same level as it binds to an extracellular domain of Fn14 (e.g., comprising a sequence set forth in SEQ ID NO: 2). For example, the Fn14-binding protein binds to a peptide consisting of the sequence set forth in SEQ ID NO: 56 optionally additionally comprising six histidine residues at a terminus at a similar or substantially the same level as it binds to an extracellular domain of Fn14 (e.g., comprising a sequence set forth in SEQ ID NO: 2). In one example, the level of binding is assessed by immobilizing the peptide and contacting the peptide with the Fn14-binding protein or by expressing the peptide on the surface of a phage and contacting the phage to an immobilized Fn14 binding protein. Exemplary Fn14-binding proteins described herein having such binding characteristics comprise the variable regions and/or CDRs of an antibody designated CRCBT-06-001, CRCBT-06-002 or CRCBT-06-005. Thus, in one example, the Fn14-binding protein binds to a peptide consisting of the sequence set forth in SEQ ID NO: 56 (optionally with an additional six histidine residues at a terminus) at a similar or substantially the same level or with a similar or substantially the same affinity as an antibody designated CRCBT-06-001 or CRCBT-06-002 or CRCBT-06-005. In another example, the Fn14-binding protein competitively inhibits binding of an antibody designated CRCBT-06-001 or CRCBT-06-002 or CRCBT-06-005 to a peptide consisting of the sequence set forth in SEQ ID NO: 56 (optionally with an additional six histidine residues at a terminus).

In one example, the Fn14-binding protein binds to an extracellular domain of Fn14 comprising an alanine substituted for the histidine at position 60 of SEQ ID NO: 1 at a similar or substantially the same level as it binds to an extracellular domain of Fn14 (e.g., comprising a sequence set forth in SEQ ID NO: 2). For example, the Fn14-binding protein binds to a peptide consisting of the sequence set forth in SEQ ID NO: 63 optionally additionally comprising six histidine residues at a terminus at a similar or substantially the same level as it binds to an extracellular domain of Fn14 (e.g., comprising a sequence set forth in SEQ ID NO: 2). In one example, the level of binding is assessed by immobilizing the peptide and contacting the peptide with the Fn14-binding protein. Exemplary Fn14-binding proteins described herein having such binding characteristics comprise the variable regions and/or CDRs of an antibody designated CRCBT-06-001 or CRCBT-06-002. Thus, in one example, the Fn14-binding protein binds to a peptide consisting of the sequence set forth in SEQ ID NO: 63 (optionally with an additional six histidine residues at a terminus) at a similar or substantially the same level or with a similar or substantially the same affinity as an antibody designated CRCBT-06-001 or CRCBT-06-002. In another example, the Fn14-binding protein competitively inhibits binding of an antibody designated CRCBT-06-001 or CRCBT-06-002 to a peptide consisting of the sequence set forth in SEQ ID NO: 63 (optionally with an additional six histidine residues at a terminus).

In one example, the method comprises administering an antibody comprising one or more of the following:

(i) a $V_H$ comprising a sequence set forth in SEQ ID NO: 15 or a humanized or deimmunized version thereof and a $V_L$ comprising a sequence set forth in SEQ ID NO: 22 or a humanized or deimmunized version thereof; or (ii) a $V_H$ comprising a sequence set forth in SEQ ID NO: 16 or a humanized or deimmunized version thereof and a $V_L$ comprising a sequence set forth in SEQ ID NO: 23 or a humanized or deimmunized version thereof.

In one example, the method reduces invasiveness of a tumor into a tissue surrounding the tumor. In one example, the method reduces invasiveness of a tumor into skeletal muscle.

Given the ability of the Fn14-binding protein to reduce tissue invasion, it is also useful for reducing or preventing tumor metastasis. Thus, the present disclosure additionally provides a method for preventing metastasis or reducing the risk of metastasis in a subject suffering from cancer, the method comprising administering the Fn14-binding protein or the antibody or the nucleic acid or the expression construct or the cell or the composition of the present disclosure to the subject.

As exemplified herein, the inventors have demonstrated that an Fn14-binding protein disclosed herein is useful for treating a cancer (e.g., colon cancer) in a subject.

In one example, the Fn14-binding protein binds to recombinant human Fn14 with a $K_D$ of 0.4 nm, such as, 0.3 nM or less, for example, 0.25 nM or less. In one example, the $K_D$ is assessed by immobilizing the Fn14-binding protein (e.g., a Fab or an antibody) and assessing binding of human recombinant Fn14 to the immobilized Fn14-binding protein using surface plasmon resonance.

In one example, the $K_D$ is between about 0.01 nM and 0.3 nM, such as between about 0.05 nM and 0.25 nM.

Another exemplary Fn14-binding protein of the disclosure has a $K_D$ of about 0.2 nM (e.g., +/−0.1 nM) for recombinant human Fn14. For example, the Fn-14 binding protein is CRCBT-06-002 or an antibody comprising the antigen binding domain, variable regions or CDRs thereof.

In one example, the Fn14-binding protein binds to an extracellular domain of Fn14 comprising a proline or alanine substituted for the arginine at position 56 of SEQ ID NO: 1 at a similar or substantially the same level as it binds to an extracellular domain of Fn14 (e.g., comprising a sequence set forth in SEQ ID NO: 2). For example, the Fn14-binding protein binds to a peptide consisting of the sequence set forth in SEQ ID NO: 52 or 54 optionally additionally comprising six histidine residues at a terminus at a similar or substantially the same level as it binds to an extracellular domain of Fn14 (e.g., comprising a sequence set forth in SEQ ID NO: 2). In one example, the level of binding is assessed by immobilizing the peptide and contacting the peptide with the Fn14-binding protein. Exemplary Fn14-binding proteins described herein having such binding characteristics comprise the variable regions and/or CDRs of an antibody designated CRCBT-06-001, CRCBT-06-002 or CRCBT-06-005. Thus, in one example, the Fn14-binding protein binds to a peptide consisting of the sequence set forth in SEQ ID NO: 52 or 54 (optionally with an additional six histidine residues at a terminus) at a similar or substantially the same level or with a similar or substantially the same affinity as an antibody designated CRCBT-06-001 or CRCBT-06-002 or CRCBT-06-005. In another example, the Fn14-binding protein competitively inhibits binding of an antibody designated CRCBT-06-001 or CRCBT-06-002 or CRCBT-06-005 to a peptide consisting of the sequence set forth in SEQ ID NO: 52 or 54 (optionally with an additional six histidine residues at a terminus).

In one example, the Fn14-binding protein binds to an extracellular domain of Fn14 comprising an alanine substituted for the arginine at position 58 of SEQ ID NO: 1 at a similar or substantially the same level as it binds to an extracellular domain of Fn14 (e.g., comprising a sequence set forth in SEQ ID NO: 2). For example, the Fn14-binding protein binds to a peptide consisting of the sequence set forth in SEQ ID NO: 56 optionally additionally comprising six histidine residues at a terminus at a similar or substantially the same level as it binds to an extracellular domain of Fn14 (e.g., comprising a sequence set forth in SEQ ID NO: 2). In one example, the level of binding is assessed by immobilizing the peptide and contacting the peptide with the Fn14-binding protein or by expressing the peptide on the surface of a phage and contacting the phage to an immobilized Fn14 binding protein. Exemplary Fn14-binding proteins described herein having such binding characteristics comprise the variable regions and/or CDRs of an antibody designated CRCBT-06-001, CRCBT-06-002 or CRCBT-06-005. Thus, in one example, the Fn14-binding protein binds to a peptide consisting of the sequence set forth in SEQ ID NO: 56 (optionally with an additional six histidine residues at a terminus) at a similar or substantially the same level or with a similar or substantially the same affinity as an antibody designated CRCBT-06-001 or CRCBT-06-002 or CRCBT-06-005. In another example, the Fn14-binding protein competitively inhibits binding of an antibody designated CRCBT-06-001 or CRCBT-06-002 or CRCBT-06-005 to a peptide consisting of the sequence set forth in SEQ ID NO: 56 (optionally with an additional six histidine residues at a terminus).

In one example, the Fn14-binding protein binds to an extracellular domain of Fn14 comprising an alanine substituted for the histidine at position 60 of SEQ ID NO: 1 at a similar or substantially the same level as it binds to an extracellular domain of Fn14 (e.g., comprising a sequence set forth in SEQ ID NO: 2). For example, the Fn14-binding protein binds to a peptide consisting of the sequence set forth in SEQ ID NO: 63 optionally additionally comprising six histidine residues at a terminus at a similar or substantially the same level as it binds to an extracellular domain of Fn14 (e.g., comprising a sequence set forth in SEQ ID NO: 2). In one example, the level of binding is assessed by immobilizing the peptide and contacting the peptide with the Fn14-binding protein. Exemplary Fn14-binding proteins described herein having such binding characteristics comprise the variable regions and/or CDRs of an antibody designated CRCBT-06-001 or CRCBT-06-002. Thus, in one example, the Fn14-binding protein binds to a peptide consisting of the sequence set forth in SEQ ID NO: 63 (optionally with an additional six histidine residues at a terminus) at a similar or substantially the same level or with a similar or substantially the same affinity as an antibody designated CRCBT-06-001 or CRCBT-06-002. In another example, the Fn14-binding protein competitively inhibits binding of an antibody designated CRCBT-06-001 or CRCBT-06-002 to a peptide consisting of the sequence set forth in SEQ ID NO: 63 (optionally with an additional six histidine residues at a terminus).

In one example, the method comprises administering an antibody comprising one or more of the following:

(i) a $V_H$ comprising a sequence set forth in SEQ ID NO: 15 or a humanized or deimmunized version thereof and a $V_L$ comprising a sequence set forth in SEQ ID NO: 22 or a humanized or deimmunized version thereof; or (ii) a $V_H$ comprising a sequence set forth in SEQ ID NO: 16 or a humanized or deimmunized version thereof and a $V_L$ comprising a sequence set forth in SEQ ID NO: 23 or a humanized or deimmunized version thereof.

The present disclosure additionally provides the Fn14-binding protein or the antibody or the nucleic acid or the expression construct or the cell or the composition of the present disclosure for use in medicine.

The present disclosure additionally provides the Fn14-binding protein or the antibody or the nucleic acid or the expression construct or the cell or the composition of the present disclosure for use in the treatment or prophylaxis of an Fn14-mediated condition. In one example, the Fn14-mediated condition is cancer metastasis or tumor invasiveness.

The present disclosure additionally provides for use of the Fn14-binding protein or the antibody or the nucleic acid or the expression construct or the cell or the composition of the present disclosure in medicine.

The present disclosure additionally provides for use of the Fn14-binding protein or the antibody or the nucleic acid or the expression construct or the cell of the present disclosure in the manufacture of a medicament for the treatment or prophylaxis of an Fn14-mediated condition. In one example, the Fn14-mediated condition is cancer metastasis or tumor invasiveness.

The present disclosure additionally provides a method for detecting Fn14 in a sample, the method comprising contacting a sample with the Fn14-binding protein or antibody of the disclosure such that an antigen-protein complex forms and detecting the complex, wherein detecting the complex is indicative of Fn14 in the sample. In one example, the sample is from a subject suffering from a Fn14-mediated condition.

The present disclosure additionally provides a method for diagnosing an Fn14-mediated condition in a subject, the method comprising performing the method described herein for detecting Fn14 in a sample from the subject, wherein detection of Fn14 in the sample is indicative of the condition.

In one example, the method comprises determining the level of Fn14 in the sample, wherein an increased or decreased level of Fn14 in the sample compared to a control sample is indicative of the condition.

The present disclosure additionally provides a method for localizing and/or detecting and/or diagnosing and/or prognosing an Fn14-mediated condition, the method comprising detecting in vivo the Fn14-binding protein or antibody of the present disclosure bound to Fn14, if present, wherein the Fn14-binding protein or antibody is conjugated to a detectable tag.

In one example, the method additionally comprises administering the binding molecule to the subject.

In one example of any method of treatment/prophylaxis/diagnosis/prognosis described herein the Fn14-mediated condition is cancer, metastasis, excessive vascularization or angiogenesis, an autoimmune disease, an inflammatory disease, a neurodegenerative diseases, a wasting disorder or ischemia.

As discussed herein, the present inventors have also determined that they can treat or prevent a wasting disorder associated with a condition using an Fn14-binding protein that binds to Fn14. Accordingly, the present disclosure additionally provides a method of treating or preventing a wasting disorder which is associated with a condition, the method comprising administering to a subject an Fn14-binding protein comprising an antigen binding domain of an anti-Fn14 antibody.

In one example, the wasting disorder is selected from the group consisting of unintended body weight loss, cachexia, pre-cachexia, muscle wasting and fat wasting. For example, the wasting disorder is cachexia.

In one example, the wasting disorder is associated with a condition selected from the group consisting of cancer, metabolic acidosis, infectious diseases, diabetes, autoimmune immune deficiency syndrome (AIDS), autoimmune disorders, addiction to drugs, cirrhosis of the liver, chronic inflammatory disorders, anorexia, chronic heart failure, chronic kidney disease, osteoporosis, skeletal muscle disease, motor neuron disease, multiple sclerosis, muscle atrophy and neurodegenerative disease.

In one example, the wasting disorder is cachexia, pre-cachexia or sarcopenia (e.g., muscle wasting associated with aging).

In one example, the wasting disorder is cachexia.

In one example, the cachexia is associated with cancer, infectious disease (e.g., tuberculosis or leprosy), AIDS, autoimmune disease (including rheumatoid arthritis or type 1 diabetes), cystic fibrosis, drug addiction, alcoholism or liver cirrhosis.

In one example, the cachexia is associated with a condition selected from rheumatoid arthritis, diabetes, cardiac disease, chronic kidney disease, chronic pulmonary inflammation, intestinal inflammation, inflammatory bowel disease, age, sepsis or AIDS.

In one exemplary form of the present disclosure the wasting disorder is cachexia associated with cancer. Numerous types of cancer are associated with cachexia, including solid tumors, carcinoma, neuroma, melanoma, leukemia, lymphoma, sarcoma, fibroma, thyroid cancer, bladder cancer, lung cancer, blastoma, bone cancer, bone tumor, brain stem glioma, brain tumor, breast cancer, bronchial tumor, cervical cancer, colon cancer, colorectal cancer, neuroepithelial tumor, endometrial cancer, endometrial uterine cancer, fallopian tube cancer, kidney cancer, oral cancer, myeloma, neoplasm, neurinoma, neuroblastoma, ovarian cancer, pancreatic cancer, prostate cancer, rectal cancer or renal cell carcinoma. Additional cancers are described herein.

In one exemplary form of the present disclosure the wasting disorder is cachexia associated with diabetes.

As discussed herein, the inventors have also determined that they can treat a wasting disorder, e.g., muscle wasting (such as cachexia) by contacting Fn14 on a tissue affected by the condition associated with the wasting disorder. For example, the inventors have found that by contacting Fn14 on a cancer they can treat muscle wasting. Thus, in some examples, the method of the disclosure comprises administering an amount of the Fn14-binding protein effective to bind to Fn14 in a tissue affected by the condition associated with the wasting disease, wherein the tissue is not muscle tissue. In the case of cachexia associated with cancer, the method comprises administering an amount of the Fn14-binding protein effective to bind to Fn14 on the cancer cells.

In some examples, the method of the disclosure comprises administering an Fn14-binding protein for a time and under conditions effective to bind to Fn14 in a tissue affected by the condition associated with the wasting disease, wherein the tissue is not muscle tissue. In the case of cachexia associated with cancer, the method comprises administering an Fn14-binding protein for a time and under conditions effective to bind to Fn14 on the cancer cells.

In one example, the method comprises administering the Fn14-binding protein to a subject suffering from a condition associated with a wasting disorder, wherein the condition is associated with or caused by a cell expressing Fn14. For example, the method comprises administering the Fn14-binding protein to a subject suffering from cancer cachexia, wherein the subject suffers from a cancer expressing Fn14.

In one example, the method additionally comprises selecting a subject suffering from a wasting disorder associated with a condition associated with or caused by a cell expressing Fn14. For example, the method additionally comprises selecting a subject suffering from cancer cachexia, wherein the subject suffers from a cancer expressing Fn14.

In one example, the Fn14-binding protein modulates Tweak-mediated Fn14 signaling.

For example, the inventors have shown that antibodies that antagonize Tweak-mediated NFκB signaling are useful in the methods of the disclosure. In one example, the Fn14-binding protein is the Fn14-binding protein or antibody of the present disclosure.

The inventors have also shown that antibodies that antagonize or agonize Tweak-mediated IL-8 secretion are useful in the methods of the disclosure. The inventors have shown antibodies having a slow off-rate or high affinity dissociation constant are useful in the methods of the disclosure. Such antibodies are shown herein to provide a superior effect compared to other anti-Fn4 antibodies.

For example, the Fn14-binding protein binds to recombinant human Fn14 with a $K_D$ of 1 nM or less, such as, 0.9 nM or less, for example, 0.8 nM or less, for example, 0.7 nM or less, for example, 0.6 nM or less. In one example, the $K_D$ is assessed by immobilizing the Fn14-binding protein (e.g., a Fab or an antibody) and assessing binding of human recombinant Fn14 to the immobilized Fn14-binding protein using surface plasmon resonance. Additional exemplary $K_D$ values are described herein and are to be taken to apply mutatis mutandis to this example of the disclosure.

In another example, the Fn14-binding protein binds to recombinant human Fn14 with a Kd of about $8\times10^{-4}$ $s^{-1}$ or less, such as, $5\times10^{-4}$ $s^{-1}$ or less, for example, $4\times10^{-4}$ $s^{-1}$ or less, for example, $2\times10^{-4}$ $s^{-1}$ or less. In one example, the Kd is assessed by immobilizing the Fn14-binding protein (e.g., a Fab or an antibody) and assessing binding of recombinant human Fn14 to the immobilized Fn14-binding protein using surface plasmon resonance. Additional exemplary Kd values are described herein and are to be taken to apply mutatis mutandis to this example of the disclosure.

In one example, the Fn14-binding protein binds to an extracellular domain of Fn14 comprising a proline or alanine substituted for the arginine at position 56 of SEQ ID NO: 1 at a similar or substantially the same level as it binds to an extracellular domain of Fn14 (e.g., comprising a sequence set forth in SEQ ID NO: 2). For example, the Fn14-binding protein binds to a peptide consisting of the sequence set forth in SEQ ID NO: 52 or 54 optionally additionally comprising six histidine residues at a terminus at a similar or substantially the same level as it binds to an extracellular domain of Fn14 (e.g., comprising a sequence set forth in SEQ ID NO: 2). In one example, the level of binding is assessed by immobilizing the peptide and contacting the peptide with the Fn14-binding protein. Exemplary Fn14-binding proteins described herein having such binding characteristics comprise the variable regions and/or CDRs of an antibody designated CRCBT-06-001, CRCBT-06-002 or CRCBT-06-005. Thus, in one example, the Fn14-binding protein binds to a peptide consisting of the sequence set forth in SEQ ID NO: 52 or 54 (optionally with an additional six histidine residues at a terminus) at a similar or substantially the same level or with a similar or substantially the same affinity as an antibody designated CRCBT-06-001 or CRCBT-06-002 or CRCBT-06-005. In another example, the Fn14-binding protein competitively inhibits binding of an antibody designated CRCBT-06-001 or CRCBT-06-002 or CRCBT-06-005 to a peptide consisting of the sequence set forth in SEQ ID NO: 52 or 54 (optionally with an additional six histidine residues at a terminus).

In one example, the Fn14-binding protein binds to an extracellular domain of Fn14 comprising an alanine substituted for the arginine at position 58 of SEQ ID NO: 1 at a similar or substantially the same level as it binds to an extracellular domain of Fn14 (e.g., comprising a sequence set forth in SEQ ID NO: 2). For example, the Fn14-binding protein binds to a peptide consisting of the sequence set forth in SEQ ID NO: 56 optionally additionally comprising six histidine residues at a terminus at a similar or substantially the same level as it binds to an extracellular domain of Fn14 (e.g., comprising a sequence set forth in SEQ ID NO: 2). In one example, the level of binding is assessed by immobilizing the peptide and contacting the peptide with the Fn14-binding protein or by expressing the peptide on the surface of a phage and contacting the phage to an immobilized Fn14 binding protein. Exemplary Fn14-binding proteins described herein having such binding characteristics comprise the variable regions and/or CDRs of an antibody designated CRCBT-06-001, CRCBT-06-002 or CRCBT-06-005. Thus, in one example, the Fn14-binding protein binds to a peptide consisting of the sequence set forth in SEQ ID NO: 56 (optionally with an additional six histidine residues at a terminus) at a similar or substantially the same level or with a similar or substantially the same affinity as an antibody designated CRCBT-06-001 or CRCBT-06-002 or CRCBT-06-005. In another example, the Fn14-binding protein competitively inhibits binding of an antibody designated CRCBT-06-001 or CRCBT-06-002 or CRCBT-06-005 to a peptide consisting of the sequence set forth in SEQ ID NO: 56 (optionally with an additional six histidine residues at a terminus).

In one example, the Fn14-binding protein binds to an extracellular domain of Fn14 comprising an alanine substituted for the histidine at position 60 of SEQ ID NO: 1 at a similar or substantially the same level as it binds to an extracellular domain of Fn14 (e.g., comprising a sequence set forth in SEQ ID NO: 2). For example, the Fn14-binding protein binds to a peptide consisting of the sequence set forth in SEQ ID NO: 63 optionally additionally comprising six histidine residues at a terminus at a similar or substantially the same level as it binds to an extracellular domain of Fn14 (e.g., comprising a sequence set forth in SEQ ID NO: 2). In one example, the level of binding is assessed by immobilizing the peptide and contacting the peptide with the Fn14-binding protein. Exemplary Fn14-binding proteins described herein having such binding characteristics comprise the variable regions and/or CDRs of an antibody designated CRCBT-06-001 or CRCBT-06-002. Thus, in one example, the Fn14-binding protein binds to a peptide consisting of the sequence set forth in SEQ ID NO: 63 (optionally with an additional six histidine residues at a terminus) at a similar or substantially the same level or with a similar or substantially the same affinity as an antibody designated CRCBT-06-001 or CRCBT-06-002. In another example, the Fn14-binding protein competitively inhibits binding of an antibody designated CRCBT-06-001 or CRCBT-06-002 to a peptide consisting of the sequence set forth in SEQ ID NO: 63 (optionally with an additional six histidine residues at a terminus).

In one example, the Fn14-binding protein is an antibody comprising one or more of the following:

(i) a $V_H$ comprising a sequence set forth in SEQ ID NO: 15 or a humanized, synhumanized or deimmunized version thereof and a $V_L$ comprising a sequence set forth in SEQ ID NO: 22 or a humanized, synhumanized or deimmunized version thereof; or (ii) a $V_H$ comprising a sequence set forth in SEQ ID NO: 16 or a humanized, synhumanized or deimmunized version thereof and a $V_L$ comprising a sequence set forth in SEQ ID NO: 23 or a humanized, synhumanized or deimmunized version thereof.

In one example, the Fn14-binding protein is an antibody comprising a $V_H$ comprising a sequence set forth in SEQ ID NO: 15 or a humanized, synhumanized or deimmunized version thereof and a $V_L$ comprising a sequence set forth in SEQ ID NO: 22 or a humanized, synhumanized or deimmunized version thereof.

In one example, the Fn14-binding protein is an antibody comprising a $V_H$ comprising a sequence set forth in SEQ ID NO: 16 or a humanized, synhumanized or deimmunized version thereof and a $V_L$ comprising a sequence set forth in SEQ ID NO: 23 or a humanized, synhumanized or deimmunized version thereof.

In one example, the subject's body weight and/or general health increases within at least one week of administration of the Fn14-binding protein.

In one example, the subject's body weight and/or general health increases within at least one or two or three or four or five or six days of administration of the Fn14-binding protein.

In one example, the subject's body weight and/or general health increases within at least one or two or three or four or five or six weeks of administration of the Fn14-binding protein.

In another example, the subject to who the Fn14-binding protein is administered loses less body weight than a subject suffering from the wasting disorder to who the Fn14-binding protein is not administered.

In a further example, the subject's body weight remains detectably increased for at least 7 days after administration of the Fn14-binding protein.

In a still further example, the subject's body weight is not reduced to a level significantly below the weight prior to administration of the Fn14-binding protein at least about 7 days after administration of the Fn14-binding protein.

In another example, administration of the Fn14-binding protein extends the life of the subject compared to a subject or a population of subjects suffering from the wasting disorder to who the Fn14-binding protein has not been administered. In this regard, when comparing to a population of subjects, the extension of life may be compared to the mean or the median term of life for the population.

In one example, administration of the Fn14-binding protein significantly extends the life of the subject or a population of subjects to who it is administered compared to a subject or a population of subjects suffering from the wasting disorder to who the Fn14-binding protein has not been administered.

In one example, administration of the Fn14-binding protein extends the life of the subject to who it is administered for a time sufficient to permit one or more additional treatments of the disorder associated with the wasting compared to a subject or a population of subjects suffering from the wasting disorder to who the Fn14-binding protein has not been administered.

In one example, the subject's life is extended by at least about 1 month or 6 months or 24 months.

In one example, the subject's life is extended while the subject is receiving treatment as described herein.

In another example, the subject's life is extended by 1% or 5% or 10% or 20% or 40% of the term of life of a subject or a population of subjects suffering from the wasting disorder to who the Fn14-binding protein has not been administered.

In one example, the Fn14-binding protein is administered at a dose between 0.5 mg/kg to about 20 mg/kg. For example, the Fn14-binding protein is administered at a dose between 1 mg/kg and 15 mg/kg, such as between 2 mg/kg and 10 mg/kg.

In one example, the Fn14-binding protein is administered at a dose of at least about 2 mg/kg. For example, the Fn14-binding protein is administered at a dose of at least about 3 mg/kg or 4 mg/kg or 5 mg/kg or 6 mg/kg or 7 mg/kg or 8 mg/kg or 9 mg/kg or 10 mg/kg. In one example, the Fn14-binding protein is administered at a dose between 2 mg/kg and 20 mg/kg, such as, between 3 mg/kg and 15 mg/kg, for example, between 5 mg/kg and 10 mg/kg, inclusive. In one example the Fn14-binding protein is administered at a dose of about 5 mg/kg. In another example, the Fn14-binding protein is administered at a dose of about 10 mg/kg.

In one example, the Fn14-binding protein is administered in multiple doses.

For example, the Fn14-binding protein is administered twice weekly for at least two weeks or three weeks or four weeks.

In another example, the Fn14-binding protein is administered in multiple doses each separated by at least about 7 days or 14 days or 21 days or 28 days or one calendar month.

In a further example, the Fn14-binding protein is administered at a loading dose and at a maintenance dose. For example, the loading dose is between about 0.5 mg/kg and 2 mg/kg (such as between 0.5 mg/kg and 1 mg/kg) and the maintenance dose of about 2 mg/kg to about 20 mg/kg (such as between about 3 mg/kg and about 15 mg/kg, for example, between about 5 mg/kg and 10 mg/kg, inclusive). In one example, the loading dose is a dose of about 0.5 mg/kg or 1 mg/kg and the maintenance dose is about 5 mg/kg or 10 mg/kg. This dosing regime is also called a stepped-up dosing regime.

In one example, the maintenance dose is administered about 5 days or 6 days or 7 days or 8 days after administration of the loading dose. For example, the maintenance dose is administered about 7 days after administration of the loading dose In one example, the method of treatment further comprises measuring the subject's body weight prior to administering the Fn14-binding protein, and administering the Fn14-binding protein if the subject's weight has declined by greater than about 5% within about 30 days.

In another example, the method further comprises measuring the subject's body weight prior to administering a dose of the Fn14-binding protein, and administering the Fn14-binding protein if the subject's weight has declined by greater than approximately 1% since administration of a previous dose of the Fn14-binding protein.

In a still further example, the method further comprises assessing the subject's cachexia. For example, the subject's cachexia is assessed by measuring the subject's total body mass, lean body mass and/or body mass index. In one example, measurement of the subject's total body mass, lean body mass and/or body mass index does not include the estimated weight of the subject's tumor(s) and/or extravascular fluid collection(s).

In one example, the method additionally comprises treating the disorder associated with the wasting disorder.

In one example, the method additionally comprises treating cancer, e.g., a cancer associated with cachexia. For example, the treatment comprises administration of an anticancer drug or radiation therapy.

In one example, treatment for the cancer or disorder associated with the wasting disorder is performed or administered at the same time or after administering the Fn14-binding protein. For example, the Fn14-binding protein is administered at least once and the subject's weight permitted to increase prior to performing or administering the treatment for cancer or disorder associated with the wasting disorder.

The present disclosure also provides an Fn14-binding protein comprising an antigen binding domain of an anti-Fn14 antibody for use in treating or preventing a wasting disorder which is associated with a condition.

The present disclosure also provides for use of an Fn14-binding protein comprising an antigen binding domain of an anti-Fn14 antibody in the manufacture of a medicament for treating or preventing a wasting disorder which is associated with a condition.

The present inventors have shown that an Fn14-binding protein disclosed herein is useful for reducing or preventing invasiveness of a tumor into muscle of a subject. Accordingly, one specific example of the present disclosure provides a method for reducing or preventing tumor invasion into muscle of a subject suffering from cancer, the method comprising administering to the subject an Fn14-binding protein comprising an antigen binding domain of an anti-Fn14 antibody, wherein the Fn14-binding protein neutralizes a Tweak activity in a cell expressing Fn14.

In one example, the Fn14-binding protein reduces Tweak-induced NFκB-signaling in a cell expressing Fn14.

In one example, the Fn14-binding protein reduces Tweak-induced NFκB-signaling in a cell expressing Fn14, and wherein the Fn14-binding protein does not detectably induce NFκB-signaling when contacted to a cell expressing Fn14 in the absence of Tweak.

In one example, the method comprises administering the Fn14-binding protein or antibody of the present disclosure. In one example, the method comprises administering an antibody comprising one or more of the following:

(i) a $V_H$ comprising a sequence set forth in SEQ ID NO: 15 or a humanized or deimmunized version thereof and a $V_L$ comprising a sequence set forth in SEQ ID NO: 22 or a humanized, synhumanized or deimmunized version thereof; or (ii) a $V_H$ comprising a sequence set forth in SEQ ID NO: 16 or a humanized or deimmunized version thereof and a $V_L$ comprising a sequence set forth in SEQ ID NO: 23 or a humanized, synhumanized or deimmunized version thereof.

In one example, the method reduces invasiveness of a tumor into a tissue surrounding the tumor. In one example, the method reduces invasiveness of a tumor into skeletal muscle.

In one example, the Fn14-binding protein is administered at the same time as or prior to treatment for the tumor. Such treatment is useful for reducing metastases that can be induced or associated with treatment of tumor.

The present disclosure also provides an Fn14-binding protein comprising an antigen binding domain of an anti-Fn14 antibody for use in treating or preventing tumor invasion into a muscle.

The present disclosure also provides for use of an Fn14-binding protein comprising an antigen binding domain of an anti-Fn14 antibody in the manufacture of a medicament for treating or preventing tumor invasion into a muscle.

The inventors have also shown that antibodies that antagonize Tweak-mediated NFκB signaling are useful in treating or preventing a glucose-metabolism disorder, such as diabetes, e.g., Type 1 diabetes. In one example, the Fn14-binding protein is the Fn14-binding protein or antibody of the present disclosure.

The inventors have also shown that antibodies that antagonize or agonize Tweak-mediated IL-8 secretion are useful in the methods of the disclosure. The inventors have shown antibodies having a slow off-rate or high affinity dissociation constant are useful in the methods of the disclosure. Such antibodies are shown herein to provide a superior effect compared to other anti-Fn4 antibodies.

For example, the Fn14-binding protein binds to recombinant human Fn14 with a $K_D$ of 1 nM or less, such as, 0.9 nM or less, for example, 0.8 nM or less, for example, 0.7 nM or less, for example, 0.6 nM or less, or 0.3 nM or less or 0.25 nM or less. In one example, the $K_D$ is assessed by immobilizing the Fn14-binding protein (e.g., a Fab or an antibody) and assessing binding of human recombinant Fn14 to the immobilized Fn14-binding protein using surface plasmon resonance. Additional exemplary $K_D$ values are described herein and are to be taken to apply mutatis mutandis to this example of the disclosure.

In one example, the Fn14-binding protein binds to an extracellular domain of Fn14 comprising a proline or alanine substituted for the arginine at position 56 of SEQ ID NO: 1 at a similar or substantially the same level as it binds to an extracellular domain of Fn14 (e.g., comprising a sequence set forth in SEQ ID NO: 2). For example, the Fn14-binding protein binds to a peptide consisting of the sequence set forth in SEQ ID NO: 52 or 54 optionally additionally comprising six histidine residues at a terminus at a similar or substantially the same level as it binds to an extracellular domain of Fn14 (e.g., comprising a sequence set forth in SEQ ID NO: 2). In one example, the level of binding is assessed by immobilizing the peptide and contacting the peptide with the Fn14-binding protein. Exemplary Fn14-binding proteins described herein having such binding characteristics comprise the variable regions and/or CDRs of an antibody designated CRCBT-06-001, CRCBT-06-002 or CRCBT-06-005. Thus, in one example, the Fn14-binding protein binds to a peptide consisting of the sequence set forth in SEQ ID NO: 52 or 54 (optionally with an additional six histidine residues at a terminus) at a similar or substantially the same level or with a similar or substantially the same affinity as an antibody designated CRCBT-06-001 or CRCBT-06-002 or CRCBT-06-005. In another example, the Fn14-binding protein competitively inhibits binding of an antibody designated CRCBT-06-001 or CRCBT-06-002 or CRCBT-06-005 to a peptide consisting of the sequence set forth in SEQ ID NO: 52 or 54 (optionally with an additional six histidine residues at a terminus).

In one example, the Fn14-binding protein binds to an extracellular domain of Fn14 comprising an alanine substituted for the arginine at position 58 of SEQ ID NO: 1 at a similar or substantially the same level as it binds to an extracellular domain of Fn14 (e.g., comprising a sequence set forth in SEQ ID NO: 2). For example, the Fn14-binding protein binds to a peptide consisting of the sequence set forth in SEQ ID NO: 56 optionally additionally comprising six histidine residues at a terminus at a similar or substantially the same level as it binds to an extracellular domain of Fn14 (e.g., comprising a sequence set forth in SEQ ID NO: 2). In one example, the level of binding is assessed by immobilizing the peptide and contacting the peptide with the Fn14-binding protein or by expressing the peptide on the surface of a phage and contacting the phage to an immobilized Fn14 binding protein. Exemplary Fn14-binding proteins described herein having such binding characteristics comprise the variable regions and/or CDRs of an antibody designated CRCBT-06-001, CRCBT-06-002 or CRCBT-06-005. Thus, in one example, the Fn14-binding protein binds to a peptide consisting of the sequence set forth in SEQ ID NO: 56 (optionally with an additional six histidine residues at a terminus) at a similar or substantially the same level or with a similar or substantially the same affinity as an antibody designated CRCBT-06-001 or CRCBT-06-002 or CRCBT-06-005. In another example, the Fn14-binding protein competitively inhibits binding of an antibody designated CRCBT-06-001 or CRCBT-06-002 or CRCBT-06-005 to a peptide consisting of the sequence set forth in SEQ ID NO: 56 (optionally with an additional six histidine residues at a terminus).

In one example, the Fn14-binding protein binds to an extracellular domain of Fn14 comprising an alanine substituted for the histidine at position 60 of SEQ ID NO: 1 at a similar or substantially the same level as it binds to an extracellular domain of Fn14 (e.g., comprising a sequence set forth in SEQ ID NO: 2). For example, the Fn14-binding protein binds to a peptide consisting of the sequence set forth in SEQ ID NO: 63 optionally additionally comprising six histidine residues at a terminus at a similar or substantially the same level as it binds to an extracellular domain of Fn14 (e.g., comprising a sequence set forth in SEQ ID NO: 2). In one example, the level of binding is assessed by immobilizing the peptide and contacting the peptide with the Fn14-binding protein. Exemplary Fn14-binding proteins described herein having such binding characteristics comprise the variable regions and/or CDRs of an antibody designated CRCBT-06-001 or CRCBT-06-002. Thus, in one example, the Fn14-binding protein binds to a peptide consisting of the sequence set forth in SEQ ID NO: 63 (optionally with an additional six histidine residues at a terminus) at a similar or substantially the same level or with a similar or substantially the same affinity as an antibody designated CRCBT-06-001 or CRCBT-06-002. In another example, the Fn14-binding protein competitively inhibits binding of an antibody designated CRCBT-06-001 or CRCBT-06-002 to a peptide consisting of the sequence set forth in SEQ ID NO: 63 (optionally with an additional six histidine residues at a terminus).

In one example, the Fn14-binding protein is an antibody comprising one or more of the following:

(i) a $V_H$ comprising a sequence set forth in SEQ ID NO: 15 or a humanized, synhumanized or deimmunized version thereof and a $V_L$ comprising a sequence set forth in SEQ ID NO: 22 or a humanized, synhumanized or deimmunized version thereof; or (ii) a $V_H$ comprising a sequence set forth in SEQ ID NO: 16 or a humanized, synhumanized or deimmunized version thereof and a $V_L$ comprising a sequence set forth in SEQ ID NO: 23 or a humanized, synhumanized or deimmunized version thereof.

In one example, the Fn14-binding protein is an antibody comprising a $V_H$ comprising a sequence set forth in SEQ ID NO: 15 or a humanized, synhumanized or deimmunized version thereof and a $V_L$ comprising a sequence set forth in SEQ ID NO: 22 or a humanized, synhumanized or deimmunized version thereof.

In one example, the Fn14-binding protein is an antibody comprising a $V_H$ comprising a sequence set forth in SEQ ID NO: 16 or a humanized, synhumanized or deimmunized version thereof and a $V_L$ comprising a sequence set forth in SEQ ID NO: 23 or a humanized, synhumanized or deimmunized version thereof.

The inventors have also produced a model of a wasting disorder, e.g., cancer cachexia. Accordingly, the present disclosure also provides a non-human mammal comprising tumor cells, wherein the tumor cells capable of ectopically expressing recombinant human Fn14, and wherein the non-human mammal develops a wasting disorder. The present disclosure also provides the tumor cells capable of ectopically expressing recombinant human Fn14.

The present disclosure also provides a method for producing a non-human animal model of a wasting disorder, the method comprising administering to a non-human mammal a tumor cell of expressing recombinant human Fn14 under conditions sufficient for the Fn14 to be expressed and for the wasting disorder to develop.

In one example, the Fn14 is inducibly expressed. For example, Fn14 encoding nucleic acid is operably linked to a promoter induced by 4-hydroxytamoxifen.

In one example, the Fn14 is constitutively expressed.

In one example, the tumor cell is a fibroblast cell genetically modified to express v12Hras.

The inventors have also produced a non-signaling form of Fn14 useful as a control in experiments to assess the effect of a compound in a wasting condition, e.g., cancer cachexia. Animals to which tumor cells expressing the non-signaling fusion protein has been administered develop cancer, but do not develop the wasting condition.

In one example, the present disclosure provides a fusion protein comprising the extracellular region of Fn14 and a glycosyl-phosphatidylinositol anchor (GPI) region of a receptor but lacking the cytosolic region of the receptor. For example, the fusion protein does not mediate Tweak signaling when expressed in a cell The present disclosure also provides a recombinant cell expressing a fusion protein comprising an extracellular region of Fn14 and a glycosylphosphatidylinositol anchor (GPI) region of a receptor but lacking the cytosolic region of the receptor, wherein the fusion protein does not mediate Tweak signaling in the cell.

In one example, the extracellular region of Fn14 is the extracellular region of human Fn14.

In one example, the GPI region is from Trail Receptor 3. For example, the fusion protein comprises a sequence set forth in SEQ ID NO: 36 or between residues 28 to 126 of SEQ ID NO: 36.

The present disclosure also provides a method of identifying a compound for the treatment of a wasting disorder, the method comprising:

(i) administering the compound to the non-human mammal model of a wasting disorder described herein and inducing expression of Fn14 (if necessary) and determining the level of the wasting disorder;

(ii) comparing the level of the wasting disorder at (i) to the levels of a wasting disorder in a non-human mammal administered the cell expressing a fusion protein comprising an extracellular region of Fn14 and a glycosylphosphatidylinositol anchor (GPI) region of a receptor but lacking the cytosolic region of the receptor and determining the level of the wasting disorder, wherein a similar level of the wasting disorder at (i) compared to (ii) indicates that the compound is useful for treating a wasting disorder.

The present disclosure also provides a method of identifying a compound for the treatment of a wasting disorder, the method comprising:

(i) administering the compound to the non-human mammal model of a wasting disorder described herein and inducing expression of Fn14 (if necessary) and determining the level of the wasting disorder;

(ii) administering to a non-human mammal the cell expressing a fusion protein comprising an extracellular region of Fn14 and a glycosylphosphatidylinositol anchor (GPI) region and determining the level of the wasting disorder, wherein a similar level of the wasting disorder at (i) compared to (ii) indicates that the compound is useful for treating a wasting disorder.

In one example, the non-human mammal expressing a fusion protein comprising an extracellular region of Fn14 and a glycosylphosphatidylinositol anchor (GPI) region and determining the level of the wasting disorder, is also administered the compound.

In one example, the method additionally comprises isolating or providing the compound or the structure of the compound.

In one example, the compound is an Fn14-binding protein comprising an antigen binding domain of an anti-Fn14 antibody.

Panel A.i. shows the cell population gated on side and forward scatter for analysis of all samples. Panel Aii. shows unstained cells, Panels Aiii. & Aiv. show cells stained with sera from 2 un-immunized mice, Panels Av. & Avi. show sera from 2 mice immunized with a non-related antigen in PBS or adjuvant, respectively. Panel Avii. show anti-hFn14 positive control. Panel B. shows results using serum from mice immunized with cells suspended in PBS or Adjuvant as indicated (mice #1318-1323), with dotted boxes indicating sera from mice displaying a positive immune response to hFn14. All sera samples were used at 1:50 dilution for staining.

Figure 2A:
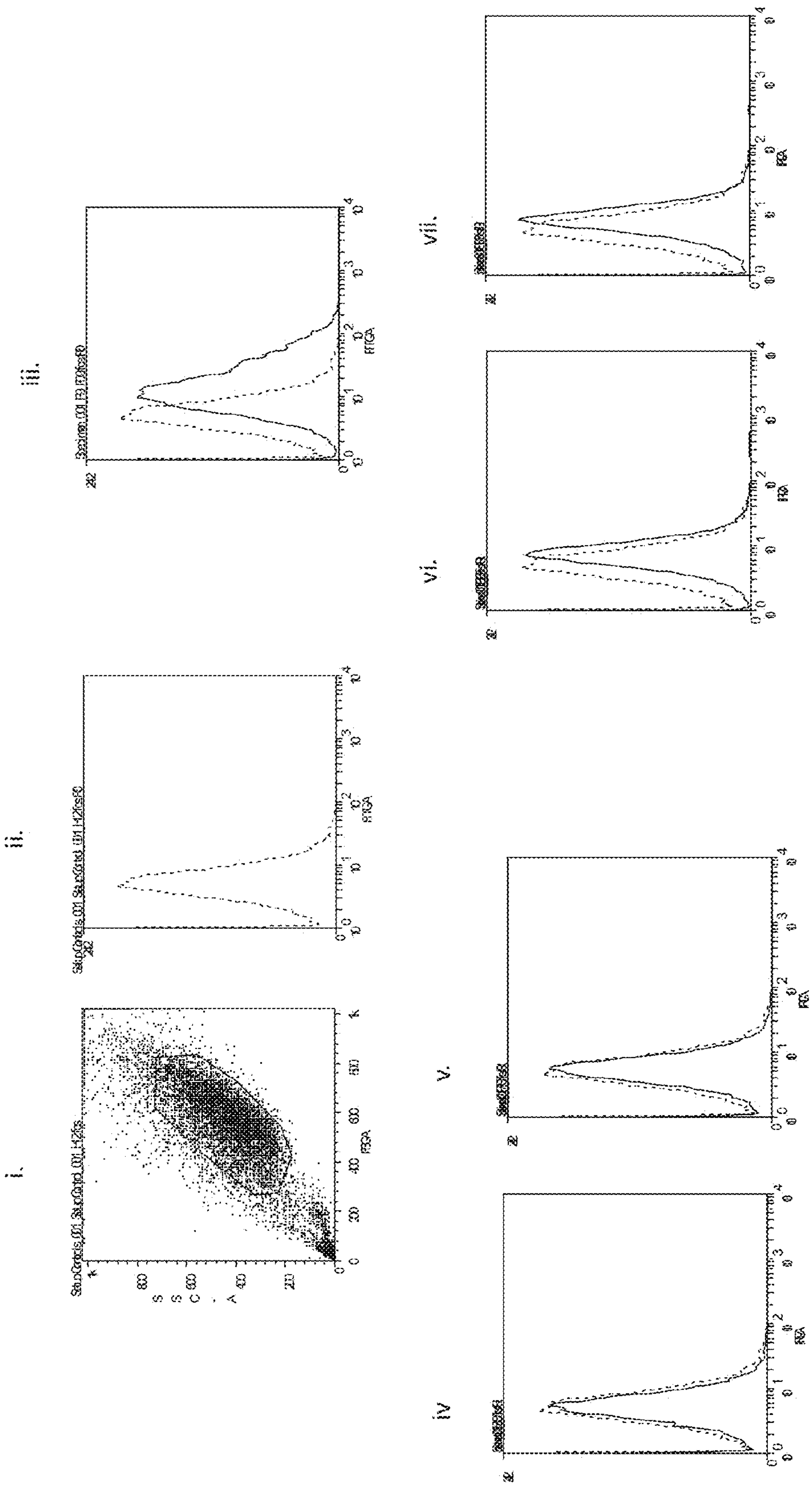
Figure 2B:
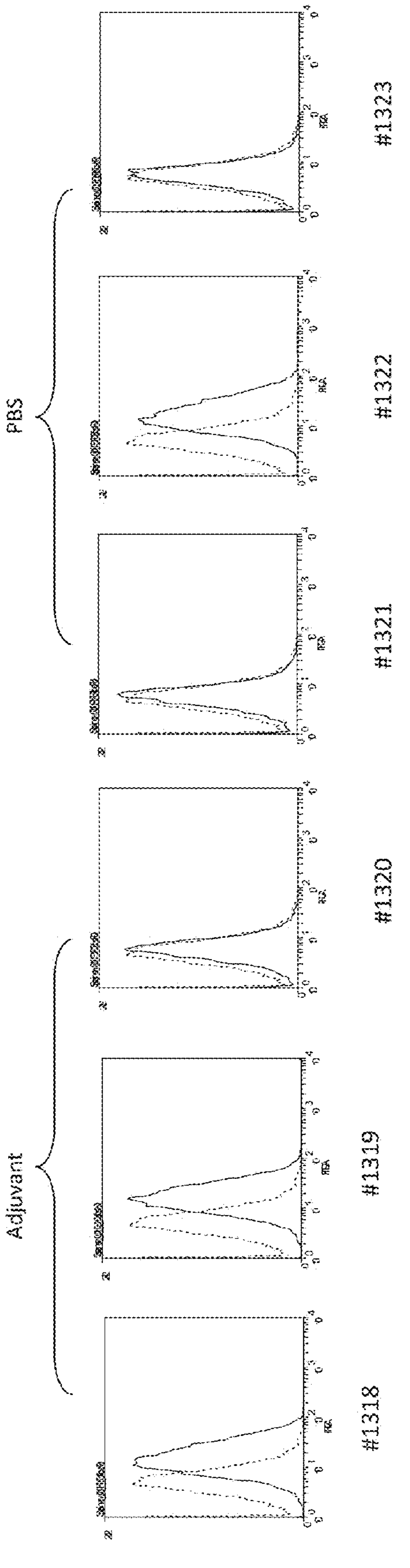

FIGS. 2A to B is a series of graphical representations showing results of screening of sera from mice immunized with recombinant Fn14-Fc on human D645 cells. Panel A shows results of screening using live D645 human glioma cells stained with mouse serum or controls and analyzed by flow cytometry. Dotted histogram traces represent unstained cells and solid traces represent stained cells. Panel A.i. shows a cell population gated for analysis of all samples, Panel ii. shows unstained cells, Panel iii. shows anti-hFn14 positive control. Panels iv. & v. show cells stained with serum from 2 un-immunized mice. Panels vi. & vii. show serum from 2 mice immunized with a non-related antigen in adjuvant or PBS, respectively. Panel B. shows sera from mice immunized with a recombinant protein comprising the extracellular domain of hFn14 in adjuvant or PBS as indicated (mice#1318-1323), with dotted boxes indicating mice with positive immune response. All sera samples were used at 1:50 dilution for staining.

Figure 3A:
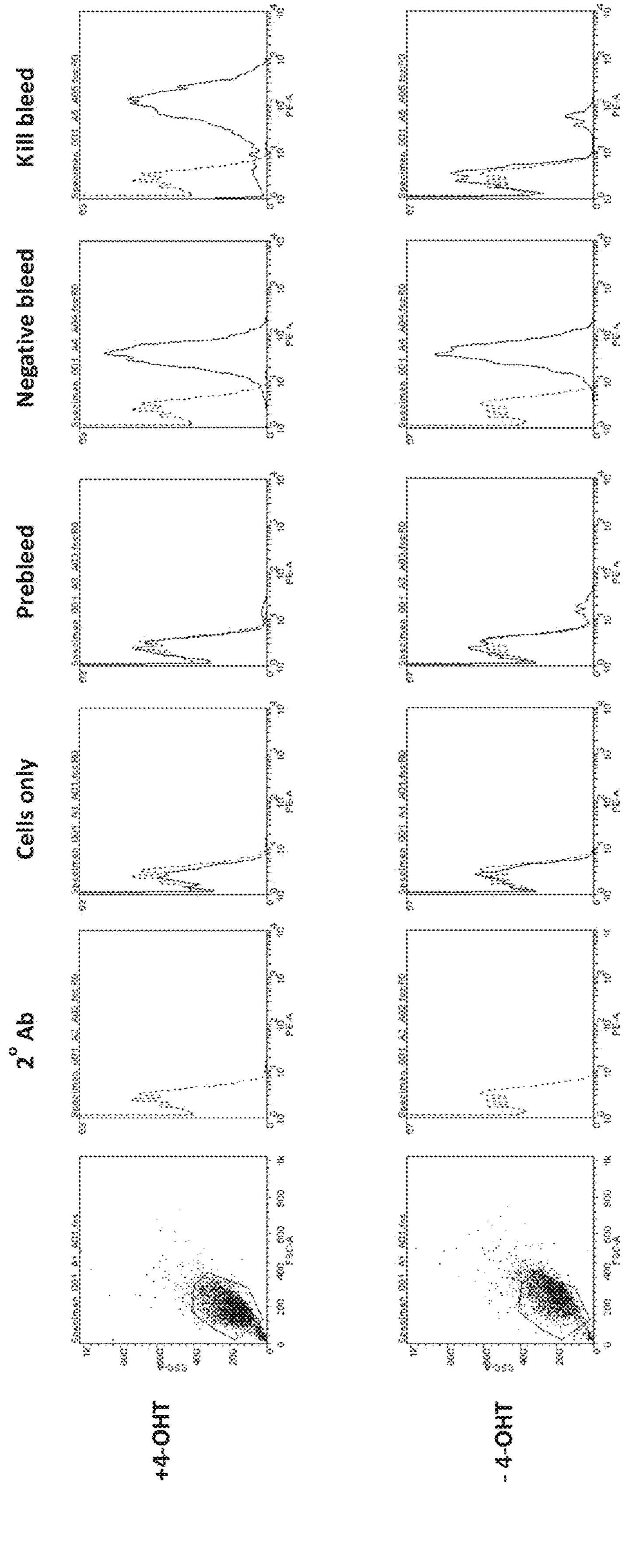
Figure 3B:
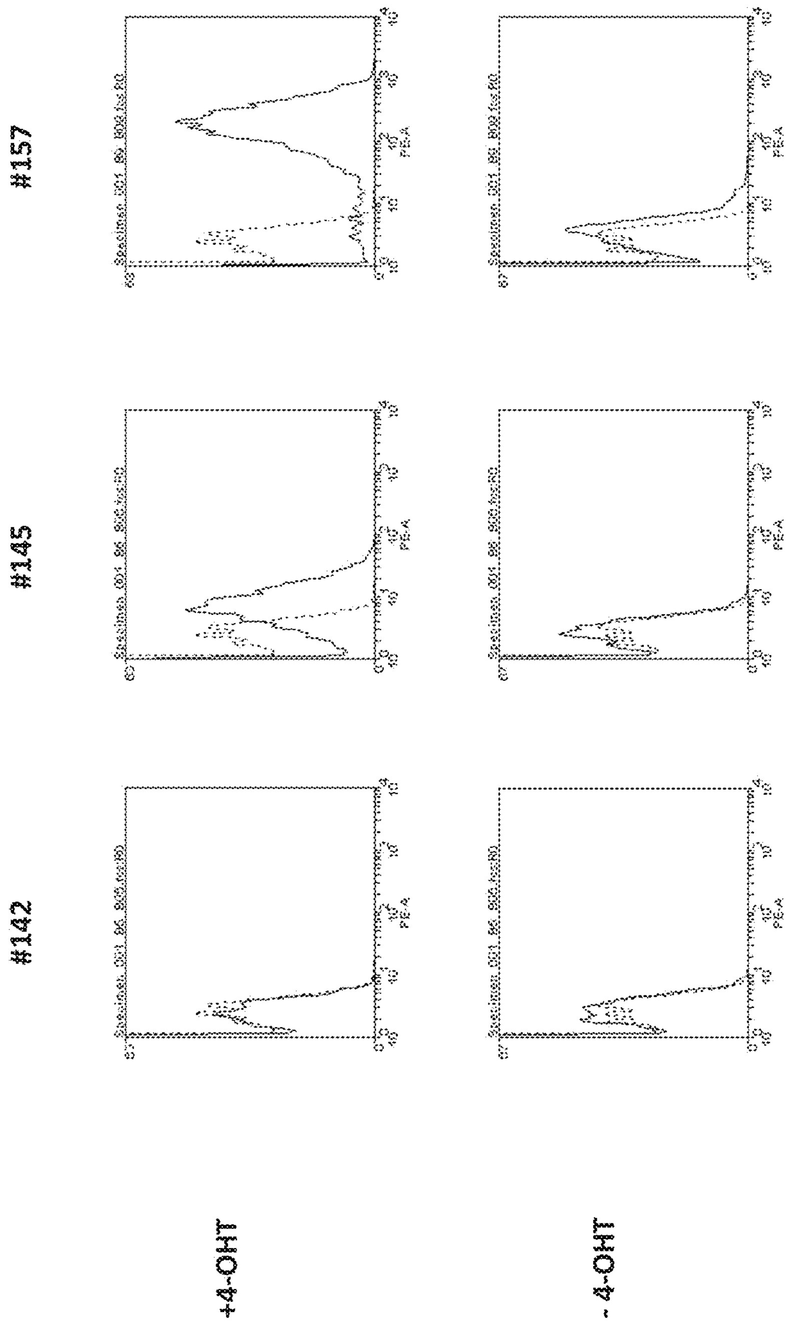
Figure 3C:
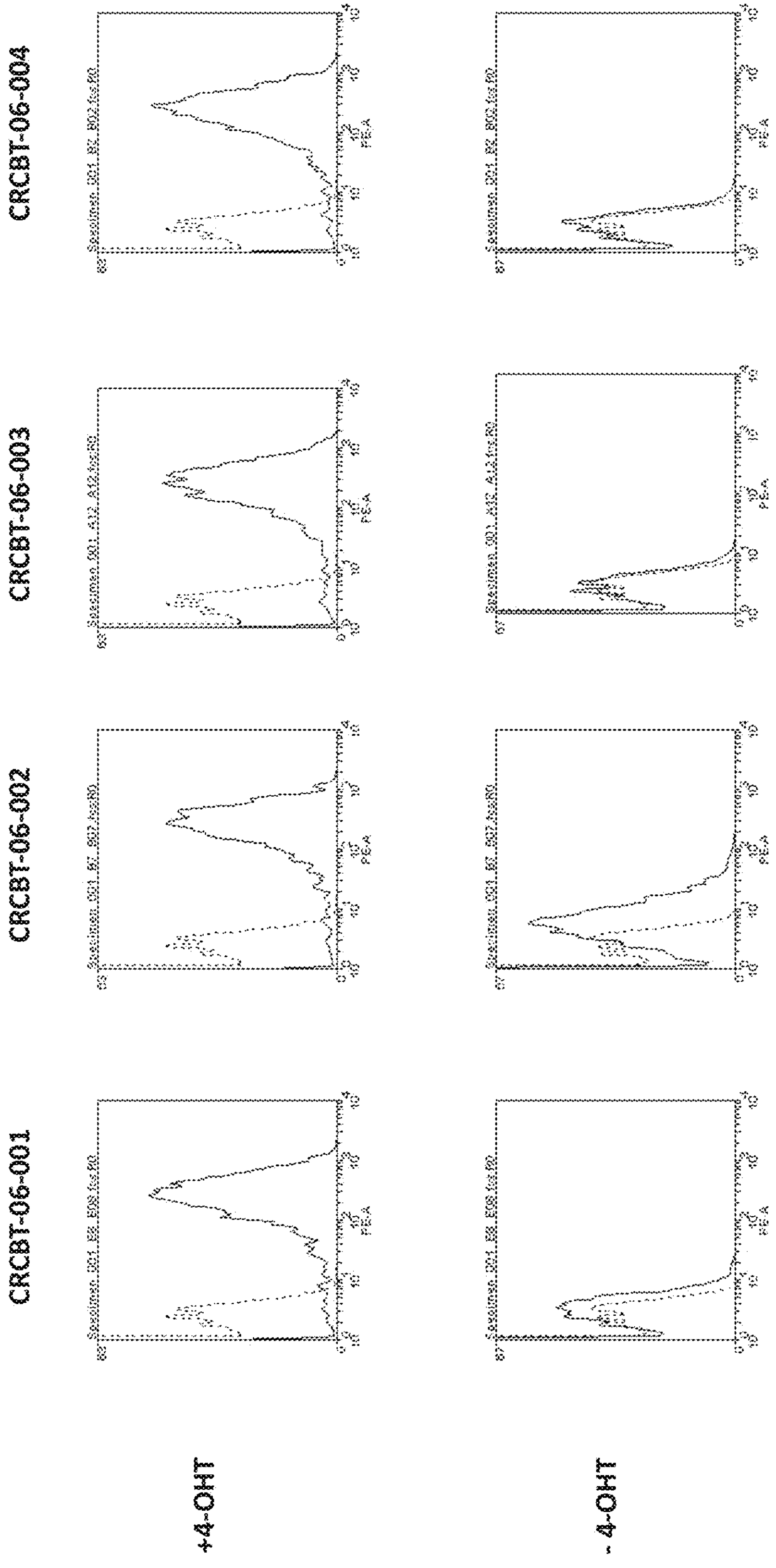

FIGS. 3A to C is a series of graphical representations showing detection of monoclonal antibodies that specifically recognize cell surface expressed human Fn14. Human Fn14 inducible MEFv12Hras cells (+/−4-OHT as indicated) were stained with control antibodies (Panel A) or hybridoma supernatant for a selection of hybridomas (Panel B) or hybridoma supernatant from clones CRCBT-06-001, CRCBT-06-002, CRCBT-06-003 and CRCBT-06-004 (Panel C). Solid traces represent supernatant staining of cells and dotted traces represent the overlay of a secondary antibody alone staining as a control (from panel A).

Figure 4A:
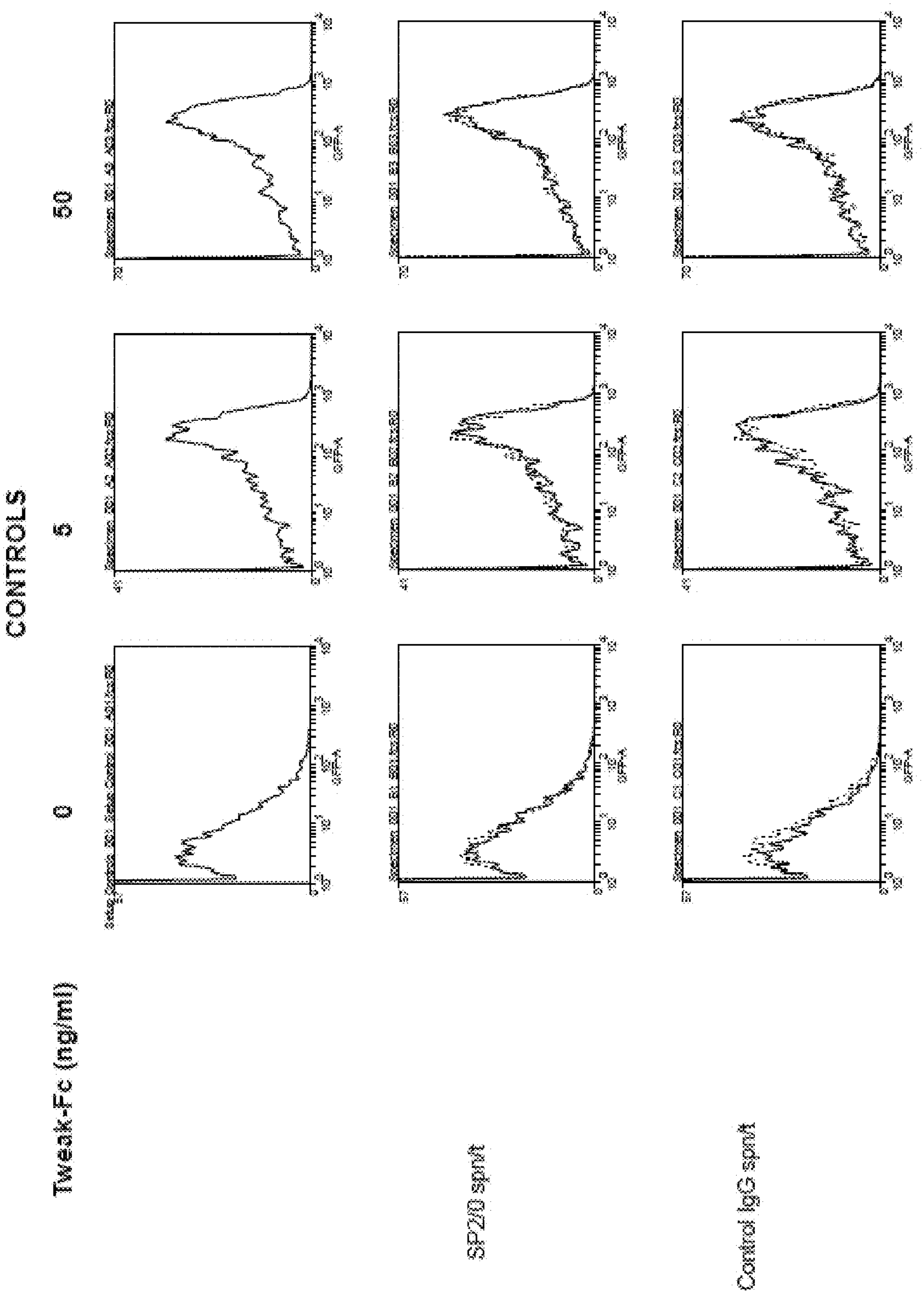
Figure 4A:
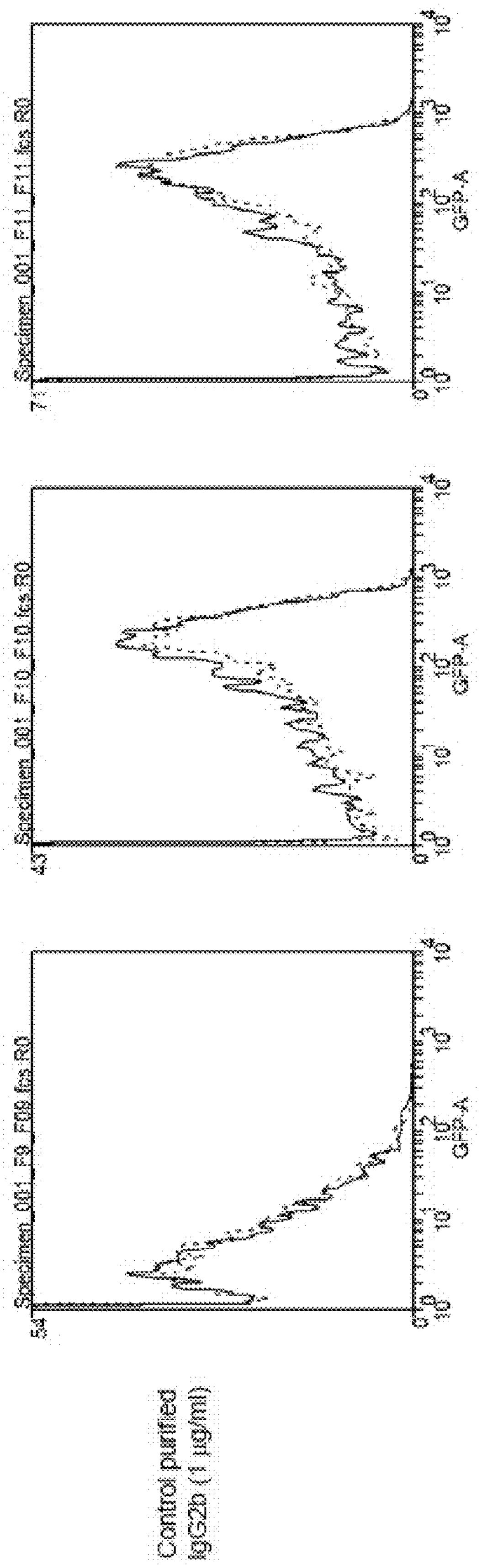
Figure 4B:
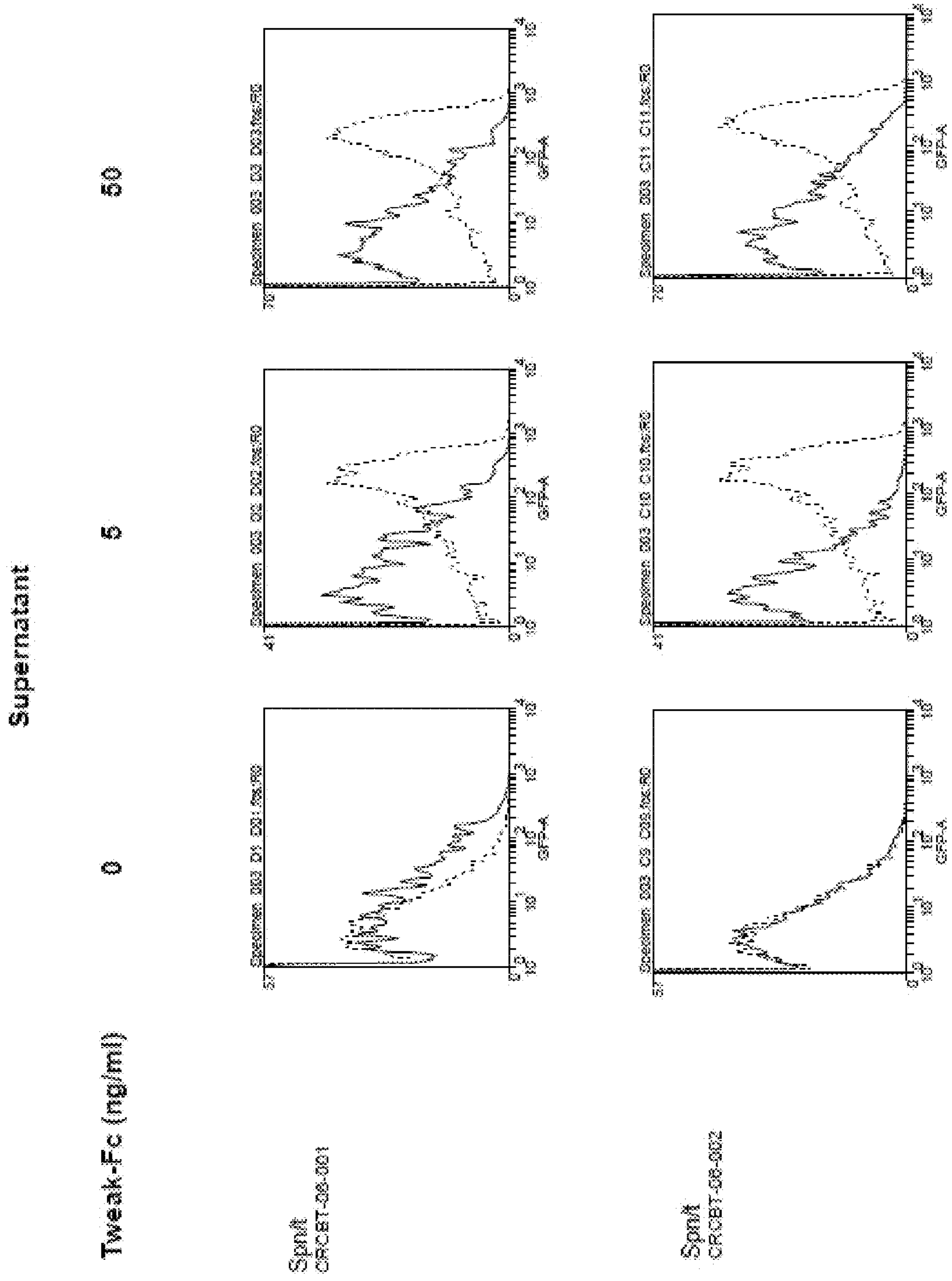
Figure 4B:
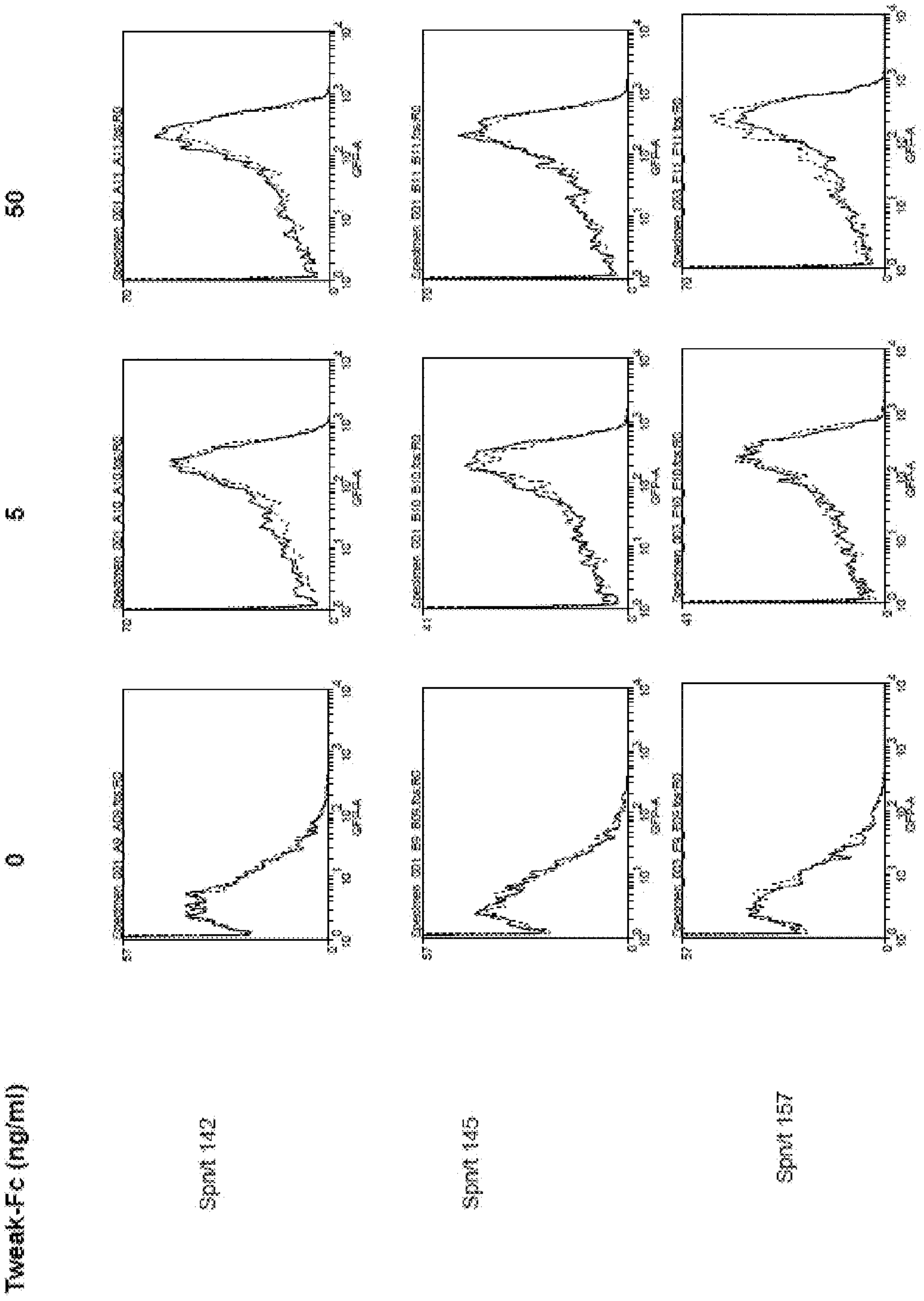
Figure 4C:
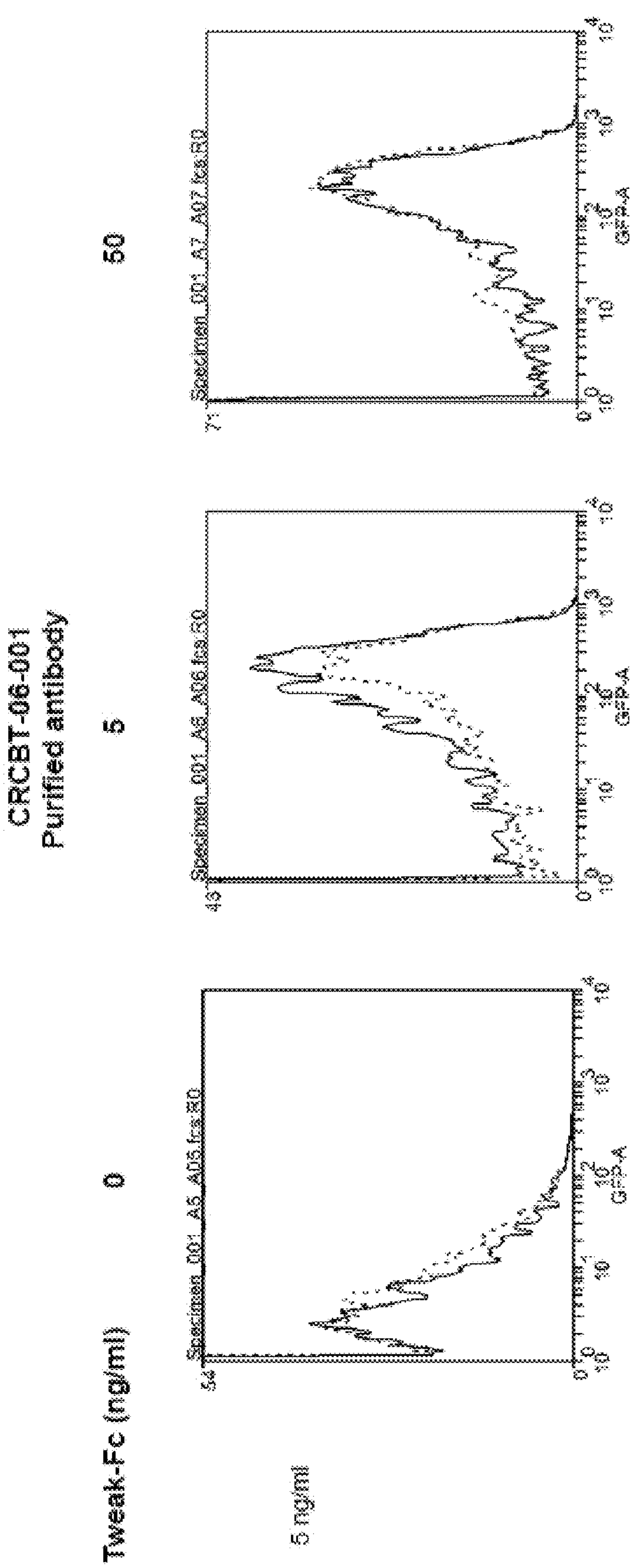
Figure 4C:
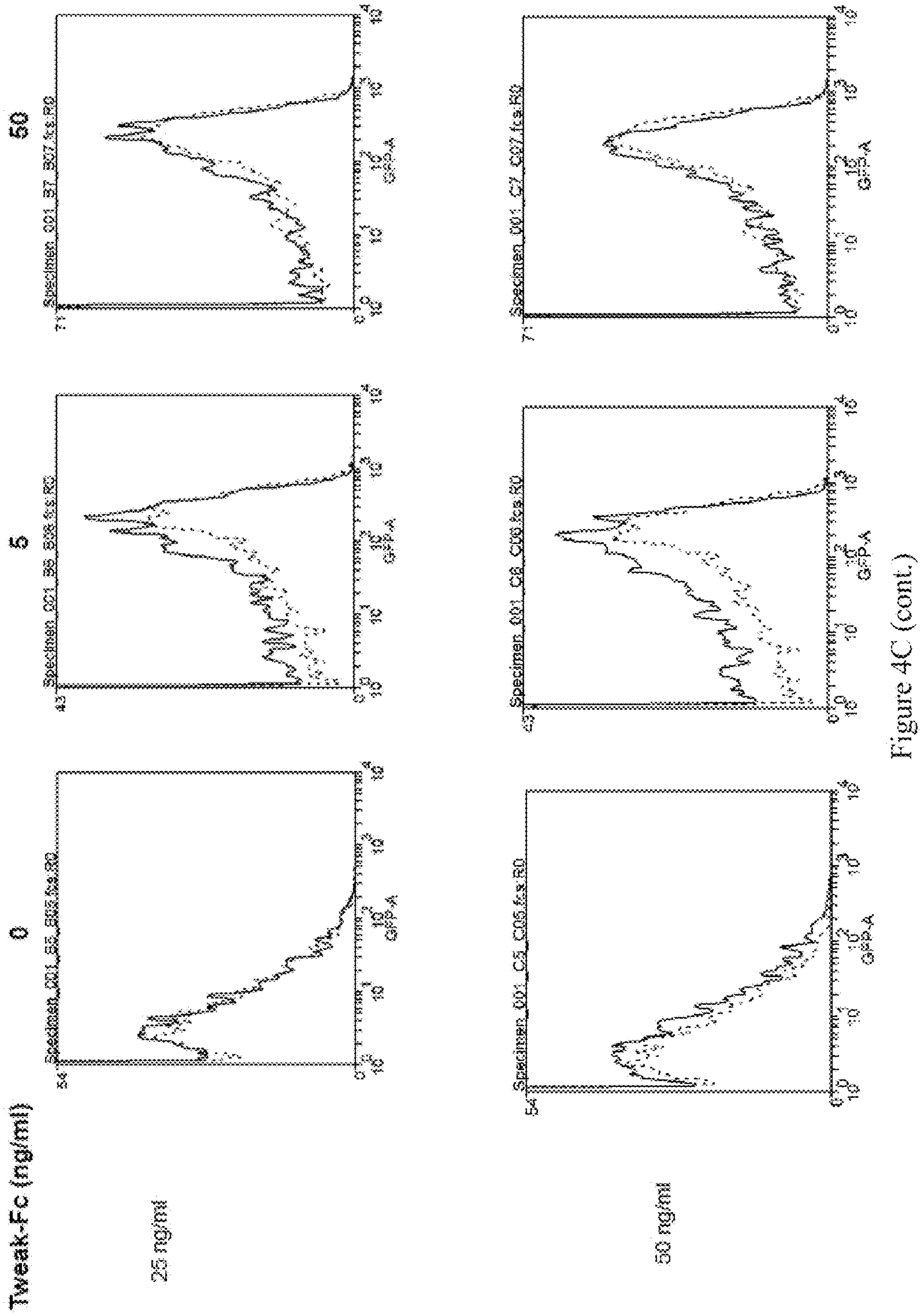
Figure 4C:
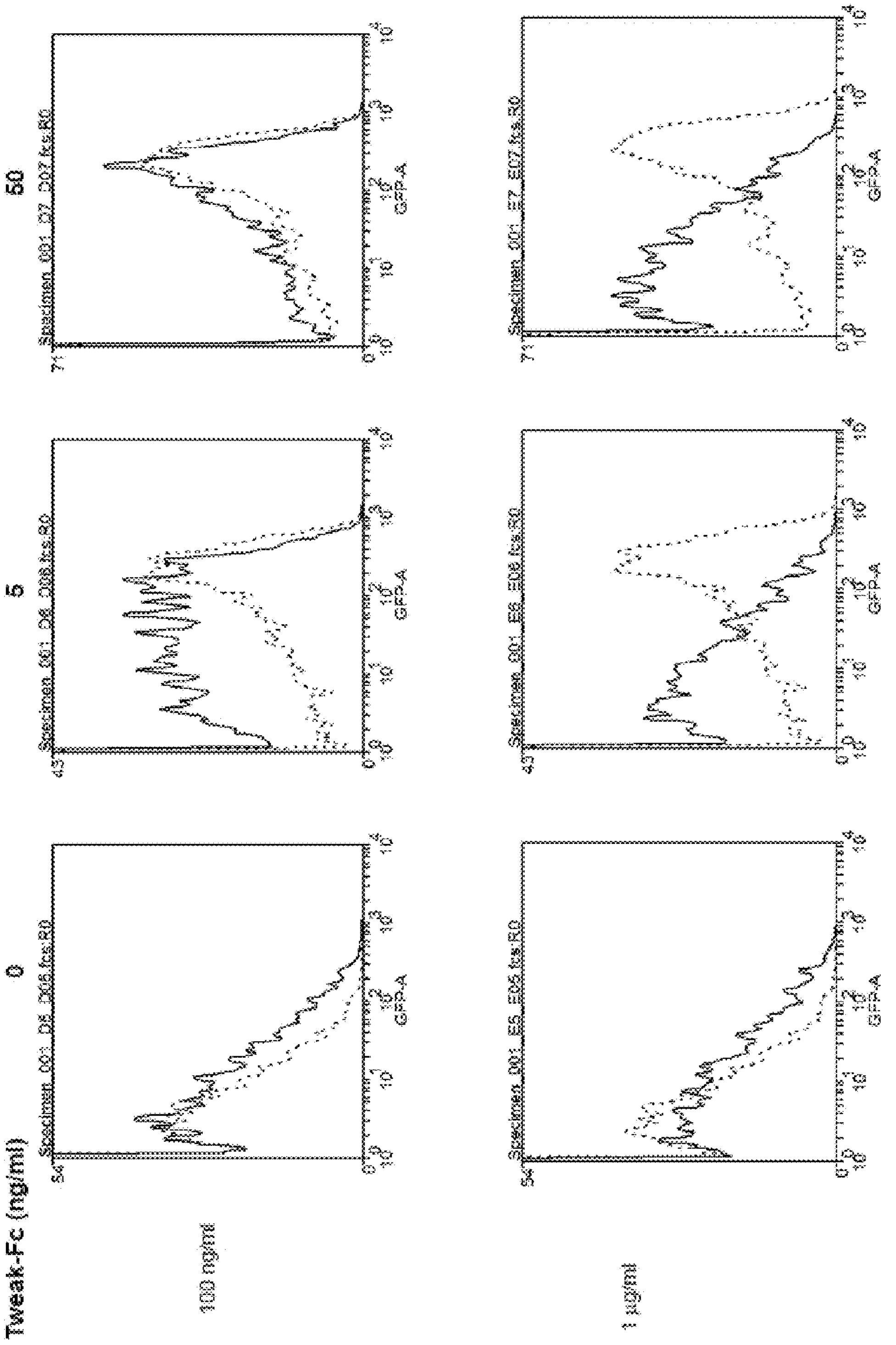
Figure 5A:
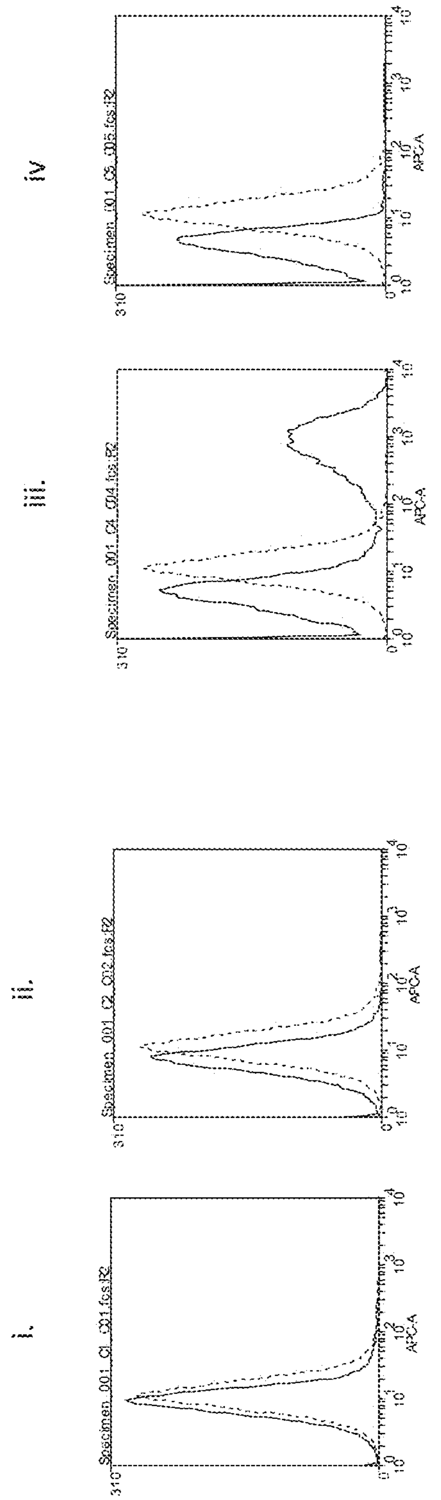
Figure 5B:
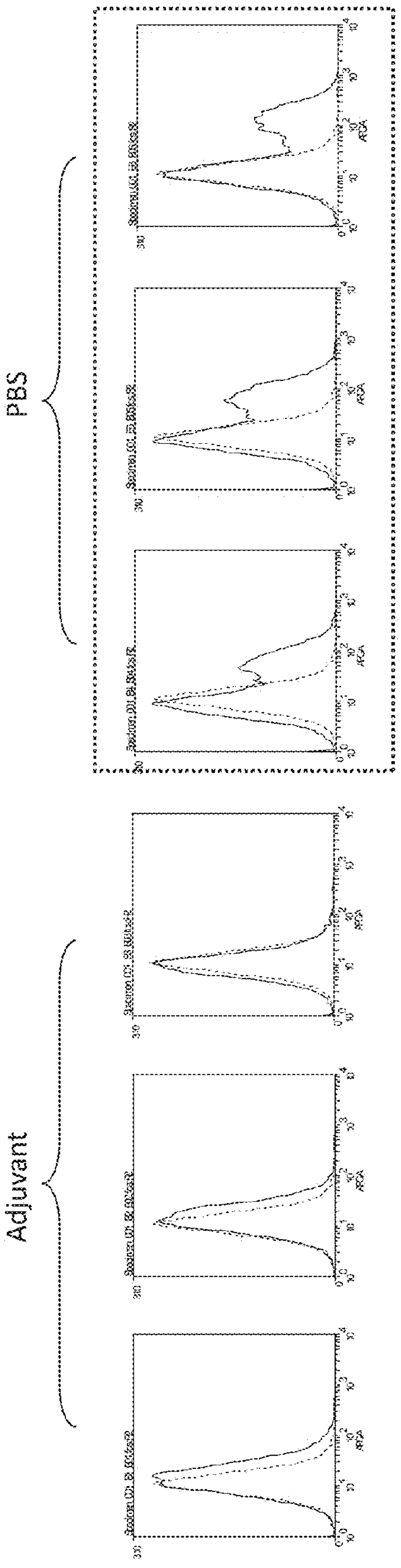

FIG. 4A to C is a series of graphical representations showing the effect of anti-hFn14 positive monoclonal antibodies on NFκB activation. HEK293T cells harboring an NFκB-responsive promoter operably linked to a GFP reporter were incubated for 24 hours in the presence/absence of Tweak-Fc (concentrations as indicated) and either control antibodies (Panel A) or supernatants from parent hybridoma clones (as indicated, Panel B) or purified monoclonal antibody CRCBT-06-001 at varying concentrations (as indicated, Panel C). Cells were harvested and GFP fluorescence assessed by flow cytometry. All supernatants were diluted 1:10 for this assay. For comparison the dotted trace overlay represents cells alone or in the presence of Tweak-Fc only at each concentration. Spn/t; supernatant FIGS. 5A to B is a series of graphical representations showing results from screening of sera from mice immunized with HEK293T cells over-expressing hFn14. Live MEFv12Hras cells expressing human Fn14 (+/−4-OHT induction) were mixed at a 1:1 ratio and stained using serum from controls (Panel A) or immunized mice (Panel B). Cells were then analyzed by flow cytometry. Dotted histogram traces represent staining of cells with serum from a mouse immunized with cells expressing a non-related antigen for comparison. Panels A.i. & show staining of cells with serum from mice immunized with HEK293T cells expressing other non-related human proteins, Panel Aiii. shows anti-hFn14 positive control and Panel Aiv. shows cells stained with secondary antibody alone. Panel B. Serum from mice immunized with HEK293T cells expressing hFn14 suspended in PBS or Adjuvant as indicated (mice#31-36), Positive response assessed based on appearance of a double peak as indicated by dotted box.

Figure 6A:
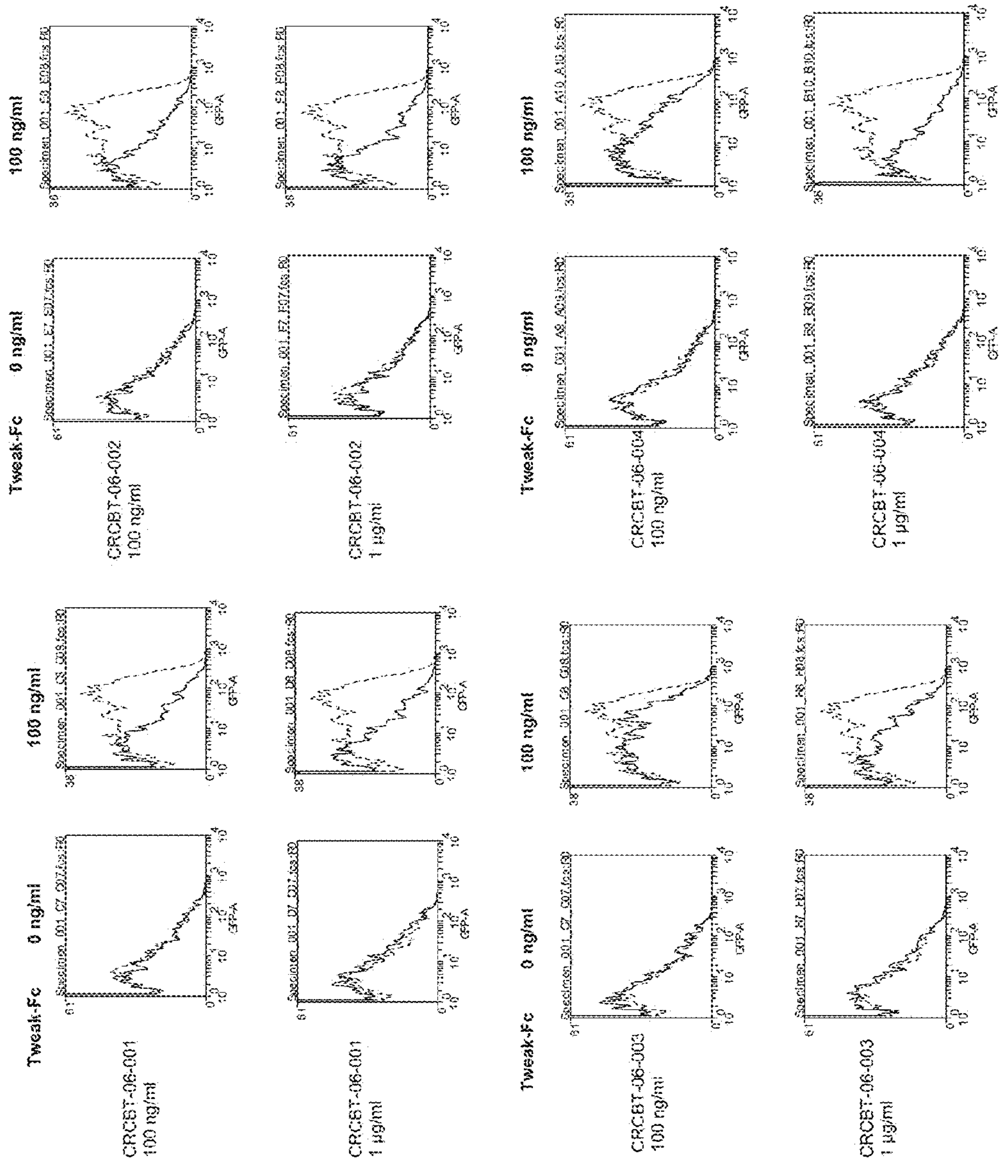

FIG. 6A is a series of graphical representations showing the effect of purified CRCBT-06-001, CRCBT-06-002, CRCBT-06-003 and CRCBT-06-0040n Tweak-induced NFκB activation. HEK293T cells harboring an NFκB-responsive promoter operably linked to a GFP reporter were incubated for 24 hours in the presence/absence of Tweak-Fc (concentrations as indicated) and purified antibody CRCBT-06-001, CRCBT-06-002, CRCBT-06-003 or CRCBT-06-004. Cells were harvested and GFP fluorescence assessed by flow cytometry. All supernatants were diluted 1:50 for this assay. For comparison, the dotted trace overlay represents cells alone or in the presence of Tweak-Fc only (as depicted in FIG. 6C panel i).

Figure 6B:
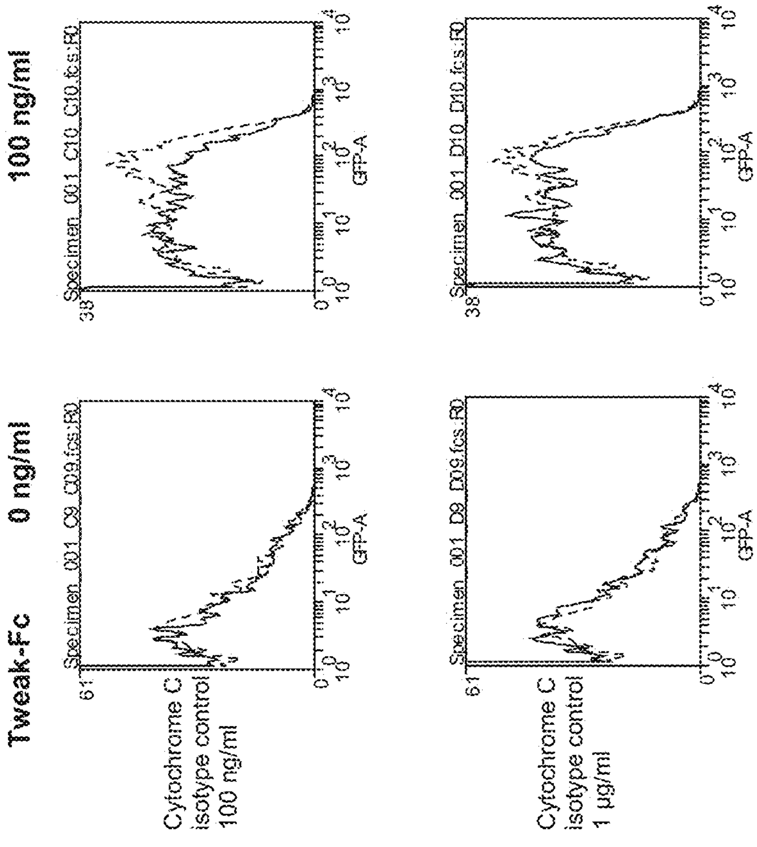

FIG. 6B is a series of graphical representations showing the effect of purified negative control antibody on Tweak induced NFκB activation. HEK293T cells harboring an NFκB-responsive promoter operably linked to a GFP reporter were incubated for 24 hours in the presence/absence of Tweak-Fc (concentrations as indicated) and purified control antibody. Cells were harvested and GFP fluorescence assessed by flow cytometry. For comparison, the dotted trace overlay represents cells alone or in the presence of Tweak-Fc only (as in FIG. 6C Panel i.).

Figure 6C:
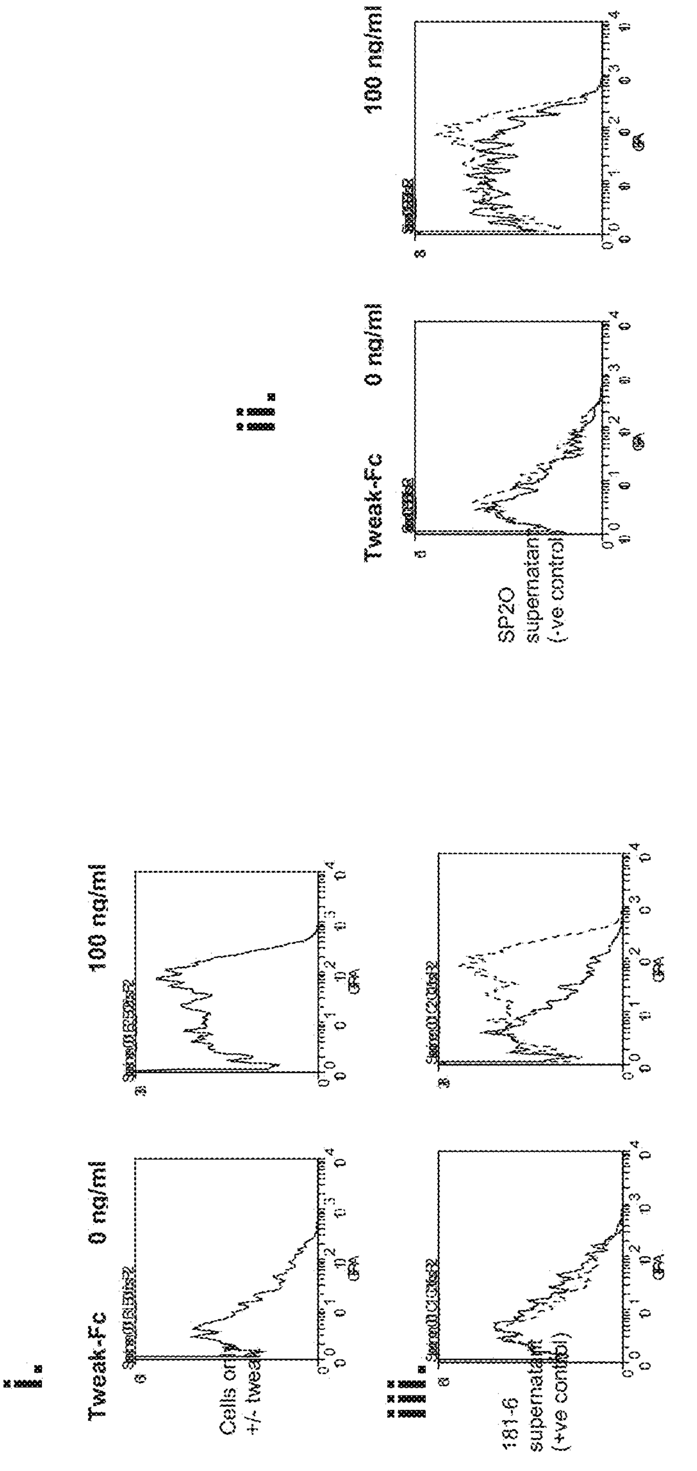

FIG. 6C is a series of graphical representations showing the effect of controls (as indicated) on Tweak induced NFκB activation. HEK293T cells harboring an NFκB-responsive promoter operably linked to a GFP reporter were incubated for 24 hours in the presence/absence of Tweak-Fc (concentrations as indicated) and controls. Cells were harvested and GFP fluorescence assessed by flow cytometry. All supernatants were diluted 1:50 for this assay. For comparison, the dotted trace overlay represents cells alone or in the presence of Tweak-Fc only (as in panel i.).

Figure 7A:
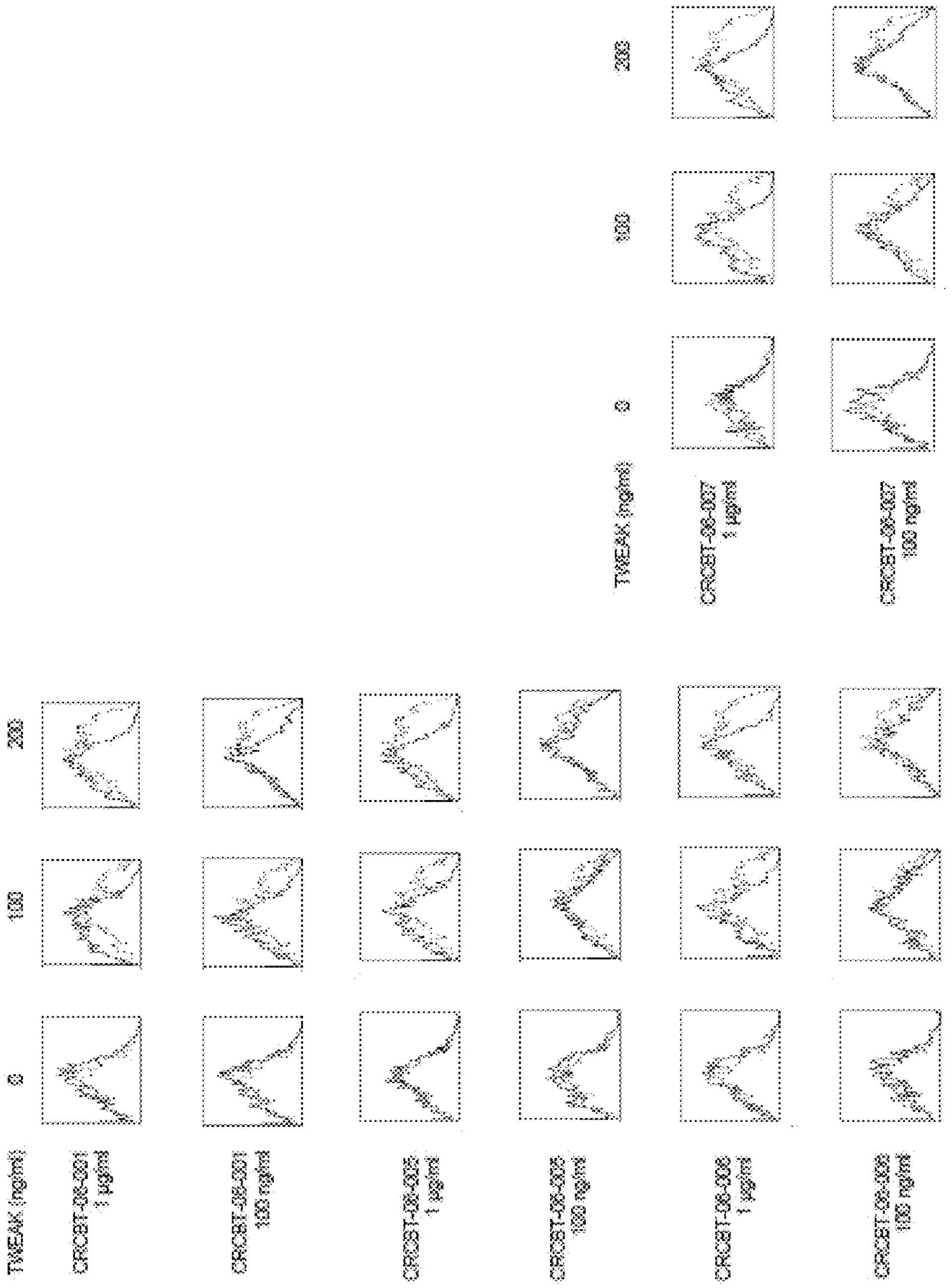

FIG. 7A is a series of graphical representations showing the effect of purified CRCBT-06-001, CRCBT-06-005, CRCBT-06-006, CRCBT-06-007, ITEM-1 and ITEM-2 on Tweak-induced NFκB activation. HEK293T cells harboring an NFκB-responsive promoter operably linked to a GFP reporter were incubated for 24 hours in the presence/absence of Tweak-Fc (100 ng/ml or 200 ng/ml) and either cells alone, isotype control IgG2b (dashed trace), purified CRCBT-06-001, CRCBT-06-005, CRCBT-06-006 or CRCBT-06-007 (solid traces; at the concentrations indicated). Cells were harvested and GFP fluorescence assessed by flow cytometry.

Figure 7B:
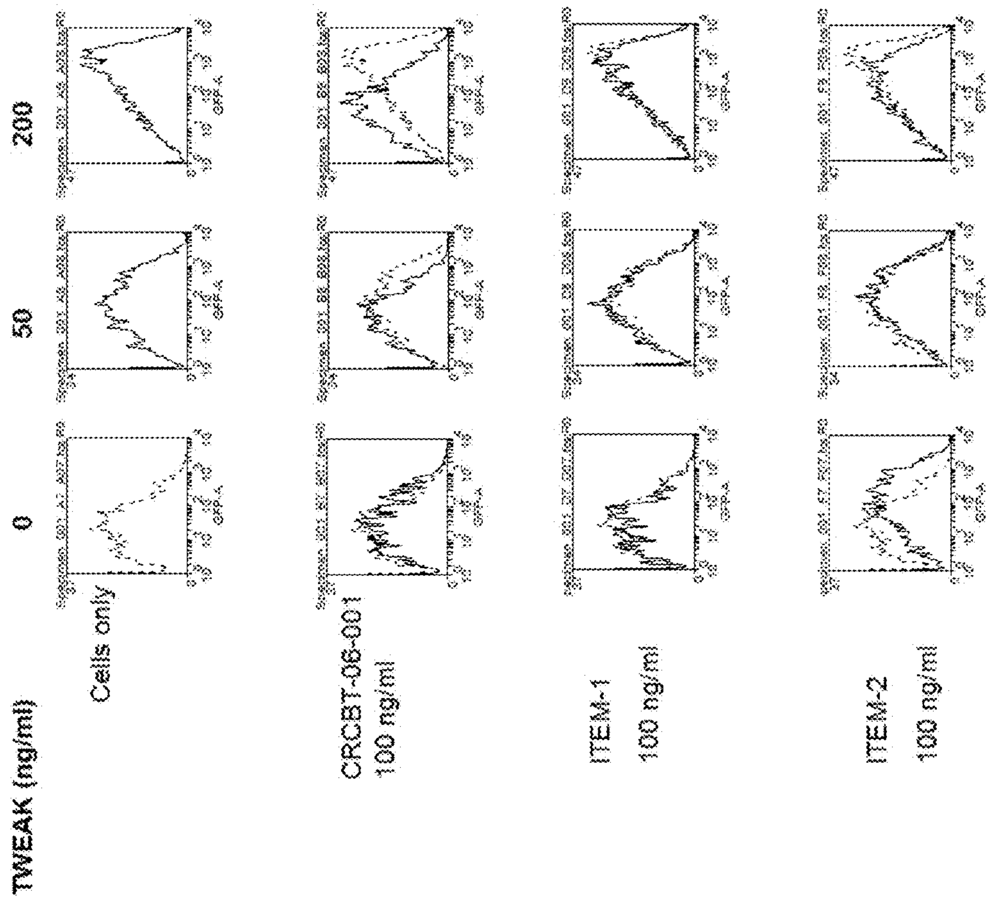

FIG. 7B is a series of graphical representations showing the effect of purified CRCBT-06-001, ITEM-1 and ITEM-2 on Tweak-induced NFκB activation. HEK293T cells harboring an NFκB-responsive promoter operably linked to a GFP reporter were incubated for 24 hours in the presence/absence of Tweak-Fc (100 ng/ml or 200 ng/ml) and either cells alone (dashed trace as underlay for antibody graphs), purified CRCBT-06-001, ITEM-1 or ITEM-2 (solid traces; at the concentrations indicated). Cells were harvested and GFP fluorescence assessed by flow cytometry.

Figure 8:
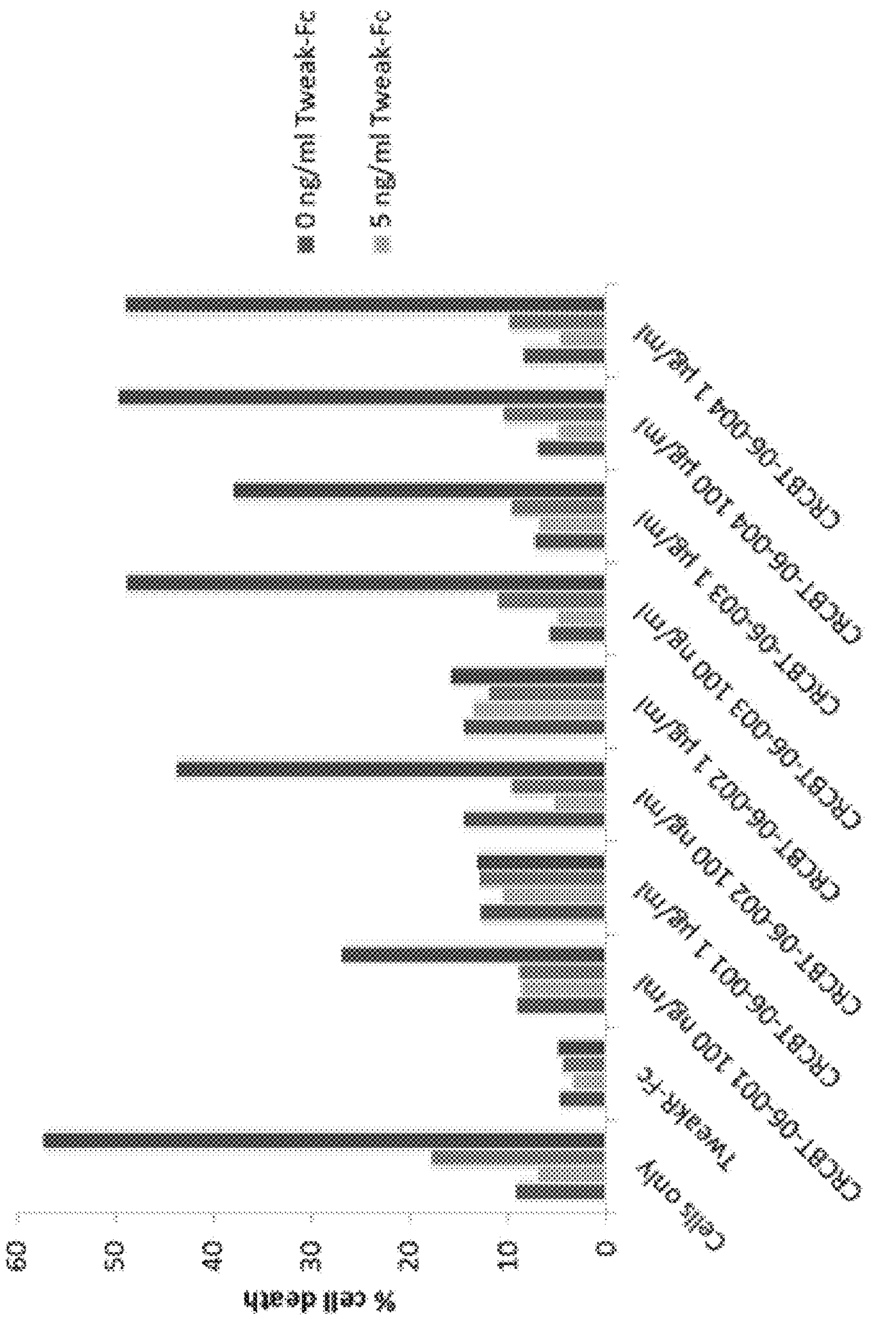

FIG. 8 is a graphical representation showing results of an assay to determine the ability of purified CRCBT-06-001, CRCBT-06-002, CRCBT-06-003 and CRCBT-06-004 to block Tweak-induced Kym1 cell death. Kym1 cells were incubated for 24 hours in the presence/absence of Tweak-Fc (concentrations as indicated) and purified antibody (at the concentrations indicated) or TweakR-Fc as positive control.

Total cells were harvested and incubated with propidium iodide. Cells were analyzed by flow cytometry and graphed as a percentage of cell death in each sample.

Figure 9:
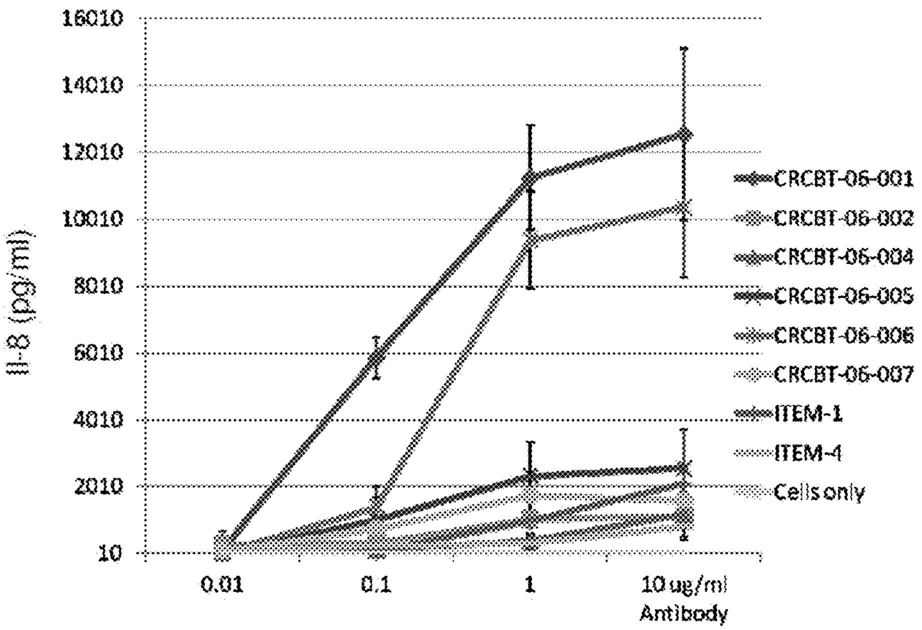

FIG. 9 is a graphical representation showing results of IL-8 secretion assay for assessing agonistic properties of antibodies. A375 cells were incubated in the presence of antibody (10, 1, 0.1 or 0.01 μg/ml) for 24 hours. Cell culture supernatants were assessed for amount of IL-8. Experiments were conducted with 3 independent biological replicates and the results averaged and graphed as IL-8 (pg/ml) with error bars representing the SEM.

Figure 10:
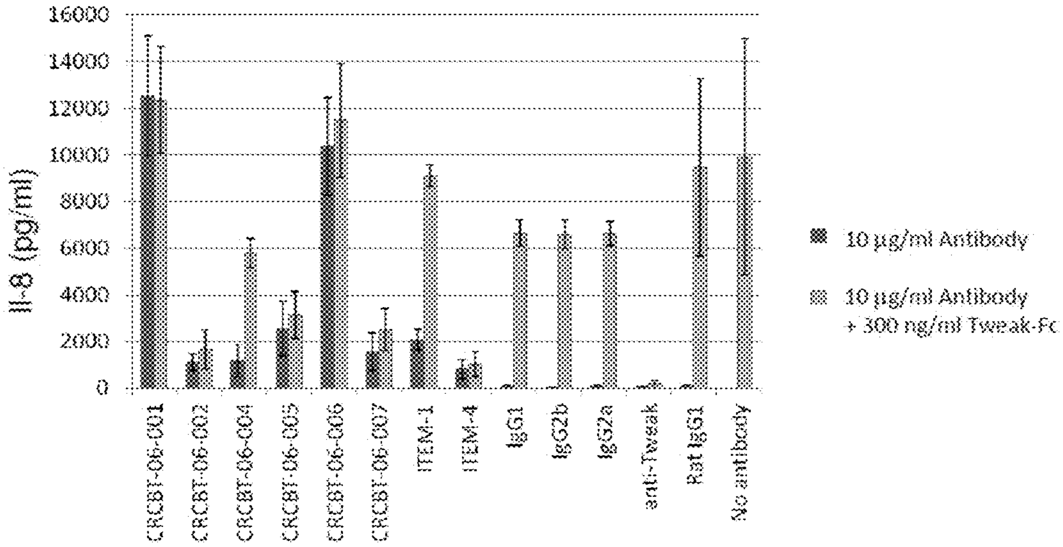

FIG. 10 is a graphical representation showing IL-8 secretion assay for determination of antibody antagonist properties of antibodies. A375 cells were incubated in the presence or absence of antibody (10 μg/ml) in the presence or absence of Tweak-Fc (300 ng/ml) for 24 hours. Cell culture supernatants were assessed for amount of IL-8. Experiments were conducted with 3 independent biological replicates and the results averaged and graphed as IL-8 (pg/ml) with error bars representing the SEM.

FIG. 11A is a diagrammatic representation showing sequences of the light chains variable regions of monoclonal antibodies CRCBT-06-001, CRCBT-06-002, CRCBT-06-003, CRCBT-06-004, CRCBT-06-005, CRCBT-06-006 and CRCBT-06-007 (labeled 001, 002, 003, 004, 005, 006 and 007, respectively). The sequences have been aligned. CDRs 1-3 and framework regions 1-4 are indicated. CDRs according to the Kabat numbering system are indicated in bold text. CDRs according to the Chothia numbering system are indicated in underlined text.

FIG. 11B is a diagrammatic representation showing sequences of a class of highly related light chains variable regions of monoclonal antibodies depicted in FIG. 11A (labeled 001, 002, 00.3, 004, 005 and 006). The sequences have been aligned. CDRs 1-3 and flanking regions 1-4 are indicated. CDRs according to the Kabat numbering system are indicated in bold text. CDRs according to the Chothia numbering system are indicated in underlined text. A consensus sequence is also shown in which "X" indicates a site of variation. Beneath the "X" is indicated all amino acids that occur at that site in the analyzed sequences.

FIG. 11C is a diagrammatic representation showing sequences of the heavy chains variable regions of monoclonal antibodies CRCBT-06-001, CRCBT-06-002, CRCBT-06-003, CRCBT-06-004, CRCBT-06-005, CRCBT-06-006 and CRCBT-06-007 (labeled 001, 002, 003, 004, 005, 006 and 007, respectively). The sequences have been aligned. CDRs 1-3 and flanking regions 1-4 are indicated. CDRs according to the Kabat numbering system are indicated in bold text. CDRs according to the Chothia numbering system are indicated in underlined text.

FIG. 11D is a diagrammatic representation showing sequences of a class of highly related heavy chains variable regions of monoclonal antibodies depicted in FIG. 11C (labeled 001, 002, 005, 006 and 007). The sequences have been aligned. CDRs 1-3 and flanking regions 1-4 (defined according to the Kabat numbering system) are indicated. CDRs according to the Kabat numbering system are indicated in bold text. CDRs according to the Chothia numbering system are indicated in underlined text. A consensus sequence is also shown in which "X" indicates a site of variation. Beneath the "X" is indicated all amino acids that occur at that site in the analyzed sequences.

Figure 12A:
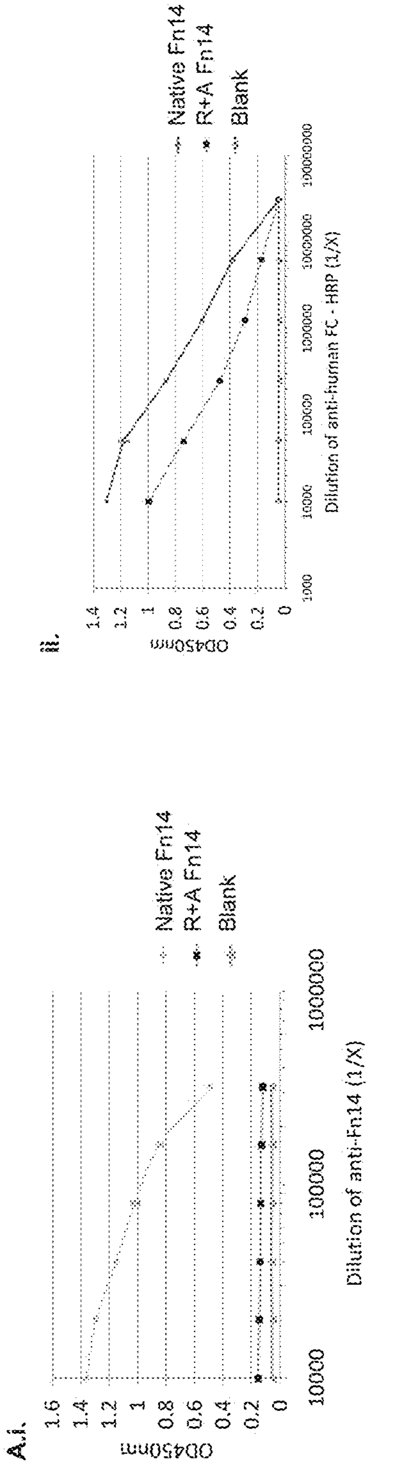

FIG. 12A is a series of graphical representations showing anti-Fn14 antibody CRCBT-06-001 recognizes a conformational epitope. Panel A.i. shows CRCBT-06-001 binds to native Fn14 but not to reduced and alkylated (R+A) Fn14 (squares) by ELISA. Panel Aii. shows Native Fn14 and R+A Fn14 retain binding to anti-Fc antibody indicating the integrity of R+A Fn14 is retained. ♦=native Fn14, ■=R+A Fn14, ▲=Blank.

Figure 12B:
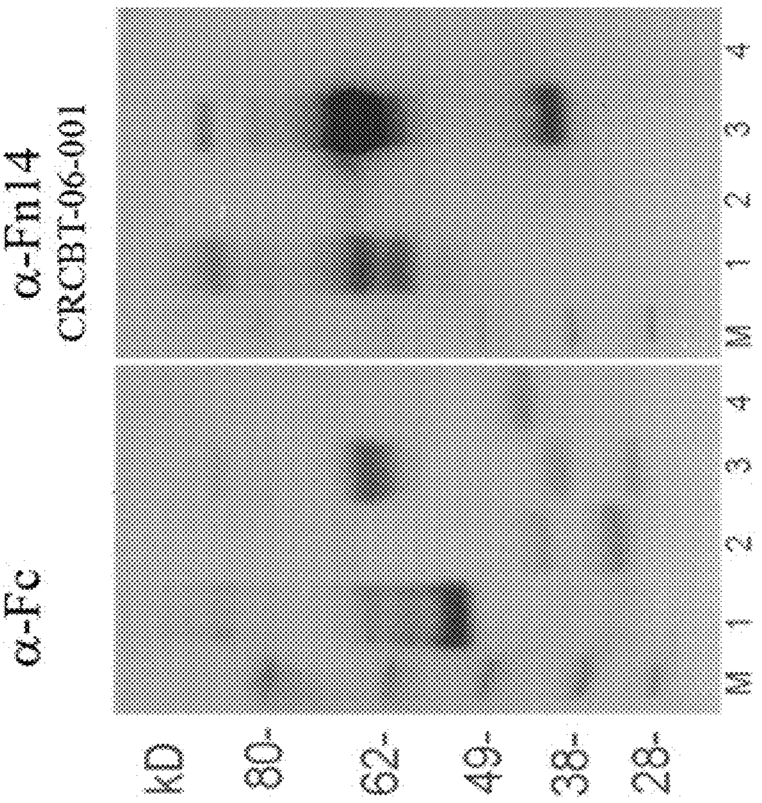

FIG. 12B is a copy of a photographic representation showing results of Western blot analysis of Fn14 and R+A Fn14 showing the R+A Fn14 is not detected by CRCBT-06-001 whereas the native Fn14 is detected strongly. Lanes labeled 1 and 2 Fn14-Fc preparation 1: Lanes 1=native Fn14-Fc, lanes 2=R+A Fn14, Lanes 3 and 4=Fn14-Fc preparation 2: lanes 3=native Fn14-Fc, lanes 4=R+A Fn14-Fc. M=molecular weight markers. α-Fc=detection using and anti-Fc antibody. αFn14=detection using CRCBT-06-001

Figure 12C:
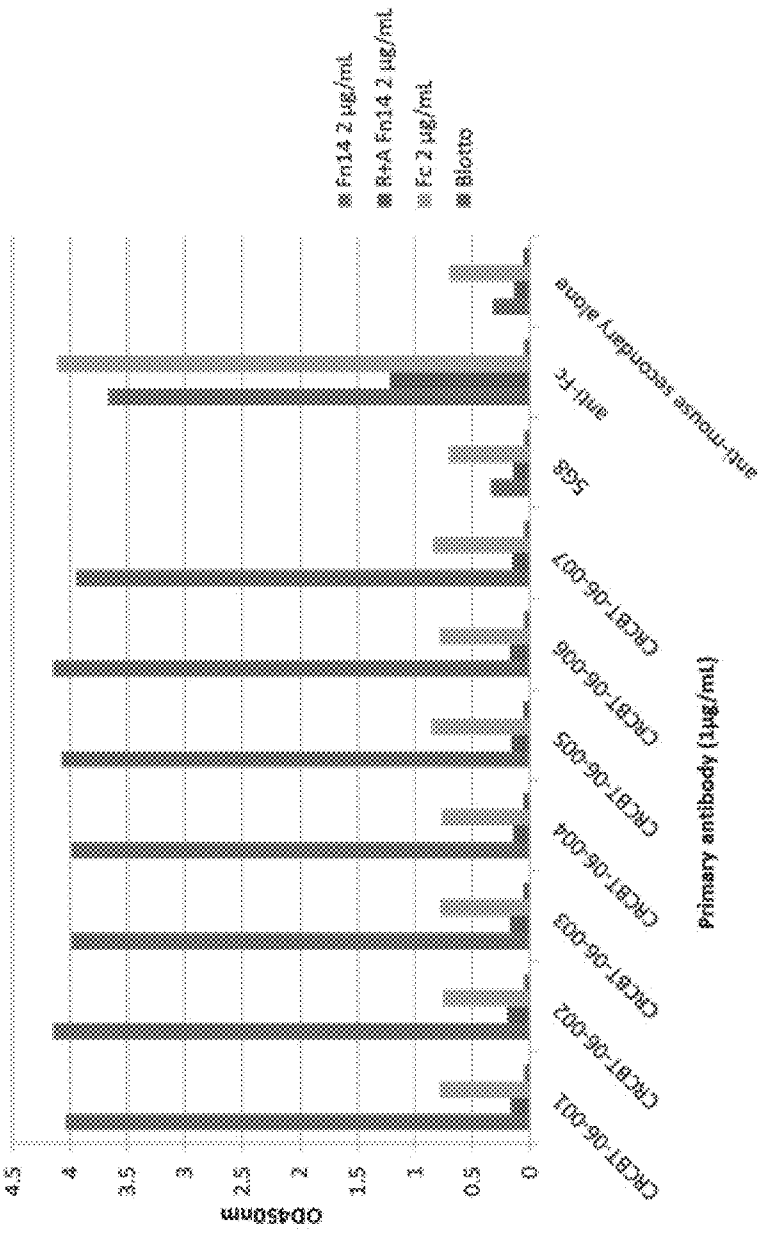

FIG. 12C is a graphical representation showing CRCBT-06-001, CRCBT-06-002, CRCBT-06-003, CRCBT-06-004, CRCBT-06-005, CRCBT-06-006 and CRCBT-06-007 recognize a conformational epitope. Antibodies were assayed by ELISA for binding to native and reduced and alkylated Fn14-Fc. Antigen was coated on the plate at 2 μg/ml and antibodies assayed at 1 μg/ml. Anti-human Fc recognized the Fc portion of Fn14 indicating that the integrity of R+A Fn14 is retained. An irrelevant antibody (5G8) and secondary antibody alone (anti-mouse HRP) were used as negative controls.

FIG. 13 is a series of representations. Panel A shows sequences of a selection of clones tested for binding to CRCBT-06-001. The shortest fragment identified by panning the phage display library (RW129) is highlighted in bold. Panel B is a graphical representation showing binding of the fragments listed in Panel A to CRCBT-06-001.

FIG. 14A is a series of graphical representations showing hFn14 extracellular domain constructs for display on phage. Panel A shows an alignment of the hFn14 constructs displayed on phage including: The full-length extracellular domain of hFn14; The D45A, K48A, M50A and D62E mutants, all known to have reduced affinity for the natural ligand Tweak; and Sub-domains 1-3.

Figure 14B:
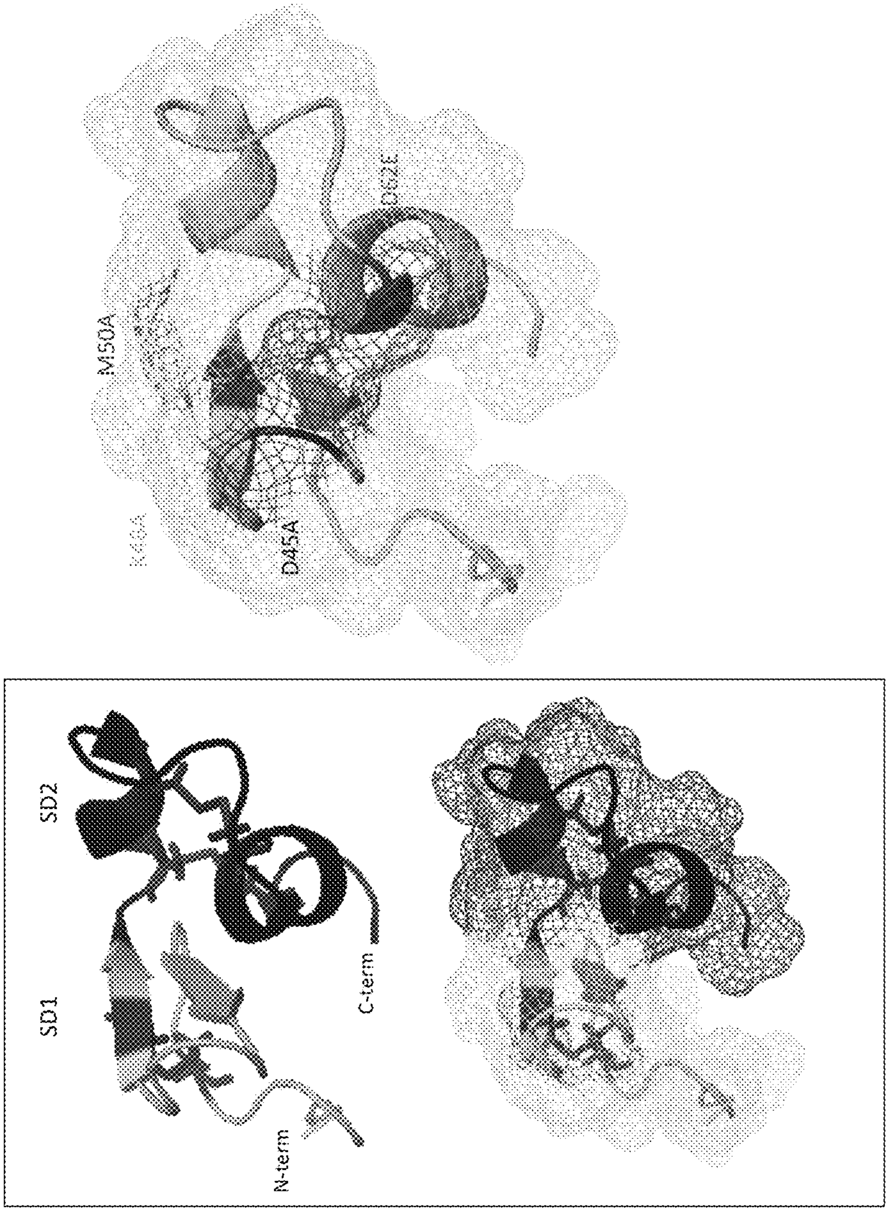

FIG. 14B shows pymol images of the solution structure solved by NMR of the human Fn14 extracellular domain structure (adapted from He et al., 2009). Subdomains 1 and 2 (SD1 and SD2, respectively) are depicted as are residues K48, D45, M50 and D62, which are known to be important for Tweak binding.

Figure 15:
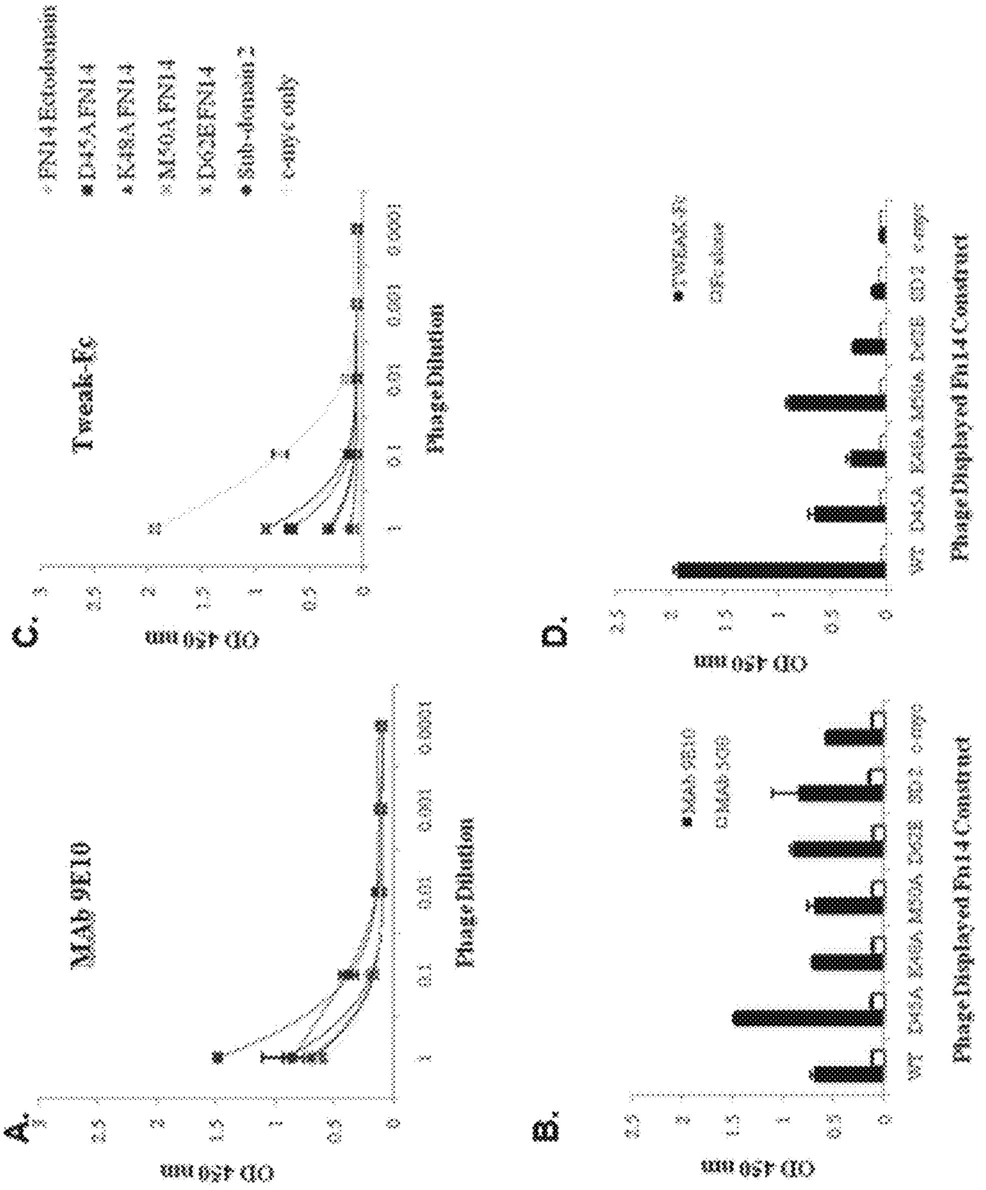

FIG. 15 is a series of graphical representations showing hFn14 extracellular domain constructs bind differentially to recombinant Tweak-Fc. Panel A shows results of an ELISA comparing the reactivity of each normalized hFn14 construct with MAb 9E10. Each phage preparation was 10-fold serially diluted and added to MAb 9E10 attached to the solid phase. Panel B shows results of the same ELISA as in Panel A comparing the binding of the highest concentration of phage with MAb 9E10 and MAb 5G8. Panel C shows results of an ELISA comparing the reactivity of each normalized phage-displayed hFn14 construct with recombinant Tweak-Fc. Panel D shows results of the same ELISA as in Panel C comparing the binding of the highest concentration of each phage preparation with recombinant Tweak-Fc and recombinant Fc alone. Binding was detected using HRP-conjugated anti-M13-phage polyclonal IgG and TMB substrate. Optical density at 450 nm was quantified using a Spectramax spectrophotometer. Error bars for each dilution represent the standard deviation of duplicate assays. In this figure, reference to "FN14 Ectodomain" or "WT" is a reference to the extracellular domain of hFn14. Methods according to Epitope mapping using phage expressed Fn14—Method 1.

Figure 16A:
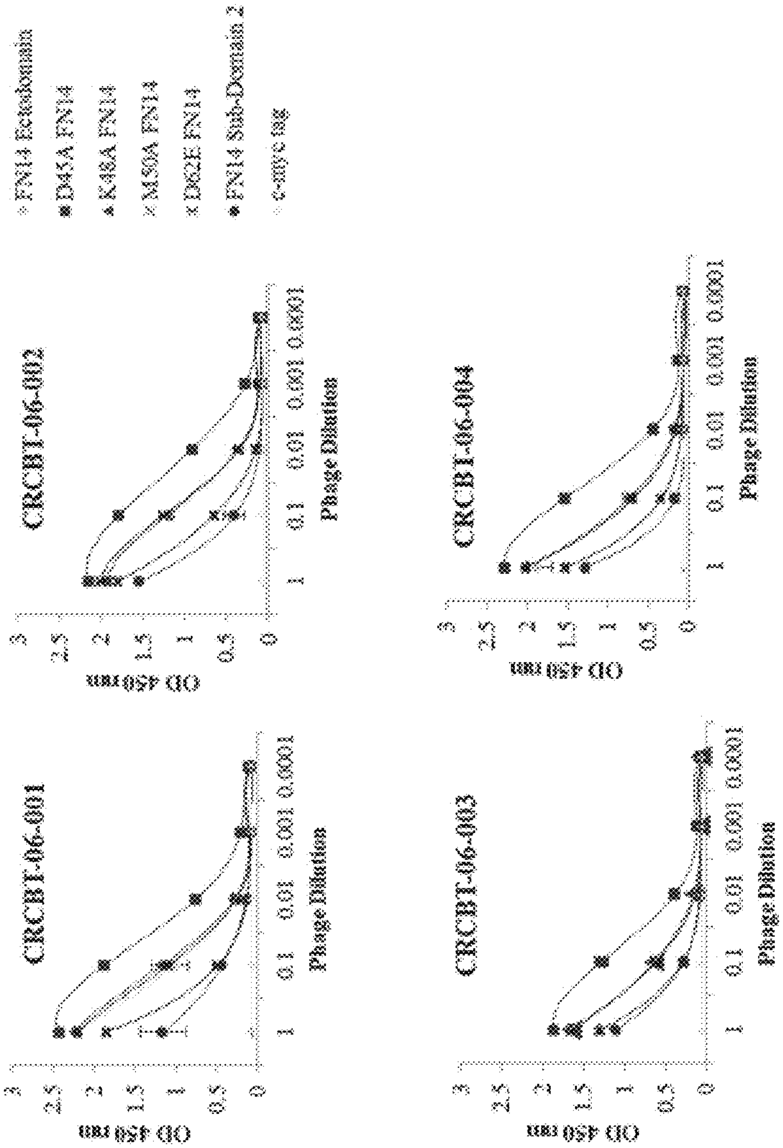

FIG. 16A is a series of graphical representations showing phage-displayed hFn14 constructs bind to anti-Fn14 MAbs.

ELISAs showing the reactivity of the repertoire of hFn14 phage constructs with the anti-Fn14 monoclonal antibodies CRCBT-06-001, CRCBT-06-002, CRCBT-06-003 and CRCBT-06-004. Binding was detected using HRP-conjugated anti-M13-phage polyclonal IgG and TMB substrate. Optical density at 450 nm was quantified using a Spectramax spectrophotometer. Error bars for each dilution represent the standard deviation of duplicate assays. In this figure, reference to "FN14 Ectodomain" is a reference to the extracellular domain of hFn14. Methods according to Epitope mapping using phage expressed Fn14—Method 1.

Figure 16B:
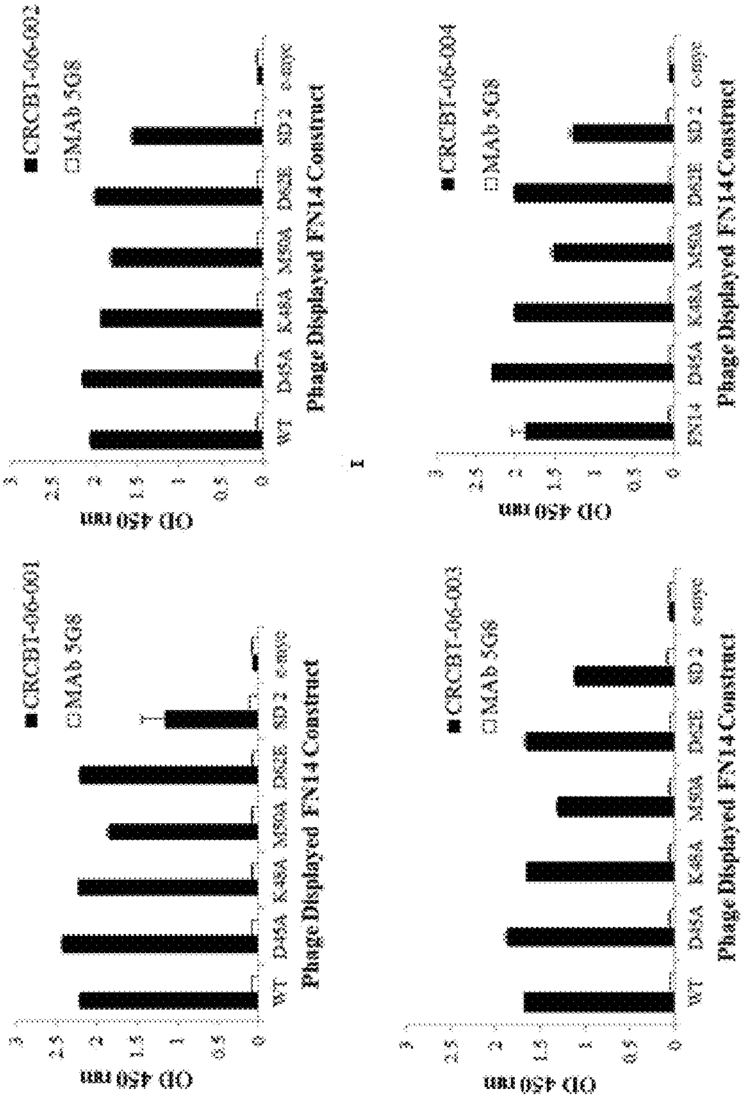

FIG. 16B is a series of graphical representations showing phage-displayed hFn14 extracellular domain constructs bind specifically to anti-Fn14 MAbs. Results depicted are from the same ELISAs as in FIG. 16A, comparing the reactivity of the repertoire of hFn14 phage constructs with the anti-Fn14 monoclonal antibodies CRCBT-06-001, CRCBT-06-002, CRCBT-06-003 and CRCBT-06-004 and MAb 5G8 (as indicated). Binding was detected using HRP-conjugated anti-M13-phage polyclonal IgG and TMB substrate. Optical density at 450 nm was quantified using a Spectramax spectrophotometer. Error bars for each dilution represent the standard deviation of duplicate assays. In this figure, reference to "WT" is a reference to the extracellular domain of hFn14.

Figure 17:
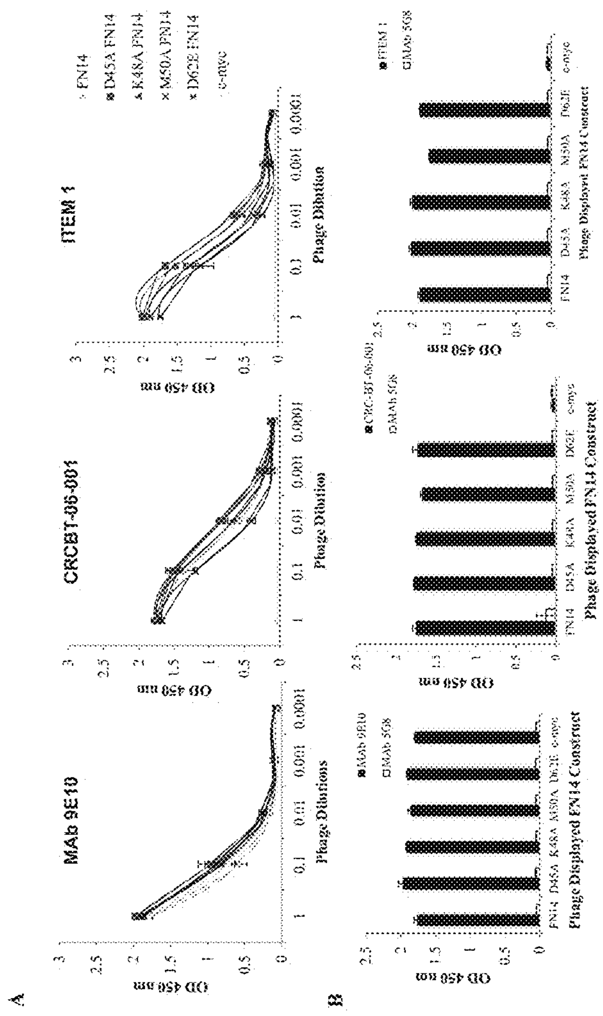

FIG. 17 is a series of graphical representations showing anti-Fn14 monoclonal antibody ITEM-1 binds well to all 4 Tweak mutants. Panel A shows results of ELISAs showing the reactivity of the repertoire of hFn14 phage constructs with MAb 9E10 and the anti-Fn14 monoclonal antibodies CRCBT-06-001 and ITEM-1. The concentration of each phage preparation was adjusted to give an approximately equal reactivity with MAb 9E10, to normalize the amount of displayed hFn14 in each phage preparation. Each normalized preparation was 10-fold serially diluted and added in solution to the MAbs attached to the solid phase. All ELISAs shown here were performed simultaneously with the same preparations of phage. Binding was detected using HRP-conjugated anti-M13 phage polyclonal IgG and TMB substrate. Optical density at 450 nm was quantified using a Spectramax spectrophotometer. Error bars for each dilution represent the standard deviation of duplicate assays. Panel B shows the results of the same ELISAs as in Panel A showing that none of the phage-displayed hFn14 constructs bind significantly to the negative control MAb 5G8. In this figure, reference to "FN14" is a reference to the extracellular domain of hFn14. Methods according to Epitope mapping using phage expressed Fn14—Method 1.

Figure 18A:
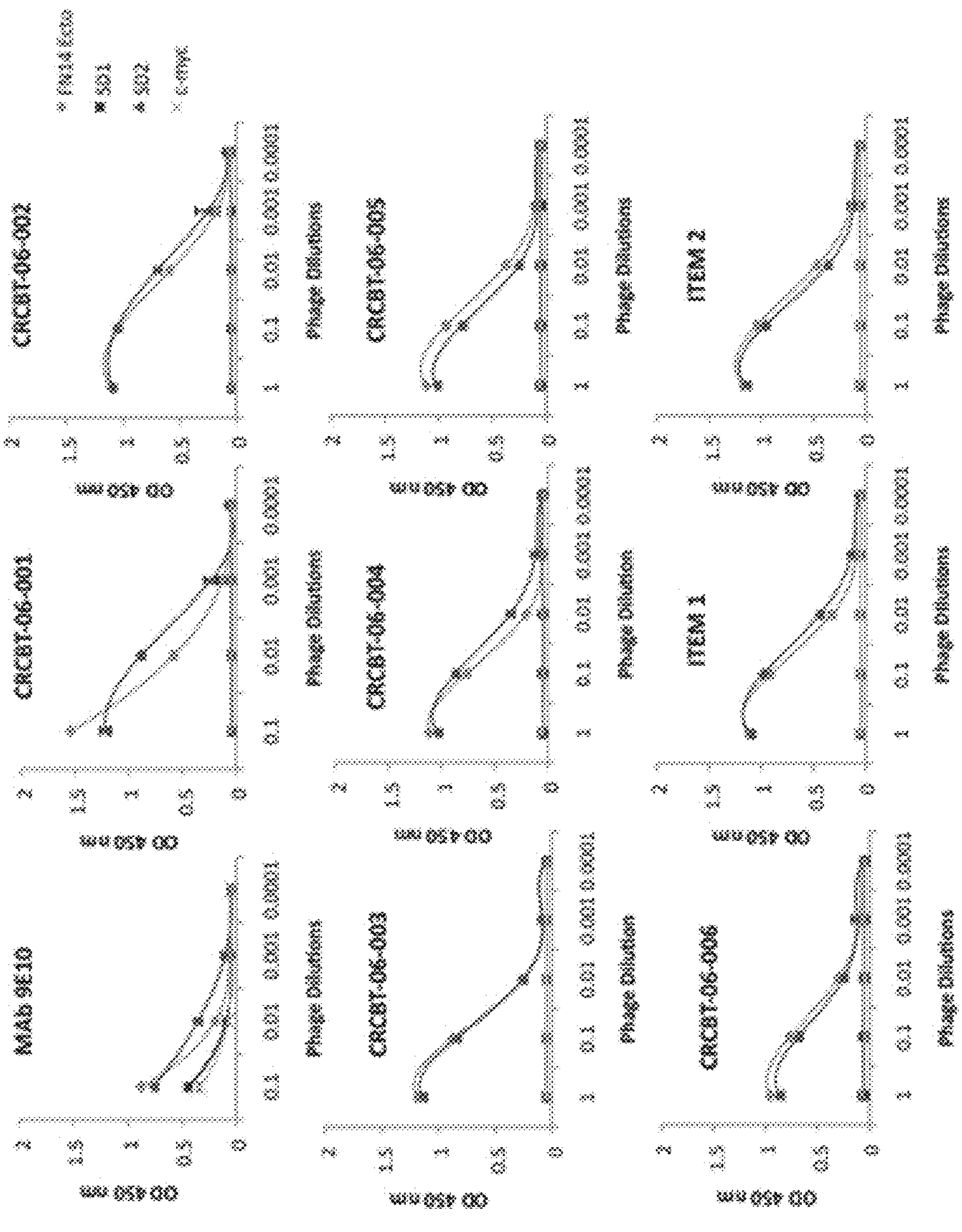

FIG. 18A is a series of graphical representations showing anti-Fn14 monoclonal antibodies bind specifically to sub-domain 2 of the hFn14 extracellular domain. Results of ELISAs are depicted showing the reactivity of the phage-displayed hFn14 extracellular domain, sub-domain 1 (SD1) and sub-domain 2 (SD2) with the anti-Fn14 monoclonal antibodies CRCBT-06-001, CRCBT-06-002, CRCBT-06-003, CRCBT-06-004, CRCBT-06-005, CRCBT-06-006, ITEM-1 and ITEM-2. The concentration of each phage preparation was adjusted to give an approximately equal reactivity with MAb 9E10, to normalize the amount of displayed hFn14 in each phage preparation. Each normalized preparation was 10-fold serially diluted and added in solution to the MAbs attached to the solid phase. All ELISAs shown were performed simultaneously with the same preparations of phage. Binding was detected using HRP-conjugated anti-M13 phage polyclonal IgG and TMB substrate. Optical density at 450 nm was quantified using a Spectramax spectrophotometer. Error bars for each dilution represent the standard deviation of duplicate assays. In this figure, reference to "FN14 Ecto" is a reference to the extracellular domain of hFn14. Methods according to Epitope mapping using phage expressed Fn14—Method 1.

Figure 18B:
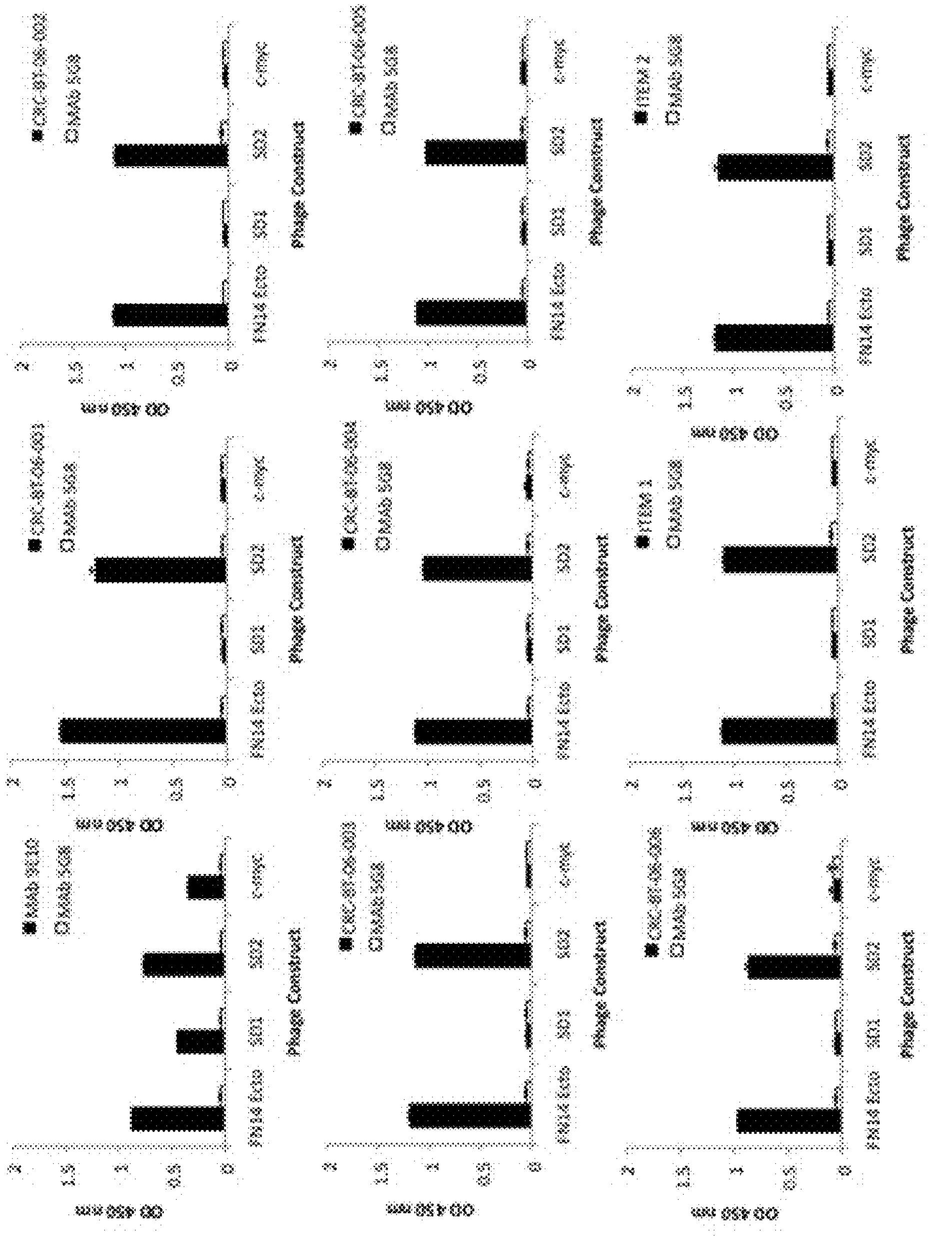

FIG. 18B is a series of graphical representations showing results of ELISAs using the same phage constructs as in FIG. 18A and showing that none of the phage-displayed hFn14 constructs bind significantly to the negative control MAb 5G8. ELISAs were performed under similar conditions to those described for FIG. 16A. In this figure, reference to "FN14 Ecto" is a reference to the extracellular domain of hFn14.

Figure 19:
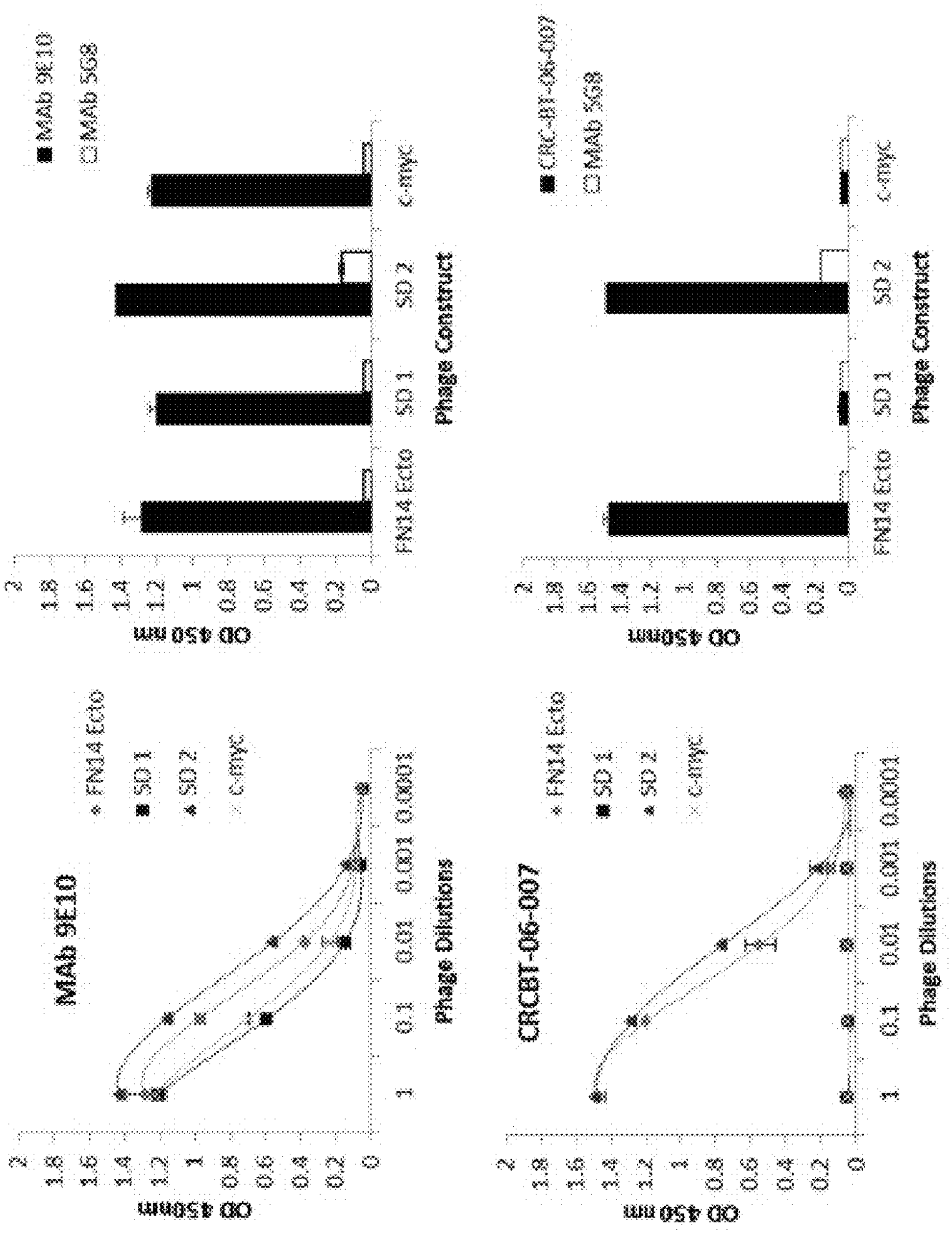

FIG. 19 is a series of graphical representations showing anti-Fn14 monoclonal antibody CRCBT-06-007 binds specifically to sub-domain 2 of the hFn14 extracellular domain. Panel A Results of ELISAs are depicted showing the reactivity of the phage-displayed hFn14 extracellular domain (Fn14 Ecto), sub-domain 1 (SD1) and sub-domain 2 (SD2) with the anti-Fn14 monoclonal antibody CRCBT-06-007. The concentration of each phage preparation was adjusted to give an approximately equal reactivity with MAb 9E10, to normalize the amount of displayed hFn14 in each phage preparation. Each normalized preparation was 10-fold serially diluted and added in solution to the MAbs attached to the solid phase. ELISAs shown here were performed simultaneously with the same preparations of phage. Binding was detected using HRP-conjugated anti-M13 phage polyclonal IgG and TMB substrate. Optical density at 450 nm was quantified using a Spectramax spectrophotometer. Error bars for each dilution represent the standard deviation of duplicate assays. Panel B shows results of ELISAs using the same phage constructs as in Figure Panel A and showing that none of the phage-displayed hFn14 constructs bind significantly to the negative control MAb 5G8. ELISAs were performed under similar conditions to those described for Panel A. Methods according to Epitope mapping using phage expressed Fn14—Method 1.

Figure 20:

FIG. 20 is a series of schematic representations. Panel A. shows the Fn14 extracellular domain, Panel B. shows the Fn14 sub-domain 1p (a longer form of sub-domain 1 expressed on phage), Panel C. shows the Fn14 sub-domain 2 and Panel D. shows the Fn14 sub-domain 3. Panel E. shows the Fn14 sub-domain 2 in which the third and sixth cysteine residues in Fn14 ECD that form disulfide bonds are mutated to serine (designated herein "Sub-domain 2 Cys 3&6 ΔS"). Panel F. shows the Fn14 sub-domain 2 in which the fourth and fifth cysteine residues in Fn14 ECD that form disulfide bonds are mutated to serine (designated herein "Sub-domain 2 Cys 4&5 ΔS"). All panels show disulfide connectivity according to the solution structure (He et al., 2009). Bold large case "S" represents serine residue substituted in place of naturally-occurring cysteine residue.

Figure 21A:
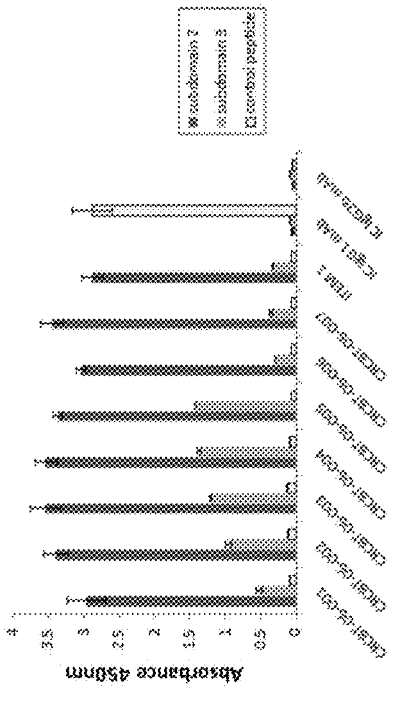

FIG. 21A is a graphical representation showing specificity of anti-Fn14 mAbs. Anti-Fn14 mAbs CRCBT-06-001, CRCBT-06-002, CRCBT-06-003, CRCBT-06-004, CRCBT-06-005, CRCBT-06-006 and CRCBT-06-007 are reactive with sub-domains 2 and 3 but not sub-domain 1. Very low reactivity to the control peptide was observed for all anti-Fn14 mAbs. The control peptide was also reactive with its cognate (isotype control) antibody.

Figure 21B:
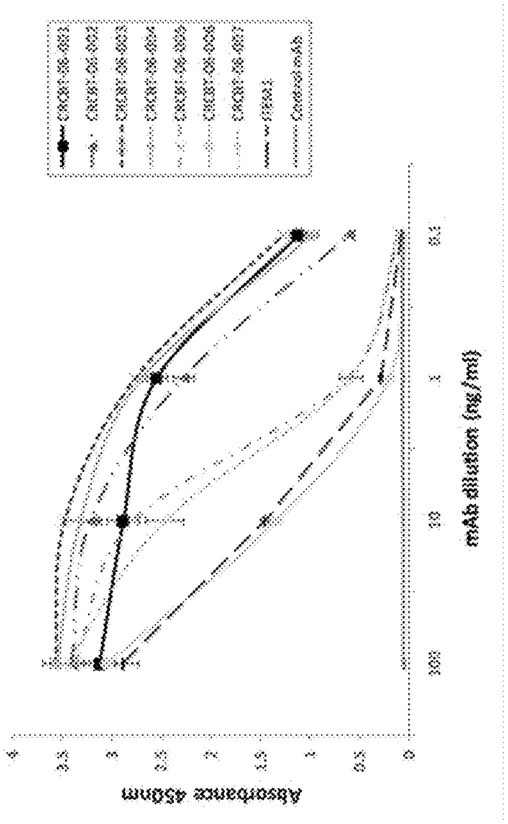

FIG. 21B is a graphical representation showing reactivity of anti-Fn14 mAbs CRCBT-06-001, CRCBT-06-002, CRCBT-06-003, CRCBT-06-004, CRCBT-06-005, CRCBT-06-006, CRCBT-06-007 and ITEM-1 with a synthetic peptide representing sub-domain 2 of Fn14. Plates were coated with sub-domain 2 peptide and various dilutions of antibody were allowed to bind, bound antibody was detected with anti-mouse HRP and TMB substrate. The average of duplicate readings are plotted, error bars represent standard deviations. The ELISA was repeated to ensure consistent results. The vertical line at 5 ng/ml within the linear part of the curves is the point at which a comparison of the reactivity of each mAb was analyzed.

Figure 21C:
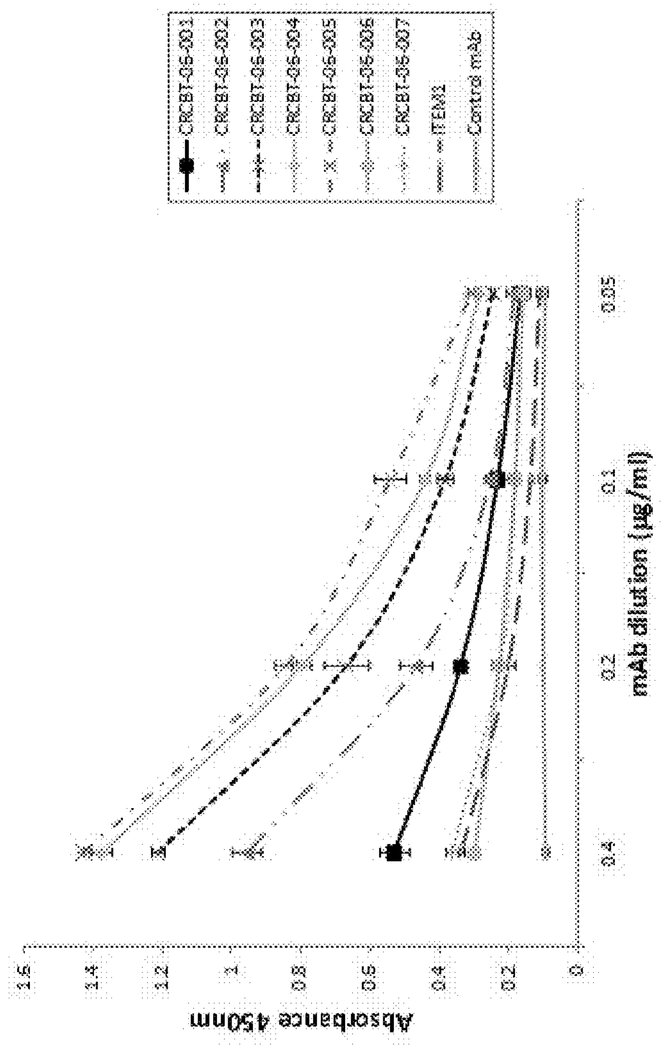

FIG. 21C is a graphical representation showing reactivity of anti-Fn14 mAbs CRCBT-06-001, CRCBT-06-002, CRCBT-06-003, CRCBT-06-004, CRCBT-06-005, CRCBT-06-006, CRCBT-06-007 and ITEM-1 with a synthetic peptide representing sub-domain 3 of Fn14. Plates were coated with sub-domain 3 peptide and various dilutions of antibody were allowed to bind, bound antibody was detected with anti-mouse HRP and TMB substrate. The average of duplicate readings are plotted, error bars represent standard deviations. The ELISA was repeated to ensure consistent results.

Figure 22:
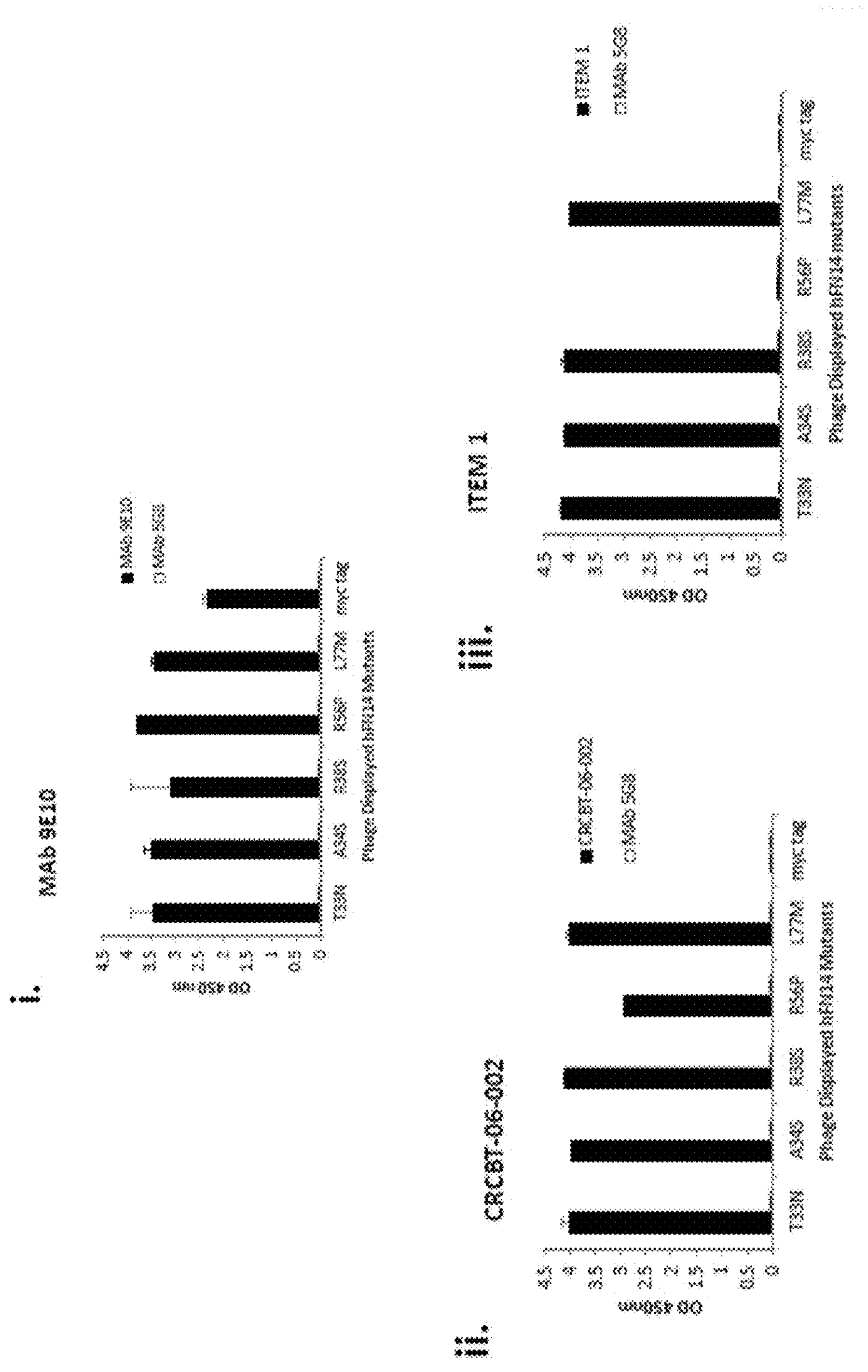

FIG. 22 is a graphical representation showing the reactivity of hFn14 phage constructs with mAb 9E10 control (Panel i), CRCBT-06-002 (Panel II) and ITEM-1 (Panel iii) to phage displayed fragments of Fn14 and mutants thereof. Binding was detected using HRP-conjugated anti-M13-phage antibody and TMB substrate. Optical density at 450 nm was quantified using a Spectramax plate reader. Error bars for each dilution represent the ranges of duplicate values. Methods according to Epitope mapping using phage expressed Fn14—Method 1

Figure 23A:
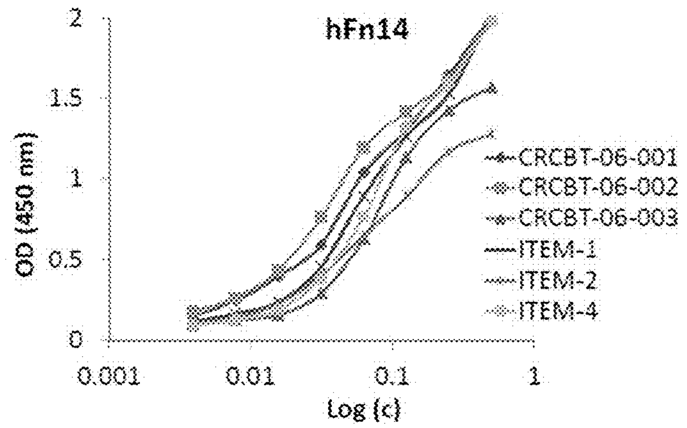

FIG. 23A is a graphical representation showing the reactivity of hFn14 with the anti-Fn14 monoclonal antibodies (as indicated in the Figure) as determined using ELISA. Binding was detected using HRP-conjugated anti-mouse IgG and TMB substrate. Optical density at 450 nm was quantified using a Spectramax spectrophotometer. Antibody concentration in μg/ml.

Figure 23B:
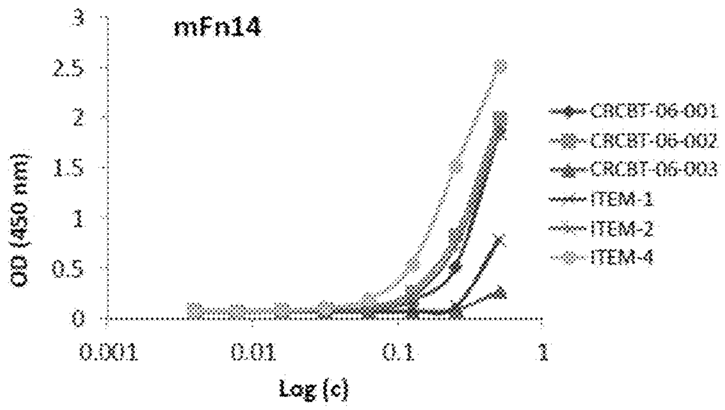
Figure 23C:
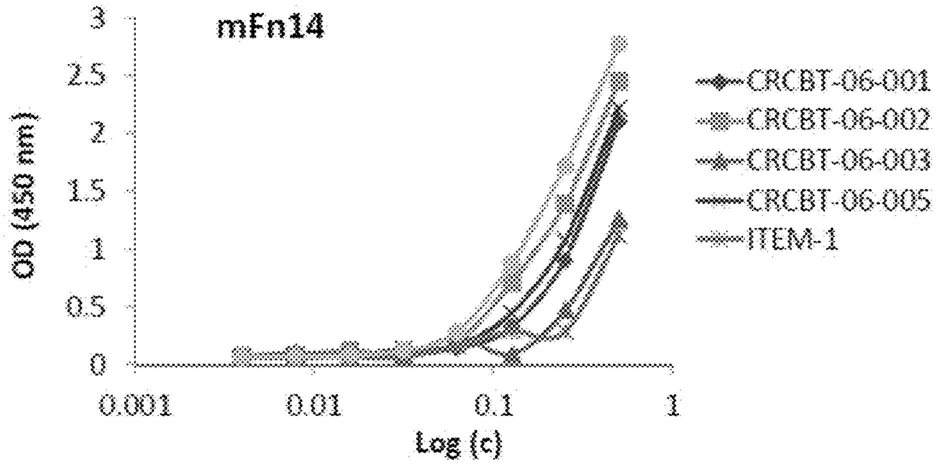
Figure 24A:
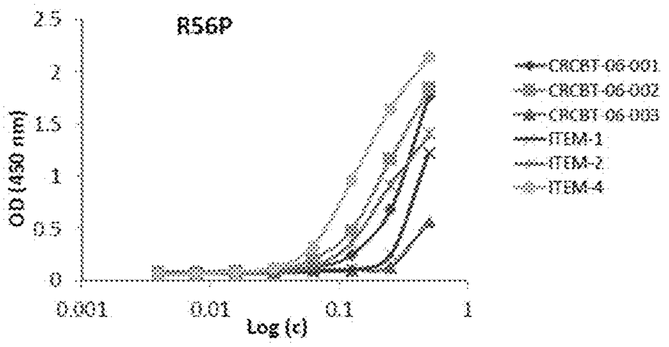
Figure 24B:
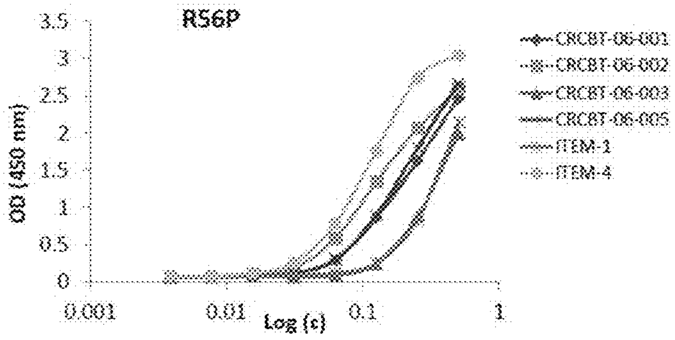
Figure 24C:
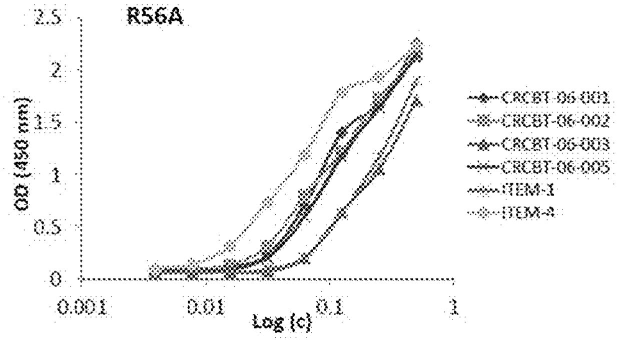
Figure 24D:
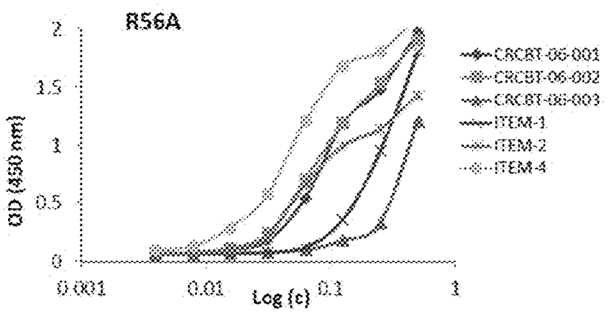
Figure 24E:
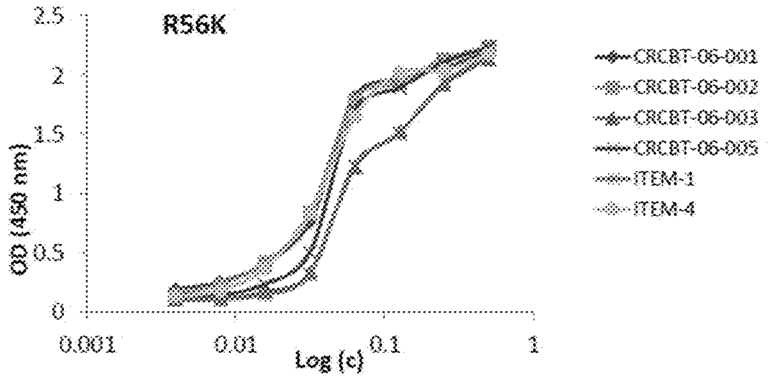
Figure 24F:
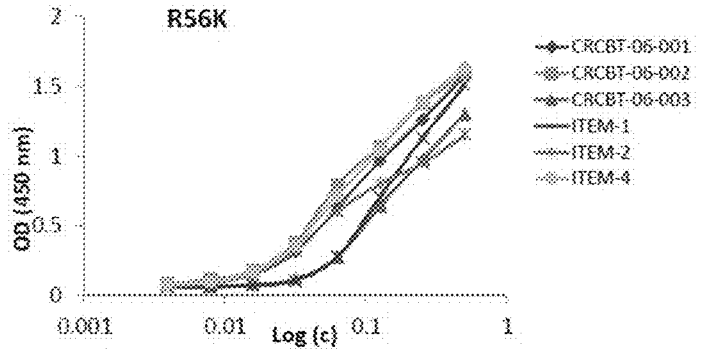

FIGS. 23B and C are graphical representations showing results of similar ELISAs as in FIG. 23A, however using mouse Fn14 to anti-Fn14 monoclonal antibodies (as indicated). Antibody concentration in μg/ml.

includes a series of graphical representations showing binding of antibodies CRCBT- FIGS. 24A-F are graphical representations showing binding of hFn14 mutants mutants R56P, R56A and R56K to anti-Fn14 antibodies. FIGS. 24A and 24B show results of ELISAs showing the reactivity of hFn14 mutant R56P with the anti-Fn14 monoclonal antibodies (as indicated in the Figure). Binding was detected using HRP-conjugated anti-mouse IgG and TMB substrate. Optical density at 450 nm was quantified using a Spectramax spectrophotometer. FIGS. 24C and D show results of ELISAs performed comparing the binding of hFn14 mutant R56A to anti-Fn14 monoclonal antibodies (as indicated). FIGS. 24E and F show results of ELISAs performed comparing the binding of hFn14 mutant R56K to anti-Fn14 monoclonal antibodies (as indicated). Antibody concentration in μg/ml.

Figure 25A:
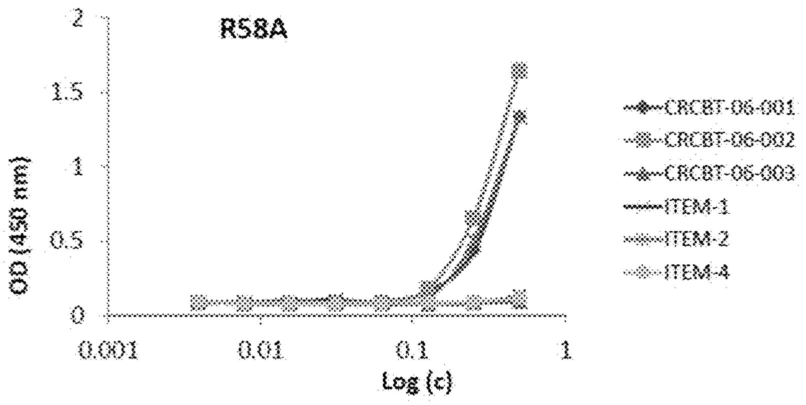

FIGS. 25A and B are graphical representations showing binding of purified hFn14 mutants R58A to anti-Fn14 antibodies (as indicated in the Figure). Binding was detected using HRP-conjugated anti-mouse IgG and TMB substrate. Optical density at 450 nm was quantified using a Spectramax spectrophotometer. Antibody concentration in μg/ml.

Figure 26:
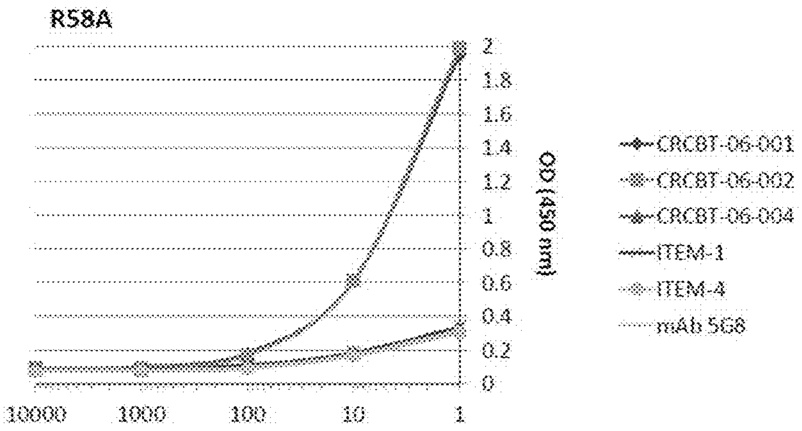

FIG. 26 is a graphical representation showing results of an ELISA testing the reactivity of mutant hFn14 phage construct comprising a R58A mutation with the anti-Fn14 monoclonal antibodies CRCBT-06-001, CRCBT-06-002, CRCBT-06-004 compared to ITEM-1 and ITEM-4. Binding was detected using Biotin-conjugated anti-M13-phage monoclonal antibody followed by HRP-conjugated Streptavidin and TMB substrate. Optical density at 450 nm was quantified using a Spectramax spectrophotometer. Error bars for each dilution represent the standard deviation of duplicate assays. X axis=dilution of phage. Methods according to Epitope mapping using phage expressed Fn14—Method 2

Figure 27A:
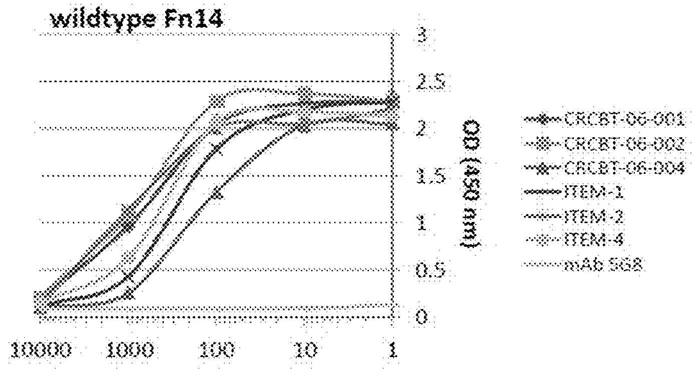
Figure 27B:
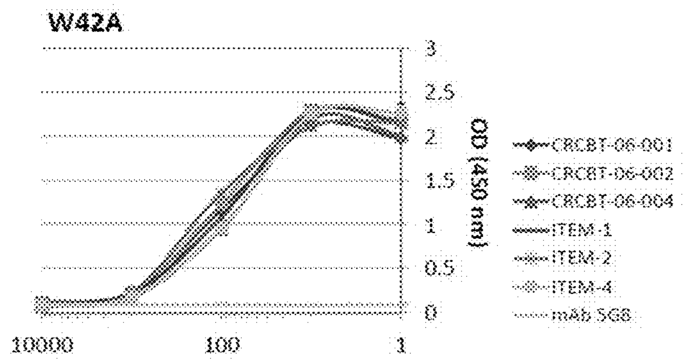
Figure 27C:
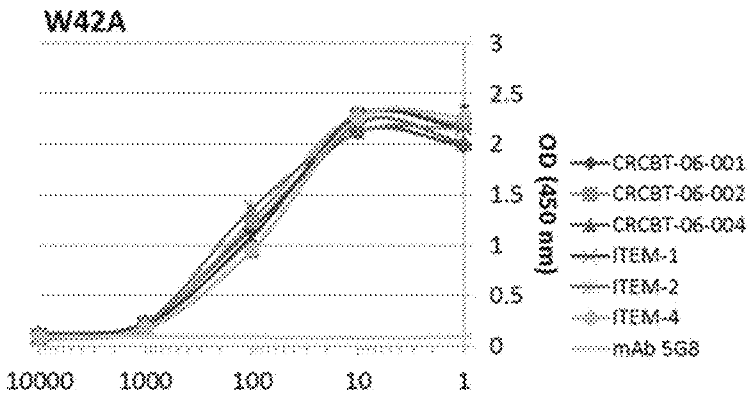
Figure 27D:
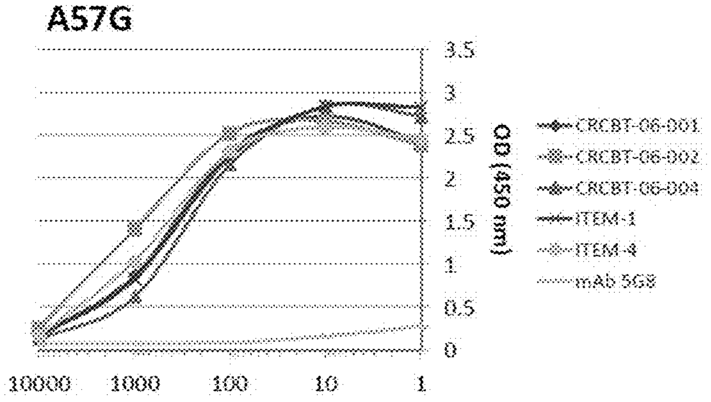
Figure 27E:
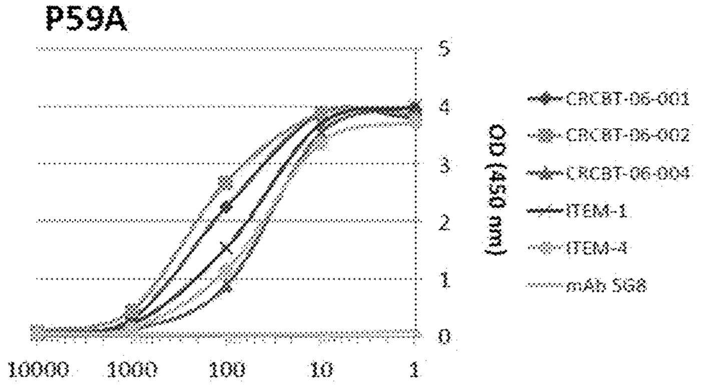
Figure 27F:
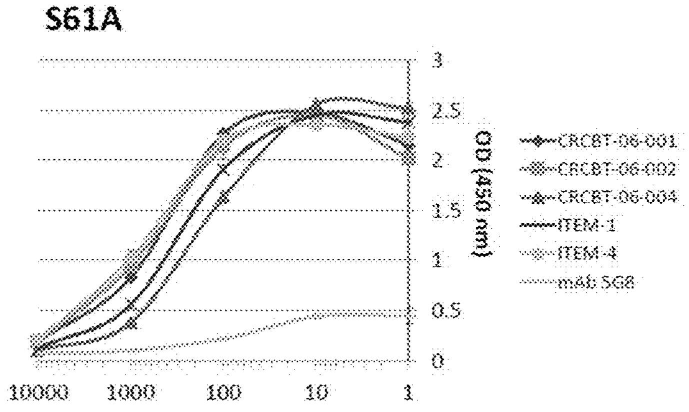
Figure 27G:
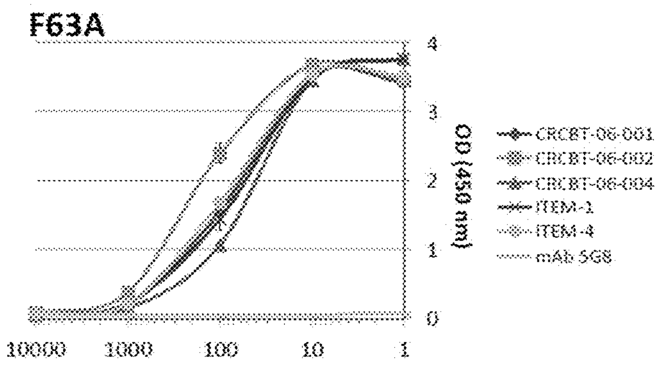
Figure 27H:
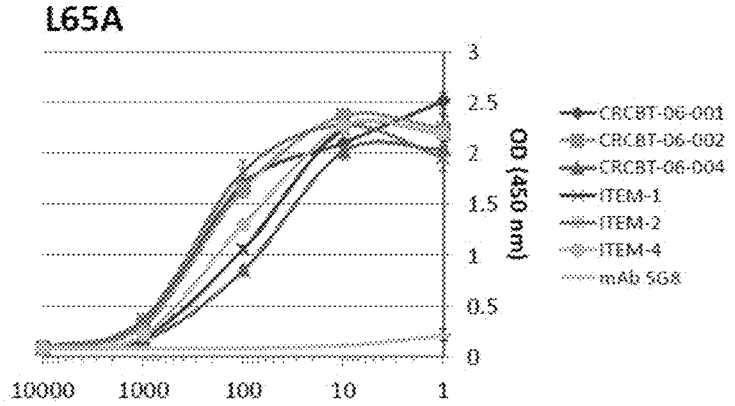

FIG. 27A to H are a series of graphical representations showing binding of phage-displayed mutant hFn14 constructs to anti-Fn14 mAbs. Results are depicted of ELISAs testing the reactivity of mutant hFn14 phage constructs with the anti-Fn14 monoclonal antibodies CRCBT-06-001, CRCBT-06-002, CRCBT-06-004 compared to ITEM-1 and ITEM-4 and in some cases ITEM-2. For mutants P59A and F63A, binding was detected using HRP-conjugated anti-M13-phage polyclonal IgG and TMB substrate. For all other mutants binding was detected using Biotin-conjugated anti-M13-phage monoclonal antibody followed by HRP-conjugated Streptavidin and TMB substrate. Optical density at 450 nm was quantified using a Spectramax spectrophotometer. Error bars for each dilution represent the standard deviation of duplicate assays. FIG. 27A. wild type Fn14, FIG. 27B. W42A, FIG. 27C. S54A, FIG. 27D. A57G, FIG. 27E. P59A, FIG. 27F. S61A, FIG. 27G. F63A, FIG. 2711. L65A. In all cases error bars represent the standard deviation. X axis=dilution of phage. Methods according to Epitope mapping using phage expressed Fn14—Method 2

Figure 28A:
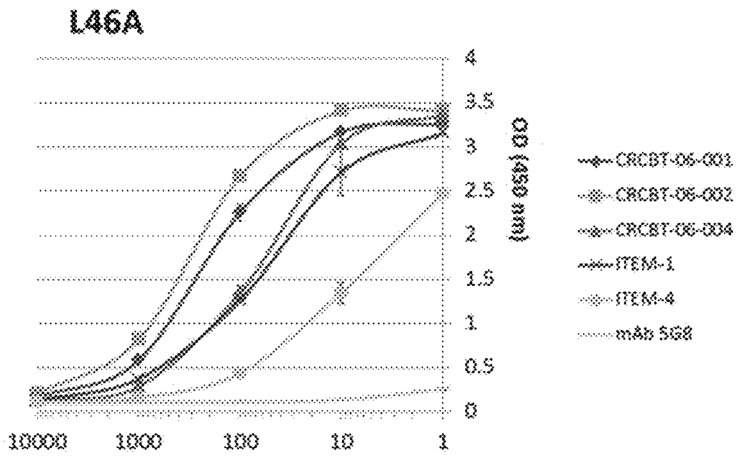
Figure 28B:
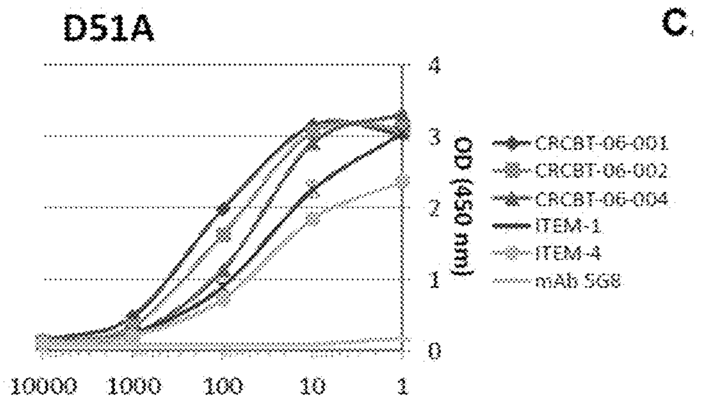
Figure 28C:
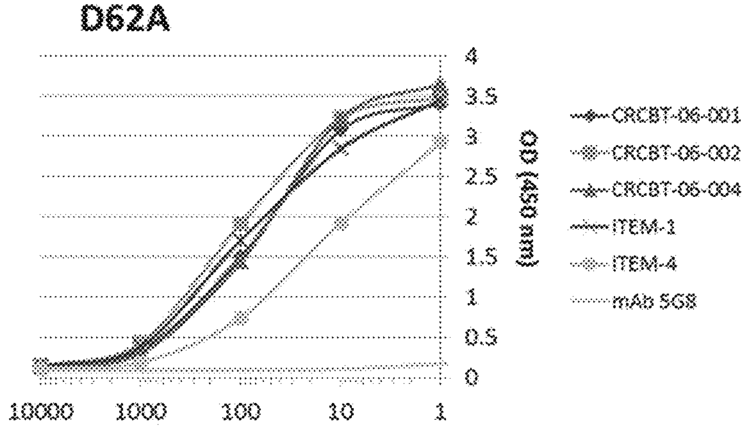

FIG. 28A to C are a series of graphical representations showing binding of phage-displayed mutant hFn14 constructs to anti-Fn14 mAbs. ELISAs showing the reactivity of mutant hFn14 phage constructs with the anti-Fn14 monoclonal antibodies CRCBT-06-001, CRCBT-06-002, CRCBT-06-004 compared to ITEM-1 and ITEM-4. Binding was detected using Biotin-conjugated anti-M13-phage monoclonal antibody followed by HRP-conjugated Streptavidin and TMB substrate. Optical density at 450 nm was quantified using a Spectramax spectrophotometer. Error bars for each dilution represent the standard deviation of duplicate assays. FIG. 28A. L46A, FIG. 28B. D51A and FIG. 28C. D62A. In all cases error bars represent the standard deviation. X axis=dilution of phage. Methods according to Epitope mapping using phage expressed Fn14—Method 2.

Figure 29A:
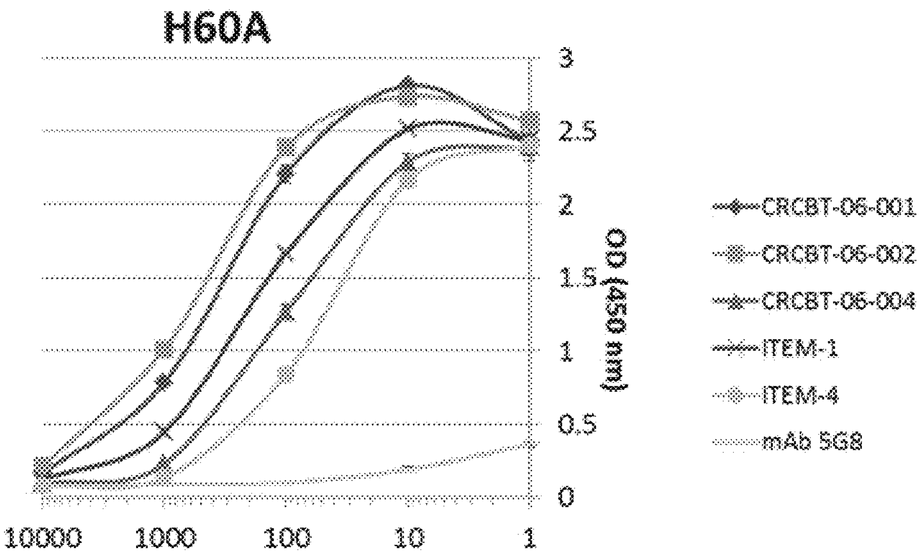
Figure 29B:
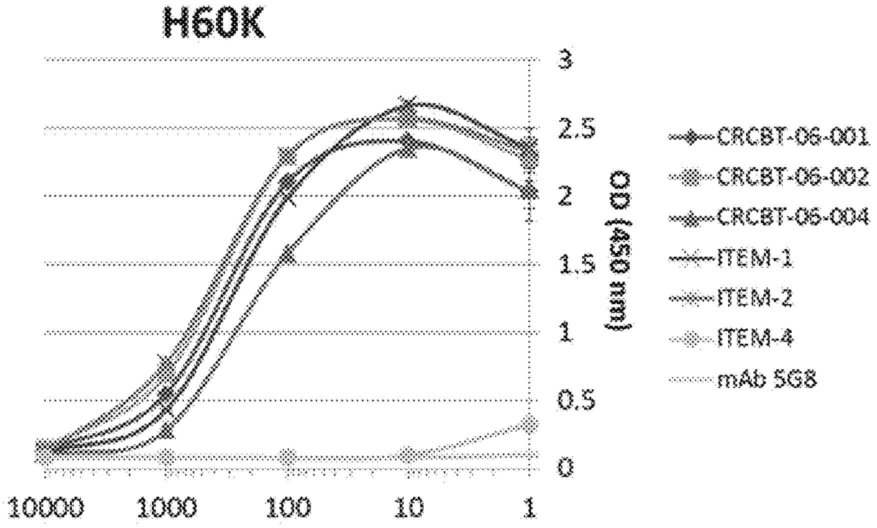

FIGS. 29A and 29B are graphical representations showing binding of phage-displayed mutant hFn14 constructs to anti-Fn14 mAbs. ELISAs showing the reactivity of mutant H60A and H60K hFn14 phage constructs with the anti-Fn14 monoclonal antibodies CRCBT-06-001, CRCBT-06-002, CRCBT-06-004 compared to ITEM-1 and ITEM-4. ITEM-2 was assessed on H60K. Binding was detected using Biotin-conjugated anti-M13-phage monoclonal antibody followed by HRP-conjugated Streptavidin and TMB substrate. Optical density at 450 nm was quantified using a Spectramax spectrophotometer. Error bars for each dilution represent the standard deviation of duplicate assays. X axis=dilution of phage. Methods according to Epitope mapping using phage expressed Fn14—Method 2.

Figure 30A:
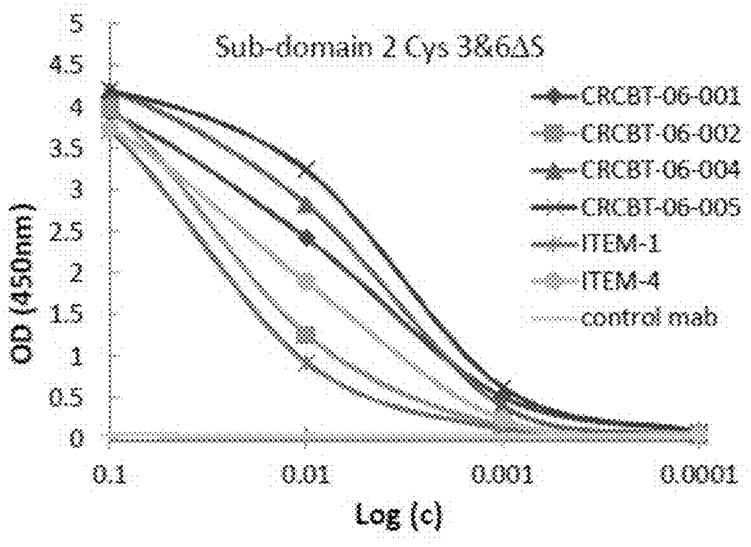
Figure 30B:
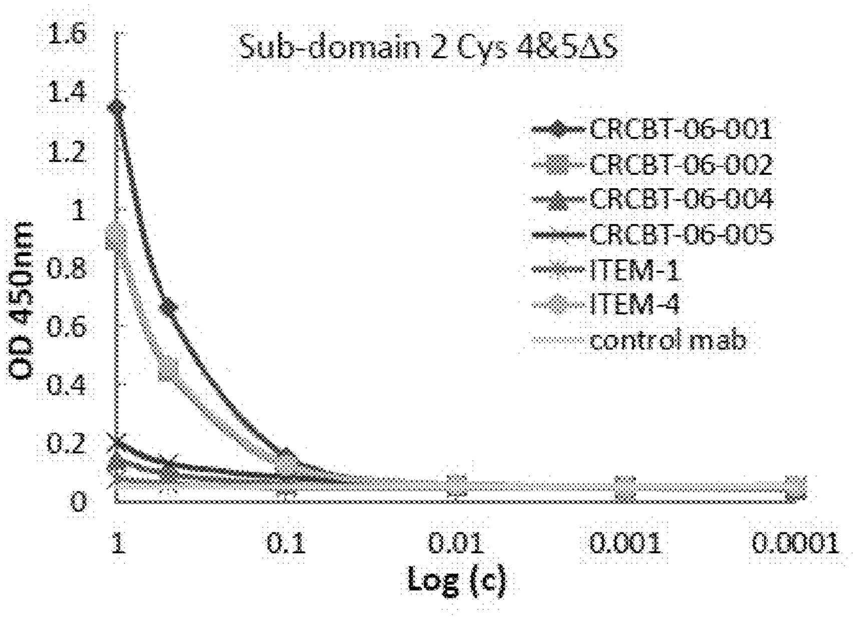

FIGS. 30A and 30B are graphical representations showing binding of anti-Fn14 antibodies to disulfide bond mutant peptides. FIG. 30A shows results of ELISAs in which anti-Fn14 antibodies were titrated (0.1-0.0001 μg/ml) and binding to sub-domain 2 cys3&6ΔS mutant was assessed. FIG. 30B is similar to FIG. 27A, however binding to sub-domain 2 cys4&5ΔS mutant was assessed (1-0.0001 μg/ml).

Figure 31:
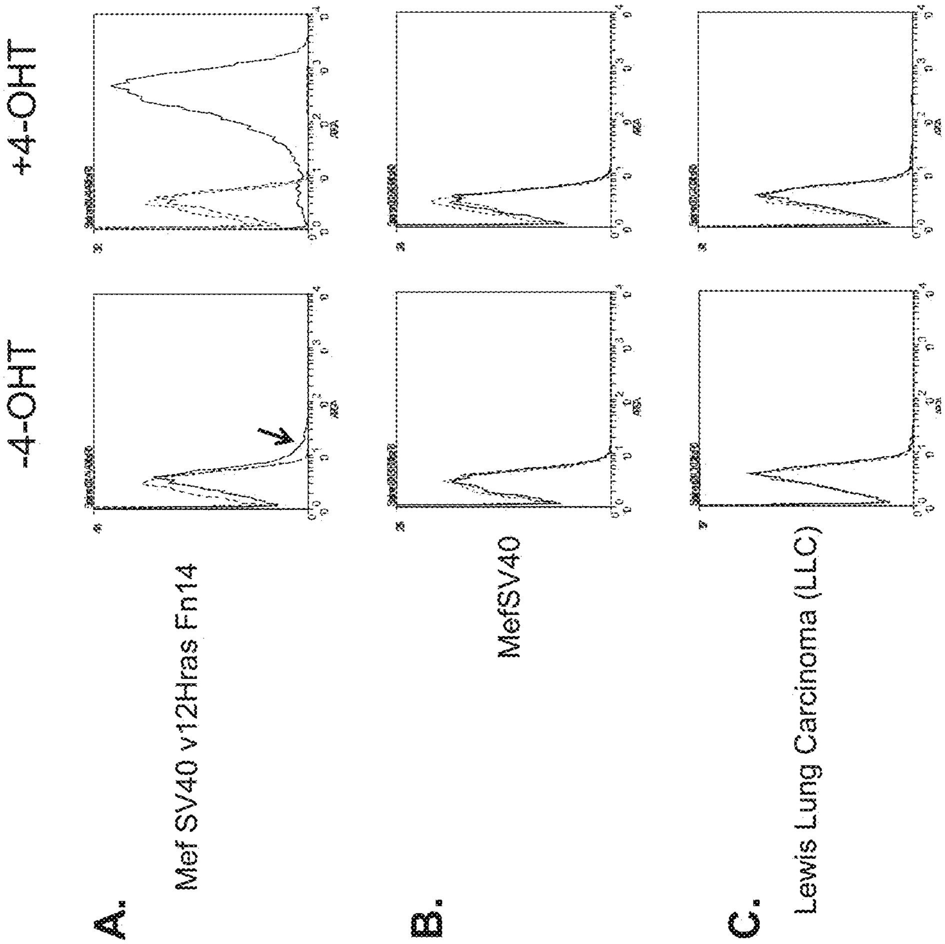

FIG. 31 is a series of graphical representations showing staining of in vitro cultured cells for Fn14 expression levels. Cells were cultured in the presence or absence of 100 nM 4-OHT for 24 hours (Panel A shows results for MEF SV40v12Hras Fn14, Panel B shows results for MEF SV40 and Panel C shows results for Lewis lung carcinoma). Cells were harvested and stained for hFn14 expression using a commercially available anti-Fn14 antibody followed by an anti-mouse Alexafluor-647 antibody for detection by flow cytometry. Staining with anti-Fn14 indicated by solid trace, secondary antibody control staining by hashed trace and unstained cells by dotted trace.

Figure 32:
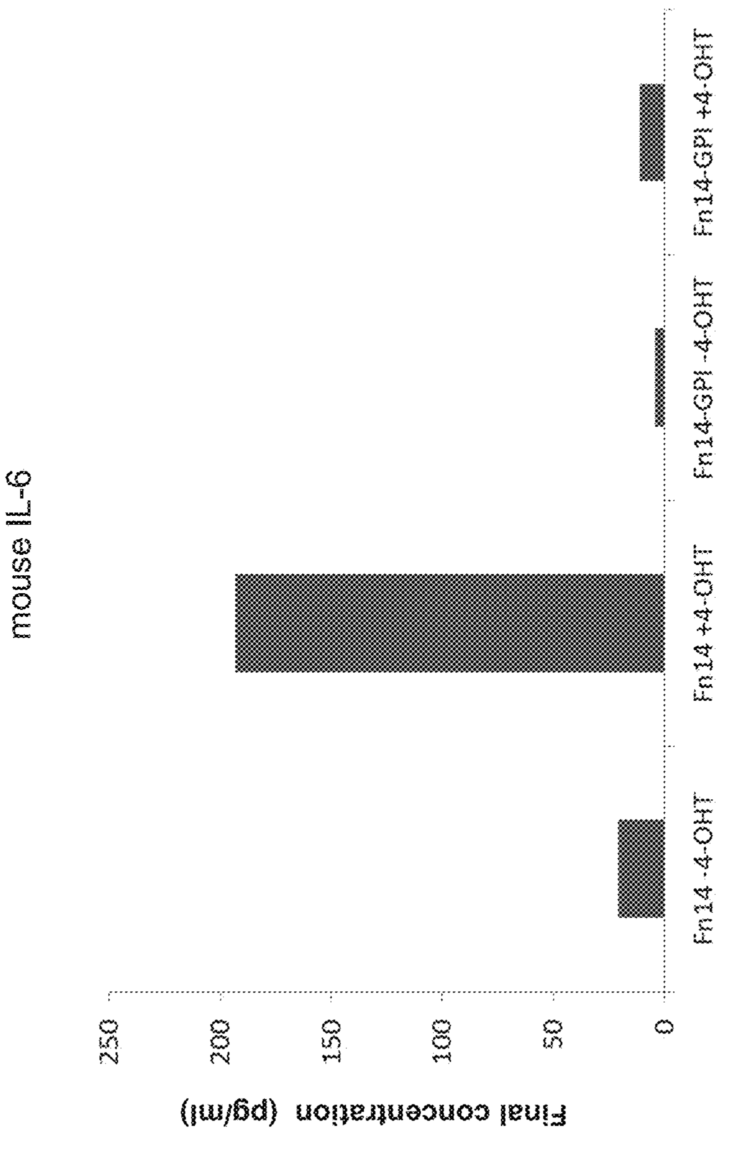

FIG. 32 is a series of graphical representations showing analysis of cytokine secretion by MEF tumor cell lines. MEF tumor cell lines containing Fn14 or Fn14-GPI were induced with 4-OHT or uninduced. After 48 hours under normal growth condition the media from cells was harvested and the levels of IL-6 were assessed using BD CBA Mouse Inflammation Kit and quantitative analysis performed using FCAP Array software (BD Biosciences).

Figure 33:
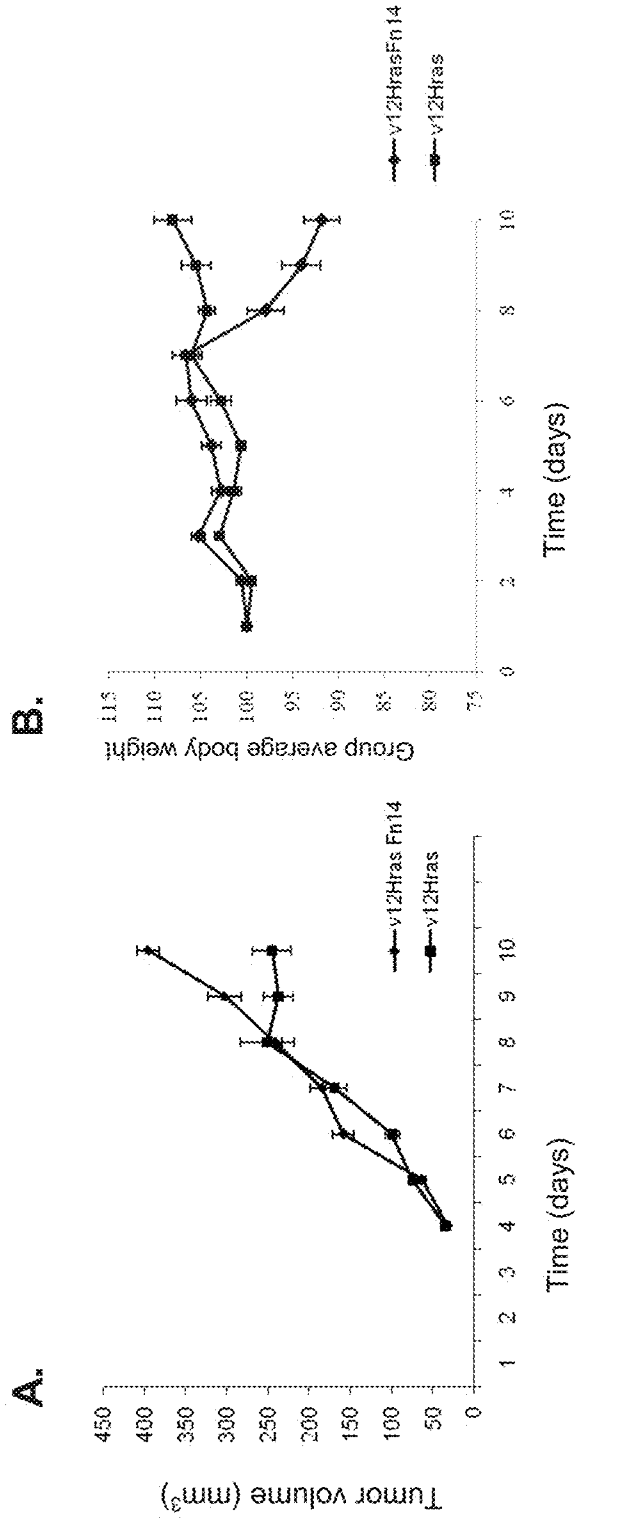

FIG. 33 is a series of representations showing creation of an Fn14 in vivo tumor model. Female C57BL/6 mice were injected with tumor cells on day 1. Panel A is a graphical representation showing results of measurements taken as tumors formed and the tumor volume for each mouse was calculated ([length*width$^2$]/2) and group averages were graphed. Panel B is a graphical representation showing results of analysis in which the body weight for each mouse assessed daily and standardized against day 1 weight as 100. The average for each group was calculated and graphed. Groups include tumors containing wildtype hFn14 (v12Hras Fn14; ♦; n=6) or parent tumor cell line (v12Hras; ■; n=6). Experiments were repeated reproducibly a number of times, data from one experiment presented. Error bars represent the SEM. Note—Panel B Y axis does not begin at 0.

FIG. 34A is a series of schematic representation of the sequence of the extracellular region of human Fn14 (BOLD) fused to the GPI anchor coding region of TrailR3 (ITALICS) to create hFn14-GPI. The predicted GPI attachment serine residue is indicated in bold text with an arrow. Underlined region indicates the Fn14 signal sequence.

Figure 34B:
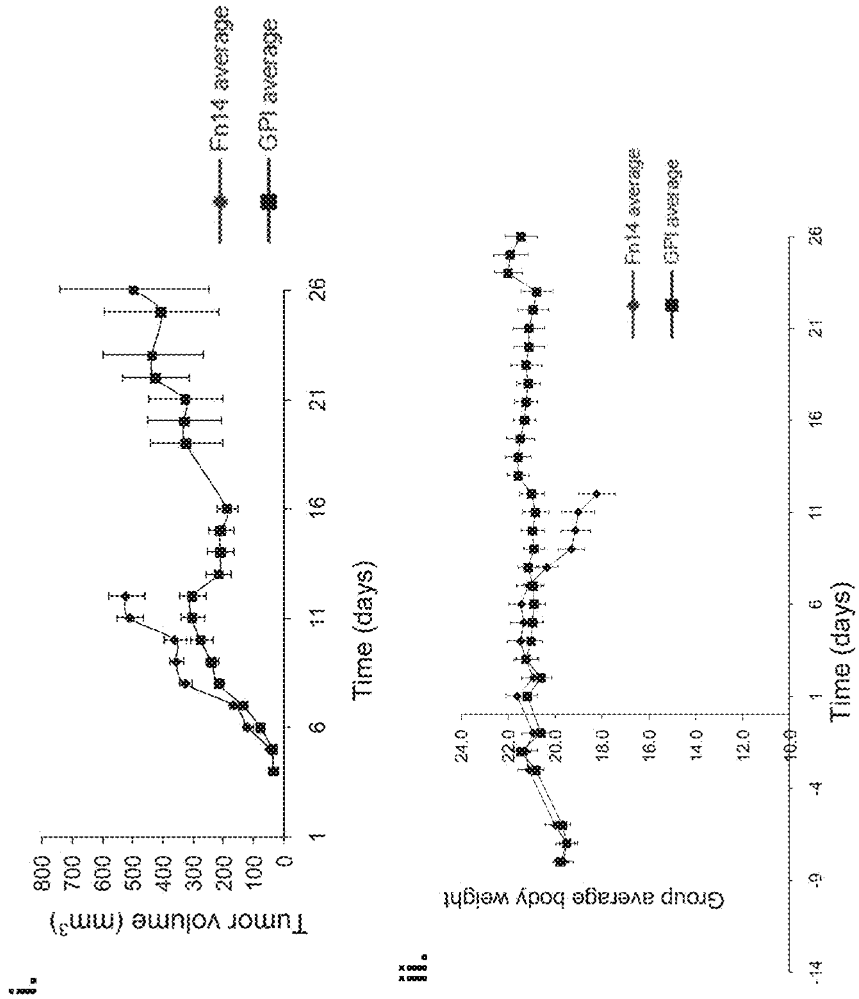

FIG. 34B includes two graphical representations showing results of introducing hFn14-expressing tumors or non-signaling hFn14-expressing tumors into mice. Female C57BL/6 mice were injected with tumor cells on day 1. Groups include tumors containing wildtype Fn14 (♦; n=14) or Fn14-GPI tumors (■; n=14). Panel i shows results of analysis performed as tumors formed, and measurements were taken and the tumor volume for each mouse was calculated ([length*width$^2$]/2). Panel ii shows results of analysis in which the body weight for each mouse. The group averages were calculated and graphed over time. Note—Panel ii Y axis does not begin at 0. Data was graphed as group averages. Experiments were repeated reproducibly a number of times, data from one representative experiment are presented. Error bars represent the SEM.

Figure 35A:
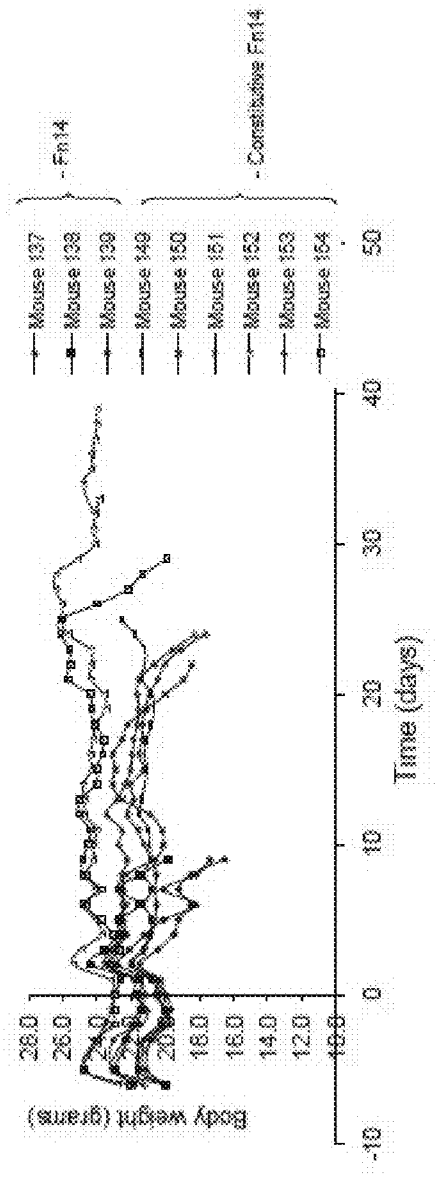
Figure 35B:
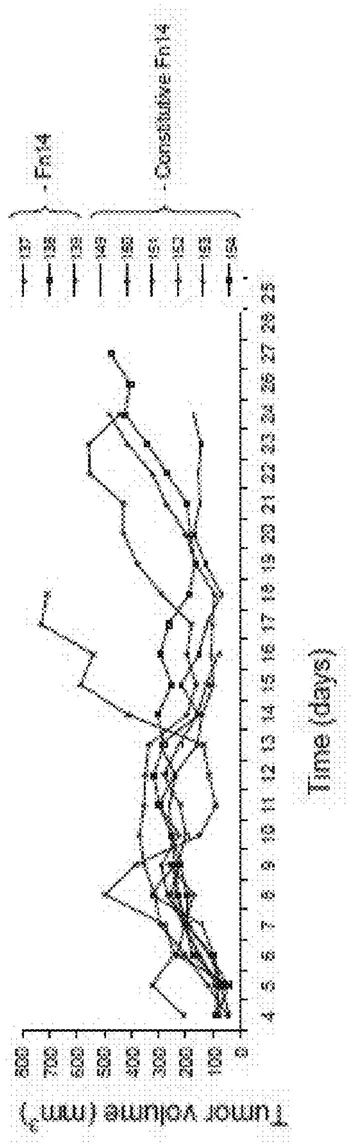

FIGS. 35A and B include two graphical representations showing effects of tumors constitutively expressing human Fn14. Female C57BL/6 mice were injected with tumor cells on day 1. Groups include tumors containing low level Fn14 (n=3, mice 137-139) and constitutively expressed Fn14 (n=6, mice 149-154) as indicated beside legend. FIG. 35A shows results of analysis in which the body weight for each mouse was assessed daily and graphed over time. Note—FIG. 35A Y axis does not begin at 0. FIG. 35B shows results of measurements of tumor volume. Measurements were taken and the tumor volume for each mouse was calculated ([length*width$^2$]/2) and graphed individually over time.

Figure 36:
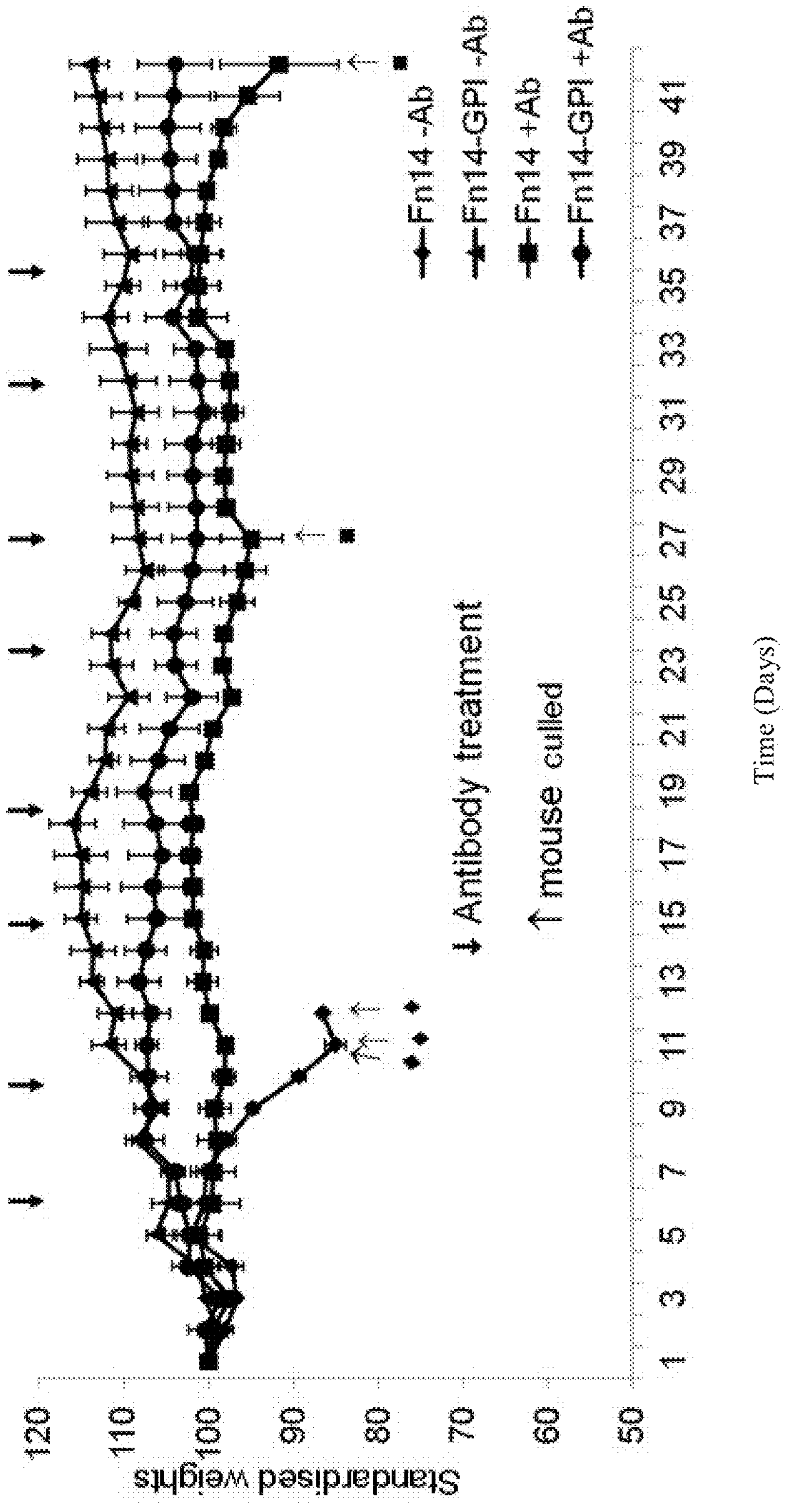

FIG. 36 is a graphical representation showing results of treatment of hFn14 tumors with CRCBT-06-001. Female C57BL/6 mice were injected with either hFn14 or hFn14-GPI tumor cells on day 1. On day 6 each group was segregated evenly and half were treated twice a week with an IP injection of CRCBT-06-001 (10 mg/kg) for a total of 4 weeks. The other half of the group received no treatment. Body weight was measured daily, standardized against starting weight as 100 and group averages were graphed. ■=Fn14 antibody treated, ♦=Fn14 untreated, ●=Fn14-GPI antibody treated, ▲=Fn14-GPI untreated. Treatment days are indicated by a black downward arrow (↓). Upward pointing arrows indicate a mouse was euthanized, the symbol underneath indicating from which group. Each group n=3 and the error bars represent SEM. Note—Y axis does not begin at 0.

Figure 37A:
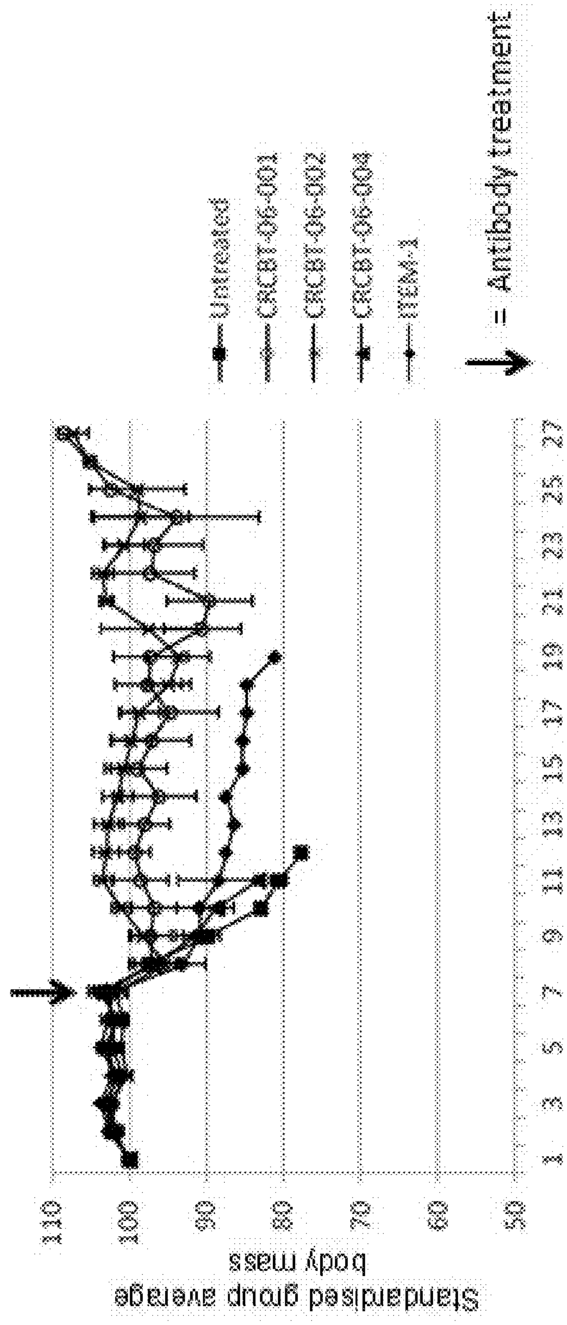

FIG. 37A is a graphical representation showing results of treatment of hFn14 tumor mice with CRCBT-06-001, CRCBT-06-002, CRCBT-06-004 or ITEM-1. Female C57BL/6 mice were injected with Fn14 tumor cells on day 1. On day 7, groups of mice (n=6) were given a single IP injection of purified antibody (5 mg/kg) or no treatment. A. Body weight was measured daily and graphed as weight standardised against starting weight as 100% and graphed as group average. Treatment day indicated by a black downward arrow (t). Error bars represent SEM. Note—Y axis does not cross at 0.

Figure 37B:
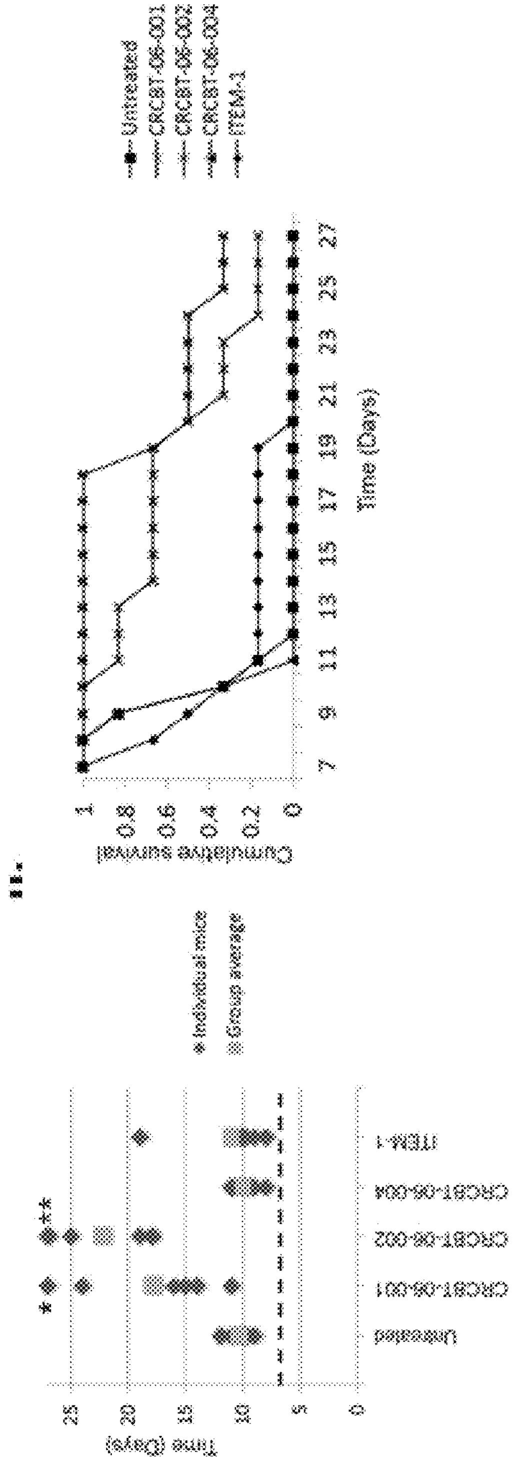

FIG. 37B includes two graphical representations showing survival of hFn14 tumor mice with CRCBT-06-001, CRCBT-06-002, CRCBT-06-004 or ITEM-1. The left-hand panel indicates the day each mouse was killed and the group average survival day. Note * indicates a data point represents healthy mice with no weight loss at the termination of the experiment (day 27). Hashed line (- -) represents antibody treatment (day 7). The right-hand panel is a Kaplan-Meier curve showing survival.

Figure 38:
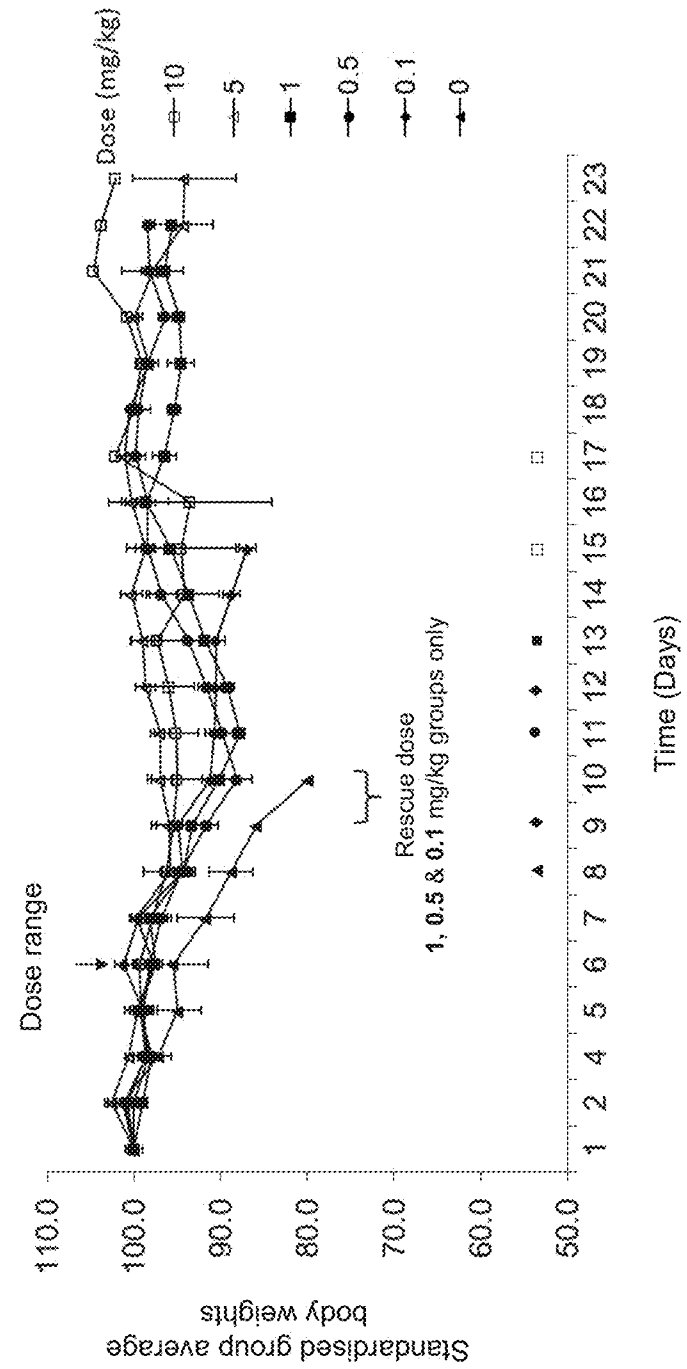

FIG. 38 is a graphical representation showing CRCBT-06-001 dose response and rescue of mice from weight loss and illness. Female C57BL/6 mice were injected with hFn14 tumor cells on day 1. On day 6 groups were treated with a single IP injection of CRCBT-06-001 (0-10 mg/kg). Untreated mice received a vehicle injection (PBS). On day 9 or 10 as indicated, mice exhibiting obvious weight loss were treated with a single IP injection of 10 mg/kg CRCBT-06-001. Body weight was measured daily, standardized against the starting weight (day 1) as 100 and group averages were graphed. The standardized weights for each group were graphed as group averages. Error bars represent the SEM. Antibody dose treatment day is indicated by a black downward arrow. Each group n=3. Symbols represent a mouse was euthanized from the group designated with that symbol. Note—Y axis does not begin at 0.

Figure 39A:
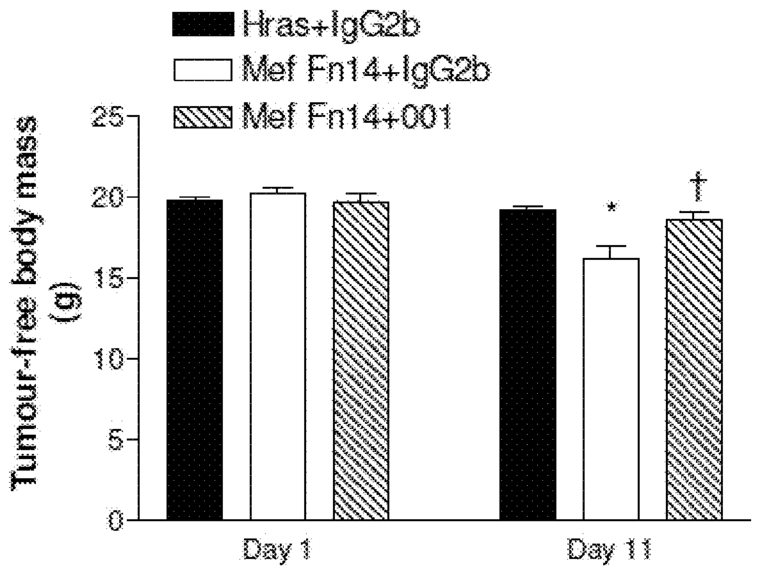

FIG. 39A is a graphical representation showing effects of CRCBT-06-001 on body mass in mice injected with MEF Fn14 cells. On day 1, female 11 week old C57BL/6 mice were given a single subcutaneous injection of MEF Fn14 or with the parent cell line (Hras). On day 6, mice were given a single intraperitoneal injection of IgG2b isotype control antibody (Hras+IgG2b, MEF Fn14+IgG2b, n=8/group) or CRCBT-06-001 (MEF Fn14+001, n=8). Body mass was measured on days 1 and 11. Data are means±SEM. *P<0.01 vs. Hras+IgG2b; †P<0.05 vs. MEFFn14+IgG2b.

Figure 39B:
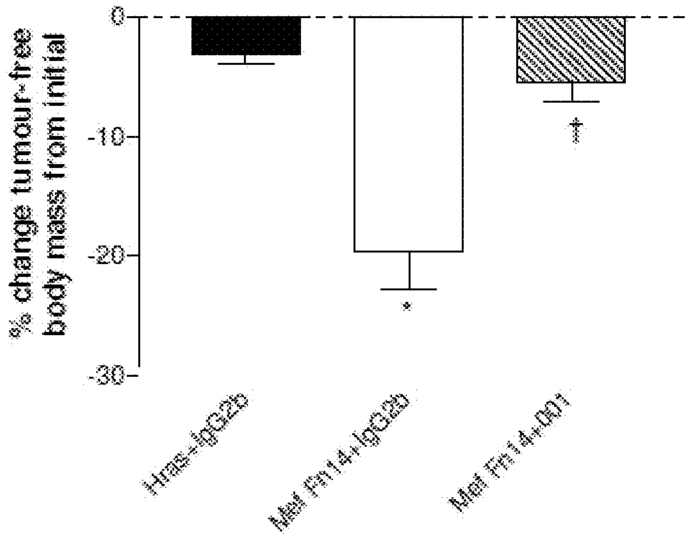

FIG. 39B is a graphical representation showing effects of CRCBT-06-001 on tumor-free body mass in mice injected with MEF Fn14 cells. On day 11, the tumor from mice described in relation to FIG. 28A was surgically excised and weighed allowing calculation of the percentage change in tumor-free body mass from pre-inoculation (B). Data are means±SEM. *P<0.01 vs. Hras+IgG2b; †P<0.05 vs. MEFFn14+IgG2b.

Figure 40A:
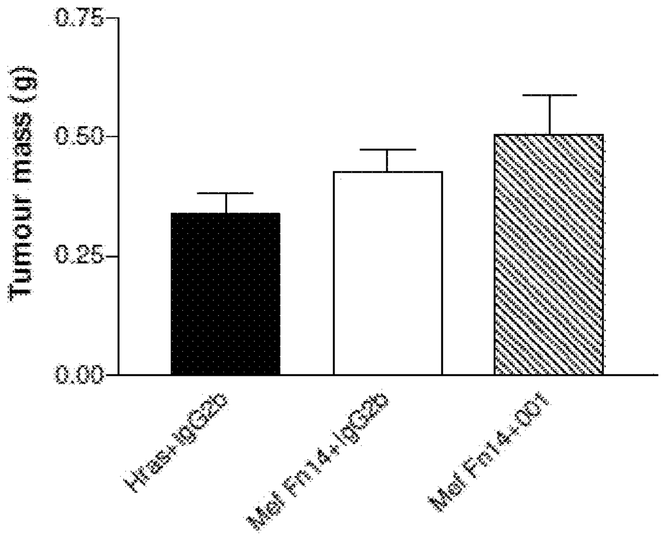

FIG. 40A is a graphical representation showing effects of CRCBT-06-001 on tumor mass in mice injected with MEF Fn14 cells. On day 11, the tumor from mice described in relation to FIG. 39A was surgically excised and weighed allowing calculation of the percentage change in tumor mass.

Figure 40B:
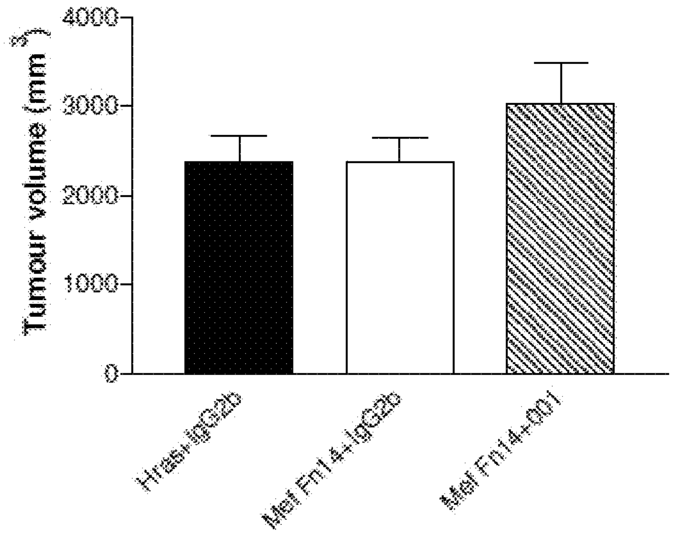

FIG. 40B is a graphical representation showing effects of CRCBT-06-001 on tumor volume in mice injected with MEF Fn14 cells. On day 11, the tumor from mice described in relation to FIG. 39A was surgically excised and tumor volume calculated.

Figure 41A:
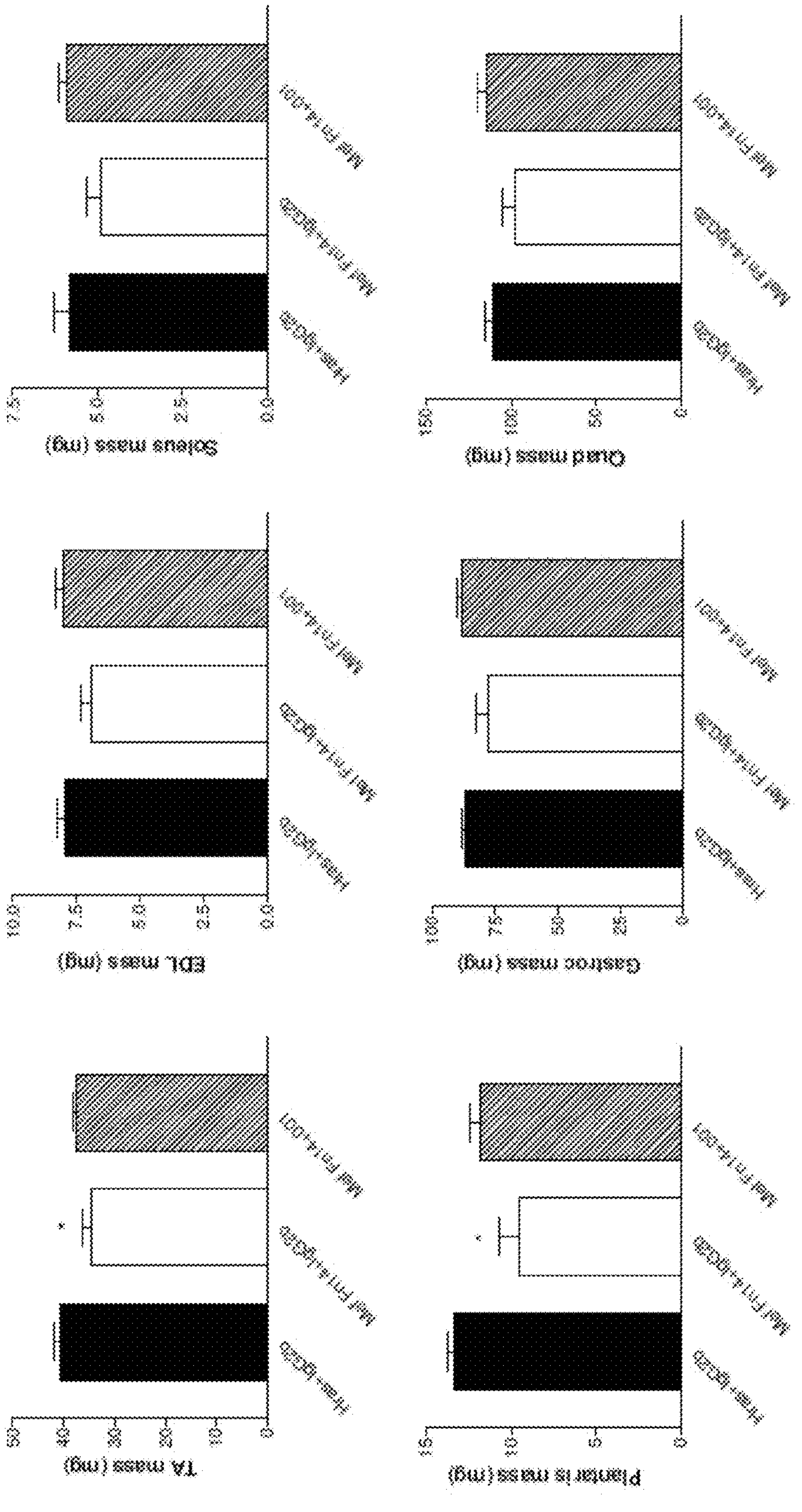

FIGS. 41A and B are a series of graphical representations showing effects of CRCBT-06-001 on muscle mass in mice injected with MEF Fn14 cells. On day 11, selected hindlimb muscles (as indicated in FIG. 41A); and epididymal fat and the heart (as indicated in FIG. 42B) were excised and weighed on an analytical balance. EDL, extensor digitorum longus; Plant, plantaris; TA, tibialis anterior; Gastroc, gastrocnemius; Quad, quadriceps. Data are means±SEM. *P<0.05 vs. Hras+IgG2b; †P<0.05 vs. MEF Fn14+IgG2b.

Figure 42A:
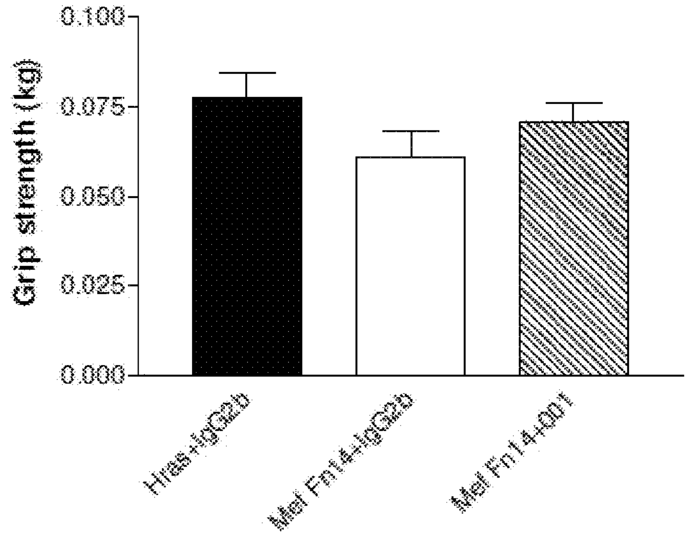
Figure 42B:
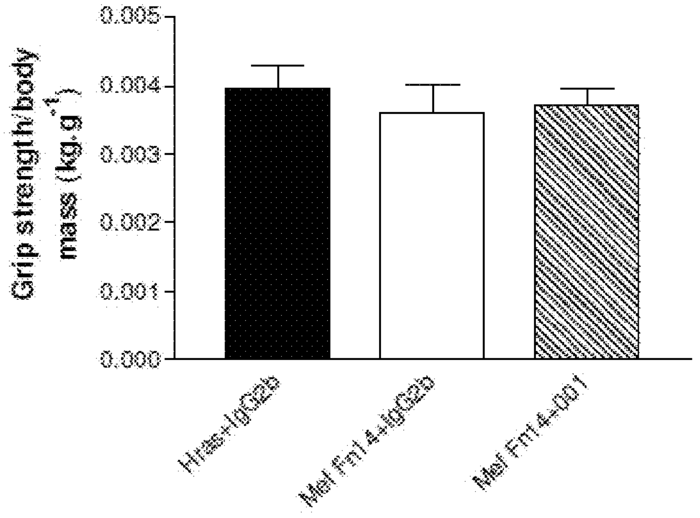

FIGS. 42A and B are graphical representations showing effects of CRCBT-06-001 on whole body strength in mice injected with MEF Fn14 cells. On day 11, whole body strength was assessed using a grip strength meter and expressed in absolute values (FIG. 42A) and normalised to body mass (FIG. 42B). Data are means±SEM.

FIGS. 43A-D are graphical representations showing effects of CRCBT-06-001 effects on functional properties of tibialis anterior (TA) muscles in situ in mice injected with MEFFn14. On day 11, peak twitch force (FIG. 43A), peak tetanic force (FIG. 43B), frequency-force relationship (FIG. 43C) and force production during and following 4 minutes of fatiguing intermittent stimulation (FIG. 43D) was assessed in TA muscles in situ. Data are means±SEM. $^{a}$P<0.05 main effect Hras+IgG2b vs MEF Fn14+IgG2b.

Figure 44:
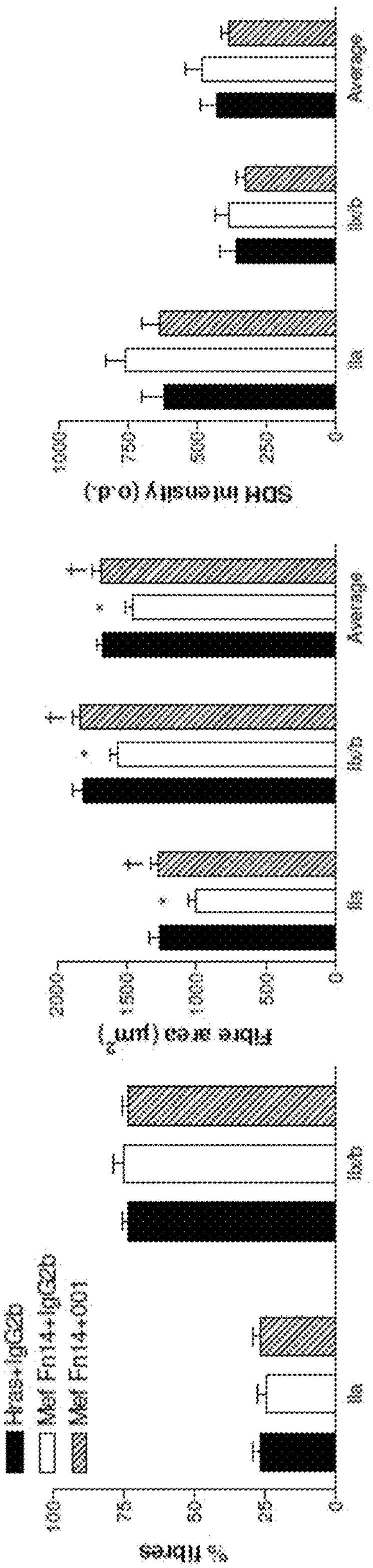

FIG. 44 is a series of graphical representations showing effects of CRCBT-06-001 on fibre size, fibre type composition and fibre oxidative enzyme capacity in tibialis anterior (TA) muscles from mice injected with MEF Fn14 cells. On day 11, TA muscles were excised and frozen for subsequent histological analyses. Quantification of laminin, N2.261 and SDH based on reaction intensity facilitated determination of the proportion of type IIa and type IIx/b fibres (non-N2.261 reacting fibres) (left panel), the area of the type IIa and type IIx/b fibres (center panel) and the SDH activity based on reaction intensity of the type IIa and type IIx/b fibres (right panel) are shown. Data are means±SEM. *P<0.05 vs. Hras+IgG2b; †P<0.05 vs. MEF Fn14+IgG2b.

Figure 45A:
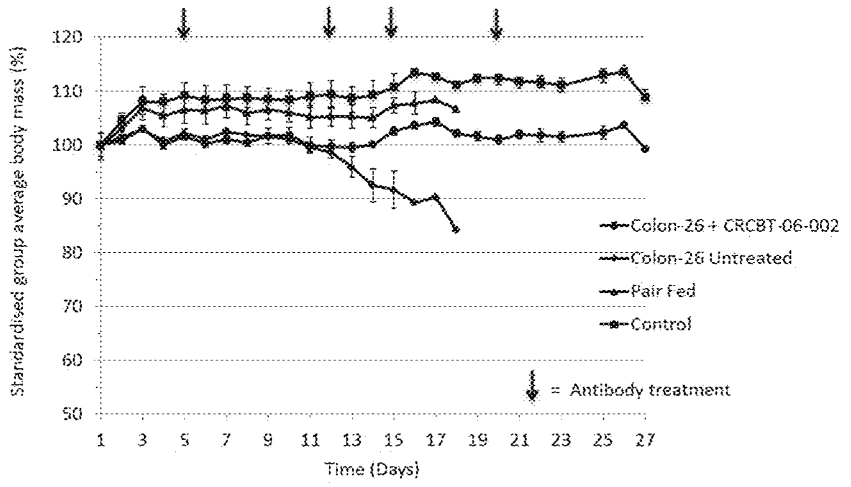

FIGS. 45A and B are graphical representations showing the effect of CRCBT-06-002 effect on Colon-26 model for cancer cachexia. Male 11 week old CD2F1 mice were inoculated with $1\times10^6$ cells s/c in the flank on day 1 to form solid tumors. Groups included Colon-26 Untreated (n=5), Colon-26+CRCBT-06-002 treated (n=5), Pair fed (n=4) and non-tumor untreated controls (n=3). On days 5, 12, 15 and 20, mice were treated with an IP injection of 10 mg/kg CRCBT-06-002 (4). Untreated mice received no treatment. For FIG. 45A, body mass was measured daily and graphed as group average weights standardised against starting weight (day 1) as 100%. For FIG. 45B daily survival after initiation of antibody treatment (day 5) was graphed as a Kaplan-Meier curve. Note—two antibody-treated mice were killed due to maximal tumor volume endpoint and therefore not included in this graph.

Figure 46A:
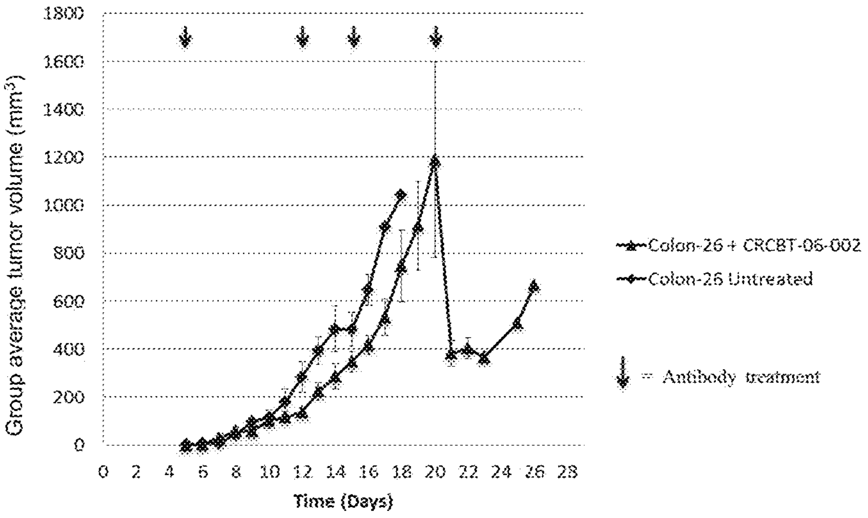
Figure 46B:
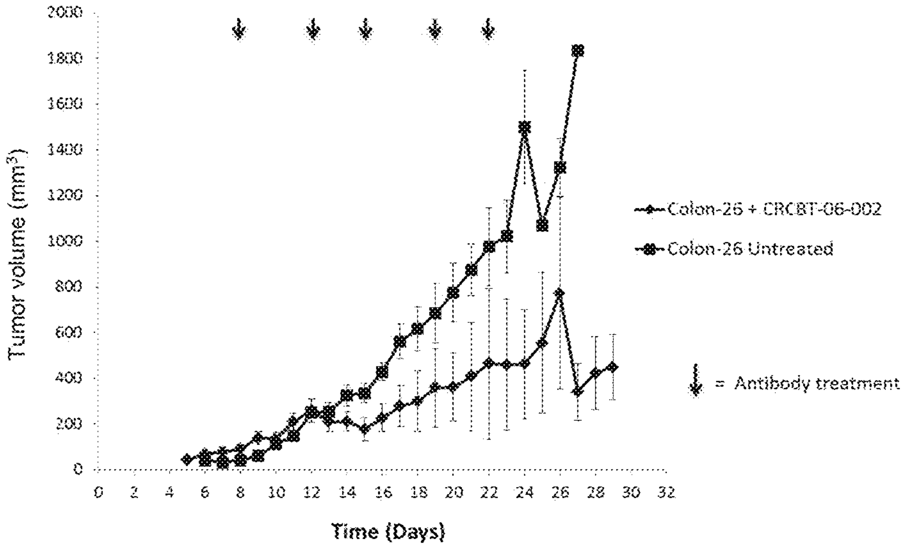

FIGS. 46A and B are graphical representations showing the effect of CRCBT-06-002 effect on tumors in the Colon-26 model for cancer cachexia. For FIG. 46A, as tumors formed, measurements were taken and the tumor volume for each mouse was calculated ([length*width$^2$]/2). Data was graphed group averages Error bars represent the SEM. The apparent drop in tumour volume (from about 1200 to 400 mm$^3$) at day 20 reflects the reduction in group number due to killing of a number of mice that had reached the maximum allowed tumour size. The surviving mice at 21 had average tumour volume of about 400 mm$^3$. For FIG. 46B, female 9-10 week old Balb/c mice were inoculated with $1\times10^6$ cells s/c in the flank on day 1 to form solid tumors. Groups included Untreated (n=5) and CRCBT-06-002 treated (n=5). On days 8, 12, 15, 19 and 22, mice were treated with an IP injection of 10 mg/kg CRCBT-06-002 as indicated. As tumors formed, measurements were taken and the tumor volume for each mouse was calculated. Data is graphed for group averages. Error bars represent the SEM.

Figure 47A:
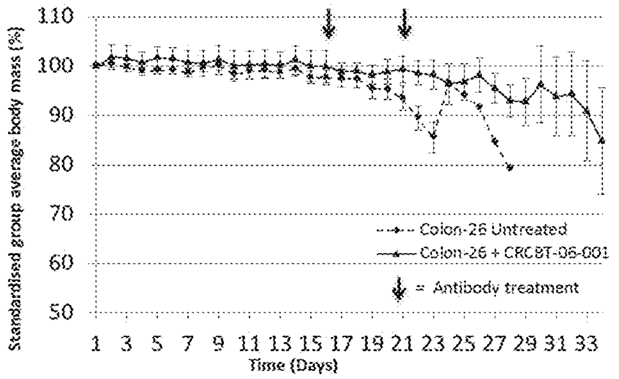
Figure 47B:
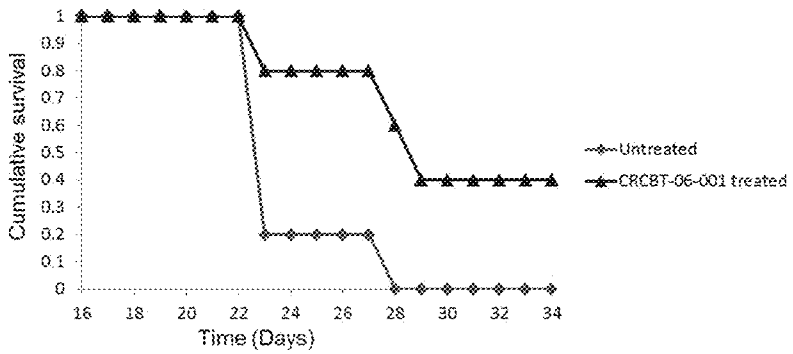
Figure 47C:
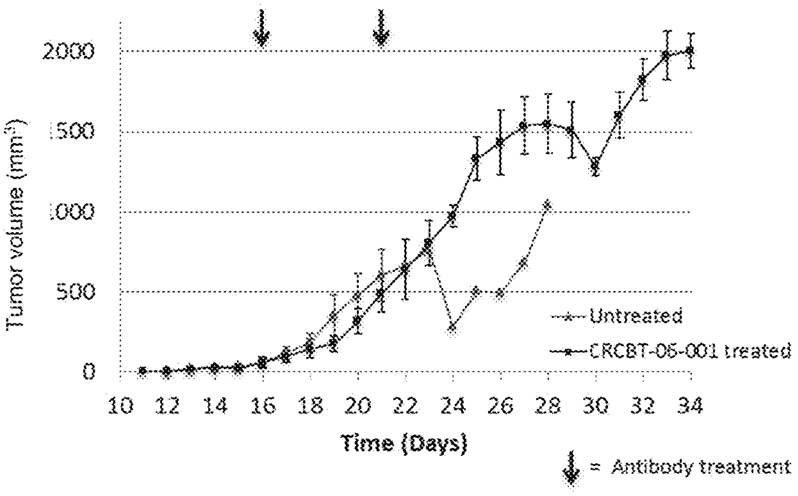

FIG. 47A to C are graphical representations showing the effect of CRCBT-06-001 on CD2F1 mice administered Colon-26 cells. Male 12 week old CD2F1 mice were inoculated with $1\times10^6$ cells s/c in the flank on day 1 to form solid tumors. Groups included Untreated (n=5; mice numbers 1-5) and CRCBT-06-001 treated (n=5; mice numbers 6-10). On days 16 and 20, mice were treated with an IP injection of 10 mg/kg CRCBT-06-001. Antibody treatment days as indicated ↓. Data was graphed standardized against starting body mass as 100% for group averages (shown in FIG. 47A) Error bars represent the SEM. FIG. 47B shows survival graphed as a Kaplan-Meier curve. FIG. 47C shows group averages of tumor volume. Error bars represent the SEM.

Figure 48A:
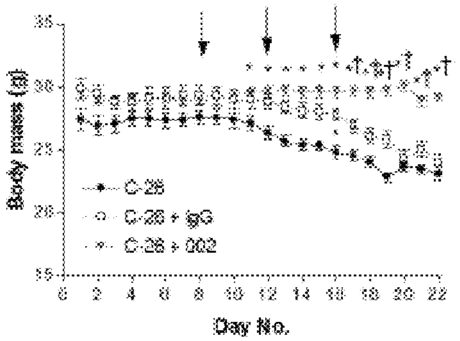
Figure 48B:
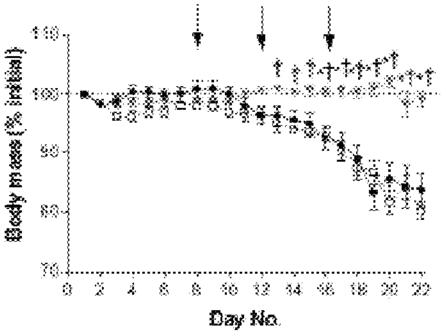
Figure 48C:
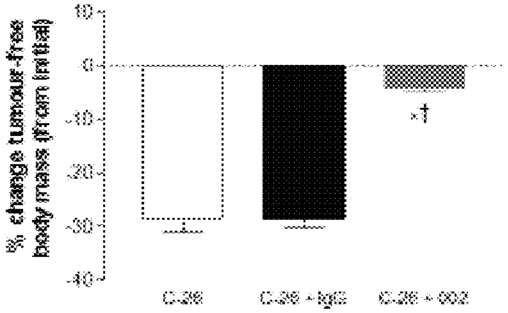

FIG. 48 A to C are graphical representations showing the effects of CRCBT-06-002 on body mass in the Colon-26 model of cancer cachexia. Male 11 week old CD2F1 mice were inoculated with $1\times10^6$ cells s/c in the flank on day 1 to form solid tumors. Groups included Untreated (n=9), IgG treated pair-fed (n=10) and CRCBT-06-002 treated pair-fed (n=10). On days 8, 12 and 16, mice were treated with an IP injection of 10 mg/kg IgG or 10 mg/kg CRCBT-06-002 (↓). Body mass was measured daily and expressed as absolute body mass (and is shown in FIG. 48A) and body mass normalised to starting weight as 100. Note: Y axis does not begin at 0 (FIG. 48B). On day 22, the tumor was surgically excised and weighed allowing calculation of the percentage change in tumor-free body mass from pre-inoculation (FIG. 48C). Data are means±SEM. *P<0.05 vs. C-26; †P<0.05 vs. C-26+IgG.

Figure 49A:
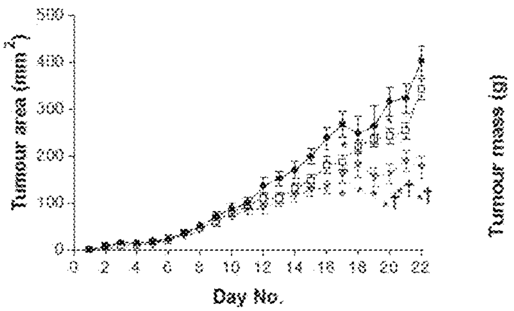
Figure 49B:
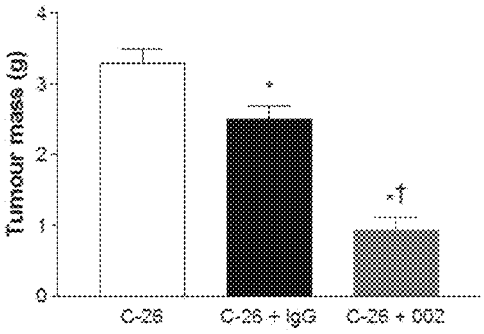
Figure 49C:
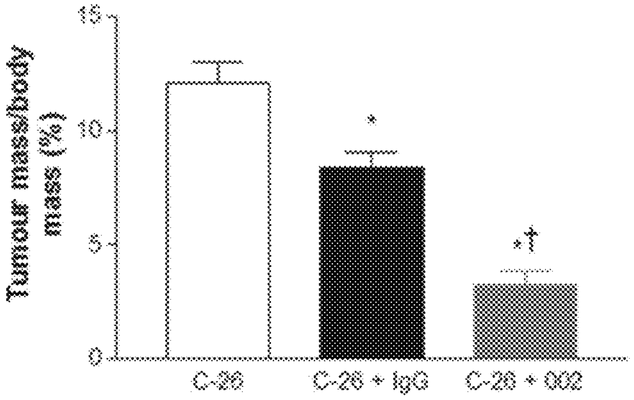

FIG. 49A to C are graphical representations showing the effect of CRCBT-06-002 on tumor size in the Colon-26 model of cancer cachexia. Tumor size was measured daily with digital calipers (results depicted in FIG. 49A). On day 22, the tumor was surgically excised and weighed (results depicted in FIG. 49B), and normalised to total body mass (as shown in FIG. 49C). Data are means±SEM. *P<0.05 vs. C-26; †P<0.05 vs. C-26+IgG FIGS. 50A and B are graphical representations showing the effects of CRCBT-06-002 on muscle mass in the Colon-26 model of cancer cachexia. On day 22, selected hindlimb muscles (FIG. 50A), epididymal fat and the heart (FIG. 50B) were excised and weighed on an analytical balance. EDL, extensor digitorum longus; Plant, plantaris; TA, tibialis anterior; Gastroc, gastrocnemius; Quad, quadriceps. Data are means±SEM. *P<0.05 vs. C-26; †P<0.05 vs. C-26+IgG.

Figure 51A:
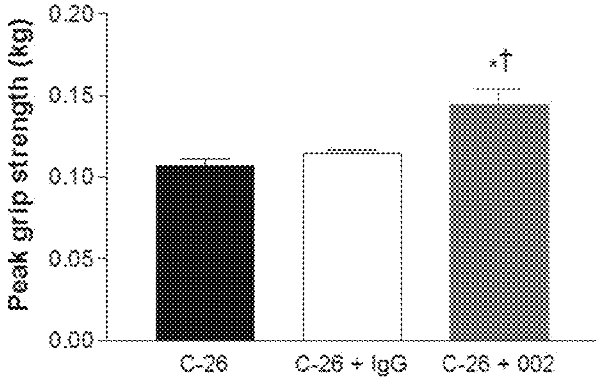
Figure 51B:
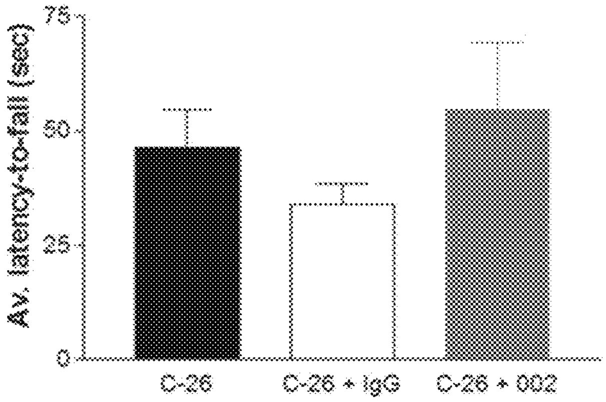

FIGS. 51A and B are graphical representations showing the effects of CRCBT-06-002 on whole body strength and mobility in the Colon-26 model of cancer cachexia. On day 21, whole body strength was assessed using a grip strength meter (FIG. 51A) and whole body mobility was assessed via latency-to-fall during a rotarod test (FIG. 51B). Data are means±SEM. *P<0.05 vs. C-26; †P<0.05 vs. C-26+IgG.

FIG. 52A to D are graphical representations showing the effect of CRCBT-06-002 effects on functional properties of tibialis anterior (TA) muscles in situ in the Colon-26 model of cancer cachexia. On day 22, peak twitch force (FIG. 52A), peak tetanic force (FIG. 52B), frequency-force relationship (FIG. 52C) and force production during and following 4 minutes of fatiguing intermittent stimulation (FIG. 52D) was assessed in TA muscles in situ. Data are means±SEM. *P<0.01 vs. C-26; †P<0.05 vs. C-26+IgG; cP<0.03 main effect C-26+002 higher than C-26+IgG.

Figure 53A:
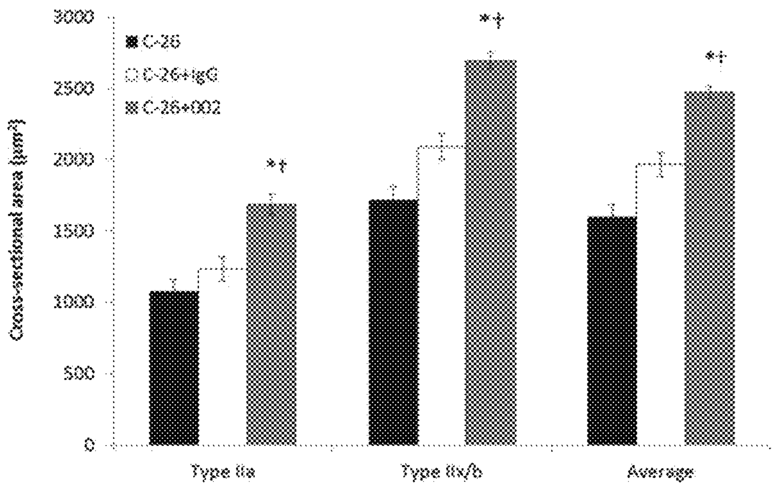
Figure 53B:
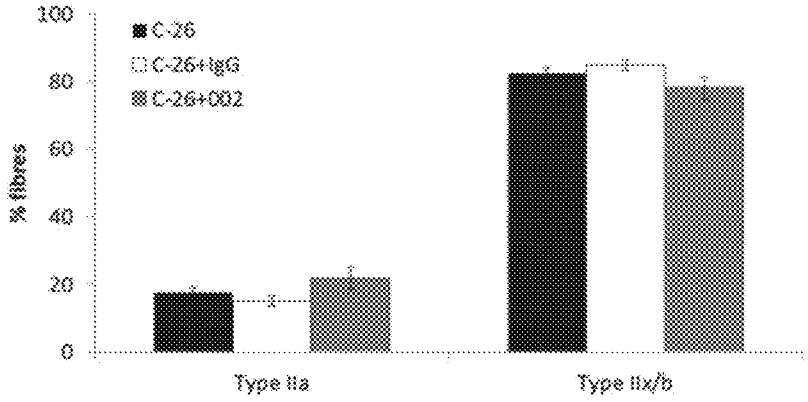
Figure 53C:
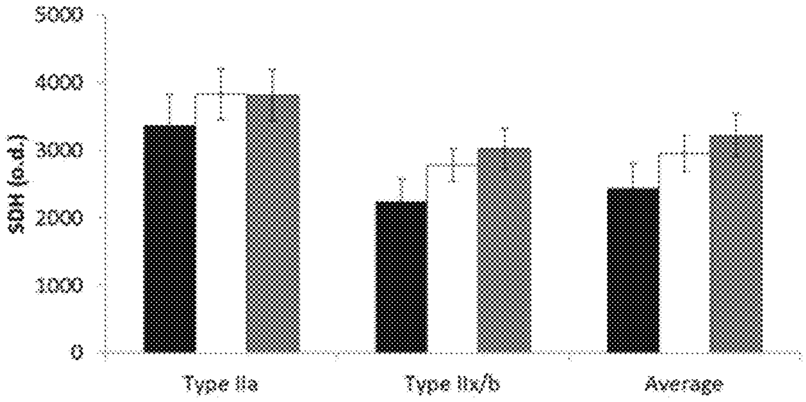

FIG. 53A to C are graphical representations showing the effects of CRCBT-06-002 on muscle fibre architecture, fibre size, fibre type composition and fibre oxidative enzyme capacity in tibialis anterior (TA) muscles from the Colon-26 model of cancer cachexia. On day 22, TA muscles were excised and frozen for subsequent analyses. Quantification of laminin and N2.261 reactions enabled assessment of the cross-sectional area (CSA) of type IIa and type IIx/b fibres as well as average muscle fibre CSA (FIG. 53A). It also enabled assessment of the proportion of type IIa and type IIx/b muscle fibres (FIG. 53B). Quantification of SDH and N2.261 allowed assessment of the oxidative enzyme capacity of type IIa and type IIx/b fibres as well as average muscle fibre oxidative enzyme capacity (FIG. 53C). *P<0.05 vs. C-26; †P<0.05 vs. C-26+IgG.

Figure 54:
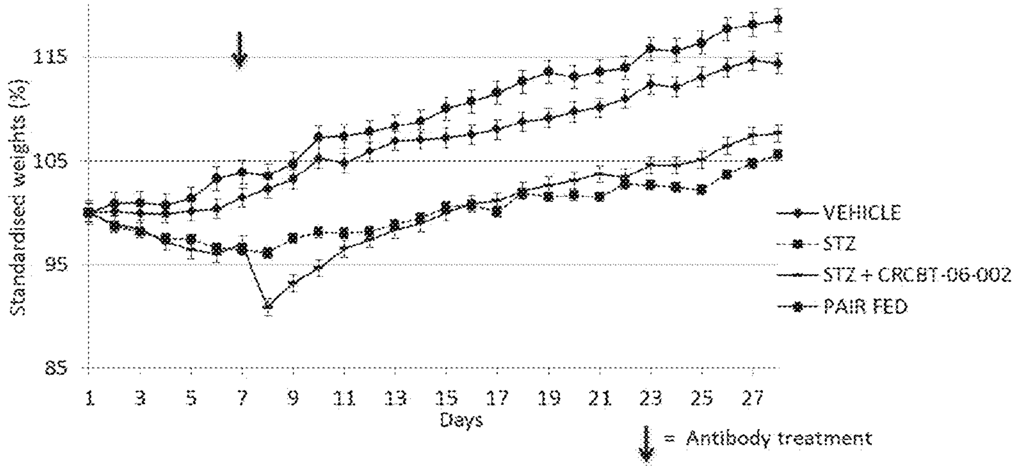

FIG. 54 is a graphical representation showing that administration of an anti-Fn14 antibody post diabetes onset partially prevents weight loss associated with streptozotocin (STZ)-induced diabetes. Diabetes was induced in male C57Bl/6 mice by multiple low dose STZ administration. Groups included STZ, Vehicle, Pair-Fed and 20 mg/kg CRCBT-06-002. ↓=Antibody treatment day. Daily body weight measurements were standardised against the starting weight (day 1) as 100% and the group averages were graphed. n=8, Error bars represent SE. Note Y axis does not cross at 0.

Figure 55:
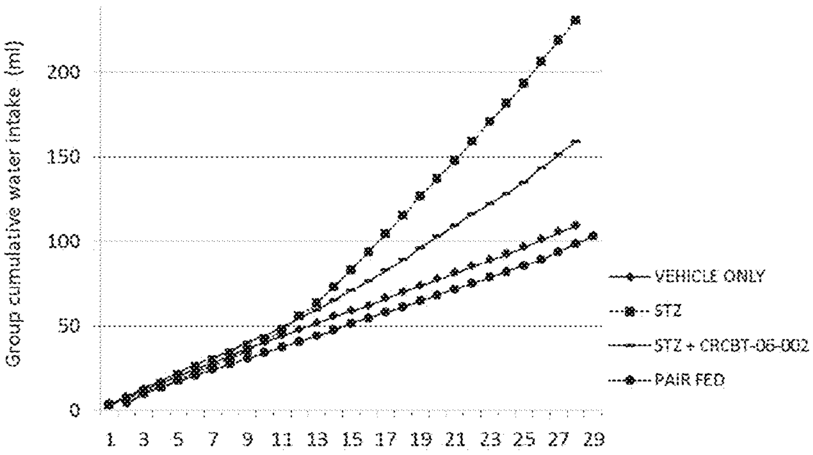

FIG. 55 is a graphical representation showing Cumulative water intake in mice depicted in FIG. 54. Water intake was measured daily for each group (n=8) and graphed as cumulative water intake.

Figure 56:
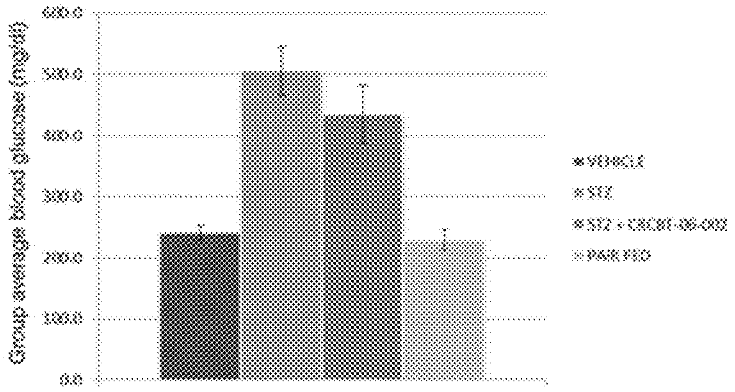
Figures 57A, 57B, 57C:
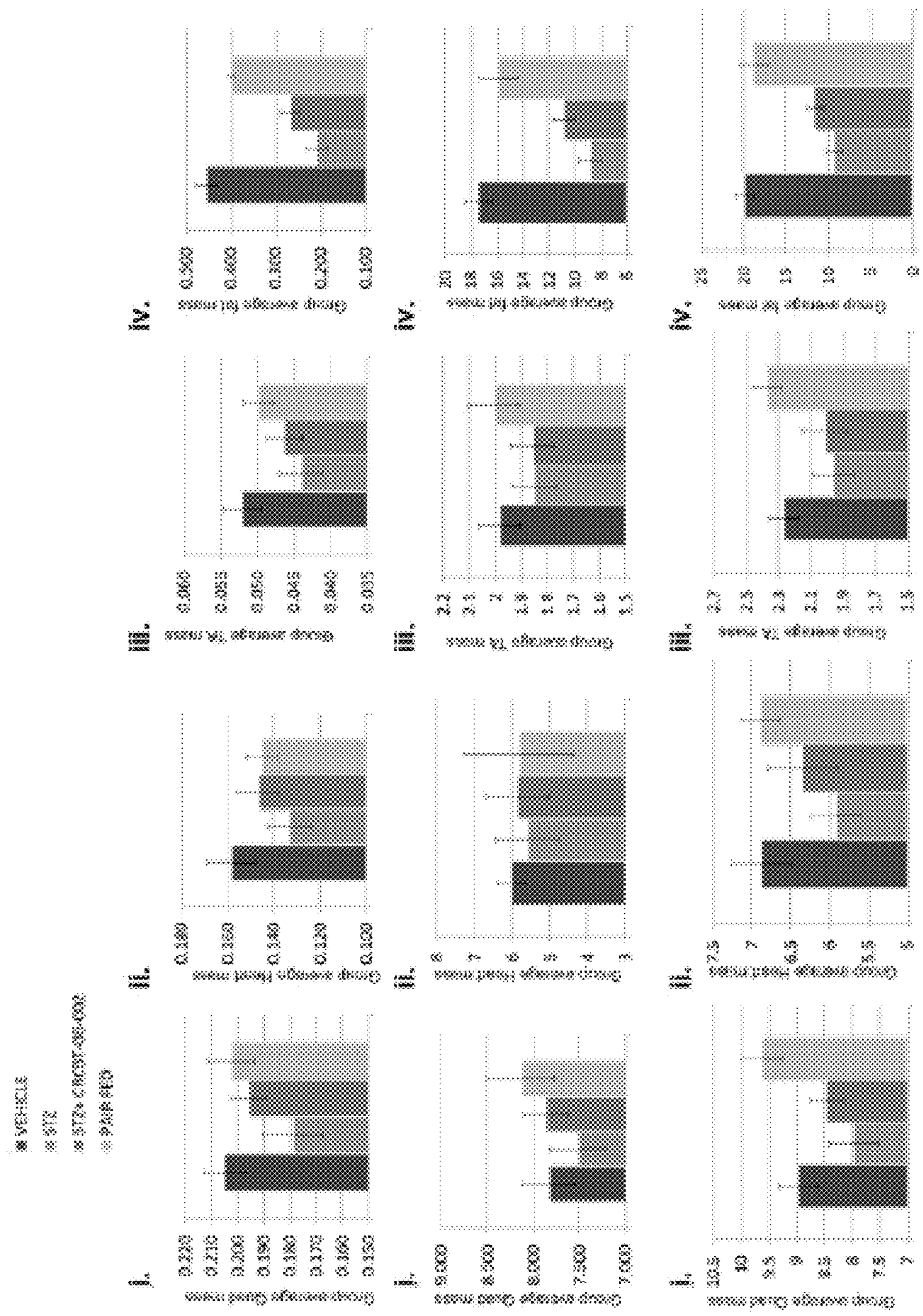

FIG. 56 is a graphical representation showing blood glucose analysis of mice treated as described in respect of FIG. 54. Blood glucose was assessed in non-fasted mice on the final day of the experiment using an Accu-check blood glucose monitor and graphed as group average. Error bars represent SEM. When a reading out of range was detected, the maximum possible reading of 600 mg/dl was assigned. n=8 per group FIGS. 57A-C are a series of graphical representations showing anti-Fn14 antibody administration post diabetes onset attenuates muscle wasting associated with STZ induced diabetes. Diabetes was induced in male C57Bl/6 mice by multiple low dose STZ administration as in FIG. 54. Groups included STZ, Vehicle, Pair-Fed and 20 mg/kg CRCBT-06-002 antibody treatment. Antibody treatment was administered on day 7. FIG. 57A shows group average tissue mass was calculated and graphed. Tissue mass was standardized to final (FIG. 57B) and starting body mass (FIG. 57C) and graphed as group averages, FIGS. 57B and C respectively show mass of i. Quadricep ii. Heart iii. Tibialis anterior iv. Epididymal fat. Error bars represent the SEM. n=8. Note some Y axis do not cross at 0.

KEY TO SEQUENCE LISTING

SEQ ID NO 1: amino acid sequence of human Fn14

SEQ ID NO 2: amino acid sequence of Fn14 extracellular domain

SEQ ID NO 3: amino acid sequence of Fn14 gene fragment RW129

SEQ ID NO 4: amino acid sequence of Fn14 gene fragment RW131

SEQ ID NO 5: amino acid sequence of Fn14 gene fragment RW127

SEQ ID NO 6: amino acid sequence of Fn14 gene fragment RW125

SEQ ID NO 7: amino acid sequence of Fn14 gene fragment RW120

SEQ ID NO 8: amino acid sequence of Fn14 gene fragment RW118

SEQ ID NO 9: amino acid sequence of Fn14 gene fragment RW114

SEQ ID NO 10: amino acid sequence of Fn14 gene fragment RW98

SEQ ID NO 11: amino acid sequence of Fn14 gene fragment RW95

SEQ ID NO 12: amino acid sequence of Fn14 gene fragment RW91

SEQ ID NO 13: amino acid sequence for consensus sequence for $V_H$

SEQ ID NO 14: amino acid sequence for consensus sequence for $V_L$

SEQ ID NO 15: amino acid sequence of $V_H$ of CRCBT-06-001

SEQ ID NO 16: amino acid sequence of $V_H$ of CRCBT-06-002

SEQ ID NO 17: amino acid sequence of $V_H$ of CRCBT-06-003

SEQ ID NO 18: amino acid sequence of $V_H$ of CRCBT-06-004

SEQ ID NO 19: amino acid sequence of $V_H$ of CRCBT-06-005

SEQ ID NO 20: amino acid sequence of $V_H$ of CRCBT-06-006

SEQ ID NO 21: amino acid sequence of $V_H$ of CRCBT-06-007

SEQ ID NO 22: amino acid sequence of $V_L$ of CRCBT-06-001

SEQ ID NO 23: amino acid sequence of $V_L$ of CRCBT-06-002

SEQ ID NO 24: amino acid sequence of $V_L$ of CRCBT-06-003

SEQ ID NO 25 amino acid sequence of $V_L$ of CRCBT-06-004

SEQ ID NO 26: amino acid sequence of $V_L$ of CRCBT-06-005

SEQ ID NO 27: amino acid sequence of $V_L$ of CRCBT-06-006

SEQ ID NO 28: amino acid sequence of $V_L$ of CRCBT-06-007

SEQ ID NO 29: amino acid sequence of hFn14 extracellular domain mutant construct D45A SEQ ID NO 30: amino acid sequence of hFn14 extracellular domain mutant construct K48A SEQ ID NO 31: amino acid sequence of hFn14 extracellular domain mutant construct M50A SEQ ID NO 32: amino acid sequence of hFn14 extracellular domain mutant construct D62E SEQ ID NO: 33: amino acid sequence of hFn14 subdomain 1

SEQ ID NO 34: amino acid sequence of hFn14 subdomain 2

SEQ ID NO: 35: amino acid sequence of hFn14 subdomain 3

SEQ ID NO 36: amino acid sequence of Fn14-GPI control

SEQ ID NO 37: nucleotide sequence of a primer for amplifying nucleic acid encoding extracellular domain of Fn14.

SEQ ID NO 38: nucleotide sequence of a primer for amplifying nucleic acid encoding extracellular domain of Fn14.

SEQ ID NO 39: nucleotide sequence of a primer for amplifying Trail R3 GPI anchor coding region.

SEQ ID NO 40: nucleotide sequence of a primer for amplifying Trail R3 GPI anchor coding region.

SEQ ID NO 41: nucleotide sequence of a primer for amplifying light chain variable region of an antibody.

SEQ ID NO 42: nucleotide sequence of a primer for amplifying light chain variable region of an antibody.

SEQ ID NO 43: nucleotide sequence of a primer for amplifying heavy chain variable region of an antibody.

SEQ ID NO 44: nucleotide sequence of a primer for amplifying heavy chain variable region of an antibody.

SEQ ID NO 45: nucleotide sequence of a primer for amplifying heavy chain variable region of an antibody.

SEQ ID NO: 46: amino acid sequence of sub-domain 1p.

SEQ ID NO: 47 Fn14 sub-domain 2 in which the third and sixth cysteine residues in Fn14 ECD that form disulfide bonds are mutated to serine (designated herein “Sub-domain 2 Cys 3&6 ΔS”).

SEQ ID NO: 48: Fn14 sub-domain 2 in which the fourth and fifth cysteine residues in Fn14 ECD that form disulfide bonds are mutated to serine (designated herein “Sub-domain 2 Cys 4&5 ΔS”).

SEQ ID NO: 49: Fn14 T33N mutant

SEQ ID NO: 50: Fn14 A34S mutant

SEQ ID NO: 51: Fn14 R38S mutant

SEQ ID NO: 52: Fn14 R56P mutant

SEQ ID NO: 53: Fn14 L77M mutant

SEQ ID NO: 54: Fn14 R56A mutant

SEQ ID NO: 55: Fn14 R56K mutant

SEQ ID NO: 56: Fn14 R58A mutant

SEQ ID NO: 57: Fn14 W42A mutant

SEQ ID NO: 58: Fn14 L46A mutant

SEQ ID NO: 59: Fn14 D51A mutant

SEQ ID NO: 60: Fn14 S54A mutant

SEQ ID NO: 61: Fn14 A57G mutant

SEQ ID NO: 62: Fn14 P59A mutant

SEQ ID NO: 63: Fn14 H60A mutant

SEQ ID NO: 64: Fn14 S61A mutant

SEQ ID NO: 65: Fn14 D62A mutant

SEQ ID NO: 66: Fn14 F63A mutant

SEQ ID NO: 67: Fn14 L65A mutant

SEQ ID NO: 68: Fn14 H60K mutant

SEQ ID NO: 69: Primer for amplifying antibody light chain

SEQ ID NO: 70: Primer for amplifying antibody light chain

DETAILED DESCRIPTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, Perbal (1984), Sambrook et al., (1989), Brown (1991), Glover and Hames (1995 and 1996), and Ausubel et al., (1988, including all updates until present), Harlow and Lane, (1988), Coligan et al., (including all updates until present) and Zola (1987).

The description and definitions of variable regions and parts thereof, immunoglobulins, antibodies and fragments thereof herein may be further clarified by the discussion in Kabat, 1987 and/or 1991, Bork et al., 1994 and/or Chothia and Lesk, 1987 and/or 1989 or Al-Lazikani et al., 1997.

The term “and/or”, e.g., “X and/or Y” shall be understood to mean either “X and Y” or “X or Y” and shall be taken to provide explicit support for both meanings or for either meaning.

Throughout this specification the word “comprise”, or variations such as “comprises” or “comprising”, will be understood to imply the inclusion of a stated element, integer or step, or group of elements, integers or steps, but not the exclusion of any other element, integer or step, or group of elements, integers or steps.

As used herein the term “derived from” shall be taken to indicate that a specified integer may be obtained from a particular source albeit not necessarily directly from that source.

In one example of the present disclosure, the X at position 103 is a glycine. In one example of the present disclosure, the X at position 103 is a glutamate or glutamic acid.

Selected Definitions

As used herein, the term “Fn14” collectively refers to Fn14 from all mammals, such as from humans and from rodents. The term “hFn14” or “human Fn14” refers to Fn14 from humans. For the purpose of nomenclature and not limitation, an amino acid sequence of an hFn14 is set forth in SEQ ID NO: 1.

For the purposes for the present disclosure, the term “antibody” includes a protein capable of specifically binding to one or a few closely related antigens (e.g., Fn14) by virtue of a Fv. This term includes four chain antibodies (e.g., two light chains and two heavy chains), recombinant or modified antibodies (e.g., chimeric antibodies, humanized antibodies, primatized antibodies, de-immunized antibodies and half antibodies, bispecific antibodies). An antibody generally comprises constant domains, which can be arranged into a constant region or constant fragment or fragment crystallizable (Fc). Exemplary forms of antibodies comprise a four-chain structure as their basic unit. Full-length antibodies comprise two heavy chains (~50-70 kDa) covalently linked and two light chains (~23 kDa each). A light chain generally comprises a variable region and a constant domain and in mammals is either a κ light chain or a λ light chain. A heavy chain generally comprises a variable region and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable region ($V_H$ or $V_L$ wherein each are ~110 amino acids in length) and one or more constant domains at the C-terminus. The constant domain of the light chain ($C_L$ which is ~110 amino acids in length) is aligned with and disulfide bonded to the first constant domain of the heavy chain ($C_H$ which is −330-440 amino acids in length). The light chain variable region is aligned with the variable region of the heavy chain. The antibody heavy chain can comprise 2 or more additional $C_H$ domains (such as, $C_H2$, $C_H3$ and the like) and can comprise a hinge region can be identified between the $C_H1$ and $C_H2$ constant domains. Antibodies can be of any type (e.g., IgG, IgE, IgM, IgD, IgA, and IgY), class (e.g., $IgG_1$, IgG2, IgG3, IgG4, $IgA_1$ and $IgA_2$) or subclass. In one example, the antibody is a murine (mouse or rat) antibody or a humanized form thereof or a primate (such as, human) antibody.

The terms “full-length antibody,” “intact antibody” or “whole antibody” are used interchangeably to refer to an antibody in its substantially intact form, as opposed to an antigen binding fragment of an antibody. Specifically, whole antibodies include those with heavy and light chains including a constant region. The constant region may be wild-type sequence constant regions (e.g., human wild-type sequence constant regions) or amino acid sequence variants thereof.

The term “Fn14-binding protein” shall be taken to include a single polypeptide chain, (i.e., a series of contiguous amino acids linked by peptide bonds), or a series of polypeptide chains covalently or non-covalently linked to one another (i.e., a polypeptide complex) capable of binding to Fn14 in the manner described and/or claimed herein. For example, the series of polypeptide chains can be covalently linked using a suitable chemical or a disulphide bond. Examples of non-covalent bonds include hydrogen bonds, ionic bonds, Van der Waals forces, and hydrophobic interactions. A non-covalent bond contemplated by the present disclosure is the interaction between a $V_H$ and a $V_L$, e.g., in some forms of diabody or a triabody or a tetrabody or a Fv.

The term “polypeptide chain” will be understood to mean from the foregoing paragraph to mean a series of contiguous amino acids linked by peptide bonds.

As the term suggests, “anti-Fn14 antibody” means an antibody that specifically binds to Fn14.

Reference herein to antibody CRCBT-06-001 is to an antibody comprising a $V_H$ comprising a sequence set forth in SEQ ID NO: 15 and a $V_L$ comprising a sequence set forth in SEQ ID NO: 22.

Reference herein to antibody CRCBT-06-002 is to an antibody comprising a $V_H$ comprising a sequence set forth in SEQ ID NO: 16 and a $V_L$ comprising a sequence set forth in SEQ ID NO: 23.

Reference herein to antibody CRCBT-06-003 is to an antibody comprising a $V_H$ comprising a sequence set forth in SEQ ID NO: 17 and a $V_L$ comprising a sequence set forth in SEQ ID NO: 24.

Reference herein to antibody CRCBT-06-004 is to an antibody comprising a $V_H$ comprising a sequence set forth in SEQ ID NO: 18 and a $V_L$ comprising a sequence set forth in SEQ ID NO: 25.

Reference herein to antibody CRCBT-06-005 is to an antibody comprising a $V_H$ comprising a sequence set forth in SEQ ID NO: 19 and a $V_L$ comprising a sequence set forth in SEQ ID NO: 26.

Reference herein to antibody CRCBT-06-006 is to an antibody comprising a $V_H$ comprising a sequence set forth in SEQ ID NO: 20 and a $V_L$ comprising a sequence set forth in SEQ ID NO: 27.

Reference herein to antibody CRCBT-06-007 is to an antibody comprising a $V_H$ comprising a sequence set forth in SEQ ID NO: 21 and a $V_L$ comprising a sequence set forth in SEQ ID NO: 28.

As used herein, “variable region” refers to the portions of the light and/or heavy chains of an antibody as defined herein that is capable of specifically binding to an antigen and includes amino acid sequences of CDRs; i.e., CDR1, CDR2, and CDR3, and FRs. For example, the variable region comprises three or four FRs (e.g., FR1, FR2, FR3 and optionally FR4) together with three CDRs. $V_H$ refers to the variable region of the heavy chain. $V_L$ refers to the variable region of the light chain.

As used herein, the term “complementarity determining regions” (syn. CDRs; i.e., CDR1, CDR2, and CDR3) refers to the amino acid residues of an antibody variable region the presence of which are major contributors to specific antigen binding. Each variable region typically has three CDR regions identified as CDR1, CDR2 and CDR3. Each complementarity determining region may comprise amino acid residues from a “complementarity determining region” as defined by Kabat et al., (1987 and/or 1991). For example, in a heavy chain variable region CDRH1 is between residues 31-35, CDRH2 is between residues 50-65 and CDRH3 is between residues 95-102. In a light chain CDRL1 is between residues 24-34, CDRL2 is between residues 50-56 and CDRL3 is between residues 89-97. These CDRs can also comprise numerous insertions, e.g., as described in Kabat (1987 and/or 1991). The present disclosure is not limited to FRs and CDRs as defined by the Kabat numbering system, but includes all numbering systems, including the canonical numbering system or of Chothia and Lesk (1987); Chothia et al. (1989); and/or Al-Lazikani et al., (1997); the numbering system of Honnegher and Plükthun (2001); the IMGT system discussed in Giudicelli et al., (1997); or the Enhanced Chothia Numbering Scheme (http://www.bioinfo.org.uk/mdex.html). In one example, the CDRs and/or FRs are defined according to the Kabat numbering system, e.g., as depicted in FIGS. 11A-11D in bold text. Optionally, heavy chain CDR2 according to the Kabat numbering system does not comprise the five C-terminal amino acids listed herein or any one or more of those amino acids are substituted with another naturally-occurring amino acid. In an additional, or alternative, option, light chain CDR1 does not comprise the four N-terminal amino acids listed herein or any one or more of those amino acids are substituted with another naturally-occurring amino acid. In this regard, Padlan et al., 1995 established that the five C-terminal amino acids of heavy chain CDR2 and/or the four N-terminal amino acids of light chain CDR1 are not generally involved in antigen binding. In one example, the CDRs and/or FRs are defined according to the Chothia numbering system, e.g., as depicted in FIGS. 9A-9D in underlined text.

As used herein, the term "Kabat numbering system" refers to the scheme for numbering antibody variable regions and identifying CDRs (hypervariable regions) as set out in Kabat et al., (1987 and/or 1991).

As used herein, the term "Chothia numbering system" refers to the scheme for numbering antibody variable regions and identifying CDRs (structural loops) as set out in of Chothia and Lesk (1987) or Al-Lazikani et al., (1997).

"Framework regions" (hereinafter FR) are those variable region residues other than the CDR residues.

As used herein, the term "Fv" shall be taken to mean any protein, whether comprised of multiple polypeptides or a single polypeptide, in which a $V_L$ and a $V_H$ associate and form a complex having an antigen binding domain, i.e., capable of specifically binding to an antigen (e.g., Fn14). The $V_H$ and the $V_L$ which form the antigen binding domain can be in a single polypeptide chain or in different polypeptide chains. Furthermore an Fv of the disclosure (as well as any protein of the disclosure) may have multiple antigen binding sites which may or may not bind the same antigen. This term shall be understood to encompass fragments directly derived from an antibody as well as proteins produced using recombinant means. In some examples, the $V_H$ is not linked to a heavy chain constant domain $C_H1$ and/or the $V_L$ is not linked to a light chain constant domain ($C_L$), e.g., a domain antibody. Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain, e.g., a minibody. A "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. An "F(ab')$_2$ fragment" of an antibody consists of a dimer of two Fab' fragments held together by two disulfide bonds, and is obtained by treating a whole antibody molecule with the enzyme pepsin, without subsequent reduction. An "Fab$_2$" fragment is a recombinant fragment comprising two Fab fragments linked using, for example a leucine zipper or a $C_H3$ domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker. A discussion of exemplary Fv containing proteins falling within the scope of this term is provided herein below.

As used herein, the term "antigen binding domain" shall be taken to mean a region of an antibody that is capable of specifically binding to an antigen, i.e., a $V_H$ or a $V_L$ or a Fv or a variable region as defined herein. The antigen binding domain need not be in the context of an entire antibody, e.g., it can be in isolation (e.g., a domain antibody) or in another form, e.g., as described herein, such as a scFv.

The term "constant region" (syn. CR) as used herein, refers to a portion of an antibody comprising at constant domains and which is generally (though not necessarily) glycosylated and which binds to one or more Fc receptors and/or components of the complement cascade (e.g., confers effector functions). The heavy chain constant region can be selected from any of the five isotypes: α, δ, ε, γ, or μ. Furthermore, heavy chains of various subclasses (such as the IgG subclasses of heavy chains) are responsible for different effector functions and thus, by choosing the desired heavy chain constant region, proteins with desired effector function can be produced. Exemplary heavy chain constant regions are gamma 1 (IgG1), gamma 2 (IgG2) and gamma 3 (IgG3).

A "constant domain" is a domain in an antibody the sequence of which is highly similar in antibodies/antibodies of the same type, e.g., IgG or IgM or IgE. A constant region of an antibody generally comprises a plurality of constant domains, e.g., the constant region of γ, α and δ heavy chains comprise three constant domains and the Fc of γ, α and δ heavy chains comprise two constant domains. A constant region of μ and ε heavy chains comprises four constant domains and the Fc region comprises two constant domains.

As used herein, the term "binds" in reference to the interaction of a protein or an antigen binding domain thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the antibody, will reduce the amount of labeled "A" bound to the antibody.

As used herein, the term "specifically binds" shall be taken to mean a protein of the disclosure reacts or associates more frequently, more rapidly, with greater duration and/or with greater affinity with a particular antigen or antigens or cell expressing same than it does with alternative antigens or cells. For example, a protein that specifically binds to an antigen binds that antigen with greater affinity (e.g., 20 fold or 40 fold or 60 fold or 80 fold to 100 fold or 150 fold or 200 fold greater affinity), avidity, more readily, and/or with greater duration than it binds to other antigens, e.g., to other TNF superfamily receptors or to antigens commonly recognized by polyreactive natural antibodies (i.e., by naturally occurring antibodies known to bind a variety of antigens naturally found in humans). It is also understood by reading this definition that, for example, a protein that specifically binds to a first antigen may or may not specifically bind to a second antigen. As such "specific binding" does not necessarily require exclusive binding or non-detectable binding of another antigen, this is meant by the term "selective binding".

As used herein, reference to a "similar" level of binding will be understood to mean that an antibody binds to an antigen at a level within about 30% or 25% or 20% of the level at which it binds to another antigen. This term can also mean that one antibody binds to an antigen at a level within about 30% or 25% or 20% of the level at which another antibody binds to the same antigen.

As used herein, reference to "substantially the same level" of binding will be understood to mean that an antibody binds to an antigen at a level within about 15% or 10% or 5% of the level at which it binds to another antigen. This term can also mean that one antibody binds to an antigen at a level within about 5% or 4% or 3% of the level at which another antibody binds to the same antigen.

As used herein, the term "epitope" (syn. "antigenic determinant") shall be understood to mean a region of Fn14 to which an antibody designated CRCBT-06-001 and/or CRCBT-06-002 and/or CRCBT-06-003 and/or CRCBT-06-004 and/or CRCBT-06-005 and/or CRCBT-06-006 and/or CRCBT-06-007 binds. This term is not necessarily limited to the specific residues or structure to which the antibody makes contacts. For example, this term includes the region spanning amino acids contacted by the antibody and/or 5-10 or 2-5 or 1-3 amino acids outside of this region. In some example, the epitope is a series of consecutive amino acids from Fn14. However, an epitope can also comprise a series of discontinuous amino acids that are positioned close to one another when Fn14 is folded, i.e., a "conformational epitope". In this regard, the term "epitope" can encompass a single polypeptide comprising some or all of the series of discontinuous amino acids sufficient to bind to an Fn14-binding protein of the present disclosure and/or can comprise a series of peptides comprising the series of amino acids. The skilled artisan will also be aware that the term "epitope" is not limited to peptides or polypeptides. For example, antibodies are capable of binding to carbohydrates or glycosylated peptides or polypeptides, phosphates or phospo-peptides or polypeptides amongst other epitopes. An epitope or peptide or polypeptide comprising same can be administered to an animal to generate antibodies against the epitope.

By "isolated" is meant that the protein is substantially removed from its naturally-occurring environment, e.g., is in a heterologous environment and/or that it is substantially free of contaminating agents, e.g., at least about 70% or 75% or 80% or 85% or 90% or 95% or 96% or 97% or 98% or 99% free of contaminating agents.

The term "competitively inhibits" shall be understood to mean that a protein of the disclosure reduces or prevents binding of a recited antibody produced to Fn14 or a fragment thereof. It will be apparent from the foregoing that the protein need not completely inhibit binding of the antibody, rather it need only reduce binding by a statistically significant amount, for example, by at least about 10% or 20% or 30% or 40% or 50% or 60% or 70% or 80% or 90% or 95%. Methods for determining competitive inhibition of binding are known in the art and/or described herein. For example, the antibody is exposed to Fn14 or a fragment thereof either in the presence or absence of the protein. If less antibody binds in the presence of the protein than in the absence of the protein, the protein is considered to competitively inhibit binding of the antibody. In one example, the protein and antibody are exposed to Fn14 substantially simultaneously. Additional methods for determining competitive inhibition of binding will be apparent to the skilled artisan and/or described herein. In one example, the antigen binding domain of the protein competitively inhibits binding of the antibody.

Reference herein to "an epitope comprising residues contained within" a recited sequence will be understood to mean that the epitope (which can be conformational) to which a protein binds comprises residues within the recited sequence, however may contain additional residues. The residues contained within the sequence are sufficient to permit the sequence to bind to a protein described herein according to any example.

By "overlapping" in the context of two epitopes shall be taken to mean that two epitopes share a sufficient number of amino acid residues to permit an antibody that binds to one epitope to competitively inhibit the binding of an antibody that binds to the other epitope. For example, the epitopes share at least one or two or three or four or five or six or seven or eight or nine or ten amino acids.

As used herein, the term "does not detectably bind" shall be understood to mean that a protein, e.g., an antibody, binds to a candidate antigen at a level less than 10%, or 8% or 6% or 5% above background. The background can be the level of binding signal detected in the absence of the protein and/or in the presence of a negative control protein (e.g., an isotype control antibody) and/or the level of binding detected in the presence of a negative control antigen. The level of binding is detected using biosensor analysis (e.g. Biacore) in which the protein is immobilized and contacted with an antigen.

As used herein, phrases referring to "reduced binding" or "binding being at a lower level" in relation to binding of an Fn14-binding protein to a peptide comprising a region of Fn14 or a mutant form thereof will be understood to mean that the protein binds to the peptide with an affinity at least about 2 fold or 5 fold or 10 fold or 20 fold or 40 fold or 60 fold less than a control epitope or antigen (e.g. Fn14 or a peptide comprising an amino acid sequence set forth in SEQ ID NO: 2).

As used herein, the term "similar level" in the context of an Fn14-binding protein will be understood to mean that a protein of the present disclosure binds to two antigens (e.g., Fn14 or a peptide comprising a sequence set forth in SEQ ID NO: 2 and a peptide comprising a sequence set forth in any one of SEQ ID NOs: 29-32, 34 or 49-68) with affinities that are within 2 fold or less of one another, e.g., within about 1 fold of one another, such as, within about 0.5 fold of one another or the levels of binding are substantially identical.

By "individually" is meant that the disclosure encompasses a Fn14-binding protein that binds to the recited antigens or groups of antigens separately, and that, notwithstanding that individual antigens or groups of antigens may not be separately listed herein the accompanying claims may define such antigens or groups of antigens separately and divisibly from each other.

By "collectively" is meant that the invention encompasses any number or combination of the recited antigens or groups of antigens, and that, notwithstanding that such numbers or combinations of antigens or groups of antigens may not be specifically listed herein the accompanying claims may define such combinations or sub-combinations separately and divisibly from any other combination of antigens or groups of antigens.

A "Tweak-mediated Fn14 signaling effect" will be understood to mean any one or group of phenotypes effected by Tweak signaling through Fn14 in a cell. Such effects include gene expression changes, NFκB-signaling, induction or inhibition of apoptosis or necrosis, induction or inhibition of angiogenesis or induction or inhibition of cytokine secretion. Suitable methods for determining Tweak-mediated Fn14 signaling effect are described herein.

As used herein, the term "Tweak-induced NFκB-signaling" will be understood to mean signal transduction that occurs within a cell expressing Fn14 that occurs via NFκB as a result of Tweak binding to Fn14. Methods for determining such signaling are known in the art and/or described herein. For example, a promoter that comprises a NFκB binding site and that facilitates gene expression as a result of NFκB binding is operably linked to a reporter gene. Tweak-induced NFκB-signaling is then determined by detecting expression of the reporter gene, e.g., detecting a fluorescent reporter gene using fluorescence activated cell sorting (FACS). Tweak-induced NFκB-signaling can also be determined by detecting the level of expression of a gene induced by NFκB, e.g., at the mRNA level or protein level.

As used herein, the term "does not detectably induce NFκB-signaling" in the context of a protein contacted to a cell expressing Fn14 in the absence of Tweak shall be taken to mean that the protein does not induce NFκB-signaling to a level significantly greater than a control protein, e.g., an isotype control antibody. In some examples, the induction of signaling is no more than 1.5 fold or 1.4 fold or 1.3 fold or 1.2 fold or 1.1 fold compared to the induction of signaling by a control protein. Methods for determining NFκB signaling are described herein.

As used herein, the term "neutralize" shall be taken to mean that a protein is capable of blocking, reducing or preventing any one or more Tweak-mediated signaling effects in a cell through Fn14. Methods for determining neutralization are known in the art and/or described herein.

The term "Fn14-mediated condition" shall be taken to encompass any disease or disorder caused by or associated with excess numbers of cells expressing Fn14 and/or over-expression of Fn14 by cells and/or excess activity of Fn14 and/or an excess level of Tweak, e.g., in serum of a subject. Exemplary Fn14-mediated conditions are cancer, metastasis, excessive vascularization or angiogenesis, autoimmune diseases, inflammatory diseases, neurodegenerative diseases, keloid scarring, graft versus host disease, graft rejection, cardiovascular disease and ischemia (including stroke).

As used herein, the term "wasting disorder" refers to a disorder which involves, results at least in part from, or includes loss of weight, muscle atrophy, fatigue, weakness in someone who is not actively trying to lose weight. Wasting disorders are commonly characterized by inadvertent and/or uncontrolled (in the absence of medical intervention) loss of muscle and/or fat. The term encompasses cachexia or other forms of wasting, e.g., denervation-induced wasting.

The term "wasting disorder associated with another condition" will be understood to mean a wasting that is observed in a subject suffering from a condition, i.e., the wasting may result from changes (e.g., metabolic changes) caused by the condition. In one example, the condition is an Fn14-mediated condition. In one example, the condition is caused by or associated with Fn14 expression in a cell (or a cell expressing Fn14) other than muscle.

As used herein, the term "cachexia" will be understood to refer to metabolic condition associated with an underlying (or another) condition, wherein cachexia is characterized by loss of body weight and loss of muscle with or without loss of fat mass. Cachexia is generally associated with increased protein catabolism due to underlying disease(s). Contributory factors to the onset of cachexia are anorexia and metabolic alterations (e.g., increased inflammatory status, increased muscle proteolysis and impaired carbohydrate, protein and lipid metabolism). A prominent clinical feature of cachexia is weight loss in adults (optionally, corrected for fluid retention) or growth failure in children (excluding endocrine disorders). Anorexia, inflammation, insulin resistance and increased muscle protein breakdown are frequently associated with cachexia. Cachexia is distinct from starvation, primary depression, malabsorption and hyperthyroidism and is associated with increased morbidity. Cachexia can be associated with or result from (directly or indirectly) various underlying disorders including cancer, metabolic acidosis (from decreased protein synthesis and increased protein catabolism), certain infectious diseases (e.g. bacterial infections, including tuberculosis, AIDS), some autoimmune disorders, addiction to drugs such as amphetamines or cocaine, chronic alcoholism and/or cirrhosis of the liver, chronic inflammatory disorders, anorexia, neurological conditions and/or neurodegenerative disease. In one example, cachexia is cancer cachexia (cachexia associated with cancer). In other examples, muscle wasting and/or unintended body weight loss associated with neurological conditions, immobility or impaired mobility due to various diseases such as neurodegenerative disease, multiple sclerosis, spinal cord injury, are included in the term. Cachexia can be diagnosed based on one or more of the following:

Weight loss of at least 5% over a period of six months (in the absence of starvation);

A BMI<20 together with weight loss; or

Appendicular skeletal muscle index consistent with sarcopenia (males <7.26 $kg/m^2$; females <5.45 $kg/m^2$) together with weight loss.

As used herein, the term "pre-cachexia" will be understood to mean a condition associated with an underlying condition (e.g., chronic condition) and characterized by unintentional weight loss of less than about 5% of a subject's body weight; and a chronic or recurrent systemic inflammatory response.

As used herein, the term "unintended body weight loss" refers to a condition where the subject is incapable of maintaining a healthy body weight or loses a considerable amount of body weight, without actually attempting to reduce body weight. For example a body mass index of less than 18.5 (or any another BMI range defined by a medical specialist) is considered underweight.

For the purposes of the present disclosure, the term "body mass index" is calculated by the following formula: mass (kg)/(height $(m)^2$).

For the purposes of the present disclosure, the term "lean body mass" is to be taken to mean the mass of tissues other than fat (e.g., white adipose tissue) in a subject. Lean body mass can be calculated or estimated by estimating a subject's percentage fat content (e.g., using calipers) and subtracting this amount from their mass or by using air displacement plethysmography or dual energy X-ray absorptiometry (DEXA).

The term "total body mass" will be understood to mean a subject's weight.

The skilled person will understand from the description herein that reference to "general health" of a subject includes one or more of lethargy or fatigue, respiratory rate, posture, pain or other scores of the health of a subject (e.g. as are known in the art). For example, treatment of a subject with an Fn14-binding protein of the disclosure resulting in improved general health results in one or more of a reduced level of lethargy or fatigue, increased respiratory rate, deeper breathing or improved posture compared to a subject suffering from the relevant condition to who the Fn14-binding protein has not been administered.

As used herein, the term "glucose metabolism disorder" shall be taken to mean any disorder in which a subject is unable to or has a reduced ability to break down or metabolize or to take up or use one or more forms of carbohydrate, generally leading to increased levels of that/those carbohydrate(s) in the blood stream of the subject. For example, the carbohydrate metabolism disorder is associated with or caused by reduced production by the pancreas of a hormone involved in breaking down a carbohydrate, e.g., production of amylase. In one example, the carbohydrate metabolism disorder is associated with or caused by reduced production by the pancreas of a hormone involved in uptake of a carbohydrate, e.g., production of insulin. Exemplary carbohydrate metabolism disorders include Type I diabetes mellitus, Type II diabetes mellitus, idiopathic Type I diabetes (Type Ib), early-onset Type II diabetes (EOD), youth-onset atypical diabetes (YOAD), maturity onset diabetes of the young (MODY), malnutrition-related diabetes, gestational diabetes, conditions of impaired glucose tolerance (IGT), conditions of impaired fasting plasma glucose, metabolic acidosis, ketosis, syndrome X, hyperglycemia, hypoinsulinemia, insulin resistance, alpha mannosidosis, beta mannosidosis, fructose intolerance, fucosidosis, galactosemia, Leigh disease, mucolipidosis, mucopolysaccharidoses or a complication of any one or more of the preceding. In one example, the glucose metabolism disorder is diabetes, for example, Type I diabetes.

In one example, a subject suffering from diabetes has a clinically accepted marker of diabetes, such as:

Fasting plasma glucose of greater than or equal to 7 mmol/L or 126 mg/dl;

Casual plasma glucose (taken at any time of the day) of greater than or equal to 11.1 mmol/L or 200 mg/dl with the symptoms of diabetes.

Oral glucose tolerance test (OGTT) value of greater than or equal to 11.1 mmol/L or 200 mg/dl measured at a two-hour interval. The OGTT is given over a two or three-hour time span.

As used herein, the terms "preventing", "prevent" or "prevention" include administering a therapeutically effective amount of a protein of the disclosure sufficient to stop or hinder the development of at least one symptom of a specified disease or condition.

As used herein, the terms "treating", "treat" or "treatment" include administering a therapeutically effective amount of a protein described herein sufficient to reduce or eliminate at least one symptom of a specified disease or condition.

As used herein, the term "subject" shall be taken to mean any animal including mammals. Exemplary subjects include humans or non-human primates. In one example, the subject is a human.

The term "sample" shall be taken to encompass the recited sample (e.g., a blood or urine sample) and any fraction thereof (e.g., plasma, serum or buffy coat) or cells derived therefrom (e.g., peripheral blood mononuclear cells) or processed forms thereof.

The term "ectopically expressed" will be understood to mean that a cell has been genetically modified to permit it to express the recited protein. For example, a cell that ectopically expresses Fn14 has been genetically modified to permit it to express Fn14. In this regard, prior to genetic modification may have or may not have expressed endogenous Fn14.

Antibody-Based Fn14 Binding Proteins

Antibodies

Methods for generating antibodies are known in the art and/or described in Harlow and Lane (1988) or Zola (1987). Generally, in such methods an Fn14 protein or immunogenic fragment or epitope-containing thereof or a cell expressing and displaying same (i.e., an immunogen), optionally formulated with any suitable or desired carrier, adjuvant, or pharmaceutically acceptable excipient, is administered to a non-human animal subject, for example, a mouse, chicken, rat, rabbit, guinea pig, dog, horse, cow, goat or pig. The immunogen may be administered intranasally, intramuscularly, sub-cutaneously, intravenously, intradermally, intraperitoneally, or by other known route.

The production of polyclonal antibodies may be monitored by sampling blood of the immunized animal at various points following immunization. One or more further immunizations may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (mAbs).

Monoclonal antibodies are exemplary antibodies contemplated by the present disclosure. The term "monoclonal antibody" or "mAb" or "MAb" refers to a homogeneous antibody population capable of binding to the same antigen(s) and, for example, to the same epitope within the antigen. This term is not intended to be limited with respect to the source of the antibody or the manner in which it is made.

For the production of mAbs any one of a number of known techniques may be used, such as, for example, the procedure exemplified in U.S. Pat. No. 4,196,265 or Harlow and Lane (1988) or Zola (1987).

For example, a suitable animal is immunized with an effective amount of the protein or immunogenic fragment or epitope thereof or cell expressing same under conditions sufficient to stimulate antibody producing cells. Rodents such as rabbits, mice and rats are exemplary animals, with mice being most commonly used. Mice genetically-engineered to express human immunoglobulin proteins, and not express murine immunoglobulin proteins, can also be used to generate an antibody of the present disclosure (e.g., as described in WO2002/066630).

Following immunization, somatic cells with the potential for producing antibodies, specifically B lymphocytes (B cells), are selected for use in the MAb generating protocol. These cells may be obtained from biopsies of spleens, tonsils or lymph nodes, or from a peripheral blood sample. The B cells from the immunized animal are then fused with cells of an immortal myeloma cell, generally derived from the same species as the animal that was immunized with the immunogen. B cells and immortal cells are fused by incubating a mixture of the cells types in the presence of an agent or agents (chemical or electrical) that promote the fusion of cell membranes. Fusion methods using Sendai virus have been described by Kohler and Milstein, (1975); and Kohler and Milstein, (1976). Methods using polyethylene glycol (PEG), such as 37% (v/v) PEG, are described by Gefter et al, (1977). The use of electrically induced fusion methods is also appropriate.

Hybrids are amplified by culture in a selective medium comprising an agent that blocks the de novo synthesis of nucleotides in the tissue culture media. Exemplary and exemplary agents are aminopterin, methotrexate and azaserine.

The amplified hybridomas are subjected to a functional selection for antibody specificity and/or titer, such as, for example, by flow cytometry and/or immunohistochemstry and/or immunoassay (e.g. radioimmunoassay, enzyme immunoassay, cytotoxicity assay, plaque assay, dot immunoassay, and the like). The present disclosure also contemplates sub-cloning of antibody producing cells, e.g., as exemplified herein.

Alternatively, ABL-MYC technology (NeoClone, Madison Wis. 53713, USA) is used to produce cell lines secreting MAbs (e.g., as described in Kumar et al, 1999).

Antibodies can also be produced or isolated by screening a display library, e.g., a phage display library, e.g., as described in U.S. Pat. No. 6,300,064 EP0368684 and/or U.S. Pat. No. 5,885,793.

Chimeric Antibodies and Proteins

In one example an antibody or Fn14-binding protein of the disclosure is a chimeric antibody or an Fn14-binding protein is a chimeric protein. The term "chimeric proteins" refers to proteins in which an antigen binding domain $V_H$ or $V_L$ is from identical with or homologous to corresponding sequences in proteins derived from a particular species (e.g., murine, such as mouse or rat) or belonging to a particular antibody class or subclass, while the remainder of the chain(s) protein is identical with or homologous to corresponding sequences in from a proteins derived from another species (e.g., primate, such as human) or belonging to another antibody class or subclass. In one example, a chimeric protein is a chimeric antibody comprising a $V_H$ and a $V_L$ from a non-human antibody (e.g., a murine antibody) and the remaining regions of the antibody are from a human antibody. The production of such chimeric proteins is known in the art, and may be achieved by standard means (as described, e.g., in U.S. Pat. Nos. 6,331,415; 5,807,715; 4,816,567 and 4,816,397).

Humanized and Human Antibodies/Proteins

The antibodies or Fn14-binding proteins of the present disclosure may be humanized or human.

The term "humanized protein" shall be understood to refer to a protein comprising a human-like variable region including CDRs from an antibody from a non-human species grafted onto or inserted into FRs from a human antibody (this type of antibody is also referred to a "CDR-grafted antibody"). Humanized proteins also include proteins in which one or more residues of the human protein are modified by one or more amino acid substitutions and/or one or more FR residues of the human protein are replaced by corresponding non-human residues. Humanized proteins may also comprise residues which are found neither in the human antibody or in the non-human antibody. Any additional regions of the protein (e.g., Fc region) are generally human. Humanization can be performed using a method known in the art, e.g., U.S. Pat. Nos. 5,225,539, 6,054,297, 7,566,771 or 5,585,089. The term "humanized protein" also encompasses a super-humanized protein, e.g., as described in U.S. Pat. No. 7,732,578.

In one example, a humanized protein comprises the regions between 27d and 34, 50 and 55, and 89 and 96 in a light chain sequence disclosed herein; and 31 and 35b, 50 and 58, and 95 and 101 in a heavy chain sequence disclosed herein (numbering according to the Kabat numbering system). In this regard, Padlan et al., *FASEB J.,* 9: 133-139, 1995 presents evidence that these regions are those most likely to bind or contact antigen.

The term "human protein" as used herein refers to proteins having variable and, optionally, constant antibody regions derived from or corresponding to sequences found in humans, e.g. in the human germline or somatic cells. The "human" antibodies can include amino acid residues not encoded by human sequences, e.g. mutations introduced by random or site directed mutations in vitro (in particular mutations which involve conservative substitutions or mutations in a small number of residues of the protein, e.g. in 1, 2, 3, 4 or 5 of the residues of the protein. These "human antibodies" do not actually need to be generated as a result of an immune response of a human, rather, they can be generated using recombinant means (e.g., screening a phage display library) and/or by a transgenic animal (e.g., a mouse) comprising nucleic acid encoding human antibody constant and/or variable regions and/or using guided selection (e.g., as described in or U.S. Pat. No. 5,565,332). This term also encompasses affinity matured forms of such antibodies. A human protein will also be considered to include a protein comprising FRs from a human antibody or FRs comprising sequences from a consensus sequence of human FRs and in which one or more of the CDRs are random or semi-random, e.g., as described in U.S. Pat. No. 6,300,064 and/or U.S. Pat. No. 6,248,516.

Human proteins or antibodies which recognize a selected epitope can also be generated using a technique referred to as "guided selection." In this approach a selected non-human monoclonal antibody, e.g., a mouse antibody, is used to guide the selection of a completely human antibody recognizing the same epitope (Jespers et al, 1988).

A human Fn14-binding protein of the disclosure comprises a variable region of a human antibody.

Synhumanized and Primatized Proteins

The Fn14-binding proteins of the present disclosure may be synhumanized proteins. The term "synhumanized protein" refers to a protein prepared by a method described in WO2007/019620. A synhumanized Fn14-binding protein includes a variable region of an antibody, wherein the variable region comprises FRs from a New World primate antibody variable region and CDRs from a non-New World primate antibody variable region. For example, a synhumanized Fn14-binding protein includes a variable region of an antibody, wherein the variable region comprises FRs from a New World primate antibody variable region and CDRs from a mouse antibody, e.g., as described herein. In one example, the synhumanized Fn14-binding protein is an Fn14-binding antibody in which one or both of the variable regions are synhumanized.

The Fn14-binding proteins of the present disclosure may be primatized proteins. A "primatized protein" comprises variable region(s) from an antibody generated following immunization of a non-human primate (e.g., a cynomolgus macaque). Optionally, the variable regions of the non-human primate antibody are linked to human constant regions to produce a primatized antibody. Exemplary methods for producing primatized antibodies are described in U.S. Pat. No. 6,113,898.

De-Immunized Antibodies and Proteins

The present disclosure also contemplates a de-immunized antibody or Fn14-binding protein. De-immunized antibodies and Fn14-binding proteins have one or more epitopes, e.g., B cell epitopes or T cell epitopes removed (i.e., mutated) to thereby reduce the likelihood that a subject will raise an immune response against the antibody or protein. Methods for producing de-immunized antibodies and proteins are known in the art and described, for example, in WO00/34317, WO2004/108158 and WO2004/064724.

Methods for introducing suitable mutations and expressing and assaying the resulting protein will be apparent to the skilled artisan based on the description herein.

Antibody Variable Region Containing Proteins

Single-Domain Antibodies

In some examples, an Fn14-binding protein of the disclosure is a single-domain antibody (which is used interchangeably with the term "domain antibody" or "dAb"). A single-domain antibody is a single polypeptide chain comprising all or a portion of the heavy chain variable region of an antibody. In certain example, a single-domain antibody is a human single-domain antibody (Domantis, Inc., Waltham, Mass.; see, e.g., U.S. Pat. No. 6,248,516; WO90/05144 and/or WO2004/058820).

Diabodies, Triabodies, Tetrabodies

Exemplary Fn14-binding proteins comprising an antibody antigen binding domain are diabodies, triabodies, tetrabodies and higher order protein complexes such as those described in WO98/044001 and WO94/007921.

For example, a diabody is a protein comprising two associated polypeptide chains, each polypeptide chain comprising the structure $V_L$-X-$V_H$ or $V_H$-X-$V_L$, wherein $V_L$ is an antibody light chain variable region, $V_H$ is an antibody heavy chain variable region, X is a linker comprising insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding site, i.e., to form an Fv molecule capable of specifically binding to one or more antigens. The $V_L$ and $V_H$ can be the same in each polypeptide chain or the $V_L$ and $V_H$ can be different in each polypeptide chain so as to form a bispecific diabody (i.e., comprising two Fvs having different specificity).

Single Chain Fv (scFv) Fragments

The skilled artisan will be aware that scFvs comprise $V_H$ and $V_L$ regions in a single polypeptide chain. The polypeptide chain further comprises a polypeptide linker between the $V_H$ and $V_L$ which enables the scFv to form the desired structure for antigen binding (i.e., for the $V_H$ and $V_L$ of the single polypeptide chain to associate with one another to form a Fv). For example, the linker comprises in excess of 12 amino acid residues with $(Gly_4Ser)_3$ being one of the more favored linkers for a scFv.

The present disclosure also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv (see, for example, Brinkmann et al., 1993).

Alternatively, or in addition, the present disclosure provides a dimeric scFv, i.e., a protein comprising two scFv molecules linked by a non-covalent or covalent linkage, e.g., by a leucine zipper domain (e.g., derived from Fos or Jun) (see, for example, Kruif and Logtenberg, 1996). Alternatively, two scFvs are linked by a peptide linker of sufficient length to permit both scFvs to form and to bind to an antigen, e.g., as described in US20060263367.

For a review of scFv, see Plückthun (1994).

Minibodies

The skilled artisan will be aware that a minibody comprises the $V_H$ and $V_L$ domains of an antibody fused to the $C_H2$ and/or $C_H3$ domain of an antibody. Optionally, the minibody comprises a hinge region between the $V_H$ and a $V_L$, sometimes this conformation is referred to as a Flex Minibody. A minibody does not comprise a $C_H1$ or a $C_L$. In one example, the $V_H$ and $V_L$ domains are fused to the hinge region and the $C_H3$ domain of an antibody. At least one of the variable regions of said minibody binds to Fn14 in the manner of the disclosure. Exemplary minibodies and methods for their production are described, for example, in WO94/09817.

Other Antibody Variable Region Containing Proteins

The present disclosure also contemplates other variable region containing Fn14-binding proteins, such as:

(i) "key and hole" bispecific proteins as described in U.S. Pat. No. 5,731,168;

(ii) heteroconjugate proteins, e.g., as described in U.S. Pat. No. 4,676,980;

(iii) heteroconjugate proteins produced using a chemical cross-linker, e.g., as described in U.S. Pat. No. 4,676,980;

(iv) Fab'-SH fragments, e.g., as described in Shalaby (1992);

(v) single chain Fab; or (vi) $Fab_3$ (e.g., as described in EP19930302894).

Non-Antibody Based Antigen Binding Domain Containing Proteins

Immunoglobulins and Immunoglobulin Fragments

An example of a compound of the present disclosure is a protein comprising a variable region of an immunoglobulin, such as a T cell receptor or a heavy chain immunoglobulin (e.g., an IgNAR, a camelid antibody).

The term "immunoglobulin" will be understood to include any antigen binding protein comprising an immunoglobulin domain. Exemplary immunoglobulins are antibodies. Additional proteins encompassed by the term "immunoglobulin" include domain antibodies, camelid antibodies and antibodies from cartilaginous fish (i.e., immunoglobulin new antigen receptors (IgNARs)). Generally, camelid antibodies and IgNARs comprise a $V_H$, however lack a $V_L$ and are often referred to as heavy chain immunoglobulins. Other "immunoglobulins" include T cell receptors.

Heavy Chain Immunoglobulins

Heavy chain immunoglobulins differ structurally from many other forms of immunoglobulin (e.g., antibodies), in so far as they comprise a heavy chain, but do not comprise a light chain. Accordingly, these immunoglobulins are also referred to as "heavy chain only antibodies". Heavy chain immunoglobulins are found in, for example, camelids and cartilaginous fish (also called IgNAR).

The variable regions present in naturally occurring heavy chain immunoglobulins are generally referred to as "VHH domains" in camelid Ig and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

Heavy chain immunoglobulins do not require the presence of light chains to bind with high affinity and with high specificity to a relevant antigen. This means that single domain binding fragments can be derived from heavy chain immunoglobulins, which are easy to express and are generally stable and soluble.

A general description of heavy chain immunoglobulins from camelids and the variable regions thereof and methods for their production and/or isolation and/or use is found inter alia in the following references WO94/04678, WO97/49805 and WO 97/49805.

A general description of heavy chain immunoglobulins from cartilaginous fish and the variable regions thereof and methods for their production and/or isolation and/or use is found inter alia in WO2005/118629.

V-Like Proteins

An example of a Fn14-binding protein of the disclosure is a T-cell receptor. T cell receptors have two V-domains that combine into a structure similar to the Fv module of an antibody. Novotny et al., *Proc Natl Acad Sci USA* 88: 8646-8650, 1991 describes how the two V-domains of the T-cell receptor (termed alpha and beta) can be fused and expressed as a single chain polypeptide and, further, how to alter surface residues to reduce the hydrophobicity directly analogous to an antibody scFv. Other publications describing production of single-chain T-cell receptors or multimeric T cell receptors comprising two V-alpha and V-beta domains include WO1999/045110 or WO2011/107595.

Other non-antibody proteins comprising antigen binding domains include proteins with V-like domains, which are generally monomeric. Examples of proteins comprising such V-like domains include CTLA-4, CD28 and ICOS. Further disclosure of proteins comprising such V-like domains is included in WO1999/045110.

Adnectins

In one example, a Fn14-binding protein of the disclosure is an adnectin. Adnectins are based on the tenth fibronectin type III ($^{10}$Fn3) domain of human fibronectin in which the loop regions are altered to confer antigen binding. For example, three loops at one end of the β-sandwich of the $^{10}$Fn3 domain can be engineered to enable an Adnectin to specifically recognize an antigen. For further details see US20080139791 or WO2005/056764.

Anticalins

In a further example, a Fn14-binding protein of the disclosure is an anticalin. Anticalins are derived from lipocalins, which are a family of extracellular proteins which transport small hydrophobic molecules such as steroids, bilins, retinoids and lipids. Lipocalins have a rigid β-sheet secondary structure with a plurality of loops at the open end of the conical structure which can be engineered to bind to an antigen. Such engineered lipocalins are known as anticalins. For further description of anticalins see U.S. Pat. No. 7,250,297B1 or US20070224633.

Affibodies

In a further example, a Fn14-binding protein of the disclosure is an affibody. An affibody is a scaffold derived from the Z domain (antigen binding domain) of Protein A of *Staphylococcus aureus* which can be engineered to bind to antigen. The Z domain consists of a three-helical bundle of approximately 58 amino acids. Libraries have been generated by randomization of surface residues. For further details see EP1641818.

Avimers

In a further example, a Fn14-binding protein of the disclosure is an Avimer. Avimers are multidomain proteins derived from the A-domain scaffold family. The native domains of approximately 35 amino acids adopt a defined disulphide bonded structure. Diversity is generated by shuffling of the natural variation exhibited by the family of A-domains. For further details see WO2002088171.

DARPins

In a further example, a Fn14-binding protein of the disclosure is a Designed Ankyrin Repeat Protein (DARPin). DARPins are derived from Ankyrin which is a family of proteins that mediate attachment of integral membrane proteins to the cytoskeleton. A single ankyrin repeat is a 33 residue motif consisting of two α-helices and a β-turn. They can be engineered to bind different target antigens by randomizing residues in the first α-helix and a β-turn of each repeat. Their binding interface can be increased by increasing the number of modules (a method of affinity maturation). For further details see US20040132028.

Other Non Antibody Polypeptides

Other non-antibody proteins comprising binding domains include those based on human γ-crystallin and human ubiquitin (affilins), kunitz type domains of human protease inhibitors, PDZ-domains of the Ras-binding protein AF-6, scorpion toxins (charybdotoxin), C-type lectin domain (tetranectins).

Constant Regions

The present disclosure encompasses Fn14-binding proteins comprising a variable region and a constant region or a domain(s) thereof, e.g., Fc, $C_H2$ and/or $C_H3$ domain. The skilled artisan will be aware of the meaning of the terms constant region and constant domain based on the disclosure herein and references discussed herein.

Constant region sequences useful for producing the Fn14-binding proteins of the present disclosure may be obtained from a number of different sources. In some examples, the constant region or portion thereof of the Fn14-binding protein is derived from a human antibody. Moreover, the constant domain or portion thereof may be derived from any antibody class, including IgM, IgG, IgD, IgA and IgE, and any antibody isotype, including IgG1, IgG2, IgG3 and IgG4. In one example, the human isotype IgG1 is used.

A variety of constant region gene sequences are available in the form of publicly accessible deposits or the sequence thereof is available from publicly available databases. Constant regions can be selected having a particular effector function (or lacking a particular effector function) or with a particular modification to reduce immunogenicity.

In one example, a protein of the present disclosure has or displays an effector function that facilitates or enables at least partial depletion, substantial depletion or elimination of cells expressing Fn14. Such an effector function may be enhanced binding affinity to Fc receptors, antibody-dependent cell-mediated cytotoxicity (ADCC), antibody-dependent cell mediated phagocytosis (ADCP) and/or complement dependent cytotoxicity (CDC).

In one example, the Fn14-binding protein is capable of inducing an enhanced level of effector function.

In one example, the level of effector function induced by the constant region is enhanced relative to a wild-type Fc region of an IgG1 antibody or a wild-type Fc region of an IgG3 antibody.

In another example, the constant region is modified to increase the level of effector function it is capable of inducing compared to the constant region without the modification. Such modifications can be at the amino acid level and/or the secondary structural level and/or the tertiary structural level and/or to the glycosylation of the Fc region.

The skilled addressee will appreciate that greater effector function may be manifested in any of a number of ways, for example as a greater level of effect, a more sustained effect or a faster rate of effect.

Exemplary constant region modifications include amino acid substitutions, such as, S239D/I332E, numbered according to the EU index of Kabat or S239D/A330L/I332E, numbered according to the EU index of Kabat.

Additional amino acid substitutions that increase ability of an Fc region to induce effector function are known in the art and/or described, for example, in U.S. Pat. Nos. 6,737,056 or 7,317,091.

In one example, the glycosylation of the constant region is altered to increase its ability to induce enhanced effector function. In some examples, Fc regions according to the present disclosure comprise a carbohydrate structure that lacks fucose attached (directly or indirectly) to an Fc region, i.e., the Fc region is "afucosylated". Such variants may have an improved ability to induce ADCC. Methods for producing afucosylated antibodies include, expressing the Fn14-binding protein in a cell line incapable of expressing α-1,6-fucosyltransferase (FUT8) (e.g., as described in Yumane-Ohnuki et al., 2004). Other methods include the use of cell lines which inherently produce antibodies capable of inducing enhanced effector function (e.g. duck embryonic derived stem cells for the production of viral vaccines, WO2008/129058; Recombinant protein production in avian EBX® cells, WO 2008/142124).

Fn14-binding proteins can also comprise an Fc region capable of inducing enhanced levels of CDC. For example, hybrids of IgG1 and IgG3 produce antibodies having enhanced CDC activity (Natsume et al., 2008).

Methods for determining the ability of an antibody or antigen binding fragment thereof to induce effector function and known in the art and/or described herein.

In another example, the protein comprises one or more amino acid substitutions that increase the half-life of the Fn14-binding protein. For example, the Fn14-binding protein comprises a constant region comprising one or more amino acid substitutions that increase the affinity of the constant region for the neonatal Fc region (FcRn). For example, the constant region has increased affinity for FcRn at lower pH, e.g., about pH 6.0, to facilitate Fc/FcRn binding in an endosome. In one example, the constant region has increased affinity for FcRn at about pH 6 compared to its affinity at about pH 7.4, which facilitates the re-release of Fc into blood following cellular recycling. These amino acid substitutions are useful for extending the half life of a protein, by reducing clearance from the blood.

Exemplary amino acid substitutions include T250Q and/or M428L or T252A, T254S and T266F or M252Y, S254T and T256E or H433K and N434F according to the EU numbering system. Additional or alternative amino acid substitutions are described, for example, in US20070135620 or U.S. Pat. No. 7,083,784.

Neutralizing Fn14-binding proteins of the present disclosure can comprise an IgG4 constant region or a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat. This position corresponds to position 228 of the hinge region according to the EU numbering system. In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulphide (S—S) bonds in the same positions (see for example WO2010/080538).

Mutant Proteins

The present disclosure provides an Fn14-binding protein having at least 80% identity to a sequence of the disclosure and having the same functional characteristics described or claimed herein.

In one example, an Fn14-binding protein of the disclosure comprises a sequence having at least 80% or 85% or 90% or 91% or 92% or 93% or 94% or 95% or 96% or 97% or 98% or 99% identity to a $V_L$ sequence disclosed herein, provided that the sequence comprises a serine at a position corresponding to residue 57 of SEQ ID NO: 14. In this regard, the inventors have identified several antibodies sharing at least about 92% identity over their entire length.

In another example, an Fn14-binding protein of the disclosure comprises a sequence having at least 70% or 75% or 80% or 85% or 90% or 91% or 92% or 93% or 94% or 95% or 96% or 97% or 98% or 99% identity to a $V_H$ of the disclosure described herein, provided that the sequence comprises one or more of a tryptophan at a position corresponding to position 31 of SEQ ID NO: 13, a glutamine at a position corresponding to position 54 of SEQ ID NO: 13, an arginine or a serine at a position corresponding to position 101 of SEQ ID NO: 13, a histidine at a position corresponding to position 107 of SEQ ID NO: 13 or a histidine at a position corresponding to position 108 of SEQ ID NO: 13. In this regard, the inventors have identified several antibodies sharing at least about 92% identity over their entire length. The inventors have also identified a series of HCDR1 according to the Kabat numbering system sharing 60% identity over their entire length. The inventors have also identified a series of HCDR2 according to the Kabat numbering system sharing 74% identity over their entire length. The inventors have also identified a series of HCDR3 according to the Kabat numbering system sharing about 63% identity over their entire length.

As discussed above, it is also known in the art that the five C-terminal residues of heavy chain CDR2 can be mutated to conservative or non-conservative amino acid substitutions (26% of residues) (Padlan et al., 1995). This combined with the variable sites identified by the inventors (five) means up to 52% variation (or at least 48% identity) to a sequence of a CDR2 (according to the Kabat numbering system) as taught herein.

The present disclosure also provides a nucleic acid encoding the foregoing proteins or nucleic acids that hybridize thereto under moderate to high stringency conditions.

The present disclosure also encompasses nucleic acids encoding a protein comprising a sequence set forth in any one of SEQ ID NOs: 13-28, which differs from a sequence exemplified herein as a result of degeneracy of the genetic code.

The % identity of a nucleic acid or polypeptide is determined by GAP (Needleman and Wunsch. 1970) analysis (GCG program) with a gap creation penalty=5, and a gap extension penalty=0.3. The query sequence is at least 50 residues in length, and the GAP analysis aligns the two sequences over a region of at least 50 residues. For example, the query sequence is at least 100 residues in length and the GAP analysis aligns the two sequences over a region of at least 100 residues. In one example, the two sequences are aligned over their entire length.

The present disclosure contemplates mutant forms of an Fn14-binding protein of the disclosure. For example, such a mutant Fn14-binding protein comprises one or more conservative amino acid substitutions compared to a sequence set forth herein. In some examples, the Fn14-binding protein comprises 10 or fewer, e.g., 9 or 8 or 7 or 6 or 5 or 4 or 3 or 2 or 1 conservative amino acid substitutions. A "conservative amino acid substitution" is one in which the amino acid residue is replaced with an amino acid residue having a similar side chain and/or hydropathicity and/or hydrophilicity.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), ft-branched side chains (e.g., threonine, valine, isoleucine) and aromatic side chains (e.g., tyrosine, phenylalanine, tryptophan, histidine). Hydropathic indices are described, for example in Kyte and Doolittle (1982) and hydrophylic indices are described in, e.g., U.S. Pat. No. 4,554,101.

The present disclosure also contemplates non-conservative amino acid changes. For example, of particular interest are substitutions of charged amino acids with another charged amino acid and with neutral or positively charged amino acids. In some examples, the Fn14-binding protein comprises 10 or fewer, e.g., 9 or 8 or 7 or 6 or 5 or 4 or 3 or 2 or 1 non-conservative amino acid substitutions.

A mutant form of an Fn14-binding protein described herein according to any example retains the ability to specifically bind to Fn14. Methods for determining specific binding to Fn14 are described herein. For example, a labeled Fn14-binding protein is brought into contact with immobilized Fn14. Following washing, bound label is detected. The labeled Fn14-binding protein is also brought into contact with immobilized Fn14 and a related protein or a mutant form of Fn14 or a fragment of Fn14 and, following washing, bound label is detected. Detection of label bound to Fn14 but not to the related or mutant protein or a fragment of Fn14 indicates that the mutant Fn14-binding protein retains the ability to specifically bind to Fn14.

In one example, the mutation(s) occur within a FR of an Fn14-binding protein of the disclosure. In another example, the mutation(s) occur within a CDR of an Fn14-binding protein of the disclosure.

Affinity Maturation

In a further example, an existing Fn14-binding protein of the disclosure is affinity matured to produce an antibody capable of binding to Fn14 with increased affinity. For example, the sequence encoding the $V_L$ and/or $V_H$ is isolated and the CDR encoding region (e.g., the region encoding CDR3 of the $V_L$ and/or $V_H$) is mutated such that one or more amino acid substitutions is introduced. The resulting mutant Fn14-binding protein is then screened for binding to Fn14, e.g., in a competitive assay.

The Fn14-binding proteins according to the disclosure may be soluble secreted proteins or may be presented as a fusion protein on the surface of a cell, or particle (e.g., a phage or other virus, a ribosome or a spore). Exemplary phage display methods are described, for example, in U.S. Pat. No. 5,821,047; 6,248,516 and 6,190,908. Phage display particles produced using these methods are then screened to identify a displayed Fn14-binding protein having a conformation sufficient for binding to a target antigen e.g., Fn14.

Protein Production

In one example, an Fn14-binding protein of the disclosure is produced by culturing a cell line, e.g., a hybridoma under conditions sufficient to produce the protein, e.g., as described herein and/or as is known in the art.

Recombinant Expression

In the case of a recombinant protein, nucleic acid encoding same is placed into one or more expression construct, e.g., expression vector(s), which is/are then transfected into host cells, such as cells that can produce a disulphide bridge or bond, such as *E. coli* cells, yeast cells, insect cells, or mammalian cells. Exemplary mammalian cells include simian COS cells, Chinese Hamster Ovary (CHO) cells, or myeloma cells that do not otherwise produce immunoglobulin protein. Molecular cloning techniques to achieve these ends are known in the art and described, for example in Ausubel or Sambrook. A wide variety of cloning and in vitro amplification methods are suitable for the construction of recombinant nucleic acids. Methods of producing recombinant antibodies are also known in the art. See U.S. Pat. No. 4,816,567; 7,923,221 and 7,022,500.

Following isolation, the nucleic acid encoding a protein of the disclosure is inserted into an expression construct or replicable vector for further cloning (amplification of the DNA) or for expression in a cell-free system or in cells. For example, the nucleic acid is operably linked to a promoter, As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Cell free expression systems are also contemplated by the present disclosure. For example, a nucleic acid encoding an Fn14-binding protein of the disclosure is operably linked to a suitable promoter, e.g., a T7 promoter, and the resulting expression construct exposed to conditions sufficient for transcription and translation. Typical expression vectors for in vitro expression or cell-free expression have been described and include, but are not limited to the TNT T7 and TNT T3 systems (Promega), the pEXP1-DEST and pEXP2-DEST vectors (Invitrogen).

Many vectors for expression in cells are available. The vector components generally include, but are not limited to, one or more of the following: a signal sequence, a sequence encoding Fn14-binding protein of the present disclosure (e.g., derived from the information provided herein), an enhancer element, a promoter, and a transcription termination sequence. The skilled artisan will be aware of suitable sequences for expression of a protein. For example, exemplary signal sequences include prokaryotic secretion signals (e.g., pelB, alkaline phosphatase, penicillinase, Ipp, or heat-stable enterotoxin II), yeast secretion signals (e.g., invertase leader, α factor leader, or acid phosphatase leader) or mammalian secretion signals (e.g., herpes simplex gD signal).

Exemplary promoters include those active in prokaryotes (e.g., phoA promoter, β-lactamase and lactose promoter systems, alkaline phosphatase, a tryptophan (trp) promoter system, and hybrid promoters such as the tac promoter).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, AUSTRALIAN CELL BANK CRL 1651); human embryonic kidney line (293 or 293 cells subcloned for growth in suspension culture; baby hamster kidney cells (BHK, AUSTRALIAN CELL BANK CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid molecule or a gene construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation, viral transduction (e.g., using a lentivirus) and microparticle bombardment such as by using DNA-coated tungsten or gold particles (Agracetus Inc., WI, USA) amongst others.

The host cells used to produce the Fn14-binding protein of this disclosure may be cultured in a variety of media, depending on the cell type used. Commercially available media such as Ham's F10 (Sigma), Minimal Essential Medium ((MEM), (Sigma), RPM1-1640 (Sigma), and Dulbecco's Modified Eagle's Medium ((DMEM), Sigma) are suitable for culturing mammalian cells. Media for culturing other cell types discussed herein are known in the art.

Isolation of Proteins

A Fn14-binding protein of the present disclosure is can be isolated or purified.

Methods for purifying an Fn14-binding protein of the disclosure are known in the art and/or described herein.

When using recombinant techniques, the Fn14-binding protein of the disclosure can be produced intracellularly, in the periplasmic space, or directly secreted into the medium. If the protein is produced intracellularly, as a first step, the particulate debris, either host cells or lysed fragments, is removed, for example, by centrifugation or ultrafiltration. Where the protein is secreted into the medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Zola (1997).

The skilled artisan will also be aware that an Fn14-binding protein of the disclosure can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. For example, the tag is a hexa-his tag. The resulting protein is then purified using methods known in the art, such as, affinity purification. For example, a protein comprising a hexa-his tag is purified by contacting a sample comprising the protein with nickel-nitrilotriacetic acid (Ni-NTA) that specifically binds a hexa-his tag immobilized on a solid or semi-solid support, washing the sample to remove unbound protein, and subsequently eluting the bound protein. Alternatively, or in addition a ligand or antibody that binds to a tag is used in an affinity purification method.

Conjugates

The present disclosure also provides conjugates of Fn14-binding proteins described herein according to any example. Examples of compounds to which a protein can be conjugated are selected from the group consisting of a radioisotope, a detectable label, a therapeutic compound, a colloid, a toxin, a nucleic acid, a peptide, a protein, a compound that increases the half life of the protein in a subject and mixtures thereof. Exemplary therapeutic agents include, but are not limited to an anti-angiogenic agent, an anti-neovascularization and/or other vascularization agent, an anti-proliferative agent, a pro-apoptotic agent, a chemotherapeutic agent or a therapeutic nucleic acid.

A toxin includes any agent that is detrimental to (e.g., kills) cells. For a description of these classes of drugs which are known in the art, and their mechanisms of action, see Goodman et al., (1990). Additional techniques relevant to the preparation of immunoglobulin-immunotoxin conjugates are provided in for instance in U.S. Pat. No. 5,194,594. Exemplary toxins include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO93/21232.

Suitable chemotherapeutic agents for forming immunoconjugates of the present disclosure include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)).

In one example, an Fn14-binding protein as described herein according to any example is conjugated or linked to another protein, including another Fn14-binding protein of the disclosure or a protein comprising an antibody variable region, such as an antibody or a protein derived therefrom, e.g., as described herein. Other proteins are not excluded. Additional proteins will be apparent to the skilled artisan and include, for example, an immunomodulator or a half-life extending protein or a peptide or other protein that binds to serum albumin amongst others.

Exemplary serum albumin binding peptides or protein are described in US20060228364 or US20080260757.

A variety of radionuclides are available for the production of radioconjugated proteins. Examples include, but are not limited to, low energy radioactive nuclei (e.g., suitable for diagnostic purposes), such as $^{13}C$, $^{15}N$, $^{2}H$, $^{125}I$, $^{123}I$, $^{99}Tc$, $^{43}K$, $^{52}Fe$, $^{67}Ga$, $^{68}Ga$, $^{111}In$ and the like. For example, the radionuclide is a gamma, photon, or positron-emitting radionuclide with a half-life suitable to permit activity or detection after the elapsed time between administration and localization to the imaging site. The present disclosure also encompasses high energy radioactive nuclei (e.g., for therapeutic purposes), such as $^{125}I$, $^{131}I$, $^{123}I$, $^{111}In$, $^{105}Rh$, $^{153}Sm$, $^{67}Cu$, $^{67}Ga$, $^{166}Ho$, $^{177}Lu$, $^{186}Re$ and $^{188}Re$. These isotopes typically produce high energy α- or β-particles which have a short path length. Such radionuclides kill cells to which they are in close proximity, for example neoplastic cells to which the conjugate has attached or has entered. They have little or no effect on non-localized cells and are essentially non-immunogenic. Alternatively, high-energy isotopes may be generated by thermal irradiation of an otherwise stable isotope, for example as in boron neutron-capture therapy (Guan et al., 1998).

In another example, the protein is conjugated to a "receptor" (such as streptavidin) for utilization in cell pretargeting wherein the conjugate is administered to the patient, followed by removal of unbound conjugate from the circulation using a clearing agent and then administration of a "ligand" (e.g., avidin) that is conjugated to a therapeutic agent (e.g., a radionucleotide).

The Fn14-binding proteins of the present disclosure can be modified to contain additional nonproteinaceous moieties that are known in the art and readily available. For example, the moieties suitable for derivatization of the protein are physiologically acceptable polymer, e.g., a water soluble polymer. Such polymers are useful for increasing stability and/or reducing clearance (e.g., by the kidney) and/or for reducing immunogenicity of an Fn14-binding protein of the disclosure. Non-limiting examples of water soluble polymers include, but are not limited to, polyethylene glycol (PEG), polyvinyl alcohol (PVA), or propropylene glycol (PPG).

In one example, an Fn14-binding protein as described herein according to any example comprises one or more detectable markers to facilitate detection and/or isolation. For example, the compound comprises a fluorescent label such as, for example, fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7, fluorescein (5-carboxyfluorescein-N-hydroxysuccinimide ester), rhodamine (5,6-tetramethyl rhodamine). The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm).

Alternatively, or in addition, the Fn14-binding protein as described herein according to any example is labeled with, for example, a fluorescent semiconductor nanocrystal (as described, for example, in U.S. Pat. No. 6,306,610).

Alternatively, or in addition, the Fn14-binding protein is labeled with, for example, a magnetic or paramagnetic compound, such as, iron, steel, nickel, cobalt, rare earth materials, neodymium-iron-boron, ferrous-chromium-cobalt, nickel-ferrous, cobalt-platinum, or strontium ferrite.

Immobilized Proteins

In one example an Fn14-binding protein is immobilized on a solid or semi-solid matrix. The term "immobilization" is to be understood to involve various methods and techniques to fix proteins onto specific matrices, e.g. as described in WO99/56126 or WO02/26292. For example, immobilization can serve to stabilize the proteins so that its activity is not reduced or adversely modified by biological, chemical or physical exposure, especially during storage or in single-batch use.

In the meaning of the disclosure, three basic methods can be used for immobilization:

Various methods for immobilizing a protein on a matrix are known in the art and include crosslinking, binding to a carrier, retention within a semi-permeable matrix.

Exemplary matrices include porous gels, aluminium oxide, bentonite, agarose, starch, nylon or polyacrylamide.

Assaying Activity of a Protein of the Disclosure

Binding Assays

One form of such an assay is an antigen binding assay, e.g., as described in Scopes (1994). Such a method generally involves labeling the Fn14-binding protein and contacting it with immobilized antigen or a fragment thereof, e.g., a protein comprising an extracellular domain of Fn14 fused to an Fc region of an antibody. Following washing to remove nonspecific bound protein, the amount of label and, as a consequence, bound protein is detected. Of course, the Fn14-binding protein can be immobilized and the antigen labeled. Panning-type assays, e.g., as described or exemplified herein can also be used.

Neutralization Assays

Assays for identifying Fn14-binding proteins that neutralize one or more Fn14-mediated Tweak activities will also be apparent to the skilled person.

For example, a neutralization assay comprises determining an Fn14-binding protein that reduces Tweak-induced NFκB-signaling in a cell expressing Fn14. In one example, a cell expressing Fn14 is produced or obtained that has incorporated into it, e.g., into its genome, a promoter operably linked to a reporter gene, wherein the promoter induces expression of the promoter in response to binding by NFκB. The cell is contacted with Tweak (or Tweak fused to an Fc region of an antibody) in the presence or absence of the Fn14-binding protein. A reduced level of expression of the reporter gene in the presence of the Fn14-binding protein compared to the absence of the Fn14-binding protein is indicative of reduction of Tweak-induced NFκB-signaling in a cell expressing Fn14. In one example, the cell is also contacted with the Fn14-binding protein in the absence of Tweak and the level of reporter gene expression determined, which permits identification of an Fn14-binding protein that does not have agonist activity. By testing multiple concentrations of the Fn14-binding protein an $IC_{50}$ is determined, i.e., a concentration at which 50% of the maximum inhibition of NFκB-signaling occurs.

Another means for testing for reduction of Tweak-induced NFκB-signaling in a cell expressing Fn14 is to test for the level of expression of a gene the expression of which is induced by NFκB. Such gene expression changes can be measured by nucleic acid-based detection assays (e.g., quantitative RT-PCR) or protein-based assays (e.g., as described herein). Exemplary genes induced by NFκB include IL-2, IL-6, TNF, BCL2, VEGF and COX2.

Another method for determining the ability of an Fn14-binding protein of the disclosure to neutralize Fn14-mediated Tweak activities is a receptor binding assay. In such a method, an Fn14 or soluble form thereof or cell expressing same is immobilized. Labeled Tweak is then contacted to the immobilized receptor or cell in the presence or absence of a test Fn14-binding protein and the amount of bound label detected. A reduction in the amount of bound label in the presence of the Fn14-binding protein compared to in the absence of the Fn14-binding protein indicates that the Fn14-binding protein reduces or prevents binding of Tweak to Fn14. By testing multiple concentrations of the Fn14-binding protein an $IC_{50}$ is determined, i.e., a concentration at which 50% of the maximum inhibition of Tweak binding to Fn14 occurs.

A further method for determining neutralization of Fn14-mediated Tweak activities is an ability of an Fn14-binding protein to reduce death of Kym1 cells in the presence of Tweak. Kym1 cells are contacted with Tweak (or Tweak fused to an Fc domain of an antibody) in the presence or absence of an Fn14-binding protein. A reduced level of cell death (e.g., assessed by propidium iodide uptake) in the presence of the Fn14-binding protein compared to in the absence of the Fn14-binding protein indicates that the Fn14-binding protein neutralizes of Fn14-mediated Tweak activities. In one example, the Kym1 cells are also contacted with the Fn14-binding protein in the absence of Tweak and the level of cell death determined, which permits identification of an Fn14-binding protein that does not have agonist activity. By testing multiple concentrations of the Fn14-binding protein an $IC_{50}$ is determined, i.e., a concentration at which 50% of the maximum inhibition of Kym1 cell death occurs.

Another method for determining the ability of an Fn14-binding protein of the disclosure to neutralize Fn14-mediated Tweak activities is to contact tumor cells with Tweak in the presence or absence of the Fn14-binding protein and to detect secretion of a cytokine, such as, IL-6. A lower level of the cytokine in the presence of the Fn14-binding protein compared to in the absence of the Fn14-binding protein indicates that the Fn14-binding protein neutralizes Fn14-mediated Tweak activities. In one example, the cells are also contacted with the Fn14-binding protein in the absence of Tweak and the level of cytokine secretion determined, which permits identification of an Fn14-binding protein that does not have agonist activity. By testing multiple concentrations of the Fn14-binding protein an $IC_{50}$ is determined, i.e., a concentration at which 50% of the maximum inhibition of cytokine secretion occurs.

Other assays for determining inhibition of Fn14-mediated Tweak activities include inhibition of tube formation by endothelial cells (e.g., HUVECs) and/or inhibition of Tweak-induced IL-8 secretion by A375 melanoma cells.

Cytokine Secretion Assays

In another example, the activity of a protein of the disclosure is determined by contacting a cell with a protein of the disclosure and determining secretion of a cytokine (e.g., IL-8) by the cell. Methods for determining IL-8 secretion are known in the art.

Cell Killing Assays

In another example, the ability of an Fn14-binding protein of the disclosure (e.g., linked to a toxic compound or a constant region) is assessed by determining their ability to induce death of a cell. In the case of a constant region-linked Fn14-binding protein it is desirable to perform such an assay in the presence of immune effector cells and/or complement (e.g., to facilitate ADCC/CDC).

In Vivo Therapeutic Efficacy Assays

A Fn14-binding protein of the disclosure can also be tested in vivo.

For example, an Fn14-binding protein can be tested in an animal model of a wasting disorder as described herein, e.g., in which a non-human mammal is administered a tumor cell expressing Fn14 under conditions for a wasting disorder to develop. an Fn14-binding protein of the disclosure is then administered and the effect on the wasting disorder is assessed, e.g., by monitoring body weight changes. A Fn14-binding protein that reduces or prevents loss of body weight or induces a gain in body weight is selected as a potential therapeutic agent.

A Fn14-binding protein of the disclosure can also be selected on the basis of its ability to reduce or prevent invasiveness of a tumor cell. For example, a tumor cell is implanted into a subject, e.g., into a muscle, and the subject is administered a test Fn14-binding protein (or for controls, no Fn14-binding protein is administered). A reduction in invasion of tissue surrounding the tumor cell (e.g., as assessed using histopathology) in the presence of the Fn14-binding protein compared to in the absence of the Fn14-binding protein indicates that the Fn14-binding protein reduces or prevent invasiveness of a tumor cell.

A Fn14-binding protein of the disclosure can also be assessed for therapeutic efficacy by determining its ability to slow or prevent development of a tumor in a xenograft model.

A Fn14-binding protein of the disclosure can also be assessed for therapeutic efficacy by determining it ability to reduce the amount of angiogenesis or vasculogenesis in a tumor in a xenograft model.

Therapeutic efficacy can also be assessed in animal models of rheumatoid arthritis e.g., a SKG strain of mouse (Sakaguchi et al.), rat type II collagen arthritis model, mouse type II collagen arthritis model; a mouse model of GVHD (e.g., as described in Trenado (2002)) or a model of ischemic stroke, e.g., aorta/vena cava occlusion, external neck torniquet or cuff, hemorrhage or hypotension, intracranial hypertension or common carotid artery occlusion, two-vessel occlusion and hypotension, four-vessel occlusion, unilateral common carotid artery occlusion (in some species only), endothelin-1-induced constriction of arteries and veins, middle cerebral artery occlusion, spontaneous brain infarction (in spontaneously hypertensive rats), macrosphere embolization, blood clot embolization or microsphere embolization.

Therapeutic efficacy can also be determined by administration of a Fn14-binding protein to a model of diabetes, e.g., type 1 diabetes. For example, the test subject is a non-obese diabetic (NOD) mouse (a model of Type I diabetes) or a mouse or rat to which streptozotocin has been administered (models of Type I and/or Type II diabetes).

Competitive Binding Assays

Assays for determining an Fn14-binding protein that competitively inhibits binding of an antibody of the disclosure will be apparent to the skilled artisan. For example, the antibody of the disclosure is conjugated to a detectable label, e.g., a fluorescent label or a radioactive label. The labeled antibody and the test Fn14-binding protein are then mixed and contacted with Fn14 or an extracellular domain thereof fused to an Fc region of an antibody or a peptide comprising an epitope thereof. The level of labeled antibody is then determined and compared to the level determined when the labeled antibody is contacted with the Fn14 or Fn14-Fc fusion or a peptide comprising an epitope thereof in the absence of the Fn14-binding protein. If the level of labeled antibody is reduced in the presence of the test Fn14-binding protein compared to the absence of the Fn14-binding protein, the Fn14-binding protein competitively inhibits binding of the antibody.

Optionally, the test Fn14-binding protein is conjugated to a different label than the antibody. This permits detection of the level of binding of the test Fn14-binding protein to the protein or epitope.

In another example, the test Fn14-binding protein is permitted to bind to Fn14 or Fn14-Fc fusion or a peptide comprising an epitope thereof prior to contacting the Fn14 or Fn14-Fc fusion or a peptide comprising an epitope thereof with an antibody described herein. A reduction in the amount of bound antibody in the presence of the Fn14-binding protein compared to in the absence of the Fn14-binding protein indicates that the Fn14-binding protein competitively inhibits binding of the antibody to Fn14. A reciprocal assay can also be performed using labeled Fn14-binding protein and first allowing the antibody to bind to Fn14 or Fn14-Fc fusion or a peptide comprising an epitope thereof. In this case, a reduced amount of labeled Fn14-binding protein bound to Fn14 or Fn14-Fc fusion or a peptide comprising an epitope thereof in the presence of the antibody compared to in the absence of antibody indicates that the Fn14-binding protein competitively inhibits binding of the antibody to Fn14.

Epitope Mapping Assays

In another example, the epitope bound by an Fn14-binding protein described herein is mapped. Epitope mapping methods will be apparent to the skilled artisan. For example, a series of overlapping peptides spanning the Fn14 sequence or a region thereof comprising an epitope of interest, e.g., peptides comprising 10-15 amino acids are produced. The Fn14-binding protein is then contacted to each peptide or a combination thereof and the peptide(s) to which it binds determined. This permits determination of peptide(s) comprising the epitope to which the Fn14-binding protein binds. If multiple non-contiguous peptides are bound by the Fn14-binding protein, the Fn14-binding protein may bind a conformational epitope.

In one example, random fragments of Fn14 are expressed on the surface of phage and the phage contacted with the Fn14-binding protein. Phage bound by the antibody can then be isolated and the amino acid sequence of the expressed peptide deduced by the encoding nucleic acid contained in the phage. By isolating a series of phage having overlapping peptides a peptide comprising a region of Fn14 comprising residues included in an epitope are identified.

Alternatively, or in addition, amino acid residues within Fn14 are mutated, e.g., by alanine scanning mutagenesis, and mutations that reduce or prevent Fn14-binding protein binding are determined. Any mutation that reduces or prevents binding of the Fn14-binding protein is likely to be within the epitope bound by the Fn14-binding protein.

A further method involves binding Fn14 or a region thereof to an immobilized Fn14-binding protein of the present disclosure and digesting the resulting complex with proteases. Peptide that remains bound to the immobilized Fn14-binding protein are then isolated and analyzed, e.g., using mass spectrometry, to determine their sequence.

A further method involves converting hydrogens in Fn14 or a region thereof to deutrons and binding the resulting protein to an immobilized Fn14-binding protein of the present disclosure. The deutrons are then converted back to hydrogen, the Fn14 or region thereof isolated, digested with enzymes and analyzed, e.g., using mass spectrometry to identify those regions comprising deutrons, which would have been protected from conversion to hydrogen by the binding of an Fn14-binding protein described herein.

In the foregoing paragraphs, reference to Fn14 encompasses recombinant Fn14, including the extracellular domain thereof.

Affinity Assays

Optionally, the dissociation constant (Kd) or association constant (Ka) or binding constant ($K_D$, i.e., Ka/Kd) of an Fn14-binding protein for Fn14 or an epitope containing peptide thereof is determined. These constants for an Fn14-binding protein is in one example measured by a radiolabeled or fluorescently-labeled Fn14 binding assay. This assay equilibrates the Fn14-binding protein with a minimal concentration of labeled Fn14 in the presence of a titration series of unlabeled Fn14. Following washing to remove unbound Fn14, the amount of label is determined. According to another example the constants are measured by using surface plasmon resonance assays, e.g., using BIAcore surface plasmon resonance (BIAcore, Inc., Piscataway, N.J.) with immobilized Fn14 or a region thereof.

Pharmaceutical Compositions and Methods of Treatment

Fn14-binding proteins of the disclosure (syn. active ingredients) are useful for formulations into a pharmaceutical composition for parenteral, topical, oral, or local administration, aerosol administration, or transdermal administration, for prophylactic or for therapeutic treatment. The pharmaceutical compositions can be administered in a variety of unit dosage forms depending upon the method of administration. For example, unit dosage forms suitable for oral administration include powder, tablets, pills, capsules and lozenges.

The pharmaceutical compositions of this disclosure are useful for parenteral administration, such as intravenous administration or subcutaneous administration or administration into a body cavity or lumen of an organ or joint. The compositions for administration will commonly comprise a solution of the Fn14-binding protein of the disclosure dissolved in a pharmaceutically acceptable carrier, such as an aqueous carrier. A variety of aqueous carriers can be used, e.g., buffered saline and the like. The compositions may contain pharmaceutically acceptable carriers as required to approximate physiological conditions such as pH adjusting and buffering agents, toxicity adjusting agents and the like, for example, sodium acetate, sodium chloride, potassium chloride, calcium chloride, sodium lactate and the like. The concentration of Fn14-binding proteins of the present disclosure in these formulations can vary widely, and will be selected primarily based on fluid volumes, viscosities, body weight and the like in accordance with the particular mode of administration selected and the patient's needs. Exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives.

The Fn14-binding protein of the disclosure can be formulated for parenteral administration, e.g., formulated for injection via the intravenous, intramuscular, sub-cutaneous, transdermal, or other such routes, including peristaltic administration and direct instillation into a tumor or disease site (intracavity administration). The preparation of an aqueous composition that contains the compounds of the present disclosure as an active ingredient will be known to those of skill in the art.

Suitable pharmaceutical compositions in accordance with the disclosure will generally include an amount of the Fn14-binding protein of the present disclosure admixed with an acceptable pharmaceutical carrier, such as a sterile aqueous solution, to give a range of final concentrations, depending on the intended use. The techniques of preparation are generally known in the art as exemplified by Remington's Pharmaceutical Sciences, 16th Ed. Mack Publishing Company, 1980.

Upon formulation, compounds of the present disclosure will be administered in a manner compatible with the dosage formulation and in such amount as is therapeutically/prophylactically effective. Suitable dosages of compounds of the present disclosure will vary depending on the specific compound, the condition to be treated and/or the subject being treated. It is within the ability of a skilled physician to determine a suitable dosage, e.g., by commencing with a sub-optimal dosage and incrementally modifying the dosage to determine an optimal or useful dosage.

Exemplary dosages and timings of administration will be apparent to the skilled artisan based on the disclosure herein.

In some examples, an Fn14-binding protein of the disclosure is administered with, prior to or after treatment for a condition, e.g., cancer. Exemplary treatments include radiation therapy, chemotherapy (e.g., caboplatin, siplatin, cyclophosphamide, docetaxal, doxorubicin, erlotinib, etoposide, fluorouracil, irinotecan, methotrexate, paclitaxel, topotecan, vincristine or vinblastine) or administration of another drug to treat a condition, e.g., a biologic such as rituximab, trastuzumab, bevacizumab, alemtuzumab, panitumumab, or cetuximab.

In one example, an Fn14-binding protein of the disclosure is administered with an appetite stimulant (e.g., a melanocortin-4 receptor antagonist, a ghrelin receptor agonist, megestrol acetate or a cannabinoid), a drug targeting an inflammatory cytokine (e.g., a TNF antagonist (e.g., etanercept, adalimumab, golimumab, infliximab), an anti-IL-6 antibody (e.g., CNTO-328, ALD-518), a β-adrenoreceptor antagonist, an anabolic steroid, myostatin, an ACE inhibitor or eicosapentaenoic acid).

Diagnostic/Prognostic Assays

It will be apparent from the description herein that the present disclosure provides various methods for diagnosing/prognosing conditions associated with Fn14 expression.

Protein Detection Assays

One example of the disclosure detects the presence of Fn14 or a cell expressing same. The amount, level or presence of a protein or cell is determined using any of a variety of techniques known to the skilled artisan such as, for example, a technique selected from the group consisting of flow cytometry, immunohistochemistry, immunofluorescence, an immunoblot, a Western blot, a dot blot, an enzyme linked immunosorbent assay (ELISA), radioimmunoassay (MA), enzyme immunoassay, fluorescence resonance energy transfer (FRET), matrix-assisted laser desorption/ionization time of flight (MALDI-TOF), electrospray ionization (ESI), mass spectrometry (including tandem mass spectrometry, e.g. LC MS/MS), biosensor technology, evanescent fiber-optics technology or protein chip technology.

In one example the assay used to determine the amount or level of a protein is a semi-quantitative assay.

In another example the assay used to determine the amount or level of a protein is a quantitative assay.

For example, the protein is detected with an immunoassay, e.g., using an assay selected from the group consisting of, immunohistochemistry, immunofluorescence, enzyme linked immunosorbent assay (ELISA), fluorescence linked immunosorbent assay (FLISA), Western blotting, radioimmunoassay (RIA), a biosensor assay, a protein chip assay and an immunostaining assay (e.g. immunofluorescence).

Standard solid-phase ELISA or FLISA formats are particularly useful in determining the concentration of a protein from a variety of samples.

In one form, an ELISA or FLISA comprises of immobilizing an Fn14-binding protein of the disclosure or a protein that binds to a different epitope of Fn14 on a solid matrix, such as, for example, a membrane, a polystyrene or polycarbonate microwell, a polystyrene or polycarbonate dipstick or a glass support. A sample is then brought into physical relation with the immobilized protein, Fn14 is bound or 'captured'. The bound Fn14 is then detected using a second labeled compound that binds to a different epitope of Fn14 (e.g., the Fn14-binding protein of the disclosure). Alternatively, a third labeled antibody can be used that binds the second (detecting) antibody.

It will be apparent to the skilled person that the assay formats described herein are amenable to high throughput formats, such as, for example automation of screening processes or a microarray format. Furthermore, variations of the above-described assay will be apparent to those skilled in the art, such as, for example, a competitive ELISA.

In an alternative example, a polypeptide is detected within or on a cell, using methods known in the art, such as, for example, immunohistochemistry or immunofluorescence. Methods using immunofluorescence are exemplary, as they are quantitative or at least semi-quantitative. Methods of quantitating the degree of fluorescence of a stained cell are known in the art and described, for example, in Cuello, 1984.

Biosensor devices generally employ an electrode surface in combination with current or impedance measuring elements to be integrated into a device in combination with the assay substrate (such as that described in U.S. Pat. No. 5,567,301). an Fn14-binding protein of the disclosure is incorporated onto the surface of a biosensor device and a biological sample contacted to said device. A change in the detected current or impedance by the biosensor device indicates protein binding to said Fn14-binding protein. Some forms of biosensors known in the art also rely on surface plasmon resonance to detect protein interactions, whereby a change in the surface plasmon resonance surface of reflection is indicative of a protein binding to a ligand or antibody (U.S. Pat. Nos. 5,485,277 and 5,492,840).

Biosensors are of particular use in high throughput analysis due to the ease of adapting such systems to micro- or nano-scales. Furthermore, such systems are conveniently adapted to incorporate several detection reagents, allowing for multiplexing of diagnostic reagents in a single biosensor unit. This permits the simultaneous detection of several proteins or peptides in a small amount of body fluids.

Imaging Methods

As will be apparent to the skilled artisan from the foregoing, the present disclosure also contemplates imaging methods using an Fn14-binding protein of the disclosure. For imaging, an Fn14-binding protein is generally conjugated to a detectable label, which can be any molecule or agent that can emit a signal that is detectable by imaging. However, a secondary labeled compound that specifically binds to an Fn14-binding protein of the disclosure may also be used. Exemplary detectable labels include a protein, a radioisotope, a fluorophore, a visible light emitting fluorophore, infrared light emitting fluorophore, a metal, a ferromagnetic substance, an electromagnetic emitting substance a substance with a specific magnetic resonance (MR) spectroscopic signature, an X-ray absorbing or reflecting substance, or a sound altering sub stance.

The Fn14-binding protein of the disclosure (and, if used the labeled secondary compound) can be administered either systemically or locally to an organ, or tissue (or tumor, in the case of a cancer) to be imaged, prior to the imaging procedure. Generally, the Fn14-binding protein is administered in doses effective to achieve the desired optical image of a tumor, tissue, or organ. Such doses may vary widely, depending upon the particular Fn14-binding protein employed, condition to be imaged, tissue, or organ subjected to the imaging procedure, the imaging equipment being used, and the like.

In some examples of the disclosure, the Fn14-binding protein is used as in vivo optical imaging agents of tissues and organs in various biomedical applications including, but not limited to, imaging of tumors, tomographic imaging of organs, monitoring of organ functions, coronary angiography, fluorescence endoscopy, laser guided surgery, photoacoustic and sonofluorescence methods, and the like.

Examples of imaging methods include magnetic resonance imaging (MRI), MR spectroscopy, radiography, computerized tomography (CT), ultrasound, planar gamma camera imaging, single-photon emission computed tomography (SPECT), positron emission tomography (PET), other nuclear medicine-based imaging, optical imaging using visible light, optical imaging using luciferase, optical imaging using a fluorophore, other optical imaging, imaging using near infrared light, or imaging using infrared light.

In some examples, an imaging agent is tested using an in vitro or in vivo assay prior to use in humans, e.g., using a model described herein.

Samples

To the extent that the method of the present disclosure is performed in vitro, on an isolated tissue sample, rather than as an in vivo based screen, reference to "sample" should be understood as a reference to any sample of biological material derived from an animal such as, but not limited to, a body fluid (e.g., blood or synovial fluid or cerebrospinal fluid), cellular material (e.g. tissue aspirate), tissue biopsy specimens or surgical specimens.

The sample which is used according to the method of the present disclosure may be used directly or may require some form of treatment prior to use. For example, a biopsy or surgical sample may require homogenization or other form of cellular dispersion prior to use. Furthermore, to the extent that the biological sample is not in liquid form, (if such form is required or desirable) it may require the addition of a reagent, such as a buffer, to mobilize the sample.

As will be apparent from the preceding description, such an assay may require the use of a suitable control, e.g. a normal or healthy individual or a typical population, e.g., for quantification.

As used herein, the term "normal individual" shall be taken to mean that the subject is selected on the basis that they do not have abnormal numbers of Fn14 expressing cells or abnormal levels of Tweak.

A "healthy subject" is one that has not been diagnosed as suffering from a condition, e.g., an Fn14-mediated condition and/or is not at risk of developing the condition.

Alternatively, or in addition, a suitable control sample is a control data set comprising measurements of the marker being assayed for a typical population of subjects known not to suffer from a condition.

In one example, a reference sample is not included in an assay. Instead, a suitable reference sample is derived from an established data set previously generated from a typical population. Data derived from processing, analyzing and/or assaying a test sample is then compared to data obtained for the sample population.

Fn14-Mediated Conditions

The present disclosure encompasses the use of an Fn14-binding protein or antibody or composition described herein to treat any Fn14-mediated condition. Exemplary conditions include cancer, metastasis, excessive vascularization or angiogenesis, an autoimmune disease, an inflammatory disease, a neurodegenerative diseases, keloid scarring, graft versus host disease, graft rejection or ischemia.

In one example, the Fn14-mediated condition is an inflammatory disease or an autoimmune disease. In one example, the condition is a connective tissue disease (including inflammatory arthritis, such as rheumatoid arthritis, psoriatic arthritis, reactive arthritis or gout), lupus (including systemic lupus erythematosus), type 1 diabetes, multiple sclerosis, vasculitis (including Wegener's granulomatosis and Henoch Schonlein Syndrome), nephritis (including glomerulonephritis and pneumonitis), atherosclerosis or inflammation of the eye (including uveitis).

In one example, the autoimmune condition is multiple sclerosis, neuritis, polymyositis, psoriasis, vitiligo, Sjogren's syndrome, arthritis (such as rheumatoid arthritis), Type 1 diabetes, autoimmune pancreatitis, inflammatory bowel diseases, Crohn's disease, ulcerative colitis, celiac disease, glomerulonephritis, scleroderma, sarcoidosis, autoimmune thyroid diseases, Hashimoto's thyroiditis, Graves disease, myasthenia gravis, Addison's disease, autoimmune uveoretinitis, pemphigus vulgaris, primary biliary cirrhosis, pernicious anemia, or systemic lupus erythematosis (SLE). In one example, the condition is rheumatoid arthritis or SLE.

In one example, the condition is a connective tissue disease, such as rheumatoid arthritis. In this regard, Dharmapatni et al., (2011) have shown that Tweak/Fn14 play a role in rheumatoid arthritis.

In one example, the condition is scleroderma (including systemic scleroderma).

In another example, the condition is graft rejection (e.g., allograft rejection) or graft versus host disease (including weight loss associated with graft versus host disease). In this regard, Tweak/Fn14 have been show to play a role in pathogenesis of graft versus host disease, e.g., by Zhao et al., (2007).

In another example, the condition is cardiac allograft vasculopathy.

In one example, the condition is graft rejection associated intimal thickening.

In another example the condition is intramyocardial infarction or ischemic repurfusion injury. In this regard, Tweak/Fn14 has been shown to play a role in ischemia by, e.g., Frauenknecht et al., (2010) and Inta et al., (2008).

In another example, the condition is associated with excessive angiogenesis and/or neovascularization, e.g., cancer (including solid tumors, leukemias, lymphoma, melanoma, glioma, breast cancer, colonic cancer, gastric cancer, esophageal cancer, renal cell cancer, ovarian cancer, cervical cancer, carcinoid cancer, testicular cancer, prostate cancer, head and neck cancer and hepatocellular carcinoma), cancer metastasis, cancer neovascularization, autoimmune disease (including psoriasis), nephropathy, retinopathy, preeclampsia, hepatitis, sepsis and macular degeneration.

In one example, the condition is cancer or a metastasis thereof. The term "cancer" refers to or describes the physiological condition in mammals that is typically characterized by unregulated cell growth/proliferation. Examples of cancer include, but are not limited to, an adenocarcinoma, a squamous cell carcinoma, a digestive/gastrointestinal cancer, an endocrine cancer, an eye cancer, a musculoskeletal cancer, a breast cancer, a neurologic cancer, a genitourinary cancer, a germ cell cancer, a head and neck cancer, a hematologic/blood cancer, a respiratory cancer, a skin cancer, an AIDS-related malignancy or a gynelogic cancer.

An adenocarcinoma is a cancer of an epithelium that originates in glandular tissue. Exemplary adenocarcinomas include forms of colorectal cancer, lung cancer, cervical cancer, prostate cancer, urachus cancer, vulval cancer, breast cancer, esophageal cancer, pancreatic cancer and gastric cancer.

Digestive/gastrointestinal cancers include anal cancer; bile duct cancer; extrahepatic bile duct cancer; appendix cancer; carcinoid tumor, gastrointestinal cancer; colon cancer; colorectal cancer including childhood colorectal cancer; esophageal cancer including childhood esophageal cancer; gallbladder cancer; gastric (stomach) cancer including childhood gastric (stomach) cancer; hepatocellular (liver) cancer including childhood hepatocellular (liver) cancer; pancreatic cancer including childhood pancreatic cancer; sarcoma, rhabdomyosarcoma; rectal cancer; and small intestine cancer.

Endocrine cancers include islet cell carcinoma (endocrine pancreas); adrenocortical carcinoma including childhood adrenocortical carcinoma; gastrointestinal carcinoid tumor; parathyroid cancer; pheochromocytoma; pituitary tumor; thyroid cancer including childhood thyroid cancer; childhood multiple endocrine neoplasia syndrome; and childhood carcinoid tumor.

Eye cancers include intraocular melanoma; and retinoblastoma.

Musculoskeletal cancers include Ewing's family of tumors; osteosarcoma/malignant fibrous histiocytoma of the bone; rhabdomyosarcoma including childhood rhabdomyosarcoma; soft tissue sarcoma including childhood soft tissue sarcoma; clear cell sarcoma of tendon sheaths; and uterine sarcoma.

Neurologic cancers include childhood brain stem glioma; brain tumor; childhood cerebellar astrocytoma; childhood cerebral astrocytoma/malignant glioma; childhood ependymoma; childhood medulloblastoma; childhood pineal and supratentorial primitive neuroectodermal tumors; childhood visual pathway and hypothalamic glioma; other childhood brain cancers; adrenocortical carcinoma; central nervous system lymphoma, primary; childhood cerebellar astrocytoma; neuroblastoma; craniopharyngioma; spinal cord tumors; central nervous system atypical teratoid/rhabdoid tumor; central nervous system embryonal tumors; and supratentorial primitive neuroectodermal tumors including childhood and pituitary tumor.

Genitourinary cancers include bladder cancer including childhood bladder cancer; renal cell (kidney) cancer; ovarian cancer including childhood ovarian cancer; ovarian epithelial cancer; ovarian low malignant potential tumor; penile cancer; prostate cancer; renal cell cancer including childhood renal cell cancer; renal pelvis and ureter, transitional cell cancer; testicular cancer; urethral cancer; vaginal cancer; vulvar cancer; cervical cancer; Wilms tumor and other childhood kidney tumors; endometrial cancer; and gestational trophoblastic tumor;

Germ cell cancers include childhood extracranial germ cell tumor; extragonadal germ cell tumor; ovarian germ cell tumor; and testicular cancer.

Head and neck cancers include lip and oral cavity cancer; childhood oral cancer; hypopharyngeal cancer; laryngeal cancer including childhood laryngeal cancer; metastatic squamous neck cancer with occult primary; mouth cancer; nasal cavity and paranasal sinus cancer; nasopharyngeal cancer including childhood nasopharyngeal cancer; oropharyngeal cancer; parathyroid cancer; pharyngeal cancer; salivary gland cancer including childhood salivary gland cancer; throat cancer; and thyroid cancer.

Hematologic/blood cell cancers include leukemia (e.g., acute lymphoblastic leukemia in adults and children; acute myeloid leukemia, e.g., in adults and children; chronic lymphocytic leukemia; chronic myelogenous leukemia; and hairy cell leukemia); a lymphoma (e.g., AIDS-related lymphoma; cutaneous T-cell lymphoma; Hodgkin's lymphoma including Hodgkin's lymphoma in adults and children; Hodgkin's lymphoma during pregnancy; non-Hodgkin's lymphoma including non-Hodgkin's lymphoma in adults and children; non-Hodgkin's lymphoma during pregnancy; mycosis fungoides; Sezary syndrome; Waldenstrom's macroglobulinemia; and primary central nervous system lymphoma); and other hematologic cancers (e.g., chronic myeloproliferative disorders; multiple myeloma/plasma cell neoplasm; myelodysplastic syndromes; and myelodysplastic/myeloproliferative disorders).

Respiratory cancers include non-small cell lung cancer; small cell lung cancer; malignant mesothelioma including malignant mesothelioma in adults and children; malignant thymoma; childhood thymoma; thymic carcinoma; bronchial adenomas/carcinoids including childhood bronchial adenomas/carcinoids; pleuropulmonary blastoma.

Skin cancers include Kaposi's sarcoma; Merkel cell carcinoma; melanoma; basal cell carcinoma and childhood skin cancer.

In a further example, the condition is a wasting disorder, such as cachexia as described in more detail herein. In one example, the wasting disorder is associated with a condition, such as, cancer, metabolic acidosis, infectious diseases, diabetes, autoimmune immune deficiency syndrome (AIDS), autoimmune disorders, addiction to drugs, cirrhosis of the liver, chronic inflammatory disorders, anorexia, chronic heart failure, chronic kidney disease, osteoporosis, skeletal muscle disease, motor neuron disease, multiple sclerosis, muscle atrophy and neurodegenerative disease.

In one example, the wasting disorder is cachexia or sarcopenia (e.g., wasting associated with aging).

In one example, the wasting disorder is cachexia.

In one example, the cachexia is associated with cancer, infectious disease (e.g., tuberculosis or leprosy), AIDS, autoimmune disease (including rheumatoid arthritis or type 1 diabetes), cystic fibrosis, drug addiction, alcoholism or liver cirrhosis.

In one example, the cachexia is associated with an autoimmune disease. In one example, the cachexia is associated with rheumatoid arthritis. In one example, the cachexia is associated with type 1 diabetes.

In one example, the cachexia is associated with cardiac disease.

In one example, the cachexia is associated with chronic kidney disease.

In one example, the cachexia is associated with chronic pulmonary inflammation.

In one example, the cachexia is associated with instestinal inflammation.

In one example, the cachexia is associated with inflammatory bowel disease.

In one example, the cachexia is associated with aging.

In one example, the cachexia is associated with sepsis.

In one example, the cachexia is associated with AIDS.

In one exemplary form of the present disclosure the wasting disorder is cachexia associated with cancer. Exemplary cancers are described supra.

In one example, the method additionally comprises identifying a subject suffering from cachexia. Such a subject can be identified, for example, based on detection of unintentiaonal weight loss following diagnosis of another condition (e.g., cancer). For example, the subject can lose at least 5% of their body weight following diagnosis of another condition (e.g., cancer) or within the previous 30 days.

Kits

The present disclosure also provides therapeutic/prophylactic/diagnostic kits comprising compounds of the present disclosure for use in the present detection/isolation/diagnostic/prognostic/treatment/prophylactic methods. Such kits will generally contain, in suitable container means, an Fn14-binding protein of the present disclosure. The kits may also contain other compounds, e.g., for detection/isolation/diagnosis/imaging or combined therapy. For example, such kits may contain any one or more of a range of anti-inflammatory drugs and/or chemotherapeutic or radiotherapeutic drugs; anti-angiogenic agents; anti-tumor cell antibodies; and/or anti-tumor vasculature or anti-tumor stroma immunotoxins or coaguligands or vaccines.

In one example, the kit is for detecting Fn14 and additionally comprises a reagent to facilitate detection (a detectable label and/or a substrate of a detectable label. Such kits may additionally comprise a positive control.

In another example, the kit is for isolating a cell or a population of cells. In such kits an Fn14-binding protein of the disclosure may be labeled with a detectable label to facilitate FACS. The Fn14-binding protein may also be labeled with a magnetic or paramagnetic particle to facilitate MACS. The Fn14-binding protein may also be immobilized on a solid or semi-solid substrate to facilitate isolation.

In a further example, the kit is for treatment or prevention of a condition. In such kits, the Fn14-binding protein may be provided in solution or in a lyophilized form, optionally with a solution for resuspension. The Fn14-binding protein may be conjugated to a therapeutic compound or the kit may include a therapeutic compound for conjugation thereto. As discussed above, the kit may also comprise additional therapeutic or prophylactic compounds.

Methods of Screening

As will be apparent to the skilled person based on the disclosure herein, the present disclosure provides methods for identifying a compound for the treatment of a wasting disorder. These methods can comprise additional steps as discussed in the following paragraphs.

The present disclosure also encompasses for the provision of information concerning the identified or isolated compound. Accordingly, the screening methods are further modified by:

(i) optionally, determining the structure of the compound; and (ii) providing the compound or the name or structure of the compound such as, for example, in a paper form, machine-readable form, or computer-readable form.

Naturally, for compound that are known, albeit not previously tested, for their function using a screen provided by the present disclosure, determination of the name and/or structure of the compound is implicit. This is because the skilled artisan will be aware of the name and/or structure of the compound at the time of performing the screen.

As used herein, the term "providing the compound" shall be taken to include any chemical or recombinant synthetic means for producing the compound or alternatively, the provision of a compound that has been previously synthesized by any person or means. This clearly includes isolating the compound.

In one example, the compound or the name or structure of the compound is provided with an indication as to its use e.g., as determined by a screen described herein.

The screening assays can be further modified by:

(i) optionally, determining the structure of the compound;

(ii) optionally, providing the name or structure of the compound such as, for example, in a paper form, machine-readable form, or computer-readable form; and (iii) providing the compound.

In one example, the synthesized/produced compound or the name or structure of the compound is provided with an indication as to its use e.g., as determined by a screen described herein.

In one example, the compound is provided in a library of compounds, each of which or a subset of which may be separated from other members (i.e., physically isolated). In such cases, a compound is isolated from the library by its identification, which then permits a skilled person to produce that compound in isolation, e.g., in the absence of other members of the library.

The present disclosure includes the following non-limiting examples.

Example 1: Generation and Characterization of Monoclonal Antibodies to Human Fn14

Methods

Production of Tumor Cells Expressing Fn14 and Non-Signaling Fn14

Cloning of Constructs for Tumor Model (Fn14 and Fn14-GPI)

The 4-hydroxytamoxifen (4-OHT) inducible lentiviral infection system (Vince et al., 2007) was used for all constructs. The full length wildtype cDNA for human Fn14 (Genbank Accession Number NM_016639) was cloned into the lentiviral vector pF_UAS_Neo at BamH I and Nhe I. The control construct containing the cDNA for the extracellular region of human Fn14 (Forward CGCGGATCCATGGCTCGGGGCTCGCTGCGC (SEQ ID NO: 37) Reverse GCTGGTGGTCATCCAAAGCAGCCGGAAGGGGGCAGG (SEQ ID NO: 38)) fused to the TrailR3 GPI anchor coding region (AF020502) was created by overlap PCR (Forward primer CGGCTGCTTTGGATGACCACCAGCCCGGGGACTCCT (SEQ ID NO: 39), Reverse primer CGCGCTAGCTTATCAAACAAACACAATCAGAAG (SEQ ID NO: 40)) to create Fn14-GPI. Constructs were confirmed by DNA sequencing.

Creation of Cell Lines for In Vivo Tumor Model (Fn14 and Fn14-GPI)

SV40 immortalized mouse embryonic fibroblasts (MEFs) from wildtype C57BL/6 mice were transformed with human v12Hras by retroviral infection. v12Hras transformed cells were then infected with lentivirus carrying DNA constructs for constitutively expressed GEV16 and either 4-hydroxytamoxifen inducible hFn14, inducible hFn14-GPI or constitutively expressing hFn14. Cells were selected with appropriate antibiotics for a minimum of 2 weeks before FACS screening was performed to confirm protein expression. For induction of protein expression, 4-OHT was added to normal growth media to a concentration of 100 nM for a minimum of 24 hours. Cells were harvested and live staining was performed using commercial antibodies to human Fn14 (Abcam ab21359) and either an anti-mouse antibody conjugated to R-phycoerythrin (R-PE; Chemicon 1030-09) or AlexaFluor 647 (Invitrogen #A21235). A minimum of 10,000 events were recorded for each sample assessed and data was subsequently analyzed.

Immunization of Mice

A purified recombinant protein comprising Fn14 extracellular domain was used for immunizations. For generation of anti-Fn14 antibodies CRCBT-06-001 and CRCBT-06-002, female Balb/c mice were immunized intraperitoneally (IP) with 15 μg of antigen in PBS emulsified at a 1:1 ratio in Complete Freund's Adjuvant (Sigma F 5881) for the primary immunization and incomplete Freund's adjuvant (Sigma F 5506) for subsequent boosts. For generation of anti-Fn14 antibodies CRCBT-06-005-CRCBT-06-007 mice were immunized with HEK293T cells either suspended in PBS and subsequent boosts performed with cells in PBS, or cells were mixed 1:1 in Complete Freund's Adjuvant (Sigma F 5881) for the primary immunization and incomplete Freund's adjuvant (Sigma F 5506) for subsequent boosts. For all mice, boosts were performed 4 weekly with a final injection given in PBS intraperitoneally 3 days before spleens were removed and the spleen cells harvested. Test bleeds were taken 5-7 days post boost and used for screening for the presence of an immune response to hFn14. Blood collected from mice was allowed to clot at 4° C. overnight. The clot was removed by centrifugation and the serum collected and stored at −20° C.

Monoclonal Antibody Production

Hybridoma fusions were performed using ClonaCell®-HY Hybridoma Kit #03800, Stemcell Technologies, Australia) essentially according to the manufacturers' instructions. Briefly, the spleen cells were isolated by spleen perfusion before fusion with mouse myeloma SP2/O (1:5 ratio). Selection and cloning steps were performed on methylcellulose-based semi-solid in 96 well plates. The culture supernatants were screened by ELISA for IgG production and subsequently by flow cytometry for specificity.

ELISA Screening of Hybridoma Supernatants

Supernatants were screened by ELISA for IgG production. Briefly 96 well plates were coated overnight at 4° C. with a polyclonal antibody to mouse IgG (Jackson Immuno Research, #715-006-150 Australia) in 0.05% carbonate-Bicarbonate coating buffer followed by blocking with 3% bovine serum albumin (BSA) diluted in phosphate buffer saline (PBS) incubated for 1 hour at room temperature (RT). Standard and samples were added (100 μl/well diluted 1:50 in PBS) for 60 min at RT. Bound monoclonal antibody was detected with goat anti mouse IgG-peroxidase (Sigma, #A25554 Australia; 100 μl/well and used at 1/50,000) incubated for 60 min at RT followed by incubation with tetramethylbenzidine (TMB) substrate (100 μl/well). Color development was stopped with 2M of sulphuric acid and the absorbance read at 450 nm.

Flow Cytometry Screening of Hybridoma Supernatants $1\times10^5$ MEF v12Hras Fn14+/− (described above) induced with 100 nM 4-OHT were used as single or mixed cell population (1:1 ratio) prior to staining. Cells were incubated at 4° C. with samples or controls for 30 min in PBS, 2% BSA. Cells were washed and incubated with secondary antibody (1:100 AlexaFluor 647-conjugated goat anti-mouse IgG, Invitrogen #A21235, Australia) for 30 min at 4° C. in the dark. The BD FACSCanto II was used to perform flow cytometry according to the manufacturer's protocol and data analysis was performed. Experiments were representative of at least three independent experiments. Purified control antibodies include IgG2b (BioLegend #401212), IgG1 (BioLegend #401405), ITEM-1 (BioLegend #314006) and ITEM-2 (eBioscience).

Monoclonal Antibody Purification/Endotoxin Removal and Testing

Purification of Antibody

Approximately 1 liter of serum free conditioned medium was collected per antibody over 4.5 days from a 4× Triple Flask 500 $cm^2$ (NUN132913 Thermofisher, Aus) of hybridomas cultured in hybridoma serum free media (12045-084, Invitrogen, Aus) supplemented with penicillin-streptomycin (10,000 U/ml). Medium was filtered through a 0.45 μm filter prior to purification. Antibodies were purified by affinity chromatography with a 5 ml column of Protein A Sepharose HiTrap MabSelect Xtra (28-4082-60, GE Healthcare, Aus). The Protein A column was equilibrated with buffer containing 0.02 M sodium phosphate, 250 mM NaCl pH 6.85, and the antibodies were eluted with 0.1 M Glycine/HCl pH 3.0, followed by neutralization with 1 M Tris/HCl pH 9.0. The neutralized eluate was concentrated and the buffer was exchanged with PBS using a vivaspin 20 column (VS2021, Sartorius, Aus). Endotoxin was removed from samples using Detoxi-Gel (20339, Thermo Scientific, Aus) and measured either with E-toxate kits (ET0100, Sigma, Aus) or using the Endosafe®-PTS Protable Test System (5-0.05 Eu/ml range cartridge) and both methods performed according to manufacturer's instructions. Endotoxin levels of all final antibody preparations used for in vivo experiments was below the level of detection of the assay (less than 0.05 EU/mg of antibody).

Antibody Isotyping

Antibodies were isotyped using the BD Cytometric Bead Array (CBA) Mouse Immunoglobulin Isotyping Kit (Catalogue No. 550026) essentially according to the manufacturer's instructions.

In Vitro Activity Assays

HEK293T NFκB GFP Assay

HEK293T cells containing a stably integrated NFκB promoter followed by GFP open reading frame were used to test for functionally active antibodies (Vince et al., 2007). Cells were incubated for 24 hours in the presence or absence of purified recombinant Tweak-Fc at a concentration of 5-200 ng/ml. In addition, hybridoma supernatant or controls were added to a final dilution of 1:10-1:100. Cells were harvested and GFP fluorescence was measured by flow cytometry (BD FACS Canto II, Diva software). A minimum of 10,000 events per sample were recorded.

As an isotype control an IgG2b anti-Cytochrome C (BD Pharmingen 556433) antibody was used at equivalent concentrations. The hybridoma supernatant from a non-antibody secreting or an irrelevant IgG producing hybridoma was used as a control.

Kym1 Death Assay

Kym1 cell death assays were performed essentially as described in Vince et al., (2007). Cells were incubated for 24 hours in the presence or absence of Tweak-Fc, and hybridoma supernatant, purified antibody or controls. Total cells were harvested and analyzed by flow cytometry in the presence of Propidium Iodide (PI; Sigma P4170) at a concentration of 50 μg/ml. Data was graphed as the percentage of cell death.

IL-8 Secretion Assay

A375 human melanoma cells were seeded at $1\times10^4$ cells per well in a 96 well flat bottom plate in Dulbecco's modified Eagle's medium (DMEM) supplemented with 10% fetal calf serum and 1% penicillin/streptomycin. Cells were allowed to attach overnight under standard cell culture conditions of 37° C. with 5% $CO_2$.

Cells were incubated with either Tweak-Fc (300 ng/ml final concentration) or with antibodies alone at the following concentrations: 10, 1, 0.1 and 0.01 μg/ml or with both Tweak-Fc and antibody at 300 ng/ml and 10 μg/ml final concentration respectively.

After the addition of reagents, cells were incubated for 24 hours under standard tissue culture conditions. Supernatants were collected and centrifuged at 700 g for 5 minutes at 4° C. Anti-Tweak antibody (MTW-1), Rat IgG1, ITEM-1, IgG2a, IgG2b, IgG1 were purchased from Biolegend, and ITEM-4 were purchased from eBioscience.

IL-8 Detection ELISA

After 24 hours, cell culture supernatants were assessed for IL-8 levels by ELISA (R&D systems) essentially according to the manufacturer's instructions. Briefly, the samples and supplied standards were incubated for 2 hours at room temperature. After several thorough washes (in the supplied wash buffer) between incubations, the IL-8 conjugate, followed by substrate solution were added to all samples and incubated at room temperature for 60 and 30 minutes, respectively. Absorbance was measured at 450 nm and 540 nm. The reading at 540 nm was subtracted from the 450 reading to account for any plate variability.

DNA Sequencing of Antibody Variable Regions mRNA was isolated from hybridoma cells using RNeasy midi kit (Qiagen, 75144). RT-PCR was done using one-step RT PCR kit (Qiagen, 210212) according to the manufacturer's instructions. Briefly, 1 μg of mRNA was used as template for cDNA synthesis and variable mouse light and heavy chains were amplified with degenerate primers as described in Wang et al, 2000.

The light chain was amplified using 10 pM of 5'-GG GAGCTC GAY ATT GTG MTS ACM CAR WCT MCA-3' (SEQ ID NO: 41) forward and 5'-GGT GCATGC GGA TAC AGT TGG TGC AGC ATC-3' (SEQ ID NO: 42) reverse primer respectively. The heavy chain was amplified using 10 pM of forward primer (MH1: 5'-CTT CCG GAATTC SAR GTN MAG CTG SAG SAG TC-3' (SEQ ID NO: 43) or MH2: 5'-CTT CCG GAATTC SAR GTN MAG CTG SAG SAG TCW GG-3' (SEQ ID NO: 44)) and the specific reverse primer (IgG1: 5'-gga agatct ATA GAC AGA TGG GGG TGT CGT TTT GGC-3' (SEQ ID NO: 45)). RT-PCR products were separated on 1.5% agarose gels, bands were excised and DNA purified using Wizard® SV Gel and PCR Clean-Up System (Promega, A9282). The purified fragments were sub-cloned into pCR®2.1-TOPO® vector using TOPO TA Cloning® Kit (Invitrogen, K4560-40) and ligations transformed into One Shot® TOP10 Electrocomp™ *E. coli* according to the manufacturer's instructions. X-Gal blue-white screening allowed the selection of white colonies that were cultured for DNA isolation using Wizard® Plus SV Minipreps DNA Purification System (Promega, A1460). For each mAb several independent clones were sent for sequencing using universal M13 primers.

To confirm the sequence of CRCBT-06-002 light chain was amplified using 10 pM of forward primer MKVP2 5'-ATG GAG WCA GAC ACA CTC CTG YTA TGG T-3' (SEQ ID NO: 69) and reverse primer 5'-TTT TAT CTC CAG CTT GGT GC-3' (SEQ ID NO: 70; adapted from Debat et al., 2001). RT-PCR products were separated on 1.5% agarose gels, bands were excised and DNA purified using Wizard® SV Gel and PCR Clean-Up System (Promega, A9282). The purified fragments were sub-cloned into pGEM®T vector using pGEM®T Vector System II (Promega, A3610) and ligations transformed into *E. coli* JM109 competent cells according to the manufacturer's instructions. X-Gal blue-white screening allowed the selection of white colonies that were cultured for DNA isolation using Wizard® Plus SV Minipreps DNA Purification System (Promega, A1460). Several independent clones were sent for sequencing using universal primers T7 and SP6

Validation of Antibody CDR/FR Sequences by Mass Spectrometric Analysis

Fab Generation

Fab fragments were generated from CRCBT-06-002 using the Thermo Scientific Pierce Mouse IgG1 Fab and F(ab')2 Preparation Kit (cat#44980) according to the manufacturer's instructions with minor modifications. Briefly, 4 mg of antibody were digested by 750 μl of immobilized Ficin in 25 mM cysteine at approximately pH 5.6 for 5 hours at 37° C. with constant mixing. After incubation, immobilized Ficin resin was centrifuged at 5,000 g for 1 min and the supernatant was kept on ice. Immobilized Ficin resin was washed with 0.5 ml of PBS three times. The wash fractions were added to the digested antibody and dialysed against 20 ml of PBS using a vivaspin20 concentrator $30K_D$ cut-off (Sartorius, cat# VS15T21) with a diafiltration cup (Sartorius, cat# VSA005) and concentrated to 0.5 ml. Undigested IgG and Fc fragments were cleared from the Fab fragments using protein G Sepharose beads according to manufacturer's instructions (GE Healthcare, 17-0618-01).

Fab from CRCBT-06-001, CRCBT-06-003, CRCBT-06-004, CRCBT-06-005, CRCBT-06-006 and CRCBT-06-007 were generated using the Thermo Scientific Pierce Fab Preparation Kit (cat#44985) according to the manufacturer's instructions with minor modifications. Briefly, 5 mg of antibody were digested by 250 μl of immobilized papain in 20 mM cysteine at approximately pH 7 for 3 hours at 37° C. with constant mixing. After incubation, immobilized papain was centrifuged at 5,000 g for 1 min and the supernatant was kept on ice. Immobilized papain was washed with 0.5 ml of PBS three times. The wash fractions were added to the digested antibody. Undigested IgG and Fc fragments were cleared from the Fab fragments using protein G Sepharose beads according to manufacturer's instructions (GE Healthcare, 17-0618-01).

Sample Preparation for Mass Spectrometric Sequence Analysis

Fab fragments generated from monoclonal antibodies were dissolved in 50 mM Tris pH 8.0 and reduced with 10 mM DTT overnight at RT, followed by alkylation with 50 mM IAA at RT in the dark for 30 minutes. Each sample of Fab was digested with either 0.5 μg of sequence grade Trypsin (Promega) or Chymotrypsin (Promega) at 40° C. for 2 hours. Additionally, each Fab was digested first and then reduced and alkylated. The peptide mixture was separated by RP-HPLC (Dionex, Ultimate 3000) prior to either direct analysis by ESI-microTOF-Q-MS/MS or by spotting onto a MALDI-MS target plate for subsequent MALDI-tof/tof-MS (both instruments: Bruker Daltonics, Germany) analysis.

The spectra obtained by either instrument were annotated by DataAnalysis and the data transferred to Biotools program (both programs: Bruker Daltonics, Germany). The Mascot search engine (Matrixscience, UK) were used to search all data against SwissProt database and the constant part and isoform of the antibodies could be confirmed. The sequences of the CDR regions were derived from the DNA sequence and those sequences were matched to the mass spectrometric data using a facility available with the Biotools program. The mass accuracy applied were a 50 ppm mass window for MS spectra and 0.8 Da tolerance was used in the MS/MS spectra.

Determining Affinity of Antibodies to Fn14 using Fn14-Fc

The interaction of mouse anti-Fn14 IgG monoclonal antibodies CRCBT-06-001 and CRCBT-06-002 with recombinant Fn14-Fc was measured using the Bio-Rad ProteOn XPR36 essentially as described by Nahshol et al., (2008). Briefly, a GLM ProteOn sensor chip was activated by flowing a mixture of 0.2 M EDC and 0.05 M sulpho-NHS over the chip (150 μl at 30 μl/min for 5 minutes). Rabbit anti-mouse IgG whole molecule (Sigma M-7023) was then coupled to the chip in the vertical orientation by flowing 150 μl of a 50 μg/ml solution in 10 mM acetate buffer (pH 4.5) at 30 μl/min. The remaining coupling sites were then deactivated by flowing 150 μl of 1 M ethanolamine-HCl (pH 8.5) at 30 μl/min. Mouse anti-Fn14 IgG monoclonal antibodies were then bound to the coupled anti-mouse IgG antibody by flowing 150 μl of 100 μg/ml IgG at 25 μl/min over a single channel of the sensor chip in the horizontal direction. Recombinant Fn14-Fc diluted in PBS Tween 20 (0.005%) was then passed over the GLM sensor chip (150 μl, 40 μl/min, contact time 90 seconds and dissociation time of 800 seconds) in the vertical direction in 5 channels at the following concentrations: 50 nM, 25 nM, 12.5 nM, 6.25 nM and 3.125 nM. PBS Tween 20 (0.005%) alone was passed over the remaining channel. Binding sensorgrams were collected and analyzed with the ProteOn Manager 2.1 XPR36 software using the Langmuir or bivalent analyte kinetic models to fit the data and determine the affinity constant $K_D$.

Determining Affinity of Antibodies to Fn14 using Fn14

The kinetic analysis of the monoclonal antibodies was performed on a ProteOn XPR36 system (BioRad) Laboratories) essentially according to the protocol from Nahshol et al (2008). Monoclonal antibodies against hFn14 (50 μg/ml) were covalently coupled to a GMC chip. Analytes were a serial dilution of bacterially expressed and purified Histidine tagged hFn14. The binding sensorgrams were collected, processed and analyzed using the integrated ProteOn Manager software (BioRad Laboratories). Binding curves were fitted using the Langmuir model describing 1:1 binding stoichiometry.

Characterizing the Nature of the Epitope Bound by CRCBT-06-001

Reduction and Alkylation of Fn14

To determine if the epitope of CRCBT-06-001 is conformational, Fn14-Fc was reduced with 10 mM Dithiothreitol (DTT) in the presence of 6M Guanidine-HCl pH 8.0 for 45 minutes at 45° C. and alkylated with 50 mM iodoacetamide (IAA) in 1M Tris-HCl pH 8.0 for 1 hour. The protein was dialyzed extensively into PBS to remove excess DTT and IAA. An ELISA was performed by coating the wells of a microtiter plate with the native Fn14 and R+An Fn14, the anti-Fn14 antibody was allowed to bind, followed by detection with an anti-mouse horse radish peroxidase (HRP) conjugate. The substrate TMB (Sigma) was used and absorbance detected at 450 nm using a microtiter plate reader. To ensure the integrity of the reduced and alkylated Fn14-Fc, the Fc portion of the fusion protein was detected using an anti-Fc-HRP.

Determining Minimal Binding Regions of Fn14 to which the mAb Binds

A phage display approach was used to construct a gene fragment library by digesting the human Fn14 gene and expressing the fragments on the surface of bacteriophage. This is a standard technique which has been used frequently for epitope mapping of both conformational and linear epitopes.

Preparation and Panning of Human Fn14 Gene Fragment Library

A variation of the method described in Coley et al. 2001 was used to prepare a human Fn14 gene fragment library expressed on M13 bacteriophage.

The phagemid vector pHENH6 (Hoogenboom et al., 1991) contains a copy of the M13 bacteriophage gene III, coding for the pIII protein on the surface of phage particles, and a multiple cloning site between the periplasmic targeting sequence and the functional gene III sequence. This vector was used for expression of hFn14 fragments as a fusion with the pIII protein. Briefly, oligonucleotide primers flanking the coding region for Fn14 were used to amplify the entire open reading frame by PCR using hFn14 DNA as template. PCR product was digested with DNase I and fragments purified and the ends blunted using Vent DNA polymerase. pHENH6 phagemid vector was digested using PstI and subsequently blunted using Vent DNA polymerase. The blunted Fn14 gene fragments generated by random digest were then ligated into the prepared pHENH6 vector. Ligated products were purified transformed into competent *E. coli* TG-1 cells by electroporation. Analysis of the resulting library indicated that coverage of the hFn14 sequence was random.

Four rounds of panning were performed by coating 10 wells of a microtiter plate (NUNC maxisorp) with 2 μg/ml of CRCBT-06-001, the wells were blocked with 5% skim milk powder in PBS and the library was allowed to bind to the antibody. After 1 hour, the plate was washed to remove unbound phage, and the adherent phage were then eluted with 0.1M glycine pH 2.2 and neutralized. The eluted phage were re-infected in TG1 *E. coli* cells, rescued, amplified and PEG precipitated for the next round of panning as described in Coley et al. 2001. Clones from round 4 were DNA sequenced in order to establish the identity of the Fn14 fragments that bound to CRCBT-06-001 antibody.

Preparation of Gene Fragments Expressed on Phage

The solution structure of Fn14 has recently been described by He et al., 2009, in addition Brown et al., 2006 identified critical residues for Tweak ligand interaction. The extracellular domain of Fn14 contains 6 cysteine residues and the disulphide pairing was described in He et al. (2009). Fragments of Fn14 as depicted in FIG. 13 were produced, expressed on phage and used to characterize the epitope bound by CRCBT-06-001.

Cloning of hFn14 Constructs for Display on M13 Phage

Oligonucleotide primers, engineered with XhoI and NotI restriction sites were designed, synthesized (Geneworks) and used to amplify the full-length extracellular domain and sub-domains 1, 2 and 3 of *Homo sapiens* Fn14 coding sequence by PCR, the products of which were subsequently A-tailed and ligated into the pGEMT vector (Promega). Plasmid from a single hFn14 extracellular domain/SD1/2/3-pGEMT clone was prepared and inserts were digested from the vector backbone using the XhoI and NotI restriction enzymes. Restricted inserts were then purified and ligated into the phagemid vector pHEN-H6 (Hoogenboom et al., 1991). For hFn14 mutants, mutagenesis was achieved using the Phusion Site-Directed Mutagenesis kit (Finnzymes) and the hFn14 extracellular domain-pHEN-H6 plasmid as template.

Epitope Mapping Using Phage Expressed Fn14—Method 1

Expressing and Purifying Phage

Glycerol stocks of TG-1 *E. coli* transformed with the phagemid constructs were used to inoculate 10 mL of YT media containing Ampicillin. Starter cultures were grown to log phase before M13K07 helper phage were added to infect the cells. Helper phage-infected cultures were then transferred to 200 ml of SB media containing Ampicillin and Kanamycin. Cultures were grown overnight at 30° C. *E. coli* were subsequently collected through centrifugation and discarded. PEG/NaCl solution was added to the culture supernatant, precipitating the phage, which were subsequently harvested through centrifugation, resuspended in phosphate buffered saline solution and stored at −80° C.

Enzyme Linked Immunosorbent Assays to Determine Binding of Phage to Antibodies

The wells of Maxisorp immunoplates (Nunc) were coated overnight at 4° C. with the target monoclonal antibodies or recombinant Tweak-Fc at a concentration of 2 μg/mL in PBS. MAb 5G8 was used as a negative control for ELISA plates coated with tested antibodies. Recombinant Fc alone was used as a negative control for ELISA plates coated with recombinant Tweak-Fc. Wells of the coated ELISA plates were subsequently blocked for 2 hrs with 10% skim milk solution in PBS. 10-fold serial dilutions of phage were made using 5% skim milk/PBS solution in 2 ml-well microtiter plates and phage dilutions were added to the coated, blocked ELISA plates for 1 hr, with vigorous shaking at room temperature. Phage were subsequently removed from the wells and the ELISA plates were washed 4× with PBS/0.05% Tween 20. HRP-conjugated anti-M13-phage polyclonal IgG diluted in PBS was then added to the wells of the ELISA plates for 1 hr, with vigorous shaking at room temperature. The antibody solution was then removed from the wells and the ELISA plates were washed 5× with PBS/0.05% Tween 20. ELISAs were developed using TMB substrate and the reaction was stopped using 2 M $H_2SO_4$ solution. Optical density at 450 nm was quantified using a Spectramax absorbance spectrophotometer.

Epitope Mapping Using Phage Expressed Fn14—Method 2

Expressing and Purifying Phage

Single colonies of TG-1 *E. coli* transformed with the phagemid constructs were used to inoculate 10 ml of 2YT media containing Ampicillin (100 □g/ml). Starter cultures were grown to log phase before M13K07 helper phage was added to rescue the phage infected *E. coli*. Helper phage-infected cultures were amplified in 200 ml of 2YT media containing Ampicillin and Kanamycin (50 □g/ml). Cultures were grown overnight at 30° C. in a shaking incubator. The culture was centrifuged and the phage (supernatant fraction) was harvested by PEG/NaCl precipitation. The phage were pelleted by centrifugation and resuspended in PBS and stored at −80° C.

Enzyme Linked Immunosorbent Assays to Measure Reactivity of mAbs with Fn14 Mutants The wells of Maxisorp immunoplates (Nunc) were coated overnight at 4° C. with the target monoclonal antibodies or recombinant Tweak-Fc at a concentration of 1.5 μg/ml in PBS. mAb 5G8 was used as a negative control for ELISA plates coated with tested antibodies. Wells of the coated ELISA plates were subsequently blocked for 2 hours with 5% skim milk solution in PBS. 10-fold serial dilutions of phage were made using PBS solution and phage dilutions were added to the coated, blocked ELISA plates for 1 hour, shaking at room temperature. Phage was subsequently removed from the wells and the ELISA plates were washed three times with PBS/0.05% Tween 20.

Detection of Phage

Two methods were used for detecting binding of phage mutants.

Method A: HRP-conjugated anti-M13-phage antibody (GE Healthcare) at a 1/5000 dilution in PBS was then added to the wells of the ELISA plates for 1 hour, shaking at room temperature. The antibody solution was then removed from the wells and the ELISA plates were washed four times with PBS/0.05% Tween 20. Method B: Biotin-conjugated anti-M13-phage antibody (GE Healthcare) diluted in PBS was then added to the wells of the ELISA plates for 1 hour shaking at room temperature. The antibody solution was then removed from the wells and the ELISA plates were washed three times with PBS/0.05% Tween 20. HRP-conjugated Streptavidin diluted in PBS was then added to the wells of the ELISA plates for 1 hour, shaking at room temperature. The solution was then removed from the wells and the ELISA plates were washed three times with PBS/0.05% Tween 20. ELISAs were developed using TMB substrate and the reaction was stopped using 2 M $H_2SO_4$ solution. Optical density at 450 nm was quantified using a Spectramax absorbance spectrophotometer.

Epitope Mapping of Antibodies Using Synthetic Peptides

Peptides representing sub-domains 1p, 2 and 3 of hFn14 (FIG. 20, Panels B and C and FIG. 14, Panel A) and for disulfide pair mutants (Cys3&6ΔS and Cys4&5ΔS; FIG. 20 Panels D and E) were synthesized by GLBiochem Ltd. (Shanghai, China) and the cysteine residues for disulfide bonds were chosen as described in the solution structure by He et al., (2009). An additional lysine residue was added to the C-terminus in order to attach a biotin moiety and to enable the peptides to bind to neutravidin coated plates (Pre-blocked; Pierce). For these experiments, a control peptide with a biotin at the C-terminus was used as a negative control and isotype control antibodies were also used.

The ELISA was performed essentially according to the manufacturer's recommended protocol (Pierce). Briefly, peptide was coated onto wells (in duplicate) at 1-10 μg/ml for 2 hours at room temperature. Wells were washed in PBS/0.05% Tween 20/0.1% BSA 3 times and dilutions of each antibody were added in wash buffer for 1 hour with gentle agitation. After another three washes anti-mouse HRP-conjugated to horse radish peroxidase (HRP; Chemicon) was added at 1/1000 dilution for 1 hour shaking. Finally, after 4 further washes the plate was developed using TMB (3,3',5,5'-tetramethylbenzidine) substrate (Pierce), and the reaction was stopped using 2M $H_2SO_4$ solution. Optical density at 450 nM was quantified using a Spectromax absorbance spectrophotometer.

Epitope Mapping of Antibodies Using Recombinant Protein

Cloning of hFn14 and mFn14 Constructs for Bacterial Expression

Oligonucleotide primers, engineered with Nde I and Bam HI restriction sites, were designed, synthesized (Geneworks) and used to amplify the full-length extracellular domain of the *H. sapiens* Fn14 (hFn14), the mouse Fn14 (mFn14) extracellular domain and mutants of hFn14 (R56P, R56A, R56K, R58K) by PCR. Subsequent products were ligated into the vector pGEM-4Z (Promega) excised with Sma I. Plasmids from single clone were prepared and inserts were digested from the vector. Restricted inserts were then purified and inserted into pET-15b (Novagen) for expression in *E. coli.*

Expression and Purification of $(His)_6$-Proteins pET-15b derived vectors were transformed into Shuffle T7 Express *E. coli* (New England BioLabs). Expression was induced by 1 mM IPTG at 30° C. for four hours. Bacterial lysate was loaded onto a 1 ml $Ni^{2+}$-nitrilotriacetic acid ($Ni^{2+}$-NTA)-agarose (Qiagen) column equilibrated with lysis buffer (20 mM Tris-HCl [pH 7.8], 300 mM NaCl, 20% [v/v] glycerol, 18 mM imidazole, 1 mM PMSF, Boehringer complete protease inhibitors). The column was first washed with 20 ml of lysis buffer and recombinant proteins were eluted by 300 mM imidazole. Recombinant proteins were dialyzed and concentrated to 1 mg/ml in 25 mM HEPES-KOH (pH 7.4), 100 mM NaCl by a Centricon Centrifugal Filter Devices YM-10 (Millipore).

Analytical Gel Filtration Chromatography $(His)_6$-proteins were further purified by gel filtration. Protein samples (1 ml) were loaded onto a HiLoad 16/60 Superdex 75 pg column (GE Healthcare) equilibrated with 25 mM HEPES-KOH (pH 7.4), 100 mM NaCl at room temperature and were chromatographed at a flow rate of 1.5 ml/min on an ÄKTAxpress system (GE Healthcare). Elution profiles were detected at 280 nm and 1.5 ml fraction were collected.

ELISA Screening of Monoclonal Antibodies with Purified $(His)_6$-Proteins

The wells of Maxisorp immunoplates (Nunc) were coated overnight at 4° C. with 2 fold serial dilutions of purified histidine tagged proteins (0.5 μg/ml to 4 ng/ml). Nonspecific protein binding sites were blocked with 1% milk in phosphate-buffered saline (PBS) for 1 hour at 37° C. Plates were washed with PBST (PBS [10 mM Na-phosphate and 150 mM NaCl], 0.05% Tween 20). Monoclonal antibodies diluted to 1 μg/ml in PBST (PBS 0.005% Tween 20, pH 7.4)+0.1% milk were added and incubated at 37° C. for 2 hours in the coated plates. After washing with PBST, a 1:15,000 dilution of peroxidase-conjugated AffiniPure goat anti-mouse IgG (H+L) (Sigma) containing 0.1% milk was added for 1 hour at 37° C. ELISAs were developed using TMB substrate and the reaction was stopped using 2 M $H_2SO_4$ solution. Optical density at 450 nm was quantified using a Spectramax absorbance spectrophotometer.

Results

Generating a Fn14 Specific Immune Response in Mice Using Recombinant Protein

Figure 1A:
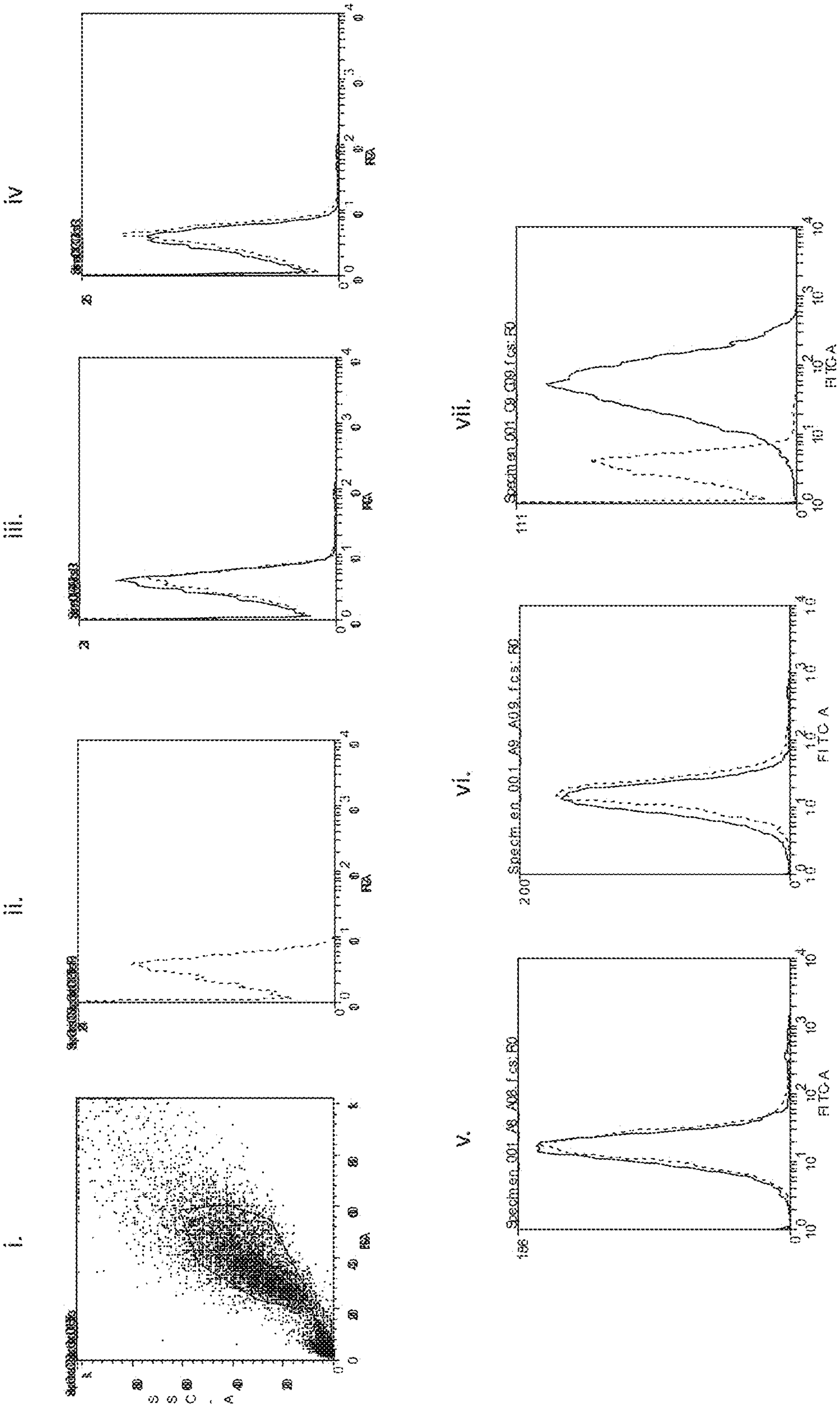
FIG. 1A to B is a series of graphical representations showing results of screening of sera from mice immunized with a recombinant protein comprising the extracellular domain of hFn14. Panel A shows results of assays in which live MEFv12Hras cells expressing human Fn14 (+/−4-OHT induction) were stained with the serum from immunized mice and subsequently analyzed by flow cytometry. Histogram traces: dotted trace represents staining on un-induced cells and solid trace represent staining on induced cells.
Figure 1B:
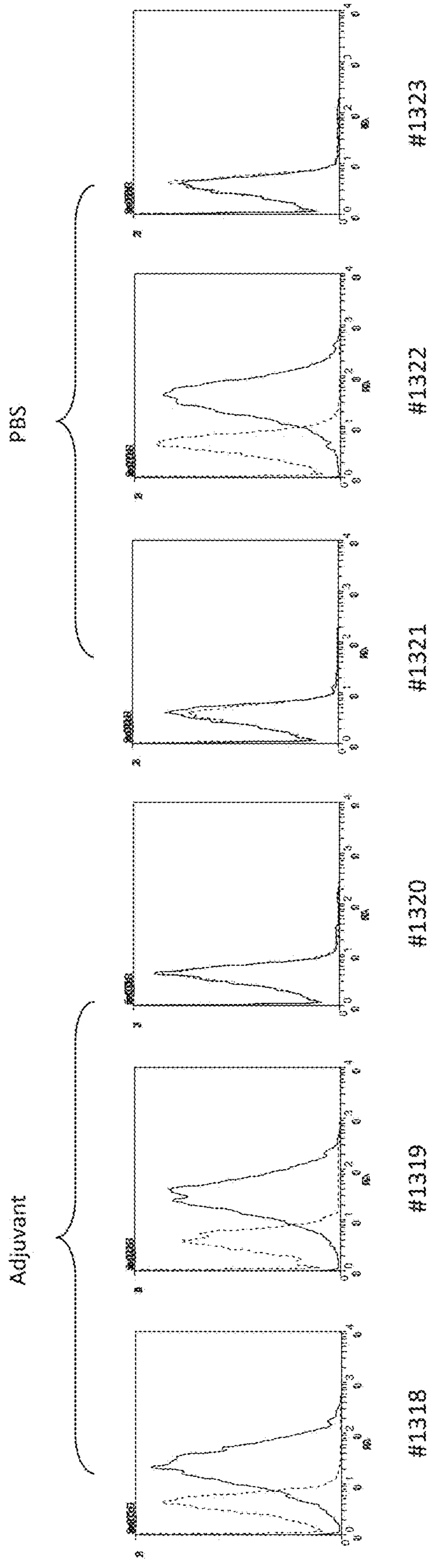

Mice were immunized using a recombinant protein comprising Fn14 extracellular domain in the presence or absence of adjuvant and after subsequent boosts a small bleed was taken and sera were isolated. Serum samples were screened for the presence of IgG antibodies specific to hFn14 by flow cytometry on live hFn14 inducible mouse embryonic fibroblasts (MEFs; FIG. 1). A number of mice displayed a good immune response to hFn14 as indicated by an increase in fluorescence on induced cells similar to that of the positive control when compared to staining of non-induced cells (panel B).

To confirm this result, sera were also screened on the human glioma cell line D645 that naturally express Fn14 when cultured in the presence of serum (FIG. 2). The same mice that tested positive on 4-OHT induced MEF cells also displayed positive staining on D645 cells, with the overall shift in fluorescence comparable to that for the positive control (panel A.iii. compared to panel B) with very minimal background staining seen when cells were stained with serum from mice immunized with a non-related antigen (panel A, vi. & vii).

Identifying Mice Producing Antagonistic Anti-Fn14 Antibodies

The serum from immunized mice was assayed for the presence of functionally active antibodies using two assays, the cell-based reporter assay for NFκB activity and the Kym1 cell death.

Results of the cell-based reporter assay for NFκB activity showed that exogenous Tweak-Fc induced a strong NFκB activation and that NFκB activation could be blocked by soluble TweakR or sera from mice that were positive for the presence of anti-hFn14 antibodies. In contrast, sera from mice immunized with a non-related antigen or that did not test positive for anti-hFn14 antibodies did not block NFκB activation.

As the serum from some mice was capable of blocking of NFκB activation, the capability of these antibodies to block Tweak induced cell death was next investigated. Results of this assay showed that culturing Kym1 cells in the presence of Tweak-Fc led to a dramatic reduction in cell survival, and that this effect could be blocked with soluble TweakR or serum from the hFn14 immunized mice that reduced Tweak induced NFκB activation, confirming the presence of antagonistic anti-hFn14 antibodies.

Monoclonal Antibody Production

The spleens from mice displaying the presence of human Fn14 specific antibodies and the capability of blocking Tweak were used for monoclonal antibody production. Hybridoma fusions were performed and subsequent clones were initially screened by ELISA for IgG secretion. The supernatants from those clones producing IgG were further assessed by staining live cells (+/−hFn14; FIG. 3). A large number of clones were generated that specifically bound to hFn14 positive cells but not those lacking hFn14. Panel B is representative of a number of the clones screened with no Fn14 binding, moderate or high binding displayed. Panel C displays four antibodies designated CRCBT-06-001, CRCBT-06-002, CRCBT-06-003 and CRCBT-06-004, which clearly display a high level of binding to cell surface expressed hFn14.

NF κB Assay to Assess Monoclonal Antibodies for Functional Activity

The supernatants from antibodies CRCBT-06-001 and CRCBT-06-002 were then assessed for functional activity in the NFκB assay described above. Substantially increased GFP fluorescence is evident in the presence of soluble Tweak-Fc but not in the presence of supernatants from either a non-IgG secreting cell line or that secreting a non-related control IgG (FIG. 4, panel A). In the presence of CRCBT-06-001 and CRCBT-06-002 containing supernatants, a strong inhibition of NFκB activation is evident, whereas in the presence of other supernatants no visible effect on activation can be seen (panel B).

Given the specificity and blocking capabilities of CRCBT-06-001 and CRCBT-06-002 these hybridomas producing the antibodies were chosen for further characterization. Each hybridoma cell line was cloned at least once and subsequent cell lines chosen. All sub-clones chosen displayed the same binding and functional characteristics of the parent cell lines.

Isotyping of monoclonal antibodies was performed. Antibodies CRCBT-06-001 and CRCBT-06-002 were found to be IgG2bκ and IgG1, respectively. CRCBT-06-003 and CRCBT-06-004 were both found to be IgG2bκ.

Monoclonal antibody CRCBT-06-001 was purified and assessed by mass spectrometry to ensure a high level of purity. Purified CRCBT-06-001 was then assayed for the level of blocking detectable in the NFκB assay (FIG. 4, panel C). At 50 ng/ml and above, CRCBT-06-001 is able to block the action of 5 or 50 ng/ml of Tweak-Fc on NFκB activation. The complete blocking of Tweak by CRCBT-06-001 can be seen at a concentration of 1 μg/ml. A minor level of activation of Fn14 is seen with higher concentrations of CRCBT-06-001, however this was not consistently seen. A purified IgG2b isotype control however showed no effect on the action of Tweak when added to 1 μg/ml (panel A, bottom series).

Transiently Transfected HEK293T Cells for the Immunization of Mice

To generate additional hFn14 antibodies, a cell based immunization strategy was used. The transient transfection of HEK293T with an hFn14 over-expression construct was optimized. Mice were immunized with transiently transfected HEK293T cells in the presence or absence of adjuvant. After 2 subsequent booster immunizations, a small bleed was taken for screening. Serum from these mice was used to stain MEF cells (+/−hFn14) for the presence of a specific immune response to hFn14 (FIG. 5). In this experiment, the Fn14 negative and positive cell populations were mixed at a ratio of 1:1 prior to staining and analysis by flow cytometry. A subsequent negative result would be indicated by the presence of either a fluorescence peak overlapping that of a negative control, or a shift in the whole peak. The appearance of a double peak would indicate a positive result (see positive control in panel A.iii.). Interestingly, only those mice immunized with live cells suspended in PBS were positive for antibodies recognizing cell surface expressed hFn14, whereas those immunized with antigen in adjuvant show no detectable response (panel B). The spleens from 2 of these anti-hFn14 positive mice were used for hybridoma fusion to generate monoclonal antibodies. This fusion yielded 15 clones that recognize cell surface expressed hFn14. Antibodies from three of these clones were purified and are designated CRCBT-06-005, CRCBT-06-006 and CRCBT-06-007. The isotype of these monoclonal antibodies was assessed and CRCBT-06-005 and CRCBT-06-007 were found to be IgG2bκ and CRCBT-06-006 was found to be IgG2a.

Characterization of Monoclonal Antibodies to Human Fn14

Tweak Induced NFκB Blocking

Antibodies CRCBT-06-001, CRCBT-06-002, CRCBT-06-003, CRCBT-06-004, CRCBT-06-005, CRCBT-06-006 and CRCBT-06-007 were purified and assessed for functional activity in vitro. All purified antibodies exhibited Tweak induced NFκB blocking activity as expected. CRCBT-06-001 and CRCBT-06-002 were able to fully block activation at 100 ng/ml (FIG. 6A). CRCBT-06-003 and CRCBT-06-004 also demonstrated good blocking ability. CRCBT-06-005, CRCBT-06-006 and CRCBT-06-007 efficiently blocked NFκB activation by 200 ng/ml of Tweak-Fc when added at a concentration of 1 μg/ml (FIG. 7A). At the lower antibody concentration of 100 ng/ml, blocking was also observed.

Antibodies ITEM-1 and ITEM-2 were also assessed for their ability to either activate NF□B or to block Tweak induced NF□B in the reporter assay (FIGS. 7A and B). ITEM-1 was unable to activate NF□B, i.e., cells cultured in the presence of ITEM-1 display no difference in NF□B activation as compared to cells alone. ITEM-1 also had no effect on the activation of NFκB by Tweak-Fc. In contrast to CRCBT-06-001, CRCBT-06-002, CRCBT-06-003, CRCBT-06-004, CRCBT-06-005, CRCBT-06-006, CRCBT-06-007 and ITEM-1, ITEM-2 induced consistent NFκB activation.

CRCBT-06-001 and CRCBT-06-002 Functional Activity in Kym1 Cell Death Assay

CRCBT-06-001, CRCBT-06-002, CRCBT-06-003 and CRCBT-06-004 were assessed for the ability to block the Tweak induced cell death of Kym1 cells in vitro. Cells alone display only a small degree of cell death and this percentage increases when cells were cultured in the presence of increasing levels of Tweak-Fc (FIG. 8). When cells were co-cultured in the presence of TweakR-Fc the Tweak-induced cell death was blocked. Similarly, when cells cultured in the presence of Tweak were co-cultured in the presence of CRCBT-06-001 or CRCBT-06-002 (1 μg/ml) the cells remain viable indicating efficient blocking of Tweak-Fc induced cell death. At a lower concentration (100 ng/ml) of antibody, Tweak induced cell death was blocked at lower concentrations of Tweak-Fc. CRCBT-06-003 and CRCBTG-06-004 also show good blocking of Tweak-induced Kym1 cell death but not to the same level as for CRCBT-06-001 and CRCBT-06-002.

IL-8 Secretion Assays

CRCBT antibodies were assessed for functional activity in an in vitro IL-8 secretion assay. The properties of the CRCBT antibodies were assessed on A375 cells by either determining if the CRCBT antibodies could trigger IL-8 secretion (agonist) or inhibit the Tweak-Fc-induced IL-8 secretion (antagonist).

A375 cells were cultured in the presence or absence of antibody at a range of concentrations (0, 0.01, 0.1, 1, 10 μg/ml; FIG. 9). Cells alone displayed no detectable background levels of IL-8. A series of isotype controls were assessed and displayed no IL-8 secretion. High IL-8 secretion was seen in the presence of CRCBT-06-001 and CRCBT-06-006. This IL-8 secretion was specific as the levels increase in an antibody concentration dependent manner. Weak IL-8 secretion is observed in the presence of CRCBT-06-002, CRCBT-06-004, CRCBT-06-005, CRCBT-06-007, ITEM-1 and ITEM-4 (FIG. 9).

Antibodies (10 μg/ml) were also assessed in the presence of 300 ng/ml Tweak-Fc to determine antagonist properties (FIG. 10). High antagonist activity was seen for CRCBT-06-002, CRCBT-06-005, CRCBT-06-007, ITEM-4 comparable to an anti-Tweak blocking antibody. Weak antagonist activity is seen for CRCBT-06-004 comparable to an anti-Tweak blocking antibody (FIG. 10).

An equation was employed to estimate the level of agonist activity as follows: (a−c)/(b−c). A similar calculation was used to estimate degree of antagonist activity: (b−d)/(b−a). Where a=the amount of IL-8 secreted in the presence of 10 μg/ml antibody, b=the amount of IL-8 secreted in the presence of 300 ng/ml Tweak-Fc, c=the amount of IL-8 secreted from cells in the absence of either antibody or Tweak-Fc, d=the amount of IL-8 secreted in the presence of 10 μg/ml antibody and 300 ng/ml Tweak-Fc. Table 1 summarizes these calculations for all antibodies tested with exception of the antagonist activity for those antibodies with strong agonist properties, as the calculation is not valid in those instances.

TABLE 1

| Calculated percentage agonist/antagonist activity in IL-8 secretion assay | | |
|---|---|---|
| | % Agonist | % Antagonist |
| CRCBT-06-001 | 128 | N/A |
| CRCBT-06-002 | 11 | 94 |
| CRCBT-06-004 | 12 | 46 |
| CRCBT-06-005 | 26 | 92 |
| CRCBT-06-006 | 106 | N/A |
| CRCBT-06-007 | 16 | 89 |
| ITEM-1 | 21 | 9 |
| ITEM-4 | 8 | 97 |
| IgG1 | 1 | 32 |
| IgG2b | 0 | 33 |
| IgG2a | 1 | 32 |
| Anti-Tweak | 0 | 99 |
| Rat IgG1 | 1 | 3 |

Thus these data together with those from assays to determine NFκB signaling and/or kym1 cell death indicate that antibodies have agonist activity in some functional assays and antagonist activity in other assays.

Affinity Measurement of Antibodies Using Fn14-Fc

A Bio-Rad ProteOn XPR36 was used to determine the affinity of mouse monoclonal anti-Fn14 antibodies CRCBT-06-001 and CRCBT-06-002 to recombinant Fn14-Fc. It is clear that both antibodies tested display a high on-rate and a low off-rate. The ProteOn software was used to fit a curve to the sensorgram based on a mathematical model, enabling the kinetics of the interaction (ka, Kd and $K_D$) to be calculated. A number of models can be used to fit the curves to the sensorgram, essentially the models used for each sensorgram were used as they provided the best fit, as evident by the low $Chi^2$ value obtained for the residuals. Results are shown in Tables 2 and 3.

TABLE 2

| Binding kinetics of CRCBT-06-001 for recombinant Fn14-Fc. | | | | |
|---|---|---|---|---|
| Parameter | ka | Kd | $K_D$ | Chi2 |
| Units | 1/Ms | 1/s | | RU |
| Scope | Global | Global | Auto Defined | |
| Type | Fitted | Fitted | Fitted | N/A |
| Kinetic-Langmuir | $2.36 \times 10^{04}$ | $1.81 \times 10^{-05}$ | $7.68 \times 10^{-10}$ | 6.66 |

TABLE 3

| Binding kinetics of CRCBT-06-002 for recombinant Fn14-Fc. | | | | |
|---|---|---|---|---|
| Parameter | ka | Kd | $K_D$ | Chi2 |
| Units | 1/Ms | 1/s | | RU |
| Scope | Global | Global | Auto Defined | |
| Type | Fitted | Fitted | Fitted | N/A |
| Kinetic-Bivalent analyte | $1.52 \times 10^{4}$ | $1.42 \times 10^{-05}$ | $9.35 \times 10^{-10}$ | 4.97 |

Affinity Measurement of Antibodies Using Fn14

Binding kinetics of anti-Fn14 antibodies CRCBT-06-001, CRCBT-06-002, CRCBT-06-004, ITEM-1 and ITEM-4 were assessed as described herein and results are set out in Table 4.

Of the selection of anti-Fn14 antibodies tested under identical experimental conditions as capture agents, CRCBT-06-004, ITEM-1 and ITEM-4 displayed much faster dissociation compared to CRCBT-06-001 and CRCBT-06-002 (Table 4).

TABLE 4

| Binding kinetics of anti-Fn14 antibodies for recombinant Fn14. | | | |
|---|---|---|---|
| Antibody | ka | Kd | KD |
| Units | 1/Ms | 1/s | M |
| CRCBT-06-001 | $1.86 \times 10^{5}$ | $1.02 \times 10^{-4}$ | $5.50 \times 10^{-10}$ |
| CRCBT-06-002 | $1.31 \times 10^{5}$ | $2.59 \times 10^{-5}$ | $1.98 \times 10^{-10}$ |
| CRCBT-06-004 | $3.45 \times 10^{5}$ | $2.03 \times 10^{-3}$ | $5.88 \times 10^{-9}$ |
| ITEM-1 | $3.58 \times 10^{5}$ | $1.47 \times 10^{-3}$ | $4.10 \times 10^{-9}$ |
| ITEM-4 | $5.1 \times 10^{5}$ | $8.64 \times 10^{-4}$ | $1.68 \times 10^{-9}$ |

DNA Sequencing of Heavy and Light Chains of Antagonistic Antibodies

The light and heavy chains were sequenced for all antibodies that antagonized NFκB signaling (FIG. 11). Subets of antibodies share a high degree of homology within their heavy and light chains with a number of differences present.

Anti-hFn14 Antibodies Bind to a Conformational Epitope

To determine if the epitope bound by CRCBT-06-001 is conformational, the Fn14-Fc purified protein was reduced and alkylated (R+A) to abolish the disulphide bond structure. ELISA results using CRCBT-06-001 clearly demonstrate that when the antigen is in the native folded state the antibody bound in a dose dependant manner. Upon reduction and alkylation however, this binding was abolished (FIG. 12Ai) demonstrating a conformational dependence for binding to CRCBT-06-001. Anti-human Fc recognized the Fc portion of Fn14 indicating the integrity of R+A Fn14 is retained (FIG. 12Aii). Western blot analysis also confirmed this finding (FIG. 12B).

ELISA was also used to determine if the epitope(s) bound by CRCBT-06-002, CRCBT-06-003, CRCBT-06-004, CRCBT-06-005, CRCBT-06-006, and CRCBT-06-007 is(are) conformationally dependent. Antibodies were tested at 1 μg/ml, and, as shown in FIG. 12C all antibodies bind to a disulfide dependant conformation of hFn14.

Generation of a Phage Library Expressing Random Fn14 Fragments

The coding region for Fn14 was amplified and digested with DNase I. Conditions that yielded fragments between 50 and 400 bp were used to produce a mixture of Fn14 gene fragments. The fragments were cloned into phagemid vector pHENH6 to create a gene fragment library with the size of ~$6 \times 10^{6}$ independent clones. A number of randomly picked clones were assessed and demonstrated the broad size distribution of the library.

Panning the Fn14 Gene Fragment Library with CRCBT-06-001

Four rounds of panning were performed to select gene fragments of Fn14 which bound to CRCBT-06-001. An ELISA was performed and very high signals were observed demonstrating enrichment in binding of gene fragments displayed on phage to CRCBT-06-001 in rounds 1-4.

Individual clones were selected from round 4 panning, a PCR performed and the resulting DNA fragments were sequenced. The sequence identity of round 4 selected Fn14 gene fragments is shown in FIG. 13, panel A. Fragments were re-assessed by ELISA for anti-hFn14 antibody binding capability (FIG. 13, panel B). Those fragments that bound comprised a portion of the extracellular region of Fn14 that contains all 6 cysteine residues that form the 3 known disulfide bonds (RW114-RW131). Fragments containing this region but also a portion of the transmembrane domain did not appear to show specific binding in this experiment. Without being bound by theory or mode of action, these data may suggest the presence of part of the transmembrane domain alters the structure or folding of these fragments (RW95 & RW98). The shortest Fn14 fragment identified in the phage library panning experiments bound by CRCBT-06-001 is indicated in bold (RW129).

Construction of hFn14 Extracellular Domain Mutants and Sub-Domains to be Expressed on Phage To further characterize the epitopes of the anti-Fn14 monoclonal antibodies, a panel of hFn14 constructs were designed to be displayed on phage. These include: The H. *Sapiens* Fn14 (hFn14) extracellular domain; four hFn14 extracellular domain mutants (D45A, K48A, M50A and D62E) known to have a decreased affinity for the natural ligand Tweak (Brown et al, 2006); and two sub-domains (1 and 2) delineated by disulfide bonds resolved in the NMR solution structure of the hFn14 extracellular domain (He et al., 2009). Sub-domain 2 is truncated at the C-terminus, since panning the hFn14 gene fragment library on CRCBT-06-001 enriched for a fragment lacking the 7 C-terminal residues of the extracellular domain, suggesting that these were not critical for antibody binding. The constructs cloned and expressed on phage are shown in FIG. 12A. The mutants illustrated in the context of the hFn14 structure homology model derived by Brown et al., (2006) are shown in FIG. 14B.

hFn14 Extracellular Domain Constructs are Expressed Successfully on the Surface of Phage To adequately assess the relative amounts of each hFn14 construct expressed on phage, a c-myc epitope tag was engineered between the pIII minor coat protein of the phage and the displayed hFn14 construct. The strong reactivity of the anti-c-myc monoclonal antibody 9E10 (MAb 9E10) with the wild type hFn14 extracellular domain and the mutants indicated that these constructs expressed well on phage. When tested simultaneously in the same ELISA, no significant binding of the phage constructs to the negative control MAb 5G8 was observed, showing that the phage preparations bound specifically to MAb 9E10.

Phage Displayed Human Extracellular Domain Mutants Show Decreased Binding to Recombinant Tweak-Fc The concentration of each phage preparation was adjusted to achieve an approximately equal reactivity with MAb 9E10. This was performed to normalize the amount of displayed hFn14 in each phage preparation for comparison. When assessed by ELISA, each phage preparation was shown to have an approximately equal reactivity with MAb 9E10, indicating that the preparations had been normalized successfully (FIG. 15, Panel A). No significant reactivity to MAb 5G8 was observed in the same ELISA, indicating that binding was specifically to MAb 9E10 (FIG. 15, Panel B). To assess the relative reactivity of each hFn14 construct with recombinant Tweak-Fc, normalized phage preparations were tested for binding to the ligand by ELISA simultaneously (FIG. 15, Panel C). In contrast to MAb 9E10, Tweak-Fc was most reactive with the wild-type hFn14 extracellular domain and less reactive with the four mutants (FIG. 15, Panel C). No significant binding of Sub-domain 2 to Tweak-Fc was observed, suggesting that regions of the extracellular domain absent in this construct contain residues critical for Tweak binding. No significant binding of phage-displayed c-myc alone to Tweak-Fc or phage-displayed hFn14 to recombinant Fc alone was observed, suggesting that the hFn14 constructs bound specifically to Tweak in these assays (FIG. 15, Panel D).

The Panel of Phage Displayed hFn14 Extracellular Domain Constructs Bind to Anti-Fn14 MAbs The relative reactivity of each phage-displayed hFn14 construct to CRCBT-06-001, CRCBT-06-002, CRCBT-06-003 and CRCBT-06-004 anti-Fn14 monoclonal antibodies was also assessed by ELISAs performed in parallel (FIG. 16A). In contrast to the pattern of reactivity observed with recombinant Tweak-Fc, all the hFn14 mutant constructs, bound well to the anti-Fn14 MAbs CRCBT-06-001, CRCBT-06-002, CRCBT-06-003 and CRCBT-06-004. As shown in previous assays, no significant binding of the phage-displayed constructs to MAb 5G8 was observed, indicating that the phage constructs were binding specifically to the anti-Fn14 MAbs (FIG. 16B). Furthermore, no significant binding of phage-displayed c-myc tag alone to any of the anti-Fn14 MAbs was observed, suggesting the antibodies were binding specifically to displayed Fn14 (FIG. 17). Binding of ITEM-1 to the 4 mutants was comparable to the binding to wildtype Fn14 extracellular domain (FIG. 17).

Anti-Fn14 Monoclonal Antibodies Bind to Sub-Domain 2, but not Sub-Domain 1 of the hFn14 Extracellular Domain To further characterize the epitopes bound by anti-Fn14 monoclonal antibodies, CRCBT-06-001, CRCBT-06-002, CRCBT-06-003, CRCBT-06-004, CRCBT-06-005, CRCBT-06-006, CRCBT-06-007, ITEM-1 and ITEM-2 were tested for binding to the phage-displayed hFn14 extracellular domain, sub-domain 1 and sub-domain 2 by ELISA (FIG. 18A, FIG. 19, Panel A). Phage were normalized according to their levels of reactivity with MAb 9E10 assayed in parallel. Consistent with previous ELISA data, CRC-BT-06-001 and CRCBT-06-002 reacted well with both the full-length extracellular domain and sub-domain 2. Furthermore, CRC-BT-06-003 to CRCBT-06-007, ITEM-1 and ITEM-2 bound well to these phage-displayed hFn14 constructs. None of the anti-Fn14 MAbs bound to phage-displayed sub-domain 1, even though this construct bound well to MAb 9E10 when assayed in parallel. As expected, none of the phage constructs bound to the negative control antibody MAb 5G8 (FIG. 18B, FIG. 19B).

Binding of Antibodies to Fn14 Sub-Domains

As described above, residues included in the epitope(s) of anti-hFn14 mAbs CRCBT-06-001, CRCBT-06-002, CRCBT-06-003, CRCBT-06-004, CRCBT-06-005, CRCBT-06-006 and CRCBT-06-007 have been shown to bind to sub-domain 2 and not to sub-domain 1 of hFn14 using phage display. Synthetic peptides corresponding to sub-domain 1p (a longer form of sub-domain 1 expressed on phage) and 2 and a further smaller region of hFn14 (termed sub-domain 3) were produced in order to confirm these findings (FIG. 20).

CRCBT-06-001, CRCBT-06-002, CRCBT-06-003, CRCBT-06-004, CRCBT-06-005, CRCBT-06-006, CRCBT-06-007 and ITEM-1 did not bind to sub-domain 1p (FIG. 21A) but were reactive with a synthetic peptide representing sub-domain 2 of Fn14 when compared to an isotype control antibody (FIG. 21A). The order of reactivity from strongest to weakest was CRCBT-06-002, CRCBT-06-001, CRCBT-06-005, CRCBT-06-007, ITEM-1 and CRCBT-06-006. The reactivity of CRCBT-06-001 and CRCBT-06-002 was similar and at 5 ng/ml (FIG. 21B). This point was in the linear part of each curve and was used to measure the percentage decrease in binding of the other mAbs to sub-domain 2. There was a 40% decrease in binding of CRCBT-06-005, 48% decrease in binding of CRCBT-06-007, 68% decrease in binding of ITEM-1 and a 76% decrease in binding of CRCBT-06-006 compared to CRCBT-06-001 and CRCBT-06-002 binding to sub-domain 2. This suggests either the affinity of CRCBT-06-001 and CRCBT-06-002 is greater for this domain, or the epitope could vary slightly for CRCBT-06-005 to CRCBT-06-007 and ITEM-1.

The reactivity of CRCBT-06-001 CRCBT-06-002, CRCBT-06-003, CRCBT-06-004, CRCBT-06-005, CRCBT- 06-006 and CRCBT-06-007 with sub-domain 3 was lower than for sub-domain 2, indicating this region may be a partial epitope for these antibodies. However, the differences in binding to this region could reveal subtle variations in the contact regions of the antibodies with hFn14. The order of binding from strongest to weakest was CRCBT-06-005, CRCBT-06-002, CRCBT-06-001, CRCBT-06-006, CRCBT-06-007 and ITEM-1. The relative binding of each antibody to sub-domain 3 at a single point in the linear region of the curves was measured at 0.2 □g/ml (FIG. 21C). There was a 43% decrease in binding of CRCBT-06-002 compared with CRCBT-06-005 for binding to sub-domain 3, 60% decrease for CRCBT-06-001, 73% decrease for CRCBT-06-006 and CRCBT-06-007 and a 76% decrease in binding of ITEM-1 to sub-domain 3 compared with CRCBT-06-005 mAb. This could indicate the epitope of ITEM-1 may differ slightly to the CRCBT antibodies based on weaker interaction with surface exposed residues in sub-domain 3.

Fn14 Homologue Mutants Bind to Anti-Fn14 mAbs

A series of mutants were generated that represent single amino acid mutations that change the human Fn14 residue to the mouse and/or rat equivalent. These were designed for expression on phage. Mutants included T33N (SEQ ID NO: 49), A34S (SEQ ID NO: 50), R38S (SEQ ID NO: 51), R56P (SEQ ID NO: 52) and L77M (SEQ ID NO: 53). The relative reactivity of each phage-displayed Fn14 constructs to the antibodies CRCBT-06-002 and ITEM-1 antibodies was assessed by ELISA. All the hFn14 constructs bound well to CRCBT-06-002. The R56P mutant although slightly reduced on CRCBT-06-002 displayed no binding to ITEM-1. Furthermore, no significant binding of phage-displayed c-myc alone to any of the anti-Fn14 mAbs was observed, suggesting the antibodies were binding specifically to the phage displayed Fn14 (FIG. 22).

As shown in previous assays, no significant binding of the phage-displayed constructs to a control mAb 5G8 was observed (FIG. 22), indicating that the phage constructs were binding specifically to the CRCBT-06-002 or ITEM-1 (FIG. 22).

Comparison of Antibody Binding to Human and Mouse Fn14 and Mutant Human Fn14

Wild type human and mouse Fn14 extracellular regions were cloned as His tagged fusion constructs for expression in bacteria. Proteins were expressed and purified to yield folded soluble protein. Assessment of the capability of each antibody to bind to human and mouse Fn14 extracellular domain was assessed by ELISA (FIGS. 23A, B and C). All antibodies were shown in this assay format to bind well to the wild type human Fn14 extracellular domain. The ability of antibodies to bind mouse Fn14 revealed differences in antibody specificity. Antibodies CRCBT-06-001, CRCBT-06-002, CRCBT-06-005, ITEM-2 and ITEM-4 all bound well to mouse Fn14 whereas CRCBT-06-003 and ITEM-1 displayed reduced binding.

Since the R56P mutant displayed no binding to ITEM-1 when expressed on phage (FIG. 22), this mutant was further assessed for binding to the suite of CRCBT antibodies along with the commercial antibodies ITEM-1, ITEM-2 and ITEM-4. A number of R56 mutants were generated in order to assess the importance of this residue. His tagged fusion proteins were generated for mutant human Fn14 R56P, R56A (SEQ ID NO: 54) and R56K (SEQ ID NO: 55) extracellular region. These were expressed in bacteria and purified to yield folded soluble protein. Assessment of the capability of each antibody to bind to this series of residue R56 mutants was assessed by ELISA (results are depicted in FIG. 24).

Binding of antibody to the R56P mutant was seen for all antibodies however slightly reduced for CRCBT-06-003 and ITEM-1 (FIGS. 24A and B). To ensure the introduction of a proline residue was not simply altering the folding state of the protein, a similar mutant was assessed where the R56 was mutated to an alanine (R56A). Binding of antibody to this mutant mirrored that obtained for the R56P mutant (FIGS. 24C and D). To further assess if the charged nature of the wild type arginine residue was the reason that CRCBT-06-003 and ITEM-1 display a reduction in binding, a R56K mutant was generated. The binding of CRCB-06-003 and ITEM-1 was mostly restored suggesting that charge is important for the antigen-antibody interaction at this residue (FIGS. 24E and F).

In combination, the data generated for the R56 mutants displays that although some reduced binding is present for CRCBT-06-003 on this mutant, all CRCBT antibodies do bind well to mutants of R56 and therefore it can be concluded that it is not a critical residue in the antibody-antigen interaction.

Figure 25B:
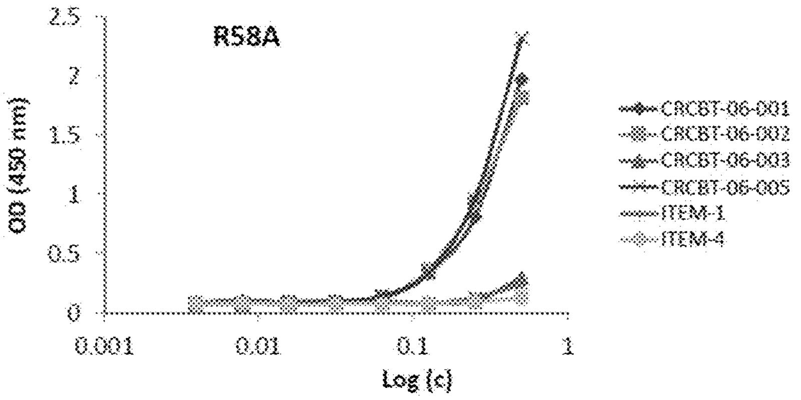

A recombinant protein for the mutation R58A (SEQ ID NO: 56) was also generated and the binding of all antibodies was assessed. The His-tagged fusion protein was expressed in bacteria and purified to yield folded soluble protein. Interestingly, this mutant segregated the antibodies into two groups, capable of binding or no binding (FIG. 25). Binding of CRCBT-06-001, CRCBT-06-002, CRCBT-06-005 and ITEM-2 was unaffected by the presence of this mutation, whereas CRCBT-06-003, ITEM-1 and ITEM-4 binding is abolished.

Further analysis of the R58A mutant was performed using a phage expressed version of the mutant. The binding of antibodies CRCBT-06-001 and CRCBT-06-002 are again unaffected. ITEM-1 and ITEM-4 binding is abolished as previously and CRCBT-06-004 additionally is unable to bind (FIG. 26).

Alanine Scan of Subdomain 2

To determine specific residues within the Fn14 epitope that are critical for binding of each antibody, an alanine scan was performed across most sub-domain 2 residues (with addition of a few residues outside this region). The suite of alanine mutants were generated as phage expressed mutants of the human Fn14 extracellular region.

The mutants assessed included W42A (SEQ ID NO: 57), L46A (SEQ ID NO: 58), D51A (SEQ ID NO: 59), S54A (SEQ ID NO: 60), A57G (SEQ ID NO: 61), R58A (SEQ ID NO: 56), P59A (SEQ ID NO: 62), H60A (SEQ ID NO: 63), S61A (SEQ ID NO: 64), D62A (SEQ ID NO: 65), F63A (SEQ ID NO: 66) and L65A (SEQ ID NO: 67). Where an alanine residue was present in the Fn14 (as in the case of A57) a glycine residue was used to generate the mutation. The binding of CRCBT-06-001, CRCBT-06-002 and CRCBT-06-004 along with ITEM-1, ITEM-4, and in some cases ITEM-2 were assessed for binding to each of the mutants (FIGS. 27 and 28). As expected, in all cases the control antibody 5G8 did not display any binding to the phage expressed proteins. All anti-Fn14 antibodies assessed bound well to wild type human Fn14 (FIG. 27A). Antibody binding was not effected for any of the antibodies on mutants W42A (FIG. 27B), S54A (FIG. 27C), A57G (FIG. 27D), P59A (FIG. 27E), S61A (FIG. 27F), F63A (FIG. 27G) and L65A (FIG. 27H) suggesting these are not important residues for antibody-antigen binding.

All antibodies bound to the L46A (FIG. 28A), D51A (FIG. 28B) and D62A (FIG. 28C) mutants however the binding of ITEM-4 is partly reduced in each case.

All antibodies were able to bind the H60A mutant however a slightly reduced binding is noted for CRCBT-06-004, ITEM-1 and ITEM-4 (FIG. 29A). This effect was not observed for CRCBT-06-004 and ITEM-1 when the mutation was replaced with a lysine, however for ITEM-4 binding was abolished (H60K; SEQ ID NO: 68; FIG. 29B). The binding of ITEM-2 to the H60K mutant vary from those in WO2009/140177 and may warrant further investigation.

Analysis of Antibody Binding Dependence on Individual Disulfide Bonds

The Fn14 extracellular region contains three disulfide bonds (cysteine residues termed 1-6) of which two reside within sub-domain 2 (cysteine residues 3-6; FIG. 20 panel C). As all the CRCBT antibodies bound well to sub-domain 2 in the context of a peptide binding assay, the need for the disulfide bonds was assessed one pair at a time. The cysteine residues 3 and 6 were mutated to serine residues (FIG. 20, Panel E) in a peptide and binding of anti-Fn14 antibodies was assessed. This disulfide bond proved dispensible with all antibodies to Fn14 tested displaying binding (FIG. 30A). The cysteine residues (4 and 5) that create the second disulfide bond were mutated to serine in a peptide of sub-domain 2 (FIG. 20, Panel F). There was a clear difference in the reactivity to this peptide with antibodies CRCBT-06-001, CRCBT-06-002 and ITEM-4 displaying good binding, whereas binding for CRCBT-06-004, CRCBT-06-005 and ITEM-1 is disrupted (FIG. 30B).

Example 2: Treatment of a Cancer-Mediated Wasting Disorder with Anti-Fn14 Antibodies Many methods used in the present Example have been previously described in Example 1. Some new methods are described in the following text, together with results of experiments.

Detection of hFn14 Expression in Cell Lines Used for Tumor Formation

To assess the level of hFn14 expression in cell lines used for in vivo tumor formation studies, induced and un-induced tumor cell lines were stained using an anti-hFn14 specific antibody and assessed by flow cytometry. Cells containing inducible hFn14 display a high level of inducible expression (FIG. 31, panel A. +4-OHT). Although in the un-induced state these cells should contain no expression of target protein, a small level of hFn14 is clearly evident (indicated by an arrow). The absence of this low level staining in the other cell lines assessed which do not contain hFn14 confirms the specificity of the antibody therefore confirming the expression in un-induced cells (FIG. 31, panels B and C).

IL-6 Secretion by Tumor Cell Lines In Vitro

MEF tumor cell lines containing hFn14 or hFn14-GPI (induced or uninduced for protein expression) were cultured for 48 hours under normal growth conditions, the media from cells was harvested and the levels of IL-6 were assessed (FIG. 32). The levels of secreted IL-6 were significantly increased in hFn14 containing cells after induction with 4-OHT (FIG. 32).

Establishment of hFn14 Tumor Model in Mice

An in vivo tumor model in wildtype C57BL/6 mice was created comprising 4-OHT inducible hFn14. To create tumor cell lines, SV40 immortalized MEF cells were transformed with human v12Hras and then stably infected with an inducible hFn14 construct described in the Materials and Methods Section of Example 1.

Mice were inoculated sub-cutaneously with cells (+/− inducible hFn14). Tumors began to form and were measurable by day 4 (FIG. 33A, panel A). The growth rate of these tumors was similar between hFn14 and controls, however the hFn14 tumors grew larger at later time points. Concurrently, from day 8 mice bearing hFn14 tumors rapidly suffered weight loss and their overall general health deteriorated (FIG. 33 B), with mice developing cachexia. All mice in this group were euthanized by day 10 due to the presence of these symptoms. Interestingly, the tumors in these mice were still in the un-induced state indicating that inducible expression in this system was not tightly regulated. On postmortem analysis, increased vasculature was noted in the hFn14 tumors as compared to the non-hFn14 control tumors.

Creation of Non-Signaling hFn14 Control Tumors

As the control tumors used in previous experiments with this system simply lacked expression of the target protein, a more suitable control construct was created for use as a control. A ‘non-signaling’ hFn14 was created whereby the extracellular region of hFn14 was fused to the C-terminal glycosylphosphatidylinositol anchor (GPI) coding region from TrailR3 to create hFn14-GPI (FIG. 34A). When expressed on cells, this protein would appear from the outside of the cell the same as wildtype hFn14 but would simply lack functional signaling. An equivalent tumor cell line harboring 4-OHT inducible GPI-anchored hFn14 was generated using this hFn14-GPI construct. Mice were injected with tumor cells on day 1 of the experiment and monitored for body weight, appearance of tumors and for general health throughout the experiment. The appearance of tumors was evident in all mice by days 4 (FIG. 34B, panel i). Similar to the non-hFn14 tumors in the previous experiments the hFn14-GPI had a slightly lower growth rate past day 8 when compared to the hFn14 tumors. In hFn14-GPI tumor mice, no weight loss or other signs of physical illness (i.e., cachexia) was noted and to ensure these mice would not simply develop symptoms at a later time point, mice were observed up to 30 days. The hFn14-GPI tumors grew large and had no effect on the overall health of the mice when compared to that seen for hFn14 tumors (FIG. 34B, panel ii). Upon postmortem assessment, hFn14-GPI control tumor vascularization appeared much like the non-expressing controls in the previous experiments.

Constitutive Fn14 Expressing Tumors

As the level of hFn14 in tumors was low and therefore difficult to detect, and given the inducible feature of this model was not being used, another method to demonstrate that wildtype hFn14 was responsible for the increased vasculature and onset of physical symptoms was generated. An independent cell line was generated with constitutive expression of hFn14. The expression of hFn14 in these cell lines was verified. A tumor experiment was performed comparing these constitutively expressing tumor cells to the previous hFn14 tumors (FIGS. 35A and B). Tumors formed in both groups however constitutively expressing hFn14 tumors did not show any signs of cachexia (i.e., weight loss and physical illness) around days 8-12 (as seen for the previous hFn14 tumors). These mice were observed over time and did eventually exhibit cachexia symptoms from approximately day 18. This result indirectly validated the involvement of hFn14 in the weight loss and deterioration of health seen when wildtype hFn14 is present in tumors.

Antibody Treatment of hFn14 Tumors

The treatment of hFn14 tumors with blocking antibodies to Fn14 was next assessed in the inducible tumor model with low level Fn14 expression. Mice were inoculated with hFn14 or hFn14-GPI tumor cells. The size of tumors, weight and overall health of mice was assessed daily. As the onset and severity of cachexia symptoms (i.e., weight loss and declining general health) is swift in this model, mice were first treated with the blocking antibody CRCBT-06-001 (10 mg/kg) 2 days prior to the expected onset of weight loss (FIG. 36). Prior to this initial antibody administration, hFn14 and hFn14-GPI groups were randomly segregated into +/− antibody treatment groups. Treatment was continued twice a week for a total of 4 weeks. Control mice received no treatment. The hFn14-GPI tumor group remained healthy as predicted throughout the course of the experiment, with the antibody treated group maintaining good general health. A small decrease in average weight was noted in the antibody treated group however mice appeared otherwise healthy. As expected, the untreated hFn14 group exhibited weight loss and deterioration of general health from day 8. All mice were euthanized by day 12. hFn14 mice that received antibody treatment not only maintained body weight and overall health throughout the course of the treatment but survived an overall of 15-25 days longer than untreated mice. Results are depicted in FIG. 36.

Assessment and Comparison of CRCBT-06-001, CRCBT-06-002, CRCBT-06-004 and ITEM-1 Efficacy Antibodies CRCBT-06-001, CRCBT-06-002, CRCBT-06-004 and ITEM-1 were in vivo in a single dose administration experiment (FIG. 37). hFn14 expressing tumors were formed in mice and on day 7 when the onset of weight loss was on average apparent, a single IP dose of 5 mg/kg antibody was administered to groups of mice. A group of hFn14 tumor mice received no treatment. As expected, CRCBT-06-001 was able to rescue the majority of mice in the group. CRCBT-06-002 rescued all mice with a prompt reversal of weight loss was evident as early as 48 hours after antibody administration. Administration of antibodies CRCBT-06-001 and CRCBT-06-002 lead to increased survival time of 17.9 and 22.3 days, respectively (see FIG. 37B; however in both cases at least one mouse remained healthy and maintained body weight at the termination of the study at day 27 meaning that the recited day is likely an underestimate). Untreated mice displayed no effect on illness progression and demonstrated a survival time of about 10.3 days. Mice treated with ITEM-1 or CRCBT-06-004 had an average survival time of 11 days and 10 days, respectively. These data demonstrate that CRCBT-06-001 and CRCBT-06-002 provide a superior benefit in treating cachexia symptoms and extending life in this mouse model.

Histopathology of Tumors

Histopathology was performed on the tumors from mice bearing hFn14 or hFn14-GPI tumors as well as a surviving CRCBT-06-002 antibody treated hFn14 tumor bearing mouse. The hFn14-GPI expressing tumor formed a discrete entity where the muscle-tumor interface was clearly defined. In contrast, hFn14 expressing tumor cells invaded the surrounding skeletal muscle and a clear boundary between tumor cells and muscle could not be identified. In mice bearing an hFn14 expressing tumor that had been treated with antibody CRCBT-06-002 and subsequently survived until day 32, no invasion of the surrounding skeletal muscle by the tumors cells wass apparent, with a clear tumor-muscle interface being visible comparable to that seen for the hFn14-GPI tumor.

CRCBT-06-001 Dose Response and Rescue Treatment

As twice weekly treatment with CRCBT-06-001 at a high dose was so successful, mice were next treated with a single injection of antibody at a range of doses (0-10 mg/kg) to assess the smallest effective amount of antibody required to observe an effect (FIG. 38). Untreated mice again suffered the expected fate however in this case the onset of weight loss (i.e., cachexia) began at day 7. Mice in the 10 mg/kg group followed the same pattern as before with a dramatic increase in overall health and maintenance of body weight compared to the untreated group. The onset of weight loss was apparent in 2 mice in this group at days 14 and 16. The other mouse survived healthy to the end of the experiment (23 days). In the 5 mg/kg treated group, all mice remained healthy and maintained weight throughout the course of the experiment with a small decrease in weight becoming apparent around day 21-22 suggesting the clearance of the antibody from the body. This dose was overall more effective than the higher dose of 10 mg/kg.

All other antibody treated groups (0.1, 0.5 and 1 mg/kg) showed some degree of improvement post treatment but these lower doses only delayed the onset of weight loss (i.e., cachexia) by a few days, with a decline in body weight seen between days 8-10. For the mice in these groups, when the onset of cachexia symptoms was definite (days 9 or 10) a single antibody dose of 10 mg/kg was administered to assess the possible rescue of these mice from further decline. The 0.5 and 1 mg/kg groups were fully rescued from further weight loss and surprisingly displayed a full reversal of weight loss within approximately 5 days post treatment. This reversal was maintained throughout the remainder of the experiment (up to day 23).

Example 3: Treatment of a Cancer-Mediated Wasting Disorder with Anti-Fn14 Antibodies Methods Experimental Animals Female C57BL/6 mice (11 week old) were given a single subcutaneous injection of mouse embryonic fibroblasts (MEF s) stably transfected with Fn14 (MEF Fn14) or the untransfected MEF Hras cells (Hras) (cell line generation described in the Materials and Methods Section of Example 1.). On day 6, mice were given a single intraperitoneal injection of IgG2b isotype control antibody (Hras+IgG2b, MEF Fn14+IgG2b, n=8/group) or CRCBT-06-001 (MEF Fn14+001, n=8). Mice were housed under a 12:12-hour light-dark cycle. Mice were assessed daily for general health, body mass, tumor size, food and water intake.

Grip Strength Test

Whole body strength was assessed on day 11 by means of a grip strength meter (Columbus Instruments, Columbus, Ohio), essentially as described in Murphy et al., 2012.

Assessment of Functional Properties of Tibialis Anterior Muscles In Situ

On day 11, mice were anaesthetised with sodium pentobarbitone (Nembutal; 60 mg/kg; Sigma-Aldrich) via intraperitoneal (IP) injection. The methods for assessment of the contractile properties of the mouse tibialis anterior (TA) muscle in situ have been described previously (Murphy et al., 2010). After determining peak tetanic force, muscles were subjected to a 4 minute intermittent stimulation protocol to induce muscle fatigue. Muscles were maximally stimulated for 1 second every 4 seconds for the duration of the fatigue protocol. Peak tetanic force was assessed at 5 minutes and 10 minutes following cessation of the fatiguing stimulation protocol. At the conclusion of the contractile measurements in situ, the TA, extensor digitorum longus (EDL), soleus, plantaris, gastrocnemius and quadriceps muscles as well as the epididymal fat and heart were carefully excised, blotted on filter paper and weighed on an analytical balance. Mice were killed as a consequence of heart excision while still anaesthetised deeply.

Skeletal Muscle Histology

Serial sections (5 μm) were cut transversely through the TA muscle using a refrigerated (−20° C.) cryostat (CTI Cryostat; IEC, Needham Heights, Mass.). Sections were reacted with: laminin (#L9393, Sigma-Aldrich) for determination of mean myofibre cross-sectional area (CSA); succinate dehydrogenase (SDH) to determine activity of oxidative enzymes; and N2.261 (developed by Dr. Helen M. Blau, obtained from the Developmental Studies Hybridoma Bank developed under the auspices of the NICHD and maintained by The University of Iowa, Department of Biology, Iowa City, Iowa, USA) to assess the percentage of myosin IIa isoforms (Murphy et al., 2010). Mouse TA muscle have been shown previously to almost lack type I fibers (Murphy et al., 2011) so all non-N2.261 reacting fibers were assumed to represent type IIx/b fibers. Optical density (o.d.) of SDH was determined after 6 min of reactivity for all samples and sections were captured in full color using bright field light microscopy and analyzed, substantially as described in Murphy et al., 2010. Digital images were obtained using an upright microscope with camera (Axio Imager D1, Carl Zeiss, Wrek, Göttingen, Germany), controlled and quantified by AxioVision AC software (AxioVision AC Rel. 4.7.1, Carl Zeiss).

Results

Injection with MEF Fn14 caused a loss of body mass, with IgG2b treated mice losing ~20% body mass during the 11 day experimental period compared with control mice that only lost ~3% body mass (FIG. 39). However, treatment with CRCBT-06-001 attenuated the loss of body mass with MEF Fn14-001 treated mice only losing ~5.5% body mass (FIG. 39). Tumor mass and volume was not significantly different between groups (FIG. 40).

Figure 41B:
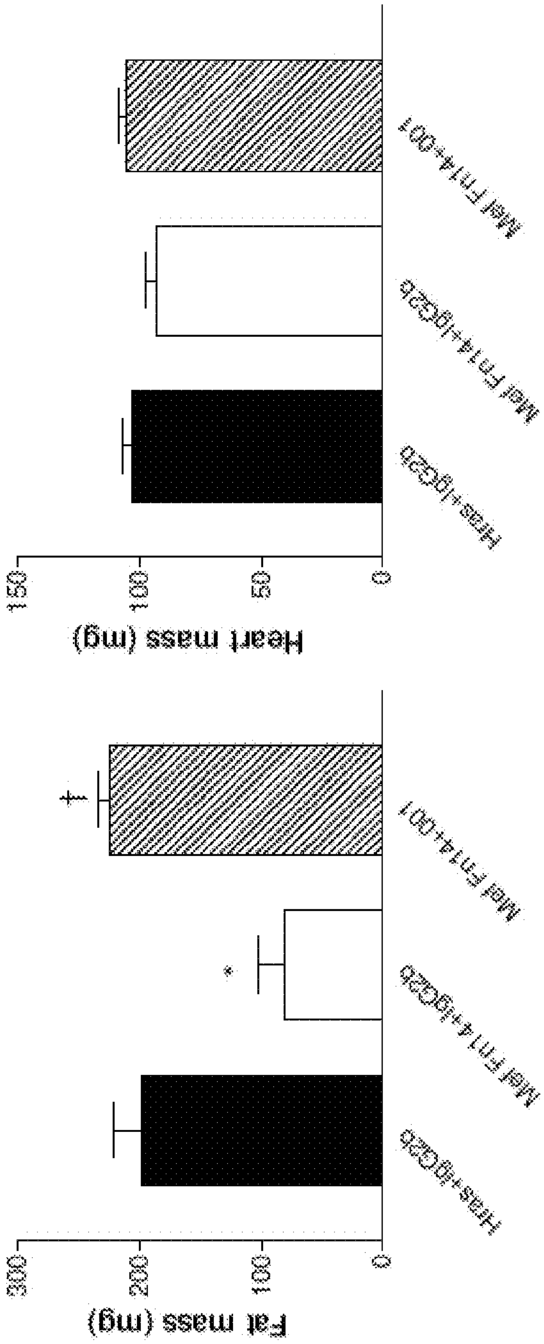

MEF Fn14 injection caused a loss of muscle and fat mass, with a 15-29% decrease in mass of the plantaris and tibialis anterior (TA) muscles and a 60% decrease in subscapular fat mass compared with control mice (FIG. 41). The loss of muscle and fat mass in MEF Fn14 injected mice was completely prevented by a single injection of CRCBT-06-001 (FIG. 41B).

Figure 43A:
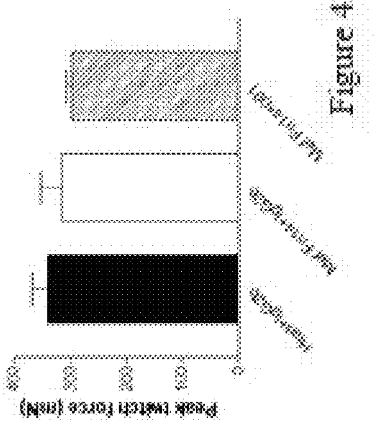
Figure 43B:
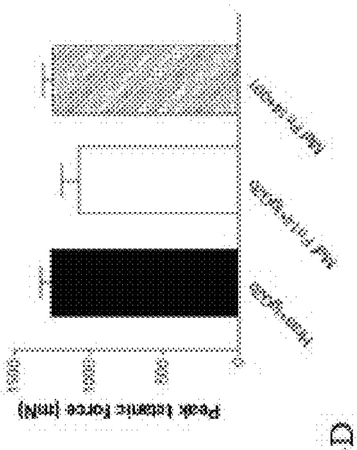
Figure 43C:
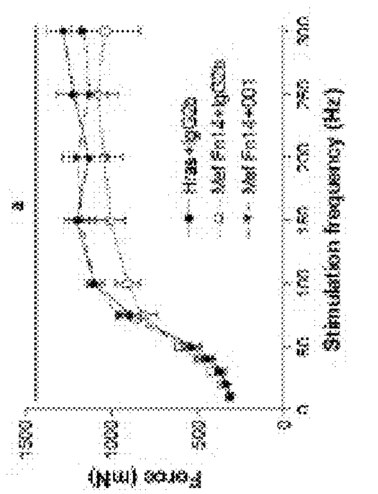
Figure 43D:
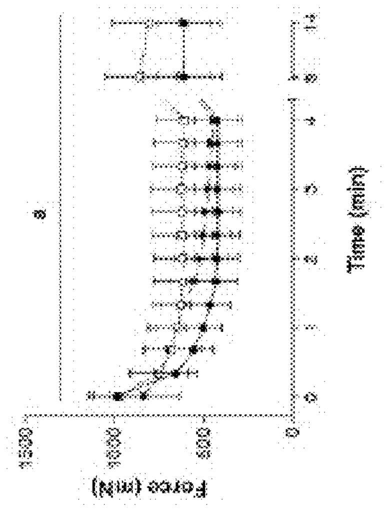

Given the short duration of the experiment, there were no differences between groups in assessments of muscle function, with similar grip strength (FIG. 42) and peak twitch and tetanic force of TA muscles (FIGS. 43A and 43B). When TA muscle strength was examined over a range of stimulation frequencies, there was a main effect for lower tetanic force production in MEF Fn14+IgG2b treated mice compared with controls (FIG. 43C). During a 4-minute intermittent fatiguing stimulation protocol, TA muscles from MEF Fn14+IgG2b treated mice produced higher forces than controls (FIG. 43D).

TA muscle sections stained with haematoxylin and eosin and sections reacted with an anti-laminin antibody revealed that MEF Fn14 injection caused a decrease in cross-sectional area of type IIa fibres (−21%) and type IIx/b fibres (−13%), and a 13% decrease in average cross-sectional area. However, a single injection of CRCBT-06-001 completely prevented the decrease in muscle fibre size. There were no differences between groups in the proportion or oxidative enzyme capacity of type IIa and type IIx/b fibres (FIG. 44).

Example 4: Treatment of a Colon Cancer-Mediated Wasting Disorder with Anti-Fn14 Antibodies Method Male CD2F1 (11 week old) or female Balb/c (9-10 week old) mice were sub-cutaneously (s/c) inoculated with $1\times10^6$ Colon-26 cells on day 1 (Cell Line Services; Germany). Mice were assessed daily for general health, body mass, food and water intake. Tumors were measured daily and tumor volume was calculated based on $(1*w^2)/2$ where 1=length and w=width. For pair fed groups feeding was achieved by monitoring the food intake of the untreated tumor group each 24 hours and then providing a non-tumor 'pair-fed' group with that amount of food for the following 24 hour period.

Results

Assessment of Antibodies in Colon-26 Mouse Cancer Model of Cachexia

The Colon-26 cancer model of cachexia is known in the cachexia literature (Murphy et al., 2012). CD2F1 mice were inoculated with Colon-26 cells to form subcutaneous solid tumors. These tumors lead to progressive weight loss in mice which includes the wasting of skeletal muscle.

Figure 45B:
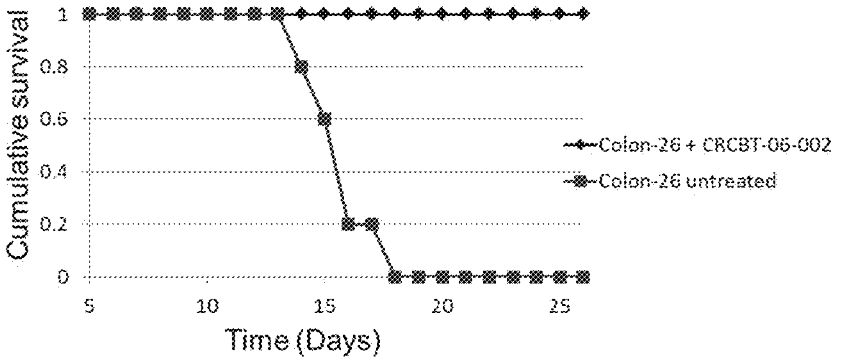

To assess the effect of anti-Fn14 antibody in this model, Colon-26-bearing mice were treated with IP antibody CRCBT-06-002 (Colon-26+CRCBT-06-002) prior to the onset of weight loss. Multiple dosing was performed throughout the course of the experiment as indicated in FIG. 45A. Additional control groups included a pair-fed non-tumor group (Pair Fed), an untreated tumor group (Colon-26 Untreated) and an untreated non-tumor group (Control). Efficacy of CRCBT-06-002 was demonstrated with treated mice maintaining body mass and overall good health throughout the experiment (longest time point measured was day 27) when compared to untreated mice that all reached the maximum allowed weight loss (based on institutional animal ethics approval) by days 14-18 (FIGS. 45A and 45B). Note, two of the five antibody treated mice were killed on day 20 due to maximal tumor mass (based on the institutional animal ethics approval) being reached and not due to weight loss or other signs of illness.

Assessment of Antibodies in Colon-26 Tumor-Bearing Balb/c Mice

Colon-26 tumors are also commonly formed in Balb/c mice and given the effect of CRCBT-06-002 that had been noted in CD2F1 mice, a similar treatment schedule was carried out in Balb/c mice bearing Colon-26 tumors. Results are depicted in FIG. 46 and show that treatment with CRCBT-06-002 reduces tumor size.

Assessment of Antibody CRCBT-06-001 in Colon-26 Tumors in CD2F1 Mice

Given the efficacy demonstrated by CRCBT-06-002 on Colon-26 cancer cachexia, the effect of CRCBT-06-001 on cachexia in this model was next assessed. CD2F1 mice were inoculated with Colon-26 cells and mice were treated with 10 mg/kg IP antibody CRCBT-06-001 on days 16 and 20 as indicted. Untreated mice were injected with Colon-26 cells but received no antibody treatment. Mice treated with CRCBT-06-001 displayed a delayed onset of weight loss as compared to the untreated controls, demonstrating the effectiveness of the antibody on the cachexia progression in this model (FIG. 47A). This can also be seen on assessment of survival over time (FIG. 47B). Despite the effectiveness of the antibody in preventing weight loss, it did not appear to have a significant effect on tumor volume (FIG. 47C).

Example 5: Treatment of a Colon Cancer-Mediated Wasting Disorder with Anti-Fn14 Antibodies Methods Experimental Animals Male CD2F1 mice (12 week old) were inoculated subcutaneously (s/c) with $5\times10^5$ Colon-26 (C-26) cells (kindly donated by Martha Belury, The Ohio State University, Columbus, Ohio) suspended in 100 μl of sterilised PBS. Mice were assessed daily for general health, body mass, tumor size, food and water intake. All mice were obtained from the Animal Resources Centre (Canning Vale, Western Australia) and housed in the Biological Research Facility at The University of Melbourne under a 12:12-hour light-dark cycle. Water was available ad libitum and both water and standard laboratory chow was provided, changed and monitored daily. Pair feeding was achieved by monitoring the food intake of the untreated group each 24 hours and then providing the pair-fed group with that amount of food for the following 24 hour period.

Grip Strength and Rotarod Test

Whole body strength and whole body mobility and coordination were assessed on day 21 by means of a grip strength meter (Columbus Instruments, Columbus, Ohio) and rotarod performance test (Rotamex-5, Columbus Instruments) essentially as described in Murphy et al., 2012.

Assessment of Functional Properties of Tibialis Anterior Muscles In Situ

On day 22, mice were anaesthetised with sodium pentobarbitone (Nembutal; 60 mg/kg; Sigma-Aldrich) via intraperitoneal (IP) injection. The methods for assessment of the contractile properties of the mouse tibialis anterior (TA) muscle in situ have been described in detail previously (Murphy et al., 2010). After determining peak tetanic force, muscles were subjected to a 4 minute intermittent stimulation protocol to induce muscle fatigue. Muscles were maximally stimulated for 1 second every 4 seconds for the duration of the fatigue protocol. Peak tetanic force was assessed at 5 minutes and 10 minutes following cessation of the fatiguing stimulation protocol. At the conclusion of the contractile measurements in situ, the TA, extensor digitorum longus (EDL), soleus, plantaris, gastrocnemius and quadriceps muscles as well as the epididymal fat and heart were carefully excised, blotted on filter paper and weighed on an analytical balance. Mice were killed as a consequence of heart excision while still anaesthetised deeply.

Skeletal Muscle Histology

Skeletal muscle histology was assessed substantially as described in Example 3.

Results

Assessment of Antibodies in Colon-26 Mouse Cancer Model of Cachexia

To further assess the effect of anti-Fn14 antibody in the Colon-26 model, mice were inoculated with Colon-26 cells and prior to the onset of weight loss, treated with antibody CRCBT-06-002 (C-26+002). Multiple dosing was performed throughout the course of the experiment as indicated. Control groups included an untreated tumor group (C-26) and a tumor group injected with IgG antibody (C-26+IgG). The C-26+IgG and C-26+002 groups were pair-fed to the untreated tumor group.

Clear efficacy of CRCBT-06-002 is demonstrated with treated mice maintaining body mass and overall good health throughout the experiment (longest time point measured was day 22) when compared to untreated mice and IgG treated mice (FIGS. 48A and B). Over the 22 day period, untreated and IgG treated tumor mice lost ~29% tumor-free body mass, whereas CRCBT-06-002 treated tumor mice only lost ~4% tumor-free body mass (FIG. 48C). Tumors were measured over time (FIG. 49A) and tumor volume was calculated and graphed for each group (FIGS. 49B and 49C).

Figure 50A:
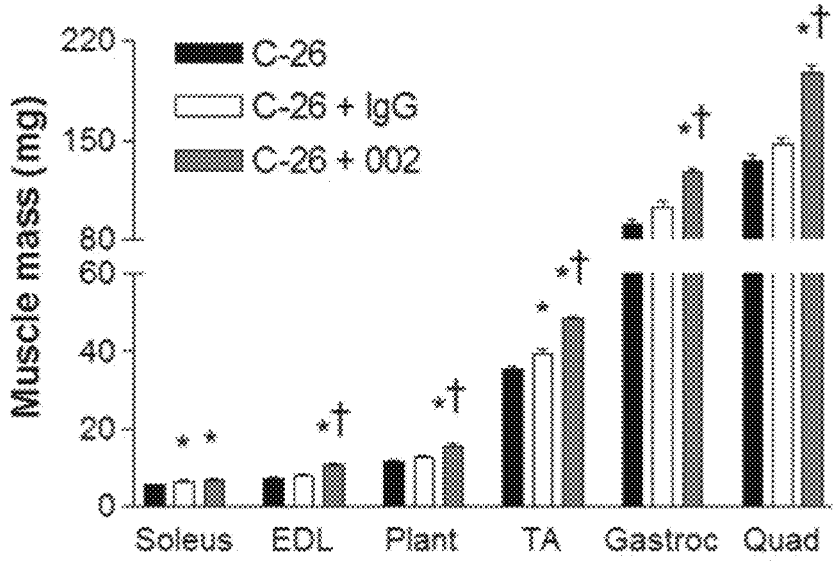
Figure 50B:
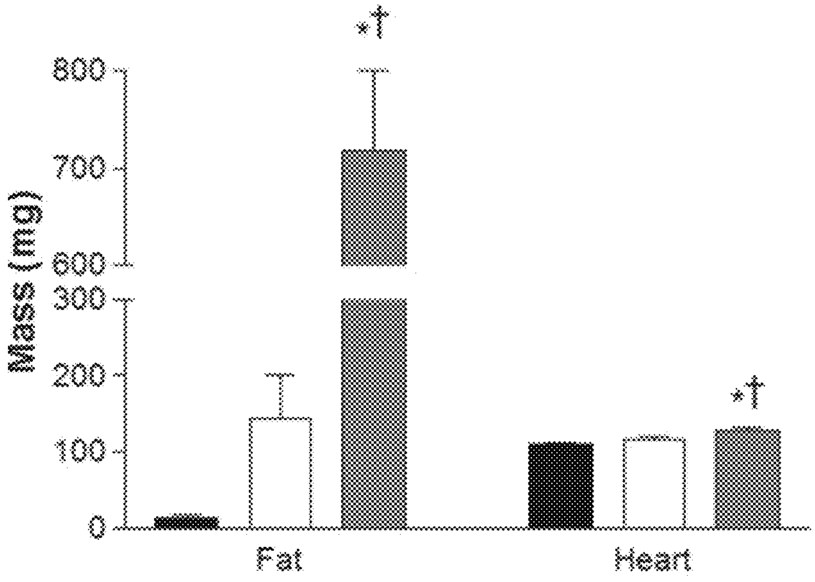

Absolute mass of the extensor digitorum longus (EDL), plantaris, tibialis anterior (TA), gastrocnemius and quadriceps muscles were 23-34% higher in the CRCBT-06-002 treated tumor mice compared to the untreated and IgG treated mice (FIG. 50A). Fat and heart mass were also higher with CRCBT-06-002 treatment (FIG. 50B).

Peak grip strength was 35% and 26% higher in CRCBT-06-002 treated tumor mice compared with untreated and IgG treated mice, respectively (FIG. 51A), whereas latency-to-fall during the rotarod test was not significantly different between groups (FIG. 51B).

Figure 52A:
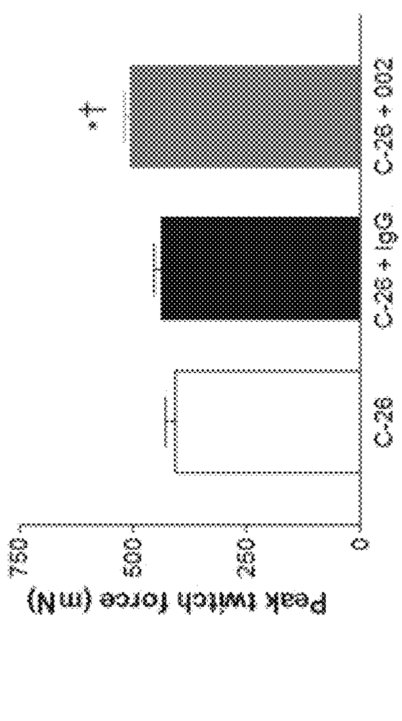
Figure 52B:
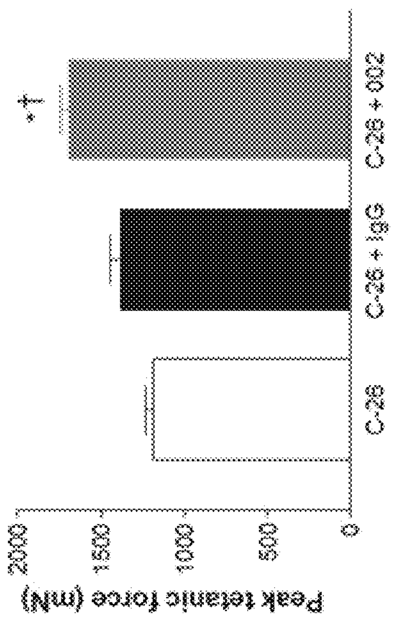
Figure 52C:
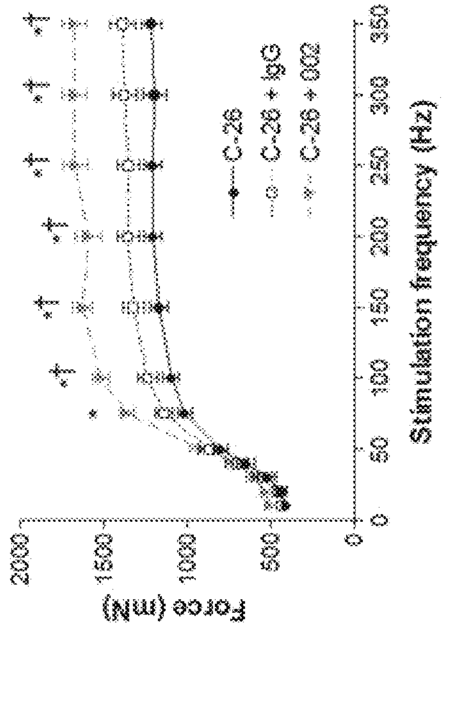
Figure 52D:
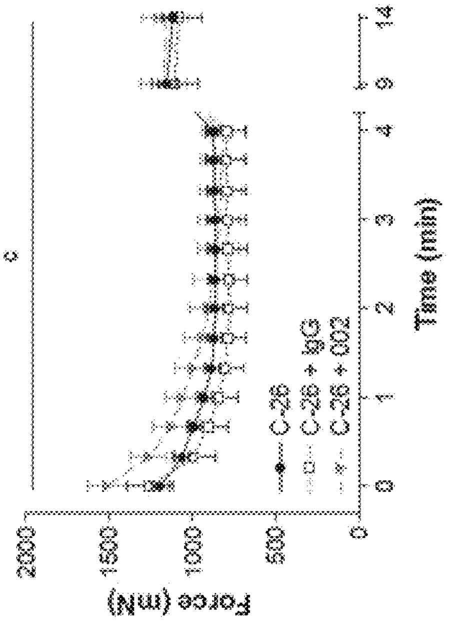

TA muscles from CRCBT-06-002 treated tumor mice were stronger than untreated and IgG treated mice, with higher peak twitch force and tetanic force over a range of stimulation frequencies (FIGS. 52A, 52B and 52C). During a 4-minute intermittent fatiguing stimulation protocol, TA muscles from 002 treated mice were stronger than untreated and IgG treated tumor mice (FIG. 52D).

TA muscle sections stained with haematoxylin and eosin and sections reacted with an anti-laminin antibody revealed that CRCBT-06-002 treated mice have bigger muscle fibres than untreated and IgG treated mice. The proportion of type IIa muscle fibres appears similar between groups, but the area of the type IIa fibres is larger in the CRCBT-06-002 treated mice. Muscle fibre oxidative capacity as assessed by SDH reaction was similar between groups.

Analysis of TA muscle sections stained with haematoxylin and eosin and sections reacted with an anti-laminin antibody revealed that cross-sectional area (CSA) of type IIa and type IIx/b fibres as well as average fibre CSA was greater in CRCBT-06-002 treated mice than untreated and IgG treated mice (FIG. 53A). The proportion of type IIa and type IIx/b muscle fibres was similar between groups (FIG. 53B). Oxidative enzyme capacity in type IIa and type IIx/b fibres as well as average fibre oxidative capacity as assessed by SDH reaction was similar between groups (FIG. 53C). These data indicate that treatment with CRCBT-06-002 increased the size of muscle fibres but did not change the constitution of muscles compared with controls.

Example 6: Treatment of Diabetes and a Diabetes-Mediated Wasting Disorder with Anti-Fn14 Antibodies Methods Diabetes was induced in 8 weeks old male C57Bl/6 mice by administering multiple low doses of Streptozotocin (STZ) essentially as described in Chen et al., 2009 and/or Motyl et al., 2009. Briefly, mice received an IP injection of 45 mg/kg STZ (Sigma S-0130) for 5 consecutive days (days 1-5). Control mice were injected with vehicle (0.1M chilled sodium citrate buffer, pH4.5). Mice were assessed for general health, body mass, food and water intake daily. The pair-fed (PF) group was fed according to the STZ injected group daily intake.

For antibody treatment, mice were administered a single IP 20 mg/kg dose of CRCBT-06-002 two days after the final streptozotocin injection (day 7). On day 28 all mice were sacrificed and blood, muscle (tibialis anterior, quadricep and heart) and epididymal fat was removed for analysis. Non-fasted blood glucose levels were measured using an Accu-check blood glucose monitor.

Results

A STZ-induced diabetes mouse model was used to assess the effect of antibody CRCBT-06-002 on diabetes-associated weight loss. Antibody was administered on day 7 to a group of STZ induced diabetic mice. Body mass was assessed daily and standardised against starting body mass as 100%. Standardised group averages were graphed (FIG. 54). The administration of antibody after diabetes induction lead to an immediate drop in body mass of this group however this weight was recovered well by 12-14 days. An overall increase in body mass was then seen from around day 18 as compared to the STZ alone group.

Over the course of the 28 day experiment, group daily intake of water was measured and graphed as the cumulative intake (FIG. 55). STZ mice water intake was higher due to the diabetic state, however the post-antibody treatment STZ group display a water intake trend over time closer to the intake of the non-diabetic control groups.

On day 28, mice were euthanized and blood glucose levels were assessed (FIG. 56). When a blood glucose level out of range of the test was obtained, the maximum level of detection was assigned (600 mg/dl). This was the case for three of the STZ group and one of the antibody treated group.

Epididymal fat, heart, tibialis anterior (TA) and quadricep were removed for analysis. Group average tissue weight was calculated and graphed (FIG. 57A) standardised to final body mass (day 28; FIG. 57B) and against starting body mass (day 1; FIG. 57C). The antibody treatment attenuated the decrease in quadriceps and heart, and partially attenuated the decrease in TA muscle and in epididymal fat.

These data demonstrate that treatment with an anti-Fn14 antibody (CRCBT-06-002) prevents or treats diabetes-induced cachexia and reduces symptoms of diabetes, such as increased daily water intake and blood glucose levels.

REFERENCES

Al-Lazikani et al., *J Mol Biol* 273, 927-948, 1997;

Ausubel et al., (editors), Current Protocols in Molecular Biology, Greene Pub. Associates and Wiley-Interscience (1988, including all updates until present);

Baecher-Allan et al, *J. Immunol.* 167:1245-1253, 2001;

Bork et al., *J Mol. Biol.* 242, 309-320, 1994;

Brinkmann et al., *Proc. Natl. Acad. Sci. USA,* 90: 7538-7542, 1993;

Brown (editor), Essential Molecular Biology: A Practical Approach, Volumes 1 and 2, IRL Press (1991);

Brown et al., *Biochem J.* 397: 297-304, 2006;

Chen et al., *Biochemical and Biophysical Research Communications*, 388:112-6, 2009;

Chothia and Lesk *J. Mol Biol.* 196:901-917, 1987;

Chothia et al., *Nature* 342, 877-883, 1989;

Coley et al., *Protein Engineering* 14: 691-698, 2001;

Coligan et al., (editors) Current Protocols in Immunology, John Wiley & Sons (including all updates until present);

Dharmapatni et al., *Arthritis Res Ther,* 13: R51, 2011;

Frauenknecht et al., *J Neuroimmunol,* 227: 1-9, 2010;

Gefter et al, *Somatic Cell Genet.* 3, 231-236, 1977;

Giudicelli et al., *Nucleic Acids Res.,* 25: 206-211 1997

Goodman et al., Goodman and Gilman's The Pharmacological Basis of Therapeutics, 8th Ed., Macmillan Publishing Co., 1990;

Glover and Hames (editors), DNA Cloning: A Practical Approach, Volumes 1-4, IRL Press (1995 and 1996);

Harlow and Lane (editors) Antibodies: A Laboratory Manual, Cold Spring Harbor Laboratory, (1988);

He et al., *Protein Science* 18: 650-656, 2009;

Hoogenboom et al., *Nucl. Acids Res.,* 19:4133-4137, 2001;

Honnegher and Plükthun *J. Mol. Biol.,* 309: 657-670, 2001

Inta et al., *J Neurol Sci* 275: 117-120, 2008;

Jespers et al, *Bio/technology* 12:899-903, 1988;

Kabat *Sequences of Proteins of Immunological Interest*, National Institutes of Health, Bethesda, Md., 1987 and 1991;

Kohler and Milstein, *Nature* 256, 495-497, 1975;

Kohler and Milstein, *Eur. j. Immunol.* 6, 511-519, 1976;

Kruif and Logtenberg *J. Biol. Chem.,* 271: 7630-7634, 1996;

Kumar et al, *Immuno. Letters* 65, 153-159, 1999;

Kyte and Doolittle *J. Mol. Biol.,* 157: 105-132, 1982;

Motyl et al., *Biol Proced Online,* 11:296-315, 2009;

Murphy et al., *FASEB J.,* 24:4433-4442, 2010;

Murphy et al., *Am J Physiol.* 301:R716-R26, 2011;

Murphy et al., *Dis Model Mech;* 5:533-545, 2012;

Nahshol et al., *Anal Biochem* 383: 52, 60, 2008;

Nakayama et al., *J. Immunol.,* 170: 341-348, 2003;

Natsume et al., *Cancer Res.* 68: 3863-3872, 2008

Needleman and Wunsch. *Mol. Biol.* 48, 443-453, 1970;

Padlan et al., *FASEB J.,* 9: 133-139, 1995;

Perbal, A Practical Guide to Molecular Cloning, John Wiley and Sons (1984);

Plückthun in The Pharmacology of Monoclonal Antibodies, vol. 113, Rosenburg and Moore eds., Springer Verlag, New York, pp. 269-315, 1994;

Sambrook et al., Molecular Cloning: A Laboratory Manual, Cold Spring Harbour Laboratory Press (1989);

Scopes In: Protein purification: principles and practice, Third Edition, Springer Verlag, 1994;

Shalaby et al, *J. Exp. Med.,* 175: 217-225, 1992;

Trenado et al., *J Clin. Invest.,* 112: 1688-1696, 2002;

Vince et al., *Cell.,* 131: 682-693, 2007;

Wang et al., *J Immunol Methods* 233): 167-177, 2000;

Yumane-Ohnuki et al., *Biotechnol Bioeng.* 87:614-22, 2004; and

Zhao et al., *J Immunol,* 179: 7949-7958, 2007

Zola, "Monoclonal Antibodies: A Manual of Techniques", CRC Press, 1987.

We claim:

1. A method of treating cancer cachexia, the method comprising administering to a subject in need thereof an Fn14-binding protein, wherein the Fn14-binding protein comprises at least a heavy chain variable region ($V_H$) and a light chain variable region ($V_L$), wherein the $V_H$ and $V_L$ bind to form a Fv comprising an antigen binding domain and wherein the Fv comprises a $V_H$ comprising CDRs 1, 2 and 3 of a $V_H$ comprising a sequence set forth in SEQ ID NO: 16 and a $V_L$ comprising CDRs 1, 2 and 3 of a $V_L$ comprising a sequence set forth in SEQ ID NO: 23.

2. The method of claim 1, wherein the method additionally comprises selecting a subject suffering from cancer cachexia, wherein the subject suffers from a cancer expressing Fn14.

3. The method of claim 1, wherein the Fn14-binding protein comprises an antigen binding domain of an anti-Fn14 antibody, wherein the antigen binding domain binds specifically to Fn14 and wherein the protein reduces Tweak-induced NFκB-signaling in a HEK293T cell expressing Fn14 and a nucleic acid encoding fluorescent protein operably linked to a promoter that facilitates gene expression as a result of NFκB signaling, and wherein the protein does not detectably induce NFκB-signaling when contacted to a HEK293T cell expressing Fn14 and a nucleic acid encoding fluorescent protein operably linked to a promoter that facilitates gene expression as a result of NFκB signaling.

4. The method of claim 1, wherein the Fn14-binding protein has one or more of the following characteristics:

(i) binds to a conformational epitope dependent on disulphide bond formation within Fn14;

(ii) binds to a peptide consisting of the sequence set forth in SEQ ID NO: 56; and/or (iii) binds to a peptide consisting of the sequence set forth in SEQ ID NO: 57 and/or SEQ ID NO: 68 at a similar or substantially the same level as it binds to an extracellular domain of Fn14.

5. The method claim 1, wherein the Fn14-binding protein is an antibody comprising:

a $V_H$ comprising the sequence set forth in SEQ ID NO: 16 and a $V_L$ comprising the sequence set forth in SEQ ID NO: 23.

* * * * *